(12) United States Patent
Bon et al.

(10) Patent No.: US 11,518,803 B2
(45) Date of Patent: Dec. 6, 2022

(54) ANTAGONIST ANTIBODIES THAT BIND TO HUMAN TGFB1, TGFB2 AND TO TGFB3 AND THEIR USE FOR THE TREATMENT OF LUNG FIBROSIS

(71) Applicant: UCB BIOPHARMA SRL, Brussels (BE)

(72) Inventors: Helene Bon, Slough (GB); Joanne Elizabeth Compson, Slough (GB); Kate Louise Dixon, Slough (GB); Carl Brendan Doyle, Slough (GB); Mark Ellis, Slough (GB); Maria Margarida Gouveia Sancho, Slough (GB); Raymond Anthony Jupp, Slough (GB); Lara Kevorkian, Slough (GB); Daniel John Lightwood, Slough (GB); Diane Marshall, Slough (GB); Andrew Charles Payne, Slough (GB); Joseph Michael David Rastrick, Slough (GB); Monika-Sarah Schulze, Slough (GB); Alison Turner, Slough (GB); Kerry Louise Tyson, Slough (GB)

(73) Assignee: UCB BIOPHARMA SRL, Brussels (BE)

( * ) Notice: Subject to any disclaimer, the term of this patent is extended or adjusted under 35 U.S.C. 154(b) by 76 days.

(21) Appl. No.: 16/925,281

(22) Filed: Jul. 9, 2020

(65) Prior Publication Data
US 2020/0407436 A1 Dec. 31, 2020

Related U.S. Application Data

(62) Division of application No. 16/307,444, filed as application No. PCT/EP2017/063796 on Jun. 7, 2017, now Pat. No. 10,766,956.

(30) Foreign Application Priority Data
Jun. 8, 2016 (GB) ..................................... 1610044

(51) Int. Cl.
C07K 16/22 (2006.01)
A61P 11/00 (2006.01)
A61K 9/00 (2006.01)
A61P 11/12 (2006.01)
A61K 39/395 (2006.01)

(52) U.S. Cl.
CPC ............ *C07K 16/22* (2013.01); *A61K 9/0075* (2013.01); *A61P 11/00* (2018.01); *A61K 39/3955* (2013.01); *A61K 39/39533* (2013.01); *A61P 11/12* (2018.01)

(58) Field of Classification Search
None
See application file for complete search history.

(56) References Cited

U.S. PATENT DOCUMENTS

2002/0141995 A1 10/2002 Irvin

FOREIGN PATENT DOCUMENTS

| CA | 2956256 A1 | 2/2016 |
|----|------------|--------|
| CN | 1835974 A | 9/2006 |
| CN | 1961003 A | 5/2007 |
| CN | 101553254 A | 10/2007 |
| CN | 104645328 A | 5/2015 |
| WO | 2005/014650 A2 | 2/2005 |
| WO | 2005/097832 A2 | 10/2005 |
| WO | 2006086469 A2 | 8/2006 |
| WO | 2007076391 A1 | 7/2007 |
| WO | 2008/060371 A1 | 5/2008 |
| WO | 2012-167143 A1 | 12/2012 |
| WO | 2014/164709 A2 | 10/2014 |
| WO | 2016/019368 A1 | 2/2016 |
| WO | 2017/141208 A1 | 8/2017 |
| WO | 2018/134681 A1 | 7/2018 |

OTHER PUBLICATIONS

Moulin et al., "Structures of a pan-specific antagonist antibody complexed to different isoforms of TGFβ reveal structural plasticity of antibody-antigen interactions," Protein Sci. 23:1698-1707 (2014).
International Search Report issued in Int'l Appl. No. PCT/EP2017/063796, dated Oct. 16, 2017.
Akhurst, Rosemary J. et al, "Targeting the TGFbeta signalling pathway in disease," Nature reviews drug discovery, Sep. 24, 2012, 790-811—XP055094901, 11(10).
Botney M D et al, "Vascular Remodeling Primary Pulmonary Hypertension Potential Role for Transforming Growth Factor-β," Am J Pathol, 1994, 286-295, vol. 144 No. 2.
Broekelmann, T J et al, "Transforming growth factor β1 is present at sites of extracellular matrix gene expression in human pulmonary fibrosis," Proc. Natl. Acad. Sci, Aug. 1991, 6642-6646, 88.
CAT-152 0102 Trabeclectomy Study Group, "A Phase III Study of Subconjunctival Human Anti-Transforming Growth Factor β2 Monoclonal Antibody (CAT-153) to prevent Scarring after First-Time Trabeculectomy," Ophthalmology, 2007, 1822-1830, 114.
Cohn et al, "A phase I dose-escalation study to a predefined dose of a transforming growth factor-β1 monoclonal antibody (TβM1) in patients with metastic cancer," International Journal of Oncology, 2014, 2221-2231, 45.
Denton, C P et al, "Recombinant Human Anti-Transforming Growth Factor β1 Antibody therapy in Systemic Sclerosis," Arthritis & Rheumatism, Jan. 2007, 323-333, vol. 56 No. 1.

(Continued)

*Primary Examiner* — Marianne P Allen
(74) *Attorney, Agent, or Firm* — Medler Ferro Woodhouse & Mills

(57) ABSTRACT

The present disclosure relates to TGF-beta antibodies and binding fragments thereof, DNA encoding the same, host cells comprising said DNA and methods of expressing the antibody or binding fragment in a host cell. The disclosure also extends to pharmaceutical compositions comprising the antibody or a binding fragment thereof and use of the antibody, binding fragment and compositions comprising the same in treatment of various diseases including fibrosis.

20 Claims, 48 Drawing Sheets

Specification includes a Sequence Listing.

(56) References Cited

OTHER PUBLICATIONS

Khalil, N et al, "Increased Production and Immunohistochemical Localization of Transforming Growth Factor-β in Idiopathic Pulmonary Fibrosis," Am J Respir Cell Mal Biol, 1991, 155-162, 5.

Lacouture, M E et al, "Cutaneous keratoacanthomas/squamous cell carcinomas associated with neutralization of transforming growth factor β by the monoclonal antibody fresolimumab (GC1008)," Cancer Immunuol Immunother, 2015, 437-446, 64.

Leask & Abraham, "TGF-β signaling and the fibrotic response," FASEB J., 2004, 816-827, 18.

Li M. 0 et al, "Transforming Growth Factor-β Regulation of Immune Responses," Ann Rev Immunol, 2006, 99-146, 24.

Rice, Lisa M et al, "Fresolimumab treatment decreases biomarkers and improves clinical symptoms in systemic sclerosis patients," Journal of clinical investigation, Jun. 22, 2015, 2795-2807—XP055394513, 125(7).

CDRL1

QASESIYSGLA SEQ ID NO: 1

CDRL2

AASDLAS SEQ ID NO: 2

CDRL3

QQTWTDGGIDNP SEQ ID NO: 3

CDRH1

GFSLSSYDMS SEQ ID NO: 4

CDRH2

IIYGGSGSTWYASWAKG SEQ ID NO: 5

CDRH3

GRDGGAGGSRNGYSL SEQ ID NO: 6

CDRH3 variant 1 – present in gH13 and gH20

GRDAGAGGSRNGYSL SEQ ID NO: 7

CDRH3 variant 2 – present in gH23

GRDAGAGGSRNAYSL SEQ ID NO: 8

CDRH3 variant 3 – present in gH29

GRDAGAGGSRDGYSL SEQ ID NO: 9

FIGURE 1B

Rabbit Ab 4856 VL region     SEQ ID NO: 10

AYDMTQTPAS VEVAVGGTVT IKCQASESIY SGLAWYQQTP GQRPKLLIYA
ASDLASGVPS RFKGSGSGTE YTLTISGVEC ADAATYYCQQ TWTDGGIDNP
FGGGTEVVVK

Rabbit Ab 4856 VL region     SEQ ID NO: 11 gcctatgata tgacccagac tccagcctct gtggaggtag ctgtgggagg
cacagtcacc atcaagtgcc aggccagtga gagcatttac agtggtttgg
cctggtatca gcagacacca gggcagcgtc ccaagctcct gatctatgct
gcatccgatc tggcatctgg ggtcccatcg cgattcaaag cagtggatc
tgggacagag tacactctca ccatcagcgg cgtggagtgt gccgatgctg
ccacttacta ctgtcaacag acttggactg atggtggtat tgataatcct
ttcggcggag ggaccgaggt ggtggtcaaa Rabbit Ab 4856 VL region with signal sequence underlined and italicised SEQ ID NO: 12

*MNMRAPTQLL GLLLLWLPGA RC*AYDMTQTP ASVEVAVGGT VTIKCQASES
IYSGLAWYQQ TPGQRPKLLI YAASDLASGV PSRFKGSGSG TEYTLTISGV
ECADAATYYC QQTWTDGGID NPFGGGTEVV VK

Rabbit Ab 4856 VL region with signal sequence underlined and italicised SEQ ID NO: 13

*atgaacatga gggcccccac tcagctgctg gggctcctgc tgctctggct
cccaggtgcc agatgt*gcct atgatatgac ccagactcca gcctctgtgg
aggtagctgt gggaggcaca gtcaccatca gtgccaggc cagtgagagc
atttacagtg gtttggcctg gtatcagcag acaccagggc agcgtcccaa
gctcctgatc tatgctgcat ccgatctggc atctggggtc ccatcgcgat
tcaaaggcag tggatctggg acagagtaca ctctcaccat cagcggcgtg
gagtgtgccg atgctgccac ttactactgt caacagactt ggactgatgg
tggtattgat aatcctttcg gcggagggac cgaggtggtg gtcaaa Rabbit Ab 4856 VH region     SEQ ID NO: 14

QSLEESGGRL VTPGTPLTLT CTASGFSLSS YDMSWVRQAP GKGLEWIGII
YGGSGSTWYA SWAKGRFTMS KTSTTVDLKI TSPTTEDMAT YFCARGRDGG
AGGSRNGYSL WGQGTLVTVS S

Rabbit Ab 4856 VH region     SEQ ID NO:15 cagtcgctgg aggagtccgg gggtcgcctg gtcacgcctg gacacccct

FIGURE 1C

```
gacactcacc tgcacagcct ctggattctc cctcagcagc tacgacatga
gctgggtccg ccaggctcca gggaaggggc tggaatggat cggaatcatt
tatggtggta gtggtagcac atggtacgcg agctgggcga aaggccgatt
caccatgtcc aaaacgtcga ccacggtgga tctgaaaatc accagtccga
cgaccgagga catggccacc tatttctgtg ccagaggacg ggatggtggt
gctggtggtt ctcgtaatgg ctattccttg tggggccaag caccctggt
caccgtctcg agt
```

Rabbit Ab 4856 VH region with signal sequence underlined and italicised SEQ ID NO: 16

*METGLRWLLL VAVLKGVQC*Q SLEESGGRLV TPGTPLTLTC TASGFSLSSY
DMSWVRQAPG KGLEWIGIIY GGSGSTWYAS WAKGRFTMSK TSTTVDLKIT
SPTTEDMATY FCARGRDGGA GGSRNGYSLW GQGTLVTVSS

Rabbit Ab 4856 VH region with signal sequence underlined and italicised SEQ ID NO: 17

*atggagactg ggctgcgctg gcttctcctg gtcgctgtgc tcaaaggtgt
ccagtgt*cag tcgctggagg agtccggggg tcgcctggtc acgcctggga
caccctgac actcacctgc acagcctctg gattctccct cagcagctac
gacatgagct gggtccgcca ggctccaggg aaggggctgg aatggatcgg
aatcatttat ggtggtagtg gtagcacatg gtacgcgagc tgggcgaaag
gccgattcac catgtccaaa acgtcgacca cggtggatct gaaaatcacc
agtccgacga ccgaggacat ggccacctat ttctgtgcca gaggacggga
tggtggtgct ggtggttctc gtaatggcta ttccttgtgg ggccaaggca
ccctggtcac cgtctcgagt Rabbit Ab 4856 light chain (V + constant) SEQ ID NO: 18

AYDMTQTPAS VEVAVGGTVT IKCQASESIY SGLAWYQQTP GQRPKLLIYA
ASDLASGVPS RFKGSGSGTE YTLTISGVEC ADAATYYCQQ TWTDGGIDNP
FGGGTEVVVK RTPVAPTVLI FPPAADQVAT GTVTIVCVAN KYFPDVTVTW
EVDGTTQTTG IENSKTPQNS ADCTYNLSST LTLTSTQYNS HKEYTCKVTQ
GTTSVVQSFN RGDC

Rabbit Ab 4856 light chain (V + constant) SEQ ID NO: 19 gcctatgata tgacccagac tccagcctct gtggaggtag ctgtgggagg
cacagtcacc atcaagtgcc aggccagtga gagcatttac agtggtttgg
cctggtatca gcagacacca gggcagcgtc ccaagctcct gatctatgct
gcatccgatc tggcatctgg ggtcccatcg cgattcaaag cagtggatc
tgggacagag tacactctca ccatcagcgg cgtggagtgt gccgatgctg
ccacttacta ctgtcaacag acttggactg atggtggtat tgataatcct
ttcggcggag ggaccgaggt ggtggtcaaa cgtacgccag ttgcacctac
```

FIGURE 1D

```
tgtcctcatc ttcccaccag ctgctgatca ggtggcaact ggaacagtca
ccatcgtgtg tgtggcgaat aaatactttc ccgatgtcac cgtcacctgg
gaggtggatg gcaccaccca aacaactggc atcgagaaca gtaaaacacc
gcagaattct gcagattgta cctacaacct cagcagcact ctgacactga
ccagcacaca gtacaacagc cacaaagagt acacctgcaa ggtgacccag
ggcacgacct cagtcgtcca gagcttcaat aggggtgact gt
```

Rabbit Ab 4856 light chain with signal sequence underlined and italicized SEQ ID NO: 20

*MNMRAPTQLL GLLLLWLPGA RC*AYDMTQTP ASVEVAVGGT VTIKCQASES
IYSGLAWYQQ TPGQRPKLLI YAASDLASGV PSRFKGSGSG TEYTLTISGV
ECADAATYYC QQTWTDGGID NPFGGGTEVV VKRTPVAPTV LIFPPAADQV
ATGTVTIVCV ANKYFPDVTV TWEVDGTTQT TGIENSKTPQ NSADCTYNLS
STLTLTSTQY NSHKEYTCKV TQGTTSVVQS FNRGDC

Rabbit Ab 4856 light chain with signal sequence underlined and italicized SEQ ID NO: 21

*atgaacatga gggcccccac tcagctgctg gggctcctgc tgctctggct*
*cccaggtgcc agatgt*gcct atgatatgac ccagactcca gcctctgtgg
aggtagctgt ggggaggcaca gtcaccatca agtgccaggc cagtgagagc
atttacagtg gtttggcctg gtatcagcag acaccagggc agcgtcccaa
gctcctgatc tatgctgcat ccgatctggc atctggggtc ccatcgcgat
tcaaaggcag tggatctggg acagagtaca ctctcaccat cagcggcgtg
gagtgtgccg atgctgccac ttactactgt caacagactt ggactgatgg
tggtattgat aatcctttcg gcggagggac cgaggtggtg gtcaaacgta
cgccagttgc acctactgtc ctcatcttcc caccagctgc tgatcaggtg
gcaactggaa cagtcaccat cgtgtgtgtg gcgaataaat actttcccga
tgtcaccgtc acctgggagg tggatggcac cacccaaaca actggcatcg
agaacagtaa aacaccgcag aattctgcag attgtaccta caacctcagc
agcactctga cactgaccag cacacagtac aacagccaca agagtacac
ctgcaaggtg acccagggca cgacctcagt cgtccagagc ttcaataggg
gtgactgt Rabbit Ab 4856 Fab heavy chain SEQ ID NO: 22

QSLEESGGRL VTPGTPLTLT CTASGFSLSS YDMSWVRQAP GKGLEWIGII
YGGSGSTWYA SWAKGRFTMS KTSTTVDLKI TSPTTEDMAT YFCARGRDGG
AGGSRNGYSL WGQGTLVTVS SGQPKAPSVF PLAPCCGDTP SSTVTLGCLV
KGYLPEPVTV TWNSGTLTNG VRTFPSVRQS SGLYSLSSVV SVTSSSQPVT
CNVAHPATNT KVDKTV

Rabbit Ab 4856 Fab heavy chain SEQ ID NO: 23

FIGURE 1E

```
cagtcgctgg aggagtccgg gggtcgcctg gtcacgcctg ggacacccct
gacactcacc tgcacagcct ctggattctc cctcagcagc tacgacatga
gctgggtccg ccaggctcca gggaaggggc tggaatggat cggaatcatt
tatggtggta gtggtagcac atggtacgcg agctgggcga aaggccgatt
caccatgtcc aaaacgtcga ccacggtgga tctgaaaatc accagtccga
cgaccgagga catggccacc tatttctgtg ccagaggacg ggatggtggt
gctggtggtt ctcgtaatgg ctattccttg tggggccaag gcaccctggt
caccgtctcg agtgggcaac ctaaggctcc atcagtcttc ccactggccc
cctgctgcgg ggacacaccc agctccacgg tgaccctggg ctgcctggtc
aaaggctacc tcccggagcc agtgaccgtg acctggaact cgggcaccct
caccaatggg gtacgcacct tcccgtccgt ccggcagtcc tcaggcctct
actcgctgag cagcgtggtg agcgtgacct caagcagcca gcccgtcacc
tgcaacgtgg cccacccagc caccaacacc aaagtggaca agaccgtt
```

Rabbit Ab 4856 Fab heavy chain with signal sequence underlined and italicized SEQ ID NO: 24

```
METGLRWLLL VAVLKGVQCQ SLEESGGRLV TPGTPLTLTC TASGFSLSSY
DMSWVRQAPG KGLEWIGIIY GGSGSTWYAS WAKGRFTMSK TSTTVDLKIT
SPTTEDMATY FCARGRDGGA GGSRNGYSLW GQGTLVTVSS GQPKAPSVFP
LAPCCGDTPS STVTLGCLVK GYLPEPVTVT WNSGTLTNGV RTFPSVRQSS
GLYSLSSVVS VTSSSQPVTC NVAHPATNTK VDKTV
```

Rabbit Ab 4856 Fab heavy chain with signal sequence underlined and italicized SEQ ID NO: 25

```
atggagactg ggctgcgctg gcttctcctg gtcgctgtgc tcaaaggtgt
ccagtgtcag tcgctggagg agtccggggg tcgcctggtc acgcctggga
caccctgac actcacctgc acagcctctg gattctccct cagcagctac
gacatgagct gggtccgcca ggctcaggg aaggggctgg aatggatcgg
aatcatttat ggtggtagtg gtagcacatg gtacgcgagc tgggcgaaag
gccgattcac catgtccaaa acgtcgacca cggtggatct gaaaatcacc
agtccgacga ccgaggacat ggccacctat ttctgtgcca gaggacggga
tggtggtgct ggtggttctc gtaatggcta ttccttgtgg ggccaaggca
ccctggtcac cgtctcgagt gggcaaccta aggctccatc agtcttccca
ctggccccct gctgcgggga cacacccagc tccacggtga ccctgggctg
cctggtcaaa ggctacctcc cggagccagt gaccgtgacc tggaactcgg
gcaccctcac caatgggta cgcacttcc cgtccgtccg gcagtcctca
ggcctctact cgctgagcag cgtggtgagc gtgacctcaa gcagccagcc
cgtcacctgc aacgtggccc acccagccac caacaccaaa gtggacaaga
ccgtt
```

FIGURE 1F

Murinised 4856 mL1.1 V-region SEQ ID NO:26

```
AYDMNQSPSS LSASLGDTIT ITCQASESIY SGLAWYQQKP GNIPKLLIYA
ASDLASGVPS RFKGSGSGTE YTLTISSLQP EDIATYYCQQ TWTDGGIDNP
FGGGTKLEIK
```

Murinised 4856 mL1.1 V-region SEQ ID NO:27

```
gcctacgaca tgaaccagtc gccatcaagc ctgagcgcct cccttggcga
caccatcacc attacttgcc aagcctccga aagcatctac tccggactcg
cctggtatca gcagaaaccg gggaacattc ccaagctcct gatctacgcc
gcttccgact tggcatcggg agtgccgtca cggttcaagg ggtccggatc
gggaaccgag tacaccctga ctatctcctc cctgcaaccc gaggatattg
cgacctacta ctgtcagcag acttggacgg atggtggaat cgacaaccct
ttcggtggcg gcaccaagct ggaaatcaag
```

Murinised 4856 mL1.1 V-region with signal sequence underlined and italicized SEQ ID NO:28

```
MSVPTQVLGL LLLWLTDARC AYDMNQSPSS LSASLGDTIT ITCQASESIY
SGLAWYQQKP GNIPKLLIYA ASDLASGVPS RFKGSGSGTE YTLTISSLQP
EDIATYYCQQ TWTDGGIDNP FGGGTKLEIK
```

Murinised 4856 mL1.1 V-region with signal sequence underlined and italicized SEQ ID NO:29

```
atgtctgtcc ccacccaagt cctcggactc ctgctactct ggcttacaga
tgccagatgc gcctacgaca tgaaccagtc gccatcaagc ctgagcgcct
cccttggcga caccatcacc attacttgcc aagcctccga aagcatctac
tccggactcg cctggtatca gcagaaaccg gggaacattc ccaagctcct
gatctacgcc gcttccgact tggcatcggg agtgccgtca cggttcaagg
ggtccggatc gggaaccgag tacaccctga ctatctcctc cctgcaaccc
gaggatattg cgacctacta ctgtcagcag acttggacgg atggtggaat
cgacaaccct ttcggtggcg gcaccaagct ggaaatcaag
```

Murinised 4856 mH2.1 V-region SEQ ID NO:30

```
EVKLLESGGG LVQPGGSLKL SCTASGFSLS SYDMSWVRQA PGKGLEWIGI
IYGGSGSTWY ASWAKGKFIM SKDSAKNTVY LQMSKVRSED MATYFCARGR
DGGAGGSRNG YSLWGQGTLV TVSS
```

Murinised 4856 mH2.1 V-region SEQ ID NO:31

```
gaggtcaagc tgctggaatc gggggggaggt ctggtgcagc cgggcggatc
tctgaagctg tcatgcaccg catccgggtt tagccttcg tcctacgaca
tgtcctgggt gcgccaggcc cccggaaagg gattggaatg gatcggcatt
atctacgggg gctccggttc cacttggtac gcgagctggg ccaaggggaa
gttcatcatg tcgaaggact ccgctaagaa caccgtgtac ctccaaatga
gcaaagtccg gagcgaggat atggccacct atttctgcgc ccggggaagg
gacggaggag ccggcggttc cagaaacggc tactcactgt ggggacaggg
caccctcgtg actgtctcga gt
```

FIGURE 1G

Murinised 4856 mH2.1 V-region with signal sequence underlined and italicized SEQ ID NO:32

*MEWSWVFLFF LSVTTGVHS*E VKLLESGGGL VQPGGSLKLS CTASGFSLSS
YDMSWVRQAP GKGLEWIGII YGGSGSTWYA SWAKGKFIMS KDSAKNTVYL
QMSKVRSEDM ATYFCARGRD GGAGGSRNGY SLWGQGTLVT VSS

Murinised 4856 mH2.1 V-region with signal sequence underlined and italicized SEQ ID NO:33

*atggaatgga gctgggtctt tctcttcttc ctgtcagtaa ctacaggagt*
*ccattct*gag gtcaagctgc tggaatcggg gggaggtctg gtgcagccgg
gcggatctct gaagctgtca tgcaccgcat ccgggtttag cctttcgtcc
tacgacatgt cctgggtgcg ccaggccccc ggaaagggat tggaatggat
cggcattatc tacgggggct ccggttccac ttggtacgcg agctgggcca
aggggaagtt catcatgtcg aaggactccg ctaagaacac cgtgtacctc
caaatgagca agtccggag cgaggatatg gccacctatt tctgcgcccg
gggaagggac ggaggagccg gcggttccag aaacggctac tcactgtggg
gacagggcac cctcgtgact gtctcgagt Mouse IGKV15-103 JK1 acceptor framework   SEQ ID NO:34

DIQMNQSPSS LSASLGDTIT ITCHASQNIN VWLSWYQQKP GNIPKLLIYK
ASNLHTGVPS RFSGSGSGTG FTLTISSLQP EDIATYYCQQ GQSYPWTFGG
GTKLEIK

Mouse IGKV15-103 JK1 acceptor framework   SEQ ID NO:35 gacatccaga tgaaccagtc tccatccagt ctgtctgcat cccttggaga
cacaattacc atcacttgcc atgccagtca gaacattaat gtttggttaa
gctggtacca gcagaaacca ggaaatattc ctaaactatt gatctataag
gcttccaact tgcacacagg cgtcccatca aggtttagtg gcagtggatc
tggaacaggt ttcacattaa ccatcagcag cctgcagcct gaagacattg
ccacttacta ctgtcaacag ggtcaaagtt atccttggac gttcggtgga
ggcaccaagc tggaaatcaa a Mouse IGHV4-S1 JH3 acceptor framework   SEQ ID NO:36

EVKLLESGGG LVQPGGSLKL SCAASGFDFS RYWMSWVRQA PGKGLEWIGE
INPDSSTINY TPSLKDKFII SRDNAKNTLY LQMSKVRSED TALYYCARWF
AYWGQGTLVT VSA

Mouse IGHV4-S1 JH3 acceptor framework   SEQ ID NO:37 gaggtgaagc ttctcgagtc tggaggtggc ctggtgcagc ctggaggatc
cctgaaactc tcctgtgcag cctcaggatt cgattttagt agatactgga
tgagttgggt ccggcaggct ccagggaaag gctagaatg gattggagaa
attaatccag atagcagtac gataaactat acgccatctc taaggataa
attcatcatc tccagagaca acgccaaaaa tacgctgtac ctgcaaatga
gcaaagtgag atctgaggac acagccctt attactgtgc aagatggttt
gcttactggg gccaagggac tctggtcact gtctctgca

FIGURE 1H 4856 gL3 V-region          SEQ ID NO:38

AYDMTQSPST LSASVGDRVT ITCQASESIY SGLAWYQQKP GKAPKLLIYA
ASDLASGVPS RFSGSGSGTE YTLTISSLQP DDFATYYCQQ TWTDGGIDNP
FGGGTKVEIK 4856 gL3 V-region (mammalian expression)     SEQ ID NO:39 gcctacgaca tgacccagtc cccctcaacc ctctccgctt ccgtgggaga
tcgcgtgacc atcacttgcc aagcctccga atcgatctac tcgggtctgg
cctggtatca gcagaagcca gggaaggcac ctaagctgtt gatctacgcg
gcctcagacc tggccagcgg agtgcccagc cggttctccg gctccggaag
cggcactgag tacaccctga ccatttcctc gcttcaaccg gatgacttcg
cgacctacta ctgtcagcag acttggacgg acggggcat cgacaacccg
tttggtggag gcaccaaagt cgagattaag 4856 gL3 V-region (*E. coli* expression)   SEQ ID NO:40 gcgtatgata tgacccagag tccaagcacc ctctccgcca gcgtaggcga
tcgtgtgact attacctgtc aggccagtga aagcatctat agcggcctgg
cgtggtatca gcaaaaaccg ggcaaagccc cgaagctgct catctatgcg
gcgtccgatc tggcgagcgg tgtgccaagc cgtttcagtg gcagcggcag
cggcaccgaa tatacctca caatttcgtc tctccagccg gatgatttcg
ccacttacta ttgtcagcaa acctggaccg atggcggcat tgataacccg
ttcggtggcg gcactaaagt agaaatcaaa 4856 gL3 V-region with signal sequence underlined and Italicized (mammalian expression)
SEQ ID NO:41

*MKWVTFISLL FLFSSAYS*AY DMTQSPSTLS ASVGDRVTIT CQASESIYSG
LAWYQQKPGK APKLLIYAAS DLASGVPSRF SGSGSGTEYT LTISSLQPDD
FATYYCQQTW TDGGIDNPFG GGTKVEIK 4856 gL3 V-region with signal sequence underlined and italicized (mammalian expression)
SEQ ID NO:42

*atgaagtggg tcaccttcat ctccctgctg tttctgttct cctccgccta
ctcc*gcctac gacatgaccc agtccccctc aaccctctcc gcttccgtgg
gagatcgcgt gaccatcact tgccaagcct ccgaatcgat ctactcgggt
ctggcctggt atcagcagaa gccagggaag gcacctaagc tgttgatcta
cgcggcctca gacctggcca gcggagtgcc cagccggttc tccggctccg
gaagcggcac tgagtacacc ctgaccattt cctcgcttca accggatgac
ttcgcgacct actactgtca gcagacttgg acggacgggg catcgacaa
cccgtttggt ggaggcacca aagtcgagat taag

FIGURE 1I 4856 gL3 V-region with signal sequence underlined and italicized (*E. coli* expression) SEQ ID NO:43

*MKKTAIAIAV ALAGFATVAQ A*AYDMTQSPS TLSASVGDRV TITCQASESI
YSGLAWYQQK PGKAPKLLIY AASDLASGVP SRFSGSGSGT EYTLTISSLQ
PDDFATYYCQ QTWTDGGIDN PFGGGTKVEI K 4856 gL3 V-region with signal sequence underlined and italicized (*E. coli* expression) SEQ ID NO:44

*atgaaaaaga cagctatcgc aattgcagtg gccttggctg gtttcgctac
cgtagcgcaa gct*gcgtatg atatgaccca gagtccaagc accctctccg
ccagcgtagg cgatcgtgtg actattacct gtcaggccag tgaaagcatc
tatagcggcc tggcgtggta tcagcaaaaa ccgggcaaag ccccgaagct
gctcatctat gcggcgtccg atctggcgag cggtgtgcca agccgtttca
gtggcagcgg cagcggcacc gaatataccc tcacaatttc gtctctccag
ccggatgatt tcgccactta ctattgtcag caaacctgga ccgatggcgg
cattgataac ccgttcggtg gcggcactaa agtagaaatc aaa 4856 gL3 light chain (V + constant) SEQ ID NO:45

AYDMTQSPST LSASVGDRVT ITCQASESIY SGLAWYQQKP GKAPKLLIYA
ASDLASGVPS RFSGSGSGTE YTLTISSLQP DDFATYYCQQ TWTDGGIDNP
FGGGTKVEIK RTVAAPSVFI FPPSDEQLKS GTASVVCLLN NFYPREAKVQ
WKVDNALQSG NSQESVTEQD SKDSTYSLSS TLTLSKADYE KHKVYACEVT
HQGLSSPVTK SFNRGEC 4856 gL3 light chain (V + constant) (mammalian expression) SEQ ID NO: 46 gcctacgaca tgacccagtc cccctcaacc ctctccgctt ccgtgggaga
tcgcgtgacc atcacttgcc aagcctccga atcgatctac tcgggtctgg
cctggtatca gcagaagcca gggaaggcac ctaagctgtt gatctacgcg
gcctcagacc tggccagcgg agtgcccagc cggttctccg gctccggaag
cggcactgag tacaccctga ccatttcctc gcttcaaccg gatgacttcg
cgacctacta ctgtcagcag acttggacgg acggggcat cgacaacccg
tttggtggag gcaccaaagt cgagattaag cgtacggtag cggccccatc
tgtcttcatc ttcccgccat ctgatgagca gttgaaatct ggaactgcct
ctgttgtgtg cctgctgaat aacttctatc ccagagaggc caaagtacag
tggaaggtgg ataacgccct ccaatcgggt aactcccagg agagtgtcac
agagcaggac agcaaggaca gcacctacag cctcagcagc accctgacgc
tgagcaaagc agactacgag aaacacaaag tctacgcctg cgaagtcacc
catcagggcc tgagctcgcc cgtcacaaag agcttcaaca ggggagagtg
t

FIGURE 1J 4856 gL3 light chain (V + constant) (*E.coli* expression) SEQ ID NO:47

```
gcgtatgata tgacccagag tccaagcacc ctctccgcca gcgtaggcga
tcgtgtgact attacctgtc aggccagtga agcatctat agcggcctgg
cgtggtatca gcaaaaaccg ggcaaagccc cgaagctgct catctatgcg
gcgtccgatc tggcgagcgg tgtgccaagc cgtttcagtg cagcggcag
cggcaccgaa tatacccctca caattcgtc tctccagccg gatgatttcg
ccacttacta ttgtcagcaa acctggaccg atggcggcat tgataacccg
ttcggtggcg gcactaaagt agaaatcaaa cgtacggtag cggccccatc
tgtcttcatc ttcccgccat ctgatgagca gttgaaatct ggaactgcct
ctgttgtgtg cctgctgaat aacttctatc cagagaggc caaagtacag
tggaaggtgg ataacgccct ccaatcgggt aactcccagg agagtgtcac
agagcaggac agcaaggaca gcacctacag cctcagcagc accctgacgc
tgagcaaagc agactacgag aaacacaaag tctacgcctg cgaagtcacc
catcagggcc tgagctcacc agtaacaaaa agttttaata gagggagtg
t
```

4856 gL3 light chain with signal sequence underlined and italicized (mammalian expression)
SEQ ID NO: 48

```
MKWVTFISLL FLFSSAYSAY DMTQSPSTLS ASVGDRVTIT CQASESIYSG
LAWYQQKPGK APKLLIYAAS DLASGVPSRF SGSGSGTEYT LTISSLQPDD
FATYYCQQTW TDGGIDNPFG GGTKVEIKRT VAAPSVFIFP PSDEQLKSGT
ASVVCLLNNF YPREAKVQWK VDNALQSGNS QESVTEQDSK DSTYSLSSTL
TLSKADYEKH KVYACEVTHQ GLSSPVTKSF NRGEC
```

4856 gL3 light chain with signal sequence underlined and italicized (mammalian expression)
SEQ ID NO: 49

```
atgaagtggg tcaccttcat ctccctgctg tttctgttct cctccgccta
ctccgcctac gacatgaccc agtccccctc aacctctcc gcttccgtgg
gagatcgcgt gaccatcact tgccaagcct ccgaatcgat ctactcgggt
ctggcctggt atcagcagaa gccagggaag gcacctaagc tgttgatcta
cgcggcctca gacctggcca gcggagtgcc cagccggttc tccggctccg
gaagcggcac tgagtacacc ctgaccattt cctcgcttca accggatgac
ttcgcgacct actactgtca gcagacttgg acggacgggg gcatcgacaa
cccgtttggt ggaggcacca aagtcgagat taagcgtacg gtagcggccc
catctgtctt catcttcccg ccatctgatg agcagttgaa atctggaact
gcctctgttg tgtgcctgct gaataacttc tatcccagag aggccaaagt
acagtggaag gtggataacg ccctccaatc gggtaactcc caggagagtg
tcacagagca ggacagcaag gacagcacct acagcctcag cagcaccctg
acgctgagca agcagacta cgagaaacac aaagtctacg cctgcgaagt
cacccatcag gcctgagct cgcccgtcac aaagagcttc aacaggggag
agtgt
```

FIGURE 1K

4856 gL3 light chain with signal sequence underlined and italicized (*E. coli* expression) SEQ ID NO:50

*MKKTAIAIAV ALAGFATVAQ A*AYDMTQSPS TLSASVGDRV TITCQASESI
YSGLAWYQQK PGKAPKLLIY AASDLASGVP SRFSGSGSGT EYTLTISSLQ
PDDFATYYCQ QTWTDGGIDN PFGGGTKVEI KRTVAAPSVF IFPPSDEQLK
SGTASVVCLL NNFYPREAKV QWKVDNALQS GNSQESVTEQ DSKDSTYSLS
STLTLSKADY EKHKVYACEV THQGLSSPVT KSFNRGEC 4856 gL3 light chain with signal sequence underlined and italicized (*E. coli* expression) SEQ ID NO:51

*atgaaaaaga cagctatcgc aattgcagtg gccttggctg gtttcgctac*
*cgtagcgcaa gct*gcgtatg atatgaccca gagtccaagc accctctccg
ccagcgtagg cgatcgtgtg actattacct gtcaggccag tgaaagcatc
tatagcggcc tggcgtggta tcagcaaaaa ccgggcaaag ccccgaagct
gctcatctat gcggcgtccg atctggcgag cggtgtgcca agccgtttca
gtggcagcgg cagcggcacc gaatataccc tcacaatttc gtctctccag
ccggatgatt tcgccactta ctattgtcag caaacctgga ccgatggcgg
cattgataac ccgttcggtg gcggcactaa agtagaaatc aaacgtacgg
tagcggcccc atctgtcttc atcttcccgc catctgatga gcagttgaaa
tctggaactg cctctgttgt gtgcctgctg aataacttct atcccagaga
ggccaaagta cagtggaagg tggataacgc cctccaatcg ggtaactccc
aggagagtgt cacagagcag gacagcaagg acagcaccta cagcctcagc
agcaccctga cgctgagcaa agcagactac gagaaacaca agtctacgc
ctgcgaagtc acccatcagg gcctgagctc accagtaaca aaaagtttta
atagagggga gtgt

FIGURE 1L

4856gH13 V-region SEQ ID NO:52

EVQLVESGGG LVKPGGSLRL SCAASGFSLS SYDMSWVRQA PGKGLEWIGI
IYGGSGSTWY ASWAKGRFTI SRDSAKNSVY LQMNSLRAED TAVYYCARGR
DAGAGGSRNG YSLWGQGTLV TVSS

4856gH13 V-region (mammalian expression) SEQ ID NO:53 gaagtgcaac tggtggaaag cggaggaggt tggtgaaac cgggagggtc
actgcggctc tcctgtgccg cctccggatt cagcctctcg tcctacgaca
tgagctgggt cagacaggcc cccgggaagg gcctggagtg gattggtatc
atctacggcg gctccggctc gacttggtac gcttcgtggg ccaagggacg
gttcaccatc tcccgcgatt ccgcgaagaa cagcgtgtat ctgcagatga
actctctgcg ggccgaggac accgcagtgt actactgcgc gaggggcgc
gacgccggcg ccggggatc acgcaacggt tactcccttt ggggacaggg
aaccctggtc actgtctcca gc 4856gH13 V-region (E. coli expression) SEQ ID NO:54 gaggttcagc tggtcgagtc tggaggcggg cttgtcaaac tggagggag
cctgcgtctc tcttgtgcag caagcggctt cagcctgtcc tcttacgata
tgtcctgggt cgccaggca cctgggaagg gcctggagtg gattggcatt
atttatggcg gcagcggcag cacatggtac gcgagctggg cgaaggccg
tttcaccatc tcccgggaca gcgcaaagaa tagcgtgtac ctccagatga
actctctccg cgcagaggac acagcagtct attactgtgc gcggggccgc
gatgcaggcg cgggcggcag ccgcaacggc tatagcctgt ggggacaggg
gacccttgtg acagtctcga gc 4856gH13 V-region with signal sequence underlined and italicized (mammalian expression)
SEQ ID NO:55

*MKWVTFISLL FLFSSAYS*EV QLVESGGGLV KPGGSLRLSC AASGFSLSSY
DMSWVRQAPG KGLEWIGIIY GGSGSTWYAS WAKGRFTISR DSAKNSVYLQ
MNSLRAEDTA VYYCARGRDA GAGGSRNGYS LWGQGTLVTV SS

4856gH13 V-region with signal sequence underlined and italicized (mammalian expression)
SEQ ID NO:56

*atgaagtggg tcaccttcat ctccctgctg tttctgttct ccagcgccta*
*ctcc*gaagtg caactggtgg aaagcggagg aggtttggtg aaaccgggag
ggtcactgcg gctctcctgt gccgcctccg gattcagcct ctcgtcctac
gacatgagct gggtcagaca ggccccgggg aagggcctgg agtggattgg
tatcatctac ggcggctccg gctcgacttg gtacgcttcg tgggccaagg
gacggttcac catctcccgc gattccgcga agaacagcgt gtatctgcag

FIGURE 1M

```
atgaactctc tgcgggccga ggacaccgca gtgtactact gcgcgagggg
gcgcgacgcc ggcgccgggg gatcacgcaa cggttactcc ctttggggac
agggaaccct ggtcactgtc tccagc
```

4856gH13 V-region with signal sequence underlined and italicized (*E. coli* expression) SEQ ID NO:57

*MKKTAIAIAV ALAGFATVAQ A*EVQLVESGG GLVKPGGSLR LSCAASGFSL
SSYDMSWVRQ APGKGLEWIG IIYGGSGSTW YASWAKGRFT ISRDSAKNSV
YLQMNSLRAE DTAVYYCARG RDAGAGGSRN GYSLWGQGTL VTVSS

4856gH13 V-region with signal sequence underlined and italicized (*E. coli* expression) SEQ ID NO:58

```
atgaagaaga ctgctatagc aattgcagtg gcgctagctg gtttcgccac
cgtggcgcaa gctgaggttc agctggtcga gtctggaggc gggcttgtca
aacctggagg gagcctgcgt ctctcttgtg cagcaagcgg cttcagcctg
tcctcttacg atatgtcctg ggtgcgccag gcacctggga agggcctgga
gtggattggc attatttatg gcggcagcgg cagcacatgg tacgcgagct
gggcgaaggg ccgtttcacc atctcccggg acagcgcaaa gaatagcgtg
tacctccaga tgaactctct ccgcgcagag gacacagcag tctattactg
tgcgcggggc cgcgatgcag gcgcgggcgg cagccgcaac ggctatagcc
tgtggggaca ggggacccctt gtgacagtct cgagc
```

4856 gH13 Fab heavy chain (V + human gamma-1 CH1) SEQ ID NO:59

EVQLVESGGG LVKPGGSLRL SCAASGFSLS SYDMSWVRQA PGKGLEWIGI
IYGGSGSTWY ASWAKGRFTI SRDSAKNSVY LQMNSLRAED TAVYYCARGR
DAGAGGSRNG YSLWGQGTLV TVSSASTKGP SVFPLAPSSK STSGGTAALG
CLVKDYFPEP VTVSWNSGAL TSGVHTFPAV LQSSGLYSLS SVVTVPSSSL
GTQTYICNVN HKPSNTKVDK KVEPKSC 4856 gH13 Fab heavy chain (V + human gamma-1 CH1) (mammalian expression) SEQ ID NO:60

```
gaagtgcaac tggtggaaag cggaggaggt ttggtgaaac cgggagggtc
actgcggctc tcctgtgccg cctccggatt cagcctctcg tcctacgaca
tgagctgggt cagacaggcc cccgggaagg gcctggagtg gattggtatc
atctacggcg gctccggctc gacttggtac gcttcgtggg ccaagggacg
gttcaccatc tcccgcgatt ccgcgaagaa cagcgtgtat ctgcagatga
actctctgcg ggccgaggac accgcagtgt actactgcgc gaggggcgc
gacgccggcg cggggggatc acgcaacggt tactcccttt ggggacaggg
aaccctggtc actgtctcca gcgcttctac aaagggccca tcggtcttcc
ccctggcacc ctcctccaag agcacctctg ggggcacagc ggccctgggc
tgcctggtca aggactactt ccccgaaccg gtgacggtgt cgtggaactc
aggcgccctg accagcggcg tgcacacctt cccggctgtc ctacagtcct
```

FIGURE 1N

```
caggactcta ctccctcagc agcgtggtga ccgtgccctc cagcagcttg
ggcacccaga cctacatctg caacgtgaat cacaagccca gcaacaccaa
ggtggacaag aaagttgagc ccaaatcttg t
```

4856 gH13 Fab heavy chain (V + human gamma-1 CH1) (*E. coli* expression) SEQ ID NO: 61

```
gaggttcagc tggtcgagtc tggaggcggg cttgtcaaac ctggagggag
cctgcgtctc tcttgtgcag caagcggctt cagcctgtcc tcttacgata
tgtcctgggt gcgccaggca cctgggaagg gcctggagtg gattggcatt
atttatggcg gcagcggcag cacatggtac gcgagctggg cgaagggccg
tttcaccatc tcccgggaca gcgcaaagaa tagcgtgtac ctccagatga
actctctccg cgcagaggac acagcagtct attactgtgc gcggggccgc
gatgcaggcg cgggcggcag ccgcaacggc tatagcctgt ggggacaggg
gacccttgtg acagtctcga gcgcttctac aaagggccca tcggtcttcc
ccctggcacc ctcctccaag agcacctctg ggggcacagc ggccctgggc
tgcctggtca aggactactt ccccgaaccg gtgacggtgt cgtggaactc
aggcgccctg accagcggcg tgcacacctt cccggctgtc ctacagtcct
caggactcta ctccctcagc agcgtggtga ccgtgccctc cagcagcttg
ggcacccaga cctacatctg caacgtgaat cacaagccca gcaacaccaa
ggtcgacaag aaagttgagc ccaaatcttg t
```

4856 gH13 Fab heavy chain with signal sequence underlined and italicized (mammalian expression)
SEQ ID NO: 62

```
MKWVTFISLL FLFSSAYSEV QLVESGGGLV KPGGSLRLSC AASGFSLSSY
DMSWVRQAPG KGLEWIGIIY GGSGSTWYAS WAKGRFTISR DSAKNSVYLQ
MNSLRAEDTA VYYCARGRDA GAGGSRNGYS LWGQGTLVTV SSASTKGPSV
FPLAPSSKST SGGTAALGCL VKDYFPEPVT VSWNSGALTS GVHTFPAVLQ
SSGLYSLSSV VTVPSSSLGT QTYICNVNHK PSNTKVDKKV EPKSC
```

4856 gH13 Fab heavy chain with signal sequence underlined and italicized (mammalian expression)
SEQ ID NO: 63

```
atgaagtggg tcaccttcat ctccctgctg tttctgttct ccagcgccta
ctccgaagtg caactggtgg aaagcggagg aggtttggtg aaaccgggag
ggtcactgcg gctctcctgt gccgcctccg gattcagcct ctcgtcctac
gacatgagct gggtcagaca ggcccccggg aagggcctgg agtggattgg
tatcatctac ggcggctccg gctcgacttg gtacgcttcg tgggccaagg
gacggttcac catctcccgc gattccgcga agaacagcgt gtatctgcag
atgaactctc tgcgggccga ggacaccgca gtgtactact gcgcgagggg
gcgcgacgcc ggcgccgggg gatcacgcaa cggttactcc ctttggggac
agggaaccct ggtcactgtc tccagcgctt ctacaaaggg cccatcggtc
ttccccctgg caccctcctc aagagcacct ctgggggcac agcggccct
gggctgcctg gtcaaggact acttccccga accggtgacg gtgtcgtgga
```

FIGURE 1O

```
actcaggcgc cctgaccagc ggcgtgcaca ccttcccggc tgtcctacag
tcctcaggac tctactccct cagcagcgtg gtgaccgtgc cctccagcag
cttgggcacc cagacctaca tctgcaacgt gaatcacaag cccagcaaca
ccaaggtgga caagaaagtt gagcccaaat cttgt
```

**4856 gH13 Fab heavy chain with signal sequence underlined and italicized (*E. coli* expression)**
SEQ ID NO:64

*MKKTAIAIAV ALAGFATVAQ A*EVQLVESGG GLVKPGGSLR LSCAASGFSL
SSYDMSWVRQ APGKGLEWIG IIYGGSGSTW YASWAKGRFT ISRDSAKNSV
YLQMNSLRAE DTAVYYCARG RDAGAGGSRN GYSLWGQGTL VTVSSASTKG
PSVFPLAPSS KSTSGGTAAL GCLVKDYFPE PVTVSWNSGA LTSGVHTFPA
VLQSSGLYSL SSVVTVPSSS LGTQTYICNV NHKPSNTKVD KKVEPKSC

**4856 gH13 Fab heavy chain with signal sequence underlined and italicized (*E. coli* expression)**
SEQ ID NO:65

*atgaagaaga ctgctatagc aattgcagtg gcgctagctg gtttcgccac*
*cgtggcgcaa gct*gaggttc agctggtcga gtctggaggc gggcttgtca
aacctggagg gagcctgcgt ctctcttgtg cagcaagcgg cttcagcctg
tcctcttacg atatgtcctg ggtgcgccag gcacctggga agggcctgga
gtggattggc attatttatg gcggcagcgg cagcacatgg tacgcgagct
gggcgaaggg ccgtttcacc atctcccggg acagcgcaaa gaatagcgtg
tacctccaga tgaactctct ccgcgcagag gacacagcag tctattactg
tgcgcggggc cgcgatgcag gcgcgggcgg cagccgcaac ggctatagcc
tgtggggaca ggggaccctt gtgacagtct cgagcgcttc tacaaagggc
ccatcggtct tccccctggc accctcctcc aagagcacct ctggggggcac
agcggccctg ggctgcctgg tcaaggacta cttccccgaa ccggtgacgg
tgtcgtggaa ctcaggcgcc ctgaccagcg gcgtgcacac cttcccggct
gtcctacagt cctcaggact ctactcctcc agcagcgtgg tgaccgtgcc
ctccagcagc ttgggcaccc agacctacat ctgcaacgtg aatcacaagc
ccagcaacac caaggtcgac aagaaagttg agcccaaatc ttgt

FIGURE 1P

4856gH20 V-region SEQ ID NO:66

EVQLVESGGG LVKPGGSLRL SCAASGFSLS SYDMSWVRQA PGKGLEWISI
IYGGSGSTWY ASWAKGRFTM SKDSAKNSVY LQMNSLRAED TAVYYCARGR
DAGAGGSRNG YSLWGQGTLV TVSS

4856gH20 V-region (mammalian expression) SEQ ID NO:67 gaagtgcaac tggtggaaag cggaggaggt ttggtgaaac cgggagggtc
actgcggctc tcctgtgccg cctccggatt cagcctctcg tcctacgaca
tgagctgggt cagacaggcc cccgggaagg gcctggagtg gatttccatc
atctacggcg gctccggctc gacttggtac gcttcgtggg ccaaggacg
gttcaccatg tccaaggatt ccgcgaagaa cagcgtgtat ctgcagatga
actctctgcg ggccgaggac accgcagtgt actactgcgc gaggggcgc
gacgccggcg ccggggatc acgcaacggt tactcccttt ggggacaggg
aaccctggtc actgtctcca gc

**4856gH20 V-region (*E. coli* expression)** SEQ ID NO:68 gaggttcagc tggtcgagtc tggaggcggg cttgtcaaac ctggagggag
cctgcgtctc tcttgtgcag caagcggctt cagcctgtcc tcttacgata
tgtcctgggt gcgccaggca cctgggaagg gcctggagtg gatttctatt
atttatggcg gcagcggcag cacatggtac gcgagctggg cgaagggccg
tttcaccatg tccaaagaca gcgcaaagaa tagcgtgtac ctccagatga
actctctccg cgcagaggac acagcagtct attactgtgc gcggggccgc
gatgcaggcg cgggcggcag ccgcaatggg tatagcctgt ggggacaggg
gacccttgtg acagtctcga gc

4856gH20 V-region with signal sequence underlined and italicized (mammalian expression)
SEQ ID NO:69
*MKWVTFISLL FLFSSAYS*EV QLVESGGGLV KPGGSLRLSC AASGFSLSSY
DMSWVRQAPG KGLEWISIIY GGSGSTWYAS WAKGRFTMSK DSAKNSVYLQ
MNSLRAEDTA VYYCARGRDA GAGGSRNGYS LWGQGTLVTV SS

4856gH20 V-region with signal sequence underlined and italicized (mammalian expression)
SEQ ID NO:70
*atgaagtggg tcaccttcat ctccctgctg tttctgttct ccagcgccta
ctcc*gaagtg caactggtgg aaagcggagg aggtttggtg aaaccgggag
ggtcactgcg gctctcctgt gccgcctccg gattcagcct ctcgtcctac
gacatgagct gggtcagaca ggccccgggg aagggcctgg agtggatttc
catcatctac ggcggctccg gctcgacttg gtacgcttcg tgggccaagg
gacggttcac catgtccaag gattccgcga agaacagcgt gtatctgcag
atgaactctc tgcgggccga ggacaccgca gtgtactact gcgcgagggg
gcgcgacgcc ggcgccgggg gatcacgcaa cggttactcc ctttggggac

FIGURE 1Q

```
agggaaccct ggtcactgtc tccagc
```

4856gH20 V-region with signal sequence underlined and italicized (*E. coli* expression)
SEQ ID NO:71
*MKKTAIAIAV ALAGFATVAQ A*EVQLVESGG GLVKPGGSLR LSCAASGFSL
SSYDMSWVRQ APGKGLEWIS IIYGGSGSTW YASWAKGRFT MSKDSAKNSV
YLQMNSLRAE DTAVYYCARG RDAGAGGSRN GYSLWGQGTL VTVSS 4856gH20 V-region with signal sequence underlined and italicized (*E. coli* expression)
SEQ ID NO:72
```
atgaagaaga ctgctatagc aattgcagtg gcgctagctg gtttcgccac
cgtggcgcaa gctgaggttc agctggtcga gtctggaggc gggcttgtca
aacctggagg gagcctgcgt ctctcttgtg cagcaagcgg cttcagcctg
tcctcttacg atatgtcctg ggtgcgccag gcacctggga agggcctgga
gtggatttct attatttatg gcggcagcgg cagcacatgg tacgcagct
gggcgaaggg ccgtttcacc atgtccaaag acagcgcaaa gaatagcgtg
tacctccaga tgaactctct ccgcgcagag gacacagcag tctattactg
tgcgcggggc cgcgatgcag gcgcgggcgg cagccgcaat gggtatagcc
tgtggggaca ggggacccct tgtgacagtct cgagc
```

4856 gH20 Fab heavy chain (V + human gamma-1 CH1) SEQ ID NO:73

EVQLVESGGG LVKPGGSLRL SCAASGFSLS SYDMSWVRQA PGKGLEWISI
IYGGSGSTWY ASWAKGRFTM SKDSAKNSVY LQMNSLRAED TAVYYCARGR
DAGAGGSRNG YSLWGQGTLV TVSSASTKGP SVFPLAPSSK STSGGTAALG
CLVKDYFPEP VTVSWNSGAL TSGVHTFPAV LQSSGLYSLS SVVTVPSSSL
GTQTYICNVN HKPSNTKVDK KVEPKSC 4856 gH20 Fab heavy chain (V + human gamma-1 CH1) (mammalian expression) SEQ ID NO:74

```
gaagtgcaac tggtggaaag cggaggaggt ttggtgaaac cgggagggtc
actgcggctc tcctgtgccg cctccggatt cagcctctcg tcctacgaca
tgagctgggt cagacaggcc cccgggaagg gcctggagtg gatttccatc
atctacggcg gctccggctc gacttggtac gcttcgtggg ccaagggacg
gttcaccatg tccaaggatt ccgcaagaa cagcgtgtat ctgcagatga
actctctgcg ggccgaggac accgcagtgt actactgcgc gaggggcgc
gacgccggcg ccggggatc acgcaacggt tactcccttt ggggacaggg
aaccctggtc actgtctcca gcgcttctac aaagggccca tcggtcttcc
ccctggcacc ctcctccaag agcacctctg ggggcacagc ggccctgggc
tgcctggtca aggactactt ccccgaaccg gtgacggtgt cgtggaactc
aggcgccctg accagcggcg tgcacacctt cccggctgtc ctacagtcct
caggactcta ctccctcagc agcgtggtga ccgtgccctc cagcagcttg
ggcacccaga cctacatctg caacgtgaat cacaagccca gcaacaccaa
```
ggtggacaag aaagttgagc ccaaatcttg t
FIGURE 1R

4856 gH20 Fab heavy chain (V + human gamma-1 CH1) (*E. coli* expression) SEQ ID NO:75

```
gaggttcagc tggtcgagtc tggaggcggg cttgtcaaac ctggagggag
cctgcgtctc tcttgtgcag caagcggctt cagcctgtcc tcttacgata
tgtcctgggt gcgccaggca cctgggaagg gcctggagtg gatttctatt
atttatggcg gcagcggcag cacatggtac gcgagctggg cgaagggccg
tttcaccatg tccaaagaca gcgcaaagaa tagcgtgtac ctccagatga
actctctccg cgcagaggac acagcagtct attactgtgc gcggggccgc
gatgcaggcg cgggcggcag ccgcaatggg tatagcctgt ggggacaggg
gacccttgtg acagtctcga gcgcttctac aaagggccca tcggtcttcc
ccctggcacc ctcctccaag agcacctctg ggggcacagc ggccctgggc
tgcctggtca aggactactc ccccgaaccg gtgacggtgt cgtggaactc
aggcgccctg accagcggcg tgcacacctt cccggctgtc ctacagtcct
caggactcta ctccctcagc agcgtggtga ccgtgccctc agcagcttg
ggcacccaga cctacatctg caacgtgaat cacaagccca gcaacaccaa
ggtcgacaag aaagttgagc ccaaatcttg t
```

4856 gH20 Fab heavy chain with signal sequence underlined and italicized (mammalian expression)
SEQ ID NO:76

*MKWVTFISLL FLFSSAYS*EV QLVESGGGLV KPGGSLRLSC AASGFSLSSY
DMSWVRQAPG KGLEWISIIY GGSGSTWYAS WAKGRFTMSK DSAKNSVYLQ
MNSLRAEDTA VYYCARGRDA GAGGSRNGYS LWGQGTLVTV SSASTKGPSV
FPLAPSSKST SGGTAALGCL VKDYFPEPVT VSWNSGALTS GVHTFPAVLQ
SSGLYSLSSV VTVPSSSLGT QTYICNVNHK PSNTKVDKKV EPKSC 4856 gH20 Fab heavy chain with signal sequence underlined and italicized (mammalian expression)
SEQ ID NO:77

*atgaagtggg tcaccttcat ctccctgctg tttctgttct ccagcgccta*
*ctcc*gaagtg caactggtgg aaagcggagg aggtttggtg aaaccgggag
ggtcactgcg gctctcctgt gccgcctccg gattcagcct ctcgtcctac
gacatgagct gggtcagaca ggccccggg aagggcctgg agtggatttc
catcatctac ggcggctccg gctcgacttg gtacgcttcg tgggccaagg
gacggttcac catgtccaag gattccgcga agaacagcgt gtatctgcag
atgaactctc tgcgggccga ggacaccgca gtgtactact gcgcgagggg
gcgcgacgcc ggcgccgggg gatcacgcaa cggttactcc ctttggggac
agggaacccct ggtcactgtc tccagcgctt ctacaaaggg cccatcggtc
ttccccctgg caccctcctc aagagcacc tctgggggca gcggccct
gggctgcctg gtcaaggact acttcccga accggtgacg gtgtcgtgga
actcaggcgc cctgaccagc ggcgtgcaca ccttcccggc tgtcctacag
tcctcaggac tctactccct cagcagcgtg gtgaccgtgc cctccagcag
cttgggcacc cagacctaca tctgcaacgt gaatcacaag cccagcaaca
ccaaggtgga caagaaagtt gagcccaaat cttgt 4856 gH20 Fab heavy chain with signal sequence underlined and italicized (*E. coli* expression)

FIGURE 1S

SEQ ID NO:78
*MKKTAIAIAV ALAGFATVAQ A*EVQLVESGG GLVKPGGSLR LSCAASGFSL
SSYDMSWVRQ APGKGLEWIS IIYGGSGSTW YASWAKGRFT MSKDSAKNSV
YLQMNSLRAE DTAVYYCARG RDAGAGGSRN GYSLWGQGTL VTVSSASTKG
PSVFPLAPSS KSTSGGTAAL GCLVKDYFPE PVTVSWNSGA LTSGVHTFPA
VLQSSGLYSL SSVVTVPSSS LGTQTYICNV NHKPSNTKVD KKVEPKSC 4856 gH20 Fab heavy chain with signal sequence underlined and italicized (*E. coli* expression)
SEQ ID NO:79
*atgaagaaga ctgctatagc aattgcagtg gcgctagctg gtttcgccac*
*cgtggcgcaa gct*gaggttc agctggtcga gtctggaggc gggcttgtca
aacctggagg gagcctgcgt ctctcttgtg cagcaagcgg cttcagcctg
tcctcttacg atatgtcctg ggtgcgccag gcacctggga agggcctgga
gtggatttct attatttatg gcggcagcgg cagcacatgg tacgcgagct
gggcgaaggg ccgtttcacc atgtccaaag acagcgcaaa gaatagcgtg
tacctccaga tgaactctct ccgcgcagag gacacagcag tctattactg
tgcgcggggc cgcgatgcag gcgcgggcgg cagccgcaat gggtatagcc
tgtggggaca ggggacccct gtgacagtct cgagcgcttc tacaaagggc
ccatcggtct tccccctggc accctcctcc aagagcacct ctgggggcac
agcggccctg ggctgcctgg tcaaggacta cttccccgaa ccggtgacgg
tgtcgtggaa ctcaggcgcc ctgaccagcg gcgtgcacac cttcccggct
gtcctacagt cctcaggact ctactcctc agcagcgtgg tgaccgtgcc
ctccagcagc ttgggcaccc agacctacat ctgcaacgtg aatcacaagc
ccagcaacac caaggtcgac aagaaagttg agcccaaatc ttgt

FIGURE 1T

4856gH23 V-region SEQ ID NO:80

EVQLVESGGG LVKPGGSLRL SCAASGFSLS SYDMSWVRQA PGKGLEWIGI
IYGGSGSTWY ASWAKGRFTI SRDSAKNSVY LQMNSLRAED TAVYYCARGR
DAGAGGSRNA YSLWGQGTLV TVSS

4856gH23 V-region (mammalian expression) SEQ ID NO:81

```
gaagtgcaac tggtggaaag cggaggaggt ttggtgaaac cgggagggtc
actgcggctc tcctgtgccg cctccggatt cagcctctcg tcctacgaca
tgagctgggt cagacaggcc cccgggaagg gcctggagtg gattggtatc
atctacggcg gctccggctc gacttggtac gcttcgtggg ccaagggacg
gttcaccatc tcccgcgatt ccgcgaagaa cagcgtgtat ctgcagatga
actctctgcg ggccgaggac accgcagtgt actactgcgc gaggggcgc
gacgccggcg ccggggatc acgcaacgcct actcccttt ggggacaggg
aaccctggtc actgtctcca gc
```

4856gH23 V-region (*E. coli* expression) SEQ ID NO:82

```
gaggttcagc tggtcgagtc tggaggcggg cttgtcaaac ctggagggag
cctgcgtctc tcttgtgcag caagcggctt cagcctgtcc tcttacgata
tgtcctgggt gcgccaggca cctgggaagg gcctggagtg gattggcatt
atttatggcg gcagcggcag cacatggtac gcgagctggg cgaagggccg
tttcaccatc tcccgggaca gcgcaaagaa tagcgtgtac ctccagatga
actctctccg cgcagaggac acagcagtct attactgtgc gcggggccgc
gatgcaggcg cgggcggcag ccgcaacgcg tatagcctgt ggggacaggg
gaccttgtg acagtctcga gc
```

4856gH23 V-region with signal sequence underlined and italicized (mammalian expression)
SEQ ID NO:83
*MKWVTFISLL FLFSSAYS*EV QLVESGGGLV KPGGSLRLSC AASGFSLSSY
DMSWVRQAPG KGLEWIGIIY GGSGSTWYAS WAKGRFTISR DSAKNSVYLQ
MNSLRAEDTA VYYCARGRDA GAGGSRNAYS LWGQGTLVTV SS 4856gH23 V-region with signal sequence underlined and italicized (mammalian expression)
SEQ ID NO:84
*atgaagtggg tcaccttcat ctccctgctg tttctgttct ccagcgccta*
*ctcc*gaagtg caactggtgg aaagcggagg aggtttggtg aaaccgggag
ggtcactgcg gctctcctgt gccgcctccg gattcagcct ctcgtcctac
gacatgagct gggtcagaca ggccccggg aagggcctgg agtggattgg
tatcatctac ggcggctccg gctcgacttg gtacgcttcg tgggccaagg
gacggttcac catctcccgc gattccgcga agaacagcgt gtatctgcag
atgaactctc tgcgggccga ggacaccgca gtgtactact gcgcgagggg

FIGURE 1U

```
gcgcgacgcc ggcgccgggg gatcacgcaa cgcctactcc ctttggggac
agggaaccct ggtcactgtc tccagc
```

**4856gH23 V-region with signal sequence underlined and italicized (*E. coli* expression)**
SEQ ID NO:85
*MKKTAIAIAV ALAGFATVAQ A*EVQLVESGG GLVKPGGSLR LSCAASGFSL
SSYDMSWVRQ APGKGLEWIG IIYGGSGSTW YASWAKGRFT ISRDSAKNSV
YLQMNSLRAE DTAVYYCARG RDAGAGGSRN AYSLWGQGTL VTVSS

**4856gH23 V-region with signal sequence underlined and italicized (*E. coli* expression)**
SEQ ID NO:86
*atgaagaaga ctgctatagc aattgcagtg gcgctagctg gtttcgccac*
*cgtggcgcaa gct*gaggttc agctggtcga gtctggaggc gggcttgtca
aacctggagg gagcctgcgt ctctcttgtg cagcaagcgg cttcagcctg
tcctcttacg atatgtcctg ggtgcgccag gcacctggga agggcctgga
gtggattggc attatttatg gcggcagcgg cagcacatgg tacgcgagct
gggcgaaggg ccgtttcacc atctcccggg acagcgcaaa gaatagcgtg
tacctccaga tgaactctct ccgcgcagag gacacagcag tctattactg
tgcgcgggc cgcgatgcag gcgcgggcgg cagccgcaac gcgtatagcc
tgtggggaca ggggacccct gtgacagtct cgagc

4856 gH23 Fab heavy chain (V + human gamma-1 CH1)
SEQ ID NO:87
EVQLVESGGG LVKPGGSLRL SCAASGFSLS SYDMSWVRQA PGKGLEWIGI
IYGGSGSTWY ASWAKGRFTI SRDSAKNSVY LQMNSLRAED TAVYYCARGR
DAGAGGSRNA YSLWGQGTLV TVSSASTKGP SVFPLAPSSK STSGGTAALG
CLVKDYFPEP VTVSWNSGAL TSGVHTFPAV LQSSGLYSLS SVVTVPSSSL
GTQTYICNVN HKPSNTKVDK KVEPKSC

4856 gH23 Fab heavy chain (V + human gamma-1 CH1) (mammalian expression)
SEQ ID NO:88
gaagtgcaac tggtggaaag cggaggaggt ttggtgaaac cgggagggtc
actgcggctc tcctgtgccg cctccggatt cagcctctcg tcctacgaca
tgagctgggt cagacaggcc cccgggaagg gcctggagtg gattggtatc
atctacggcg gctccggctc gacttggtac gcttcgtggg ccaagggacg
gttcaccatc tcccgcgatt ccgcgaagaa cagcgtgtat ctgcagatga
actctctgcg ggccgaggac accgcagtgt actactgcg gagggggcgc
gacgccggcg ccggggatc acgcaacgcc tactcccttt ggggacaggg
aaccctggtc actgtctcca gcgcttctac aaagggccca tcggtcttcc
ccctggcacc ctcctccaag agcacctctg gggcacagc ggccctgggc
tgcctggtca aggactactt ccccgaaccg gtgacggtgt cgtggaactc
aggcgccctg accagcggcg tgcacacctt cccggctgtc ctacagtcct
caggactcta ctccctcagc agcgtggtga ccgtgccctc cagcagcttg
ggcacccaga cctacatctg caacgtgaat cacaagccca gcaacaccaa
```

FIGURE 1V ggtggacaag aaagttgagc ccaaatcttg t

**4856 gH23 Fab heavy chain (V + human gamma-1 CH1) (*E. coli* expression)**
SEQ ID NO:89
gaggttcagc tggtcgagtc tggaggcggg cttgtcaaac ctggagggag
cctgcgtctc tcttgtcag caagcggctt cagcctgtcc tcttacgata
tgtcctgggt gcgccaggca cctgggaagg gcctggagtg gattggcatt
atttatggcg gcagcggcag cacatggtac gcgagctggg cgaagggccg
tttcaccatc tcccgggaca gcgcaaagaa tagcgtgtac ctccagatga
actctctccg cgcagaggac acagcagtct attactgtgc gcggggccgc
gatgcaggcg cgggcggcag ccgcaacgcg tatagcctgt ggggacaggg
gaccctgtg acagtctcga gcgcttctac aaagggccca tcggtcttcc
ccctggcacc ctcctccaag agcacctctg ggggcacagc ggccctgggc
tgcctggtca aggactactt ccccgaaccg gtgacggtgt cgtggaactc
aggcgcctg accagcggcg tgcacacctt cccggctgtc ctacagtcct
caggactcta ctccctcagc agcgtggtga ccgtgccctc agcagcttg
ggcacccaga cctacatctg caacgtgaat cacaagccca gcaacaccaa
ggtcgacaag aaagttgagc ccaaatcttg t

4856 gH23 Fab heavy chain with signal sequence underlined and italicized (mammalian expression)
SEQ ID NO:90
*MKWVTFISLL FLFSSAYS*EV QLVESGGGLV KPGGSLRLSC AASGFSLSSY
DMSWVRQAPG KGLEWIGIIY GGSGSTWYAS WAKGRFTISR DSAKNSVYLQ
MNSLRAEDTA VYYCARGRDA GAGGSRNAYS LWGQGTLVTV SSASTKGPSV
FPLAPSSKST SGGTAALGCL VKDYFPEPVT VSWNSGALTS GVHTFPAVLQ
SSGLYSLSSV VTVPSSSLGT QTYICNVNHK PSNTKVDKKV EPKSC

4856 gH23 Fab heavy chain with signal sequence underlined and italicized (mammalian expression)
SEQ ID NO:91
*atgaagtggg tcaccttcat ctccctgctg tttctgttct ccagcgccta*
*ctcc*gaagtg caactggtgg aaagcggagg aggtttggtg aaaccgggag
ggtcactgcg gctctcctgt gccgcctccg gattcagcct ctcgtcctac
gacatgagct gggtcagaca ggcccccggg aagggcctgg agtggattgg
tatcatctac ggcggctccg gctcgacttg gtacgcttcg tgggccaagg
gacggttcac catctcccgc gattccgcga agaacagcgt gtatctgcag
atgaactctc tgcgggccga ggacaccgca gtgtactact gcgcgagggg
gcgcgacgcc ggcgccgggg gatcacgcaa cgcctactcc ctttggggac
agggaaccct ggtcactgtc tccagcgctt ctacaaaggg cccatcggtc
ttccccctgg caccctcctc caagagcacc tctgggggca gcggccct
gggctgcctg gtcaaggact acttccccga accggtgacg gtgtcgtgga
actcaggcgc cctgaccagc ggcgtgcaca ccttcccggc tgtcctacag
tcctcaggac tctactccct cagcagcgtg gtgaccgtgc cctccagcag
cttgggcacc cagacctaca tctgcaacgt gaatcacaag cccagcaaca
ccaaggtgga caagaaagtt gagcccaaat cttgt

FIGURE 1W

4856 gH23 Fab heavy chain with signal sequence underlined and italicized (*E. coli* expression)
SEQ ID NO:92
*MKKTAIAIAV ALAGFATVAQ A*EVQLVESGG GLVKPGGSLR LSCAASGFSL
SSYDMSWVRQ APGKGLEWIG IIYGGSGSTW YASWAKGRFT ISRDSAKNSV
YLQMNSLRAE DTAVYYCARG RDAGAGGSRN AYSLWGQGTL VTVSSASTKG
PSVFPLAPSS KSTSGGTAAL GCLVKDYFPE PVTVSWNSGA LTSGVHTFPA
VLQSSGLYSL SSVVTVPSSS LGTQTYICNV NHKPSNTKVD KKVEPKSC 4856 gH23 Fab heavy chain with signal sequence underlined and italicized (*E. coli* expression)
SEQ ID NO:93
*atgaagaaga ctgctatagc aattgcagtg gcgctagctg gtttcgccac
cgtggcgcaa gct*gaggttc agctggtcga gtctggaggc gggcttgtca
aacctggagg gagcctgcgt ctctcttgtg cagcaagcgg cttcagcctg
tcctcttacg atatgtcctg ggtgcgccag gcacctggga agggcctgga
gtggattggc attatttatg gcggcagcgg cagcacatgg tacgcagct
gggcgaaggg ccgtttcacc atctcccggg acagcgcaaa gaatagcgtg
tacctccaga tgaactctct ccgcgcagag gacacagcag tctattactg
tgcgcggggc cgcgatgcag gcgcgggcgg cagccgcaac gcgtatagcc
tgtggggaca ggggaccctt gtgacagtct cgagcgcttc tacaaagggc
ccatcggtct tcccctggc accctcctcc aagagcacct ctgggggcac
agcggccctg ggctgcctgg tcaaggacta cttccccgaa ccggtgacgg
tgtcgtggaa ctcaggcgcc ctgaccagcg gcgtgcacac cttcccggct
gtcctacagt cctcaggact ctactccctc agcagcgtgg tgaccgtgcc
ctccagcagc ttgggcaccc agacctacat ctgcaacgtg aatcacaagc
ccagcaacac caaggtcgac aagaaagttg agcccaaatc ttgt

FIGURE 1X

4856gH29 V-region SEQ ID NO:94

```
EVQLVESGGG LVKPGGSLRL SCAASGFSLS SYDMSWVRQA PGKGLEWIGI
IYGGSGSTWY ASWAKGRFTI SRDSAKNSVY LQMNSLRAED TAVYYCARGR
DAGAGGSRDG YSLWGQGTLV TVSS
```

4856gH29 V-region (mammalian expression) SEQ ID NO:95

```
gaagtgcaac tggtggaaag cggaggaggt ttggtgaaac cgggagggtc
actgcggctc tcctgtgccg cctccggatt cagcctctcg tcctacgaca
tgagctgggt cagacaggcc cccgggaagg gcctggagtg gattggtatc
atctacggcg gctccggctc gacttggtac gcttcgtggg ccaagggacg
gttcaccatc tcccgcgatt ccgcgaagaa cagcgtgtat ctgcagatga
actctctgcg ggccgaggac accgcagtgt actactgcgc gaggggcgc
gacgccggcg ccggggatc acgcgacggt tactcccttt ggggacaggg
aaccctggtc actgtctcca gc
```

4856gH29 V-region (*E. coli* expression) SEQ ID NO:96

```
gaggttcagc tggtcgagtc tggaggcggg cttgtcaaac ctggagggag
cctgcgtctc tcttgtgcag caagcggctt cagcctgtcc tcttacgata
tgtcctgggt cgccaggca cctgggaagg gcctggagtg gattggcatt
atttatggcg gcagcggcag cacatggtac gcgagctggg cgaagggccg
tttcaccatc tcccgggaca gcgcaaagaa tagcgtgtac ctccagatga
actctctccg cgcagaggac acagcagtct attactgtgc gcggggccgc
gatgcaggcg cgggcggcag ccgcgatggg tatagcctgt ggggacaggg
gaccctttgtg acagtctcga gc
```

4856gH29 V-region with signal sequence underlined and italicized (mammalian expression)
SEQ ID NO:97
*MKWVTFISLL FLFSSAYS*EV QLVESGGGLV KPGGSLRLSC AASGFSLSSY
DMSWVRQAPG KGLEWIGIIY GGSGSTWYAS WAKGRFTISR DSAKNSVYLQ
MNSLRAEDTA VYYCARGRDA GAGGSRDGYS LWGQGTLVTV SS 4856gH29 V-region with signal sequence underlined and italicized (mammalian expression)
SEQ ID NO:98
*atgaagtggg tcaccttcat ctccctgctg tttctgttct ccagcgccta*
*ctcc*gaagtg caactggtgg aaagcggagg aggtttggtg aaaccgggag
ggtcactgcg gctctcctgt gccgcctccg gattcagcct ctcgtcctac
gacatgagct gggtcagaca ggcccccggg aagggcctgg agtggattgg
tatcatctac ggcggctccg gctcgacttg gtacgcttcg tgggccaagg
gacggttcac catctcccgc gattccgcga agaacagcgt gtatctgcag
atgaactctc tgcgggccga ggacaccgca gtgtactact gcgcgagggg

FIGURE 1Y

```
gcgcgacgcc ggcgccgggg gatcacgcga cggttactcc ctttggggac
agggaaccct ggtcactgtc tccagc
```

**4856gH29 V-region with signal sequence underlined and italicized (*E. coli* expression)**
SEQ ID NO:99
*MKKTAIAIAV ALAGFATVAQ A*EVQLVESGG GLVKPGGSLR LSCAASGFSL
SSYDMSWVRQ APGKGLEWIG IIYGGSGSTW YASWAKGRFT ISRDSAKNSV
YLQMNSLRAE DTAVYYCARG RDAGAGGSRD GYSLWGQGTL VTVSS

**4856gH29 V-region with signal sequence underlined and italicized (*E. coli* expression)**
SEQ ID NO:100
*atgaagaaga ctgctatagc aattgcagtg gcgctagctg gtttcgccac*
*cgtggcgcaa gct*gaggttc agctggtcga gtctggaggc gggcttgtca
aacctggagg gagcctgcgt ctctcttgtg cagcaagcgg cttcagcctg
tcctcttacg atatgtcctg ggtgcgccag gcacctggga agggcctgga
gtggattggc attatttatg gcggcagcgg cagcacatgg tacgcgagct
gggcgaaggg ccgtttcacc atctcccggg acagcgcaaa gaatagcgtg
tacctccaga tgaactctct ccgcgcagag gacacagcag tctattactg
tgcgcggggc cgcgatgcag gcgcgggcgg cagccgcgat gggtatagcc
tgtggggaca ggggacctt gtgacagtct cgagc

4856 gH29 Fab heavy chain (V + human gamma-1 CH1)
SEQ ID NO:101
EVQLVESGGG LVKPGGSLRL SCAASGFSLS SYDMSWVRQA PGKGLEWIGI
IYGGSGSTWY ASWAKGRFTI SRDSAKNSVY LQMNSLRAED TAVYYCARGR
DAGAGGSRDG YSLWGQGTLV TVSSASTKGP SVFPLAPSSK STSGGTAALG
CLVKDYFPEP VTVSWNSGAL TSGVHTFPAV LQSSGLYSLS SVVTVPSSSL
GTQTYICNVN HKPSNTKVDK KVEPKSC

4856 gH29 Fab heavy chain (V + human gamma-1 CH1) (mammalian expression)
SEQ ID NO:102
gaagtgcaac tggtggaaag cggaggaggt ttggtgaaac cgggagggtc
actgcggctc tcctgtgccg cctccggatt cagcctctcg tcctacgaca
tgagctgggt cagacaggcc cccgggaagg gcctggagtg gattggtatc
atctacggcg gctccggctc gacttggtac gcttcgtggg ccaagggacg
gttcaccatc tcccgcgatt ccgcgaagaa cagcgtgtat ctgcagatga
actctctgcg ggccgaggac accgcagtgt actactgcg gaggggcgc
gacgccggcg ccgggggatc acgcgacggt tactcctt ggggacaggg
aaccctggtc actgtctcca gcgcttctac aaagggccca tcggtcttcc
ccctggcacc ctcctccaag agcacctctg gggcacagc ggccctgggc
tgcctggtca aggactactt ccccgaaccg gtgacggtgt cgtggaactc
aggcgccctg accagcggcg tgcacacctt cccggctgtc ctacagtcct
caggactcta ctccctcagc agcgtggtga ccgtgccctc cagcagcttg
ggcacccaga cctacatctg caacgtgaat cacaagccca gcaacaccaa
```

FIGURE 1Z

```
ggtggacaag aaagttgagc ccaaatcttg t
```

**4856 gH29 Fab heavy chain (V + human gamma-1 CH1) (*E. coli* expression)**
SEQ ID NO:103
```
gaggttcagc tggtcgagtc tggaggcggg cttgtcaaac ctggagggag
cctgcgtctc tcttgtgcag caagcggctt cagcctgtcc tcttacgata
tgtcctgggt gcgccaggca cctgggaagg gcctggagtg gattggcatt
atttatggcg gcagcggcag cacatggtac gcgagctggg cgaagggccg
tttcaccatc tcccgggaca gcgcaaagaa tagcgtgtac ctccagatga
actctctccg cgcagaggac acagcagtct attactgtgc gcggggccgc
gatgcaggcg cgggcggcag ccgcgatggg tatagcctgt ggggacaggg
gaccttgtg acagtctcga gcgcttctac aaagggccca tcggtcttcc
ccctggcacc ctcctccaag agcacctctg ggggcacagc ggccctgggc
tgcctggtca aggactactt ccccgaaccg gtgacggtgt cgtggaactc
aggcgccctg accagcggcg tgcacacctt cccggctgtc ctacagtcct
caggactcta ctccctcagc agcgtggtga ccgtgccctc cagcagcttg
ggcacccaga cctacatctg caacgtgaat cacaagccca gcaacaccaa
ggtcgacaag aaagttgagc ccaaatcttg t
```

4856 gH29 Fab heavy chain with signal sequence underlined and italicized (mammalian expression)
SEQ ID NO:104
*MKWVTFISLL FLFSSAYS*EV QLVESGGGLV KPGGSLRLSC AASGFSLSSY
DMSWVRQAPG KGLEWIGIIY GGSGSTWYAS WAKGRFTISR DSAKNSVYLQ
MNSLRAEDTA VYYCARGRDA GAGGSRDGYS LWGQGTLVTV SSASTKGPSV
FPLAPSSKST SGGTAALGCL VKDYFPEPVT VSWNSGALTS GVHTFPAVLQ
SSGLYSLSSV VTVPSSSLGT QTYICNVNHK PSNTKVDKKV EPKSC

4856 gH29 Fab heavy chain with signal sequence underlined and italicized (mammalian expression)
SEQ ID NO:105
*atgaagtggg tcaccttcat ctccctgctg tttctgttct ccagcgccta*
*ctcc*gaagtg caactggtgg aaagcggagg aggtttggtg aaaccgggag
ggtcactgcg gctctcctgt gccgcctccg gattcagcct ctcgtcctac
gacatgagct gggtcagaca ggcccccggg aagggcctgg agtggattgg
tatcatctac ggcggctccg gctcgacttg gtacgcttcg tgggccaagg
gacggttcac catctcccgc gattccgcga agaacagcgt gtatctgcag
atgaactctc tgcgggccga ggacaccgca gtgtactact gcgcgagggg
gcgcgacgcc ggcgcggggg gatcacgcga cggttactcc ctttggggac
agggaaccct ggtcactgtc tccagcgctt ctacaagggg cccatcggtc
ttccccctgg caccctcctc aagagcacc tctgggggca gcggccct
gggctgcctg gtcaaggact acttccccga accggtgacg gtgtcgtgga
actcaggcgc cctgaccagc ggcgtgcaca ccttcccggc tgtcctacag
tcctcaggac tctactccct cagcagcgtg gtgaccgtgc cctccagcag
cttgggcacc cagacctaca tctgcaacgt gaatcacaag cccagcaaca
ccaaggtgga caagaaagtt gagcccaaat cttgt

FIGURE 1AA

4856 gH29 Fab heavy chain with signal sequence underlined and italicized (*E. coli* expression)
SEQ ID NO:106
*MKKTAIAIAV ALAGFATVAQ A*EVQLVESGG GLVKPGGSLR LSCAASGFSL
SSYDMSWVRQ APGKGLEWIG IIYGGSGSTW YASWAKGRFT ISRDSAKNSV
YLQMNSLRAE DTAVYYCARG RDAGAGGSRD GYSLWGQGTL VTVSSASTKG
PSVFPLAPSS KSTSGGTAAL GCLVKDYFPE PVTVSWNSGA LTSGVHTFPA
VLQSSGLYSL SSVVTVPSSS LGTQTYICNV NHKPSNTKVD KKVEPKSC 4856 gH29 Fab heavy chain with signal sequence underlined and italicized (*E. coli* expression)
SEQ ID NO:107
*atgaagaaga ctgctatagc aattgcagtg gcgctagctg gtttcgccac*
*cgtggcgcaa gct*gaggttc agctggtcga gtctggaggc gggcttgtca
aacctggagg gagcctgcgt ctctcttgtg cagcaagcgg cttcagcctg
tcctcttacg atatgtcctg ggtgcgccag gcacctggga agggcctgga
gtggattggc attatttatg gcggcagcgg cagcacatgg tacgcgagct
gggcgaaggg ccgtttcacc atctcccggg acagcgcaaa gaatagcgtg
tacctccaga tgaactctct ccgcgcagag gacacagcag tctattactg
tgcgcggggc cgcgatgcag gcgcgggcgg cagccgcgat gggtatagcc
tgtggggaca ggggaccctt gtgacagtct cgagcgcttc tacaaagggc
ccatcggtct tccccctggc accctcctcc aagagcacct ctgggggcac
agcggccctg ggctgcctgg tcaaggacta cttccccgaa ccggtgacgg
tgtcgtggaa ctcaggcgcc ctgaccagcg gcgtgcacac cttcccggct
gtcctacagt cctcaggact ctactcctc agcagcgtgg tgaccgtgcc
ctccagcagc ttgggcaccc agacctacat ctgcaacgtg aatcacaagc
ccagcaacac caaggtcgac aagaaagttg agcccaaatc ttgt 4856 scFv
SEQ ID NO:108
EVQLVESGGG LVKPGGSLRL SCAASGFSLS SYDMSWVRQA PGKCLEWIGI
IYGGSGSTWY ASWAKGRFTI SRDSAKNSVY LQMNSLRAED TAVYYCARGR
DAGAGGSRNG YSLWGQGTLV TVSSGGGGSG GGGSGGGGSG GGGSAYDMTQ
SPSTLSASVG DRVTITCQAS ESIYSGLAWY QQKPGKAPKL LIYAASDLAS
GVPSRFSGSG SGTEYTLTIS SLQPDDFATY YCQQTWTDGG IDNPFGCGTK
VEIKRTENLY FQ

FIGURE 1AB

Human IGKV1-5 JK4 acceptor framework SEQ ID NO:109

```
DIQMTQSPST LSASVGDRVT ITCRASQSIS SWLAWYQQKP GKAPKLLIYD
ASSLESGVPS RFSGSGSGTE FTLTISSLQP DDFATYYCQQ YNSYSLTFGG
GTKVEIK
```

Human IGKV1-5 JK4 acceptor framework SEQ ID NO:110

```
gacatccaga tgacccagtc tccttccacc ctgtctgcat ctgtaggaga
cagagtcacc atcacttgcc gggccagtca gagtattagt agctggttgg
cctggtatca gcagaaacca gggaaagccc taagctcct gatctatgat
gcctccagtt tggaaagtgg ggtcccatca aggttcagcg gcagtggatc
tgggacagaa ttcactctca ccatcagcag cctgcagcct gatgattttg
caacttatta ctgccaacag tataatagtt attctctcac tttcggcgga
gggaccaagg tggagatcaa a
```

Human IGHV3-21 JH5 acceptor framework SEQ ID NO:111

```
EVQLVESGGG LVKPGGSLRL SCAASGFTFS SYSMNWVRQA PGKGLEWVSS
ISSSSSYIYY ADSVKGRFTI SRDNAKNSLY LQMNSLRAED TAVYYCARNW
FDSWGQGTLV TVSS
```

Human IGHV3-21 JH5 acceptor framework SEQ ID NO:112

```
gaggtgcagc tggtggagtc tgggggaggc ctggtcaagc ctggggggtc
cctgagactc tcctgtgcag cctctggatt caccttcagt agctatagca
tgaactgggt ccgccaggct ccagggaagg ggctggagtg ggtctcatcc
attagtagta gtagtagtta catatactac gcagactcag tgaagggccg
attcaccatc tccagagaca acgccaagaa ctcactgtat ctgcaaatga
acagcctgag agccgaggac acggctgtgt attactgtgc gagaaactgg
ttcgactcct ggggccaagg aaccctggtc accgtctcct ca
```

Figure 2A

LIGHT CHAIN Graft 4856

```
              1       5        10       15       20       25       30       35       40       45       50       55       60       65       70       75       80       85       90       95abc   100  105
Light 4856    AYDMTQTPASVEVAVGGTVTIKCQASESIYSGLAWYQQTPGQRPKLLIYAASDLASGVPSRFKGSGSGTEYTLTISGVECADAATYYCQQTWTDGGIDNPFGGGTEVVK
              |||   ||||||| ||        ||   |||||||||||   ||    |||||||||||||||||   |||||||||||     |||||||||| |||||||||| |||||| ||
IGKV1-5       DIQMTQSPSTLSASVGDRVTITCRASQSISSWLAWYQQKPGKAPKLLIYDASSLESGVPSRFSGSGSGTEFTLTISSLQPDDFATYYCQQYN----SYSLTFGGGTKVEIK
              |||                |
4856gL3       AYDMTQSPSTLSASVGDRVTITCQASESIYSGLAWYQQKPGKAPKLLIYAASDLASGVPSRFSGSGSGTEYTLTISSLQPDDFATYYCQQTWTDGGIDNPFGGGTKVEIK
4856mL1.1     AYDMNQSPSSLSASLGDTITITCQASESIYSGLAWYQQKPGNIPKLLIYAASDLASGVPSRFKGSGSGTEYTLTISSLQPEDIATYYCQQTWTDGGIDNPFGGGTKLEIK
```

Legend

Light 4856 = Rabbit light chain variable region sequence (SEQ ID NO: 10)
IGKV1-5 = human germline acceptor framework VK1 sequence IGKV1-5 with JK4 (SEQ ID NO:108)

4856gL3 = Humanized graft of 4856 light chain variable region using IGKV1-5 human germline as the acceptor framework. (SEQ ID NO:38)
4856mL1.1 = Murinized graft of 4856 light chain variable region using a murine germline as the acceptor framework (SEQ ID NO:26)

CDRs are shown in bold/underlined
Donor residues are shown in bold/italic and are highlighted: A1, Y2, D3 and Y71

Figure 2B

HEAVY CHAIN Graft 4856

```
              1         5        10        15        20        25        30        35        40        45        50      a 55        60        65        70        75        80  abc 85        90        95   100abcdefg 105       110
Heavy 4856   -QSLEESGGRLVTPGTPLTLTCTASGFSLSSYDMSWVRQAPGKGLEWIGIIYGGSGSTWYASWAKGRFTMSKTST--TVDLKITSPTTEDMATYFCARGRDGGAGGSRNGYSLWGQGTLVTVSS
IGHV3-21      EVQLVESGGGLVKPGGSLRLSCAASGFTFSSYSMNWVRQAPGKGLEWVSSISSSSSYIYYADSVKGRFTISRDNAKNSLYLQMNSLRAEDTAVYYCAR-----------------NWFDSWGQGTLVTVSS
              |||                                  ||| ||                 ||  |                    ||| |||   |||||||||||||||  |||                                  ||||||||||||
4856gH13      EVQLVESGGGLVKPGGSLRLSCAASGFSLSSYDMSWVRQAPGKGLEWIGIIYGGSGSTWYASWAKGRFTISRDSAKNSVYLQMNSLRAEDTAVYYCARGRDAGAGGSRNGYSLWGQGTLVTVSS
4856gH20      EVQLVESGGGLVKPGGSLRLSCAASGFSLSSYDMSWVRQAPGKGLEWISIIYGGSGSTWYASWAKGRFTMSKDSAKNSVYLQMNSLRAEDTAVYYCARGRDAGAGGSRNGYSLWGQGTLVTVSS
4856gH23      EVQLVESGGGLVKPGGSLRLSCAASGFSLSSYDMSWVRQAPGKGLEWIGIIYGGSGSTWYASWAKGRFTISRDSAKNSVYLQMNSLRAEDTAVYYCARGRDAGAGGSRNAYSLWGQGTLVTVSS
4856gH29      EVQLVESGGGLVKPGGSLRLSCAASGFSLSSYDMSWVRQAPGKGLEWIGIIYGGSGSTWYASWAKGRFTISRDSAKNSVYLQMNSLRAEDTAVYYCARGRDAGAGGSRDGYSLWGQGTLVTVSS
4856mH2.1     EVKLLESGGGLVQPGGSLKLSCTASGFSLSSYDMSWVRQAPGKGLEWIGIIYGGSGSTWYASWAKGKFIMSKDSAKNTVYLQMSKVRSEDNATYFCARGRDGGAGGSRNGYSLWGQGTLVTVSS
```

Legend

4856 = Rabbit heavy chain variable region sequence (SEQ ID NO:14)

IGHV3-21 = human germline acceptor framework VH3 sequence IGHV3-21 with JH5 (SEQ ID NO:110)

4856gH13 (SEQ ID NO:52), gH20 (SEQ ID NO:66), gH23 (SEQ ID NO:80) and gH29 (SEQ ID NO:94)= Humanized grafts of 4856 heavy chain variable region using IGHV3-21 human germline as the acceptor framework.

4856mH2.1 = Murinized graft of 4856 heavy chain variable region using a murine germline as the acceptor framework (SEQ ID NO:30)

CDRs are shown in bold/underlined

Donor residues are shown in bold/italic and are highlighted: I48, G49, M69, K71, S73 and V78

The mutation in CDRH3 to remove a potential Aspartic acid isomerization site is shown in bold/underlined and is highlighted: A98

The mutations in CDRH3 to remove a potential Asparagine deamidation site are shown in bold/underlined and are highlighted: D100e, A100f

FIGURE 3A

HUMAN Latency-associated Peptide and Transforming growth factor beta-1 SEQ ID NO:113
LSTCKTIDMELVKRKRIEAIRGQILSKLRLASPPSQGEVPPGPLPEAVLALYNSTRDRVAGESAEPEPEPEADYYAK
EVTRVLMVETHNEIYDKFKQSTHSIYMFFNTSELREAVPEPVLLSRAELRLLRLKLKVEQHVELYQKYSNNSWRYLS
NRLLAPSDSPEWLSFDVTGVVRQWLSRGGEIEGFRLSAHCSCDSRDNTLQVDINGFTTGRRGDLATIHGMNRPFLLL
MATPLERAQHLQSSRHRRALDTNYCFSSTEKNCCVRQLYIDFRKDLGWKWIHEPKGYHANFCLGPCPYIWSLDTQYS
KVLALYNQHNPGASAAPCCVPQALEPLPIVYYVGRKPKVEQLSNMIVRSCKCS

FIGURE 3B

Mature HUMAN Transforming growth factor beta-1 SEQ ID NO:114
ALDTNYCFSSTEKNCCVRQLYIDFRKDLGWKWIHEPKGYHANFCLGPCPYIWSLDTQYSKVLALYNQHNPGASAAPC
CVPQALEPLPIVYYVGRKPKVEQLSNMIVRSCKCS

FIGURE 3C

HUMAN Latency-associated Peptide and Transforming growth factor beta-2 SEQ ID NO:115
LSTCSTLDMDQFMRKRIEAIRGQILSKLKLTSPPEDYPEPEEVPPEVISIYNSTRDLLQEKASRRAAACERERSDEE
YYAKEVYKIDMPPFFPSENAIPPTFYRPYFRIVRFDVSAMEKNASNLVKAEFRVFRLQNPKARVPEQRIELYQILKS
KDLTSPTQRYIDSKVVKTRAEGEWLSFDVTDAVHEWLHHKDRNLGFKISLHCPCCTFVPSNNYIIPNKSEELEARFA
GIDGTSTYTSGDQKTIKSTRKKNSGKTPHLLLMLLPSYRLESQQTNRRKKRALDAAYCFRNVQDNCCLRPLYIDFKR
DLGWKWIHEPKGYNANFCAGACPYLWSSDTQHSRVLSLYNTINPEASASPCCVSQDLEPLTILYYIGKTPKIEQLSN
MIVKSCKCS

FIGURE 3D

Mature HUMAN Transforming growth factor beta-2 SEQ ID NO:116
ALDAAYCFRNVQDNCCLRPLYIDFKRDLGWKWIHEPKGYNANFCAGACPYLWSSDTQH
SRVLSLYNTINPEASASPCCVSQDLEPLTILYYIGKTPKIEQLSNMIVKSCKCS

FIGURE 3E

HUMAN Latency-associated Peptide and Transforming growth factor beta-3 SEQ ID NO:117
LSTCTTLDFGHIKKKRVEAIRGQILSKLRLTSPPEPTVMTHVPYQVLALYNSTRELLEEMHGEREEGCTQENTESEY
YAKEIHKFDMIQGLAEHNELAVCPKGITSKVFRFNVSSVEKNRTNLFRAEFRVLRVPNPSSKRNEQRIELFQILRPD
EHIAKQRYIGGKNLPTRGTAEWLSFDVTDTVREWLLRRESNLGLEISIHCPCHTFQPNGDILENIHEVMEIKFKGVD
NEDDHGRGDLGRLKKQKDHHNPHLILMMIPPHRLDNPGQGGQRKKRALDTNYCFRNLEENCCVRPLYIDFRQDLGWK
WVHEPKGYYANFCSGPCPYLRSADTTHSTVLGLYNTLNPEASASPCCVPQDLEPLTILYYVGRTPKVEQLSNMVVKS
CKCS

FIGURE 3F

Mature HUMAN Transforming growth factor beta-3 SEQ ID NO:118
ALDTNYCFRNLEENCCVRPLYIDFRQDLGWKWVHEPKGYYANFCSGPCPYLRSADTTHST
VLGLYNTLNPEASASPCCVPQDLEPLTILYYVGRTPKVEQLSNMVVKSCKCS FIGURE 17A
FIGURE 17B
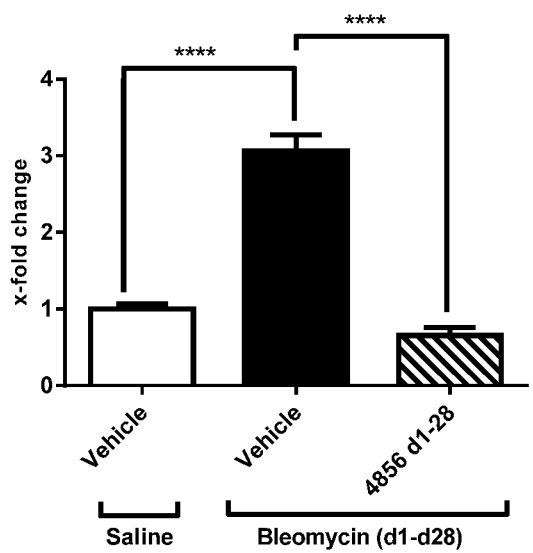
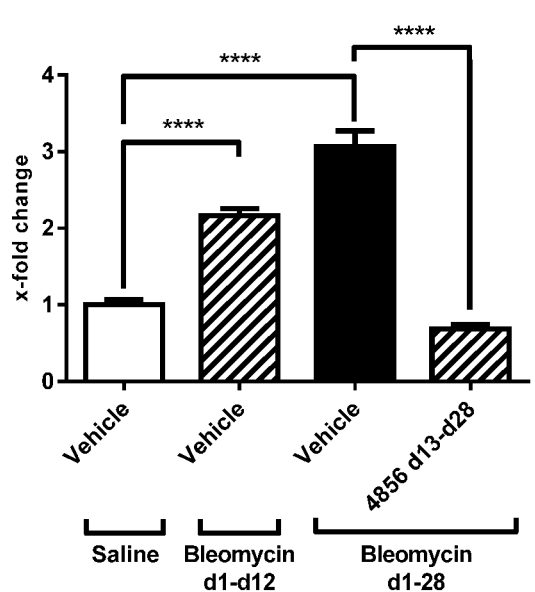

FIGURE 18A

Mature human TGF-beta 1 (SEQ ID NO:114) showing residues involved in interaction with 4856 Fab gL3gH13 (underlined) and residues critical for interaction with TbetaRI and TbetaRII (bold). Contacting residues within 4Å.

1
ALDTNYCFSSTEKNCCVRQLYIDF<u>RKDLGWKW</u>IHEPKGY

40
HANFCLGPCPYIWSLDTQYS<u>K</u>VLA<u>L</u>YNQ<u>H</u>NPGASAAPCCV

80
PQALEPLPIV<u>YYVGR</u>KP<u>K</u>V<u>EQL</u>SNMIVRSCKCS

Mature human TGF-beta 1 (SEQ ID NO:114) showing residues involved in interaction with 4856 Fab gL3gH13 (underlined) and residues critical for interaction with TbetaRI and TbetaRII (bold). Contacting residues within 5Å.

1
ALDTNYCFSSTEKNCCVRQLYIDF<u>RKDLGWKW</u>IHEPKGY

40
HANFCLGPCPYIWSLDT<u>Q</u>YS<u>K</u>VLA<u>L</u>YNQ<u>H</u>NPGASAAPCCV

80
PQALEPLP<u>I</u>V<u>YYVGRKPK</u>V<u>EQL</u>SNMIVRSCKCS

Mature human TGF-beta 2 (SEQ ID NO:116) showing residues involved in interaction with scFv 4856 (underlined). Contacting residues within 4Å.

ALDAAYCFRN VQDNCCLRPL YIDF<u>KRDLGW KWIHEPKGYN</u> ANFCAGACP<u>Y</u> LWSSDTQHS<u>R</u> VLS<u>L</u>YNT<u>I</u>NP EASASPCCVS QDLEPLTIL<u>Y</u> <u>Y</u>IGKTPKIE<u>Q</u> <u>L</u>SNMIVKSCK CS

ANTAGONIST ANTIBODIES THAT BIND TO HUMAN TGFB1, TGFB2 AND TO TGFB3 AND THEIR USE FOR THE TREATMENT OF LUNG FIBROSIS

REFERENCE TO AN ELECTRONIC SEQUENCE LISTING

The contents of the electronic sequence listing (0089-0023US2_SL.txt; Size: 140,360 bytes; and Date of Creation Nov. 20, 2018) is herein incorporated by reference in its entirety.

BACKGROUND OF THE INVENTION

There are 3 TGF-beta isoforms present in humans, TGF-beta 1, TGF-beta 2 and TGF-beta 3. The isoforms are homologous and share ~70% sequence identity. They are all synthesised and secreted as a latent complex in which TGF-beta is complexed with two other polypeptides, latent TGF-beta binding protein (LTBP) and latency-associated peptide (LAP) (a protein derived from the N-terminal region of the TGF-beta gene product). Serum proteinases such as plasmin catalyze the release of active mature TGF-beta from the complex.

In their active forms, TGF-beta isoforms exist as a ~25 KDa homodimeric protein. All 3 isoforms signal via the same transmembrane receptors TbetaRI and TbetaRII. TGF-beta first binds to TbetaRII which then forms a heterotetrameric complex with TbetaRI, leading to phosphorylation of TbetaRI and activation of subsequent signalling pathways (see Derynck & Miyazono (eds), 2008, The TGF-beta Family, Cold Spring Harbor Press). Despite signalling via the same receptor complex, distinct non-overlapping functions of the 3 isoforms have been noted which is exemplified by mice containing genetic deletions of the individual isoforms each having different phenotypes (Shull et al., 1992, Nature 359: 693-699; Sanford et al., 1997, Development 124: 2659-2670; Proetzel et al., 1995, Nature Genet., 11: 409-414).

TGF-beta is a pleotropic molecule involved in a range of biological processes. TGF-beta inhibits the proliferation of many cell types, including epithelial, endothelial, haematopoietic and immune cells. The effector functions of immune cells are also responsive to TGF-beta and TGF-beta suppresses Th1 and Th2 cell differentiation whilst stimulating Treg cells, thus TGF-beta has a predominantly immunosuppressive function (Li et al., 2006, Ann Rev Immunol., 24: 99-146; Rubtsov & Rudensky, 2007, Nat Rev Immunol., 7: 443-453). TGF-beta expression is highly regulated and involved in maintenance of tissue homeostasis. However chronic over expression of TGF-beta is linked with driving disease progression in disease states such as cancer and fibrosis.

Due to the role of human TGF-beta in a variety of human disorders, therapeutic strategies have been designed to inhibit or counteract TGF-beta activity. In particular, antibodies that bind to, and neutralize, TGF-beta have been sought as a means to inhibit TGF-beta activity. Antibodies to TGF-beta are known in the art. A systemically administered anti-TGF-beta1 antibody (CAT-192) was evaluated in a Phase I/II trial in systemic sclerosis patients, with no evidence of efficacy with doses up to 10 mg/kg (Denton et al., 2007, Arthritis Rheum, 56: 323-333). A humanised antibody (TbetaM1) optimised for activity against TGF-beta1 was assessed in a Phase1 trial in patients with metastatic cancer, but no anti-tumor effect was noted (Cohn et al., 2014, Int J Oncol., 45: 2221-2231). A human TGF-beta2 antibody (CAT-152) was evaluated for prevention of scarring after trabeculectomy, but no difference from placebo was noted (CAT-152 0102 Trabeculectomy Study Group, 2007, Ophthalmology, 114: 1822-1830). A systemically administered full length IgG specific for TGF-beta1, 2 and 3 (Fresolimumab, GC1008) has been investigated for the treatment of certain cancers and fibrotic disease. However, side effects have been reported including skin lesions that appear to be associated with systemic delivery of the antibody (Lacouture et al., 2015, Cancer Immunol Immunother., 64: 437-446).

Fibrosis is an aberrant response to wound healing wherein excess fibrous connective tissue is formed in an organ or tissue. In the remodelling phase during normal wound healing, synthesis of new collagen exceeds the rate at which it is degraded, resulting in scar formation. The final process of normal wound healing is scar resolution which occurs through a combination of reduced collagen synthesis and increased collagen degradation, a process controlled by matrix metalloproteinases (MMPs) and tissue inhibitors of metalloproteinases (TIMPS) produced by granulocytes, macrophages, epidermal cells and myofibroblasts. Thus wound healing involves a shift in metabolic equilibrium from stimulation of deposition followed by resolution. Any disruption in this equilibrium may result in excessive deposition of matrix components resulting in hardening and scarring of tissues and destruction of normal tissue architecture and a compromise in tissue function; this disruption is termed fibrosis.

Abnormal epithelial-mesenchymal interactions, altered fibroblast phenotypes, exaggerated fibroblast proliferation, and excessive deposition of collagen and extracellular matrix are all the key processes which contribute to fibrotic disease. A key cell type in this process is the myofibroblast. Activation of myofibroblasts results in their increased secretion of types I, III and IV collagen, fibronectin, laminin and proteoglycans. Other cell types considered to play a prominent role in fibrosis include epithelial cells and macrophages. TGF-beta is considered to be a master regulator of fibrosis and contributes to the fibrotic process via actions on several cell types including macrophages and fibroblasts (Leask & Abraham, 2004, FASEB J., 18: 816-827). Key profibrotic activities include the stimulation of fibroblast migration and the transformation of fibroblasts to myofibroblasts, stimulating excessive ECM deposition. TGF-beta is also involved in macrophage migration and stimulates the production of mesenchymal growth factors from macrophages such as PDGF, as well as inhibiting ECM degradation through the increased expression of protease inhibitors such as TIMP3.

Fibrotic diseases are a leading cause of morbidity and mortality and can affect many tissue and organ systems. Included in this group of diseases are interstitial lung diseases. Idiopathic pulmonary fibrosis (IPF) is the most common form of interstitial lung diseases and is one of seven distinct groups of idiopathic interstitial pneumonias (IIP). The interstitium is the microscopic space between the basement membranes of the alveolar epithelium and capillary endothelium, and forms part of the blood-gas barrier. IIPs are characterised by expansion of the interstitial compartment by inflammatory cells, with associated fibrosis particularly noted for IPF.

IPF patients present with progressive exertional dyspnoea and cough with progressive pulmonary parenchymal fibrosis, resulting in pulmonary restriction and hypoxemia. The diagnosis of IPF is established using a combination of clinical, radiographic and pathological criteria and is associated with a characteristic pathological pattern called usual interstitial pneumonia (UIP).

IPF can be diagnosed at any age, but is most prevalent in those aged over 50 years and prevalence is higher in men than women. IPF has a mortality rate higher than many neoplastic diseases, with a 3 year survival rate of 50% and a 5 year survival rate of only 20%. The cause of IPF is unknown, but it is hypothesised that there are multiple episodes of epithelial cell activation from as yet unidentified exogenous and endogenous stimuli, which if left untreated leads to progressive lung injury and ultimately fibrosis. Disruption of the alveolar epithelium is followed by migration, proliferation and activation of mesenchymal cells, resulting in the formation of fibroblastic/myofibroblastic foci with excessive accumulation of ECM.

TGF-beta expression is increased in the fibrotic lungs of IPF patients (Broekelmann et al., 1991, PNAS, 88: 6642-6646; Khalil et al., 1991, Am J Respir Cell Mol Biol, 5: 155-162) and together with the well-established role of TGF-beta in driving fibrotic mechanisms the inhibition of TGF-beta should be considered as an effective mechanism for the treatment of IPF patients.

There is no effective therapy available for IPF patients. Anti-inflammatory agents, including corticosteroids, cyclophosphamide and azothiaprine have proved to be of little benefit for patients and have associated side effects. Recently two small molecule drugs, pirfenidone and nintedanib, have been approved for the treatment of IPF. Both drugs have been shown to slow the progression of disease, but neither cures the disease and many patients continue to decline. In addition treatment-related adverse events such as gastrointestinal events, rash and photosensitivity are evident (Cottin and Maher, 2015, Eur Respir Rev, 24: 58-64; Mazzei et al., 2015, Ther Adv Respir Dis.) To date, no targeted therapies and no antibody therapies have been approved for fibrotic indications.

Furthermore, TGF-beta is also associated with pulmonary hypertension, such as pulmonary arterial hypertension (PAH). Increased expression of TGF-beta in patients with pulmonary hypertension has been shown by immunohistochemistry (Botney et al., 1994, Am J Pathol, 144: 286-295) and also noted in blood and lung homogenates from pulmonary hypertension patients (Selimovic et al., 2009, Eur Respir J, 34: 662-668; Gore et al., PLOS One (2014) 9(6):e100310). A TbetaRI kinase inhibitor has also been shown to inhibit the monocrotaline-induced model of pulmonary hypertension (Zaiman et al., 2008, Am J Respir Crit Care Med, 177: 896-905). Pulmonary hypertension is a well-recognised complication of IPF, and these data support the hypothesis that IPF patients whose symptoms are driven by both interstitial fibrosis and pulmonary hypertension could be a sub-population of patients for whom anti-TGF-beta therapies could potentially be even more effective.

Therefore, there exists a need in the art for suitable and/or improved antibodies capable of binding and inhibiting all three isoforms of TGF-beta suitable for therapeutic applications. Such antibodies may also be more effective for treating pulmonary indications and/or have fewer side effects if delivered by inhalation.

BRIEF SUMMARY OF THE INVENTION

This invention pertains to novel TGF-beta specific antibodies and binding fragments thereof, in particular antagonistic antibodies and fragments.

In one aspect there is provided an antagonistic antibody which binds human TGF-beta 1, human TGF-beta 2 and human TGF-beta 3 comprising a heavy chain, wherein the variable domain of the heavy chain comprises at least one of a CDR having the sequence given in SEQ ID NO:4 for CDR-H1, a CDR having the sequence given in SEQ ID NO:5 for CDR-H2 and a CDR having the sequence given in SEQ ID NO:6, SEQ ID NO:7, SEQ ID NO:8 or SEQ ID NO:9 for CDR-H3.

In one aspect there is provided an antagonistic antibody which binds human TGF-beta 1, human TGF-beta 2 and human TGF-beta 3, comprising a light chain, wherein the variable domain of the light chain comprises at least one of a CDR having the sequence given in SEQ ID NO:1 for CDR-L1, a CDR having the sequence given in SEQ ID NO:2 for CDR-L2 and a CDR having the sequence given in SEQ ID NO:3 for CDR-L3.

The disclosure also extends to a polynucleotide, such as DNA, encoding an antibody or fragment as described herein.

Also provided is a host cell comprising said polynucleotide.

Methods of expressing an antibody or binding fragment thereof are provided herein.

The present disclosure also relates to pharmaceutical compositions comprising said antibodies or binding fragments thereof.

In one embodiment there is provided a method of treatment comprising administering a therapeutically effective amount of an antibody, fragment or composition as described herein.

The present disclosure also extends to an antibody, binding fragment or composition according to the present disclosure for use in treatment, particularly in the treatment of cancer and/or fibrotic disease.

BRIEF DESCRIPTION OF THE DRAWINGS

FIGS. 1A-1AB show certain antibody amino acid and polynucleotide sequences of the disclosure.

FIG. 1A provides CDR sequences from antibody 4856 (SEQ ID NOs:1-9).

FIG. 1B-1E provides rabbit sequences for antibody 4856 (SEQ ID NOs:10-25).

FIG. 1F-1G provides murinised sequences for antibody 4856 (SEQ ID NOs: 26-33) as well as murine acceptor sequences (SEQ ID NOs: 34-37).

FIG. 1H-1K provides light chain (SEQ ID NOs: 45-51) and variable region sequences (SEQ ID NO:38-44) for antibody 4856 gL3.

FIG. 1L-1O provides Fab heavy chain (SEQ ID NOs: 59-65) and variable region sequences (SEQ ID NO:52-58) for antibody 4856 gH13.

FIG. 1P-1S provides Fab heavy chain (SEQ ID NOs: 73-79) and variable region sequences (SEQ ID NO:66-72) for antibody 4856 gH20.

FIG. 1T-1W provides Fab heavy chain (SEQ ID NOs: 87-93) and variable region sequences (SEQ ID NO:80-86) for antibody 4856 gH23.

FIG. 1X-1AA provides Fab heavy chain (SEQ ID NOs: 101-107) and variable region sequences (SEQ ID NO:94-100) for antibody 4856 gH29.

FIG. 1AB provides human acceptor framework sequences (SEQ ID NOs:108-111).

FIG. 2 shows alignments of the amino acid sequences of various light chain (FIG. 2A) and heavy chain (FIG. 2B) of antibody 4856 and acceptor sequences.

FIG. 3A shows the amino acid sequence of human Latency-associated Peptide and TGF-beta 1

FIG. 3B shows the amino acid sequence of mature human TGF-beta 1

FIG. 3C shows the amino acid sequence of human Latency-associated Peptide and TGF-beta 2

FIG. 3D shows the amino acid sequence of mature human TGF-beta 2

FIG. 3E shows the amino acid sequence of human Latency-associated Peptide and TGF-beta 3

FIG. 3F shows the amino acid sequence of mature human TGF-beta 3

FIGS. 17A-B The effect of intranasally administered 4856 gL3gH13 Fab from A) day 1-28 or B) 13-28 on bleomycin-induced pSmad2/3 expression in type 1 collagen expressing cells.

FIG. 18A shows the sequence of mature human TGF-beta 1 (SEQ ID NO:114) with the residues involved in interaction with 4856 Fab gL3gH13 (underlined) and residues critical for interaction with TbetaRI and TbetaRII (bold) using crystallographic data at 4 Å resolution.

FIG. 18B shows the sequence of mature human TGF-beta 1 (SEQ ID NO:114) with the residues involved in interaction with 4856 Fab gL3gH13 (underlined) and residues critical for interaction with TbetaRI and TbetaRII (bold) using crystallographic data at 5 Å resolution.

FIG. 18C shows the sequence of mature human TGF-beta 2 (SEQ ID NO:116).

DETAILED DESCRIPTION

Figure 4A:
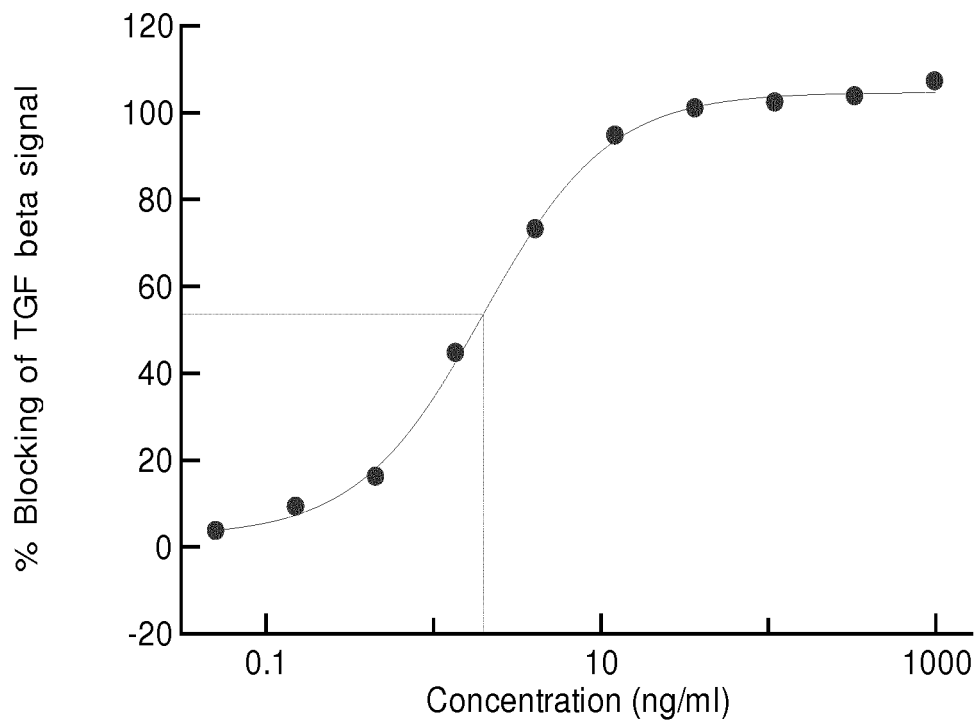
FIGS. 4A, B and C show the effect of rabbit antibody 4856 Fab in the (A) TGF-beta1, (B) TGF-beta2 and (C) TGF-beta3 HEK-Blue-TGF-beta reporter gene assay

The antibodies of the present disclosure bind TGF-beta 1, TGF-beta 2 and TGF-beta 3. In one embodiment the antibodies of the present disclosure bind all three isoforms of mature TGF-beta, mature TGF-beta 1 (SEQ ID NO:114), mature TGF-beta 2 (SEQ ID NO:115) and mature TGF-beta 3 (SEQ ID NO:118). In one embodiment the antibodies of the present disclosure bind the homodimer of each of the three isoforms of mature TGF-beta, the homodimer of mature TGF-beta 1 (SEQ ID NO:114), the homodimer of mature TGF-beta 2 (SEQ ID NO:115) and the homodimer of mature TGF-beta 3 (SEQ ID NO:118). In one embodiment the antibodies of the present disclosure do not bind the latent forms of TGF-beta 1, TGF-beta 2 and TGF-beta 3 comprising the latency-associated peptide (LAP), as shown in SEQ ID NO:113, SEQ ID NO: 115 and SEQ ID NO:117.

In one embodiment the antibodies described herein are antagonistic. As used herein, the term 'antagonistic antibody' describes an antibody that is capable of inhibiting and/or neutralising the biological signalling activity of TGF-beta 1, TGF-beta 2 and TGF-beta 3, for example by blocking binding or substantially reducing binding of TGF-beta 1, TGF-beta 2 and TGF-beta 3 to TbetaRI and/or TbetaRII and thus inhibiting the formation and activation of the TGF-beta receptor complex.

Assays suitable for determining the ability of an antibody to inhibit and/or neutralise the biological signalling activity of TGF-beta 1, TGF-beta 2 and TGF-beta 3 are described in the Examples herein, for example the HEK-Blue TGF-beta reporter gene assay using recombinant TGF-beta 1, 2 and/or 3 described in Example 1 and Example 2, or the BxPC3 and HEK-Blue TGF-beta reporter gene co-culture assay driven by the production of TGF-beta by BvPC3 cells described in Example 3.

In one embodiment, the antibody molecules of the present invention have inhibitory activity in the recombinant TGF-beta 1, TGF-beta 2 or TGF-beta 3 HEK-Blue TGF-beta reporter gene assay, wherein the antibody inhibits human TGF-beta 1 activity with an IC50 of 0.5 nM or better, inhibits human TGF-beta 2 activity with an IC50 of 0.05 nM or better and inhibits human TGF-beta 3 activity with an IC50 of 2 nM or better. In one embodiment the antibody inhibits TGF-beta in the endogenous TGF-beta HEK-Blue TGF-beta reporter gene assay with an IC50 of 10 nM or better.

The antibody molecules of the present invention suitably have a high binding affinity. Affinity may be measured using any suitable method known in the art, including techniques such as surface plasmon resonance, for example BIAcore, as described in the Examples herein, using isolated natural or recombinant TGF-beta 1, TGF-beta 2 and TGF-beta 3 or a suitable fusion protein/polypeptide. In one embodiment, the antibody molecules of the present invention have the following order of binding affinity of highest for human TGF-beta 1, followed by human TGF-beta 2 and the lowest binding affinity for human TGF-beta 3. In one embodiment, the antibody molecules of the present invention have a binding affinity for human TGF-beta 1 that is 10 to 30 times, such as 15 to 25 times, higher than the binding affinity for human TGF-beta 3. In one embodiment, the antibody molecules of the present invention have a binding affinity for human TGF-beta 2 that is 2 to 20 times, such as 5 to 15 times, higher than the binding affinity for human TGF-beta 3.

Suitably the antibody molecules of the present invention have a binding affinity for isolated human TGF-beta 1, TGF-beta 2 and TGF-beta 3 of about 2000 pM or less than 2000 pM. In one embodiment the antibody molecule of the present invention has a binding affinity for human TGF-beta 1 of 500 pM or lower, such as 200 pM or lower or 100 pM or lower. In one embodiment the antibody molecule of the present invention has a binding affinity for human TGF-beta 2 of 500 pM or lower, such as 300 pM or lower, 200 pM or lower. In one embodiment the antibody molecule of the present invention has a binding affinity for human TGF-beta 3 of 3000 pM or lower, such as 2500 pM or lower, 2000 pM or lower.

In one embodiment, the antibody of the present invention has a binding affinity for human TGF-beta 1 of 100 pM or lower, a binding affinity for human TGF-beta 2 of 200 pM or lower and a binding affinity for human TGF-beta 3 of 2000 pM or better.

The lower the numerical value of the affinity the higher the affinity of the antibody or fragment for the TGF-beta isoform.

The present inventors have provided new anti-TGF-beta antibodies, including humanised antibodies. The antibodies were generated from immunisation of rabbits with mature TGF-beta 1 and mature TGF-beta 2.

The residues in antibody variable domains are conventionally numbered according to a system devised by Kabat et al., 1987. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M., J. Mol. Biol., 196, 901-917 (1987)), the loop equivalent to CDR-H1 extends from residue 26 to residue 32. Thus unless indicated otherwise 'CDR-H1' as employed herein is intended to refer to residues 26 to 35, as described by a combination of the Kabat numbering system and Chothia's topological loop definition.

The CDRs of the light chain variable domain are located at residues 24-34 (CDR-L1), residues 50-56 (CDR-L2) and residues 89-97 (CDR-L3) according to the Kabat numbering system.

Antibodies for use in the present disclosure may be obtained using any suitable method known in the art. The TGF-beta polypeptide/protein including fusion proteins, cells (recombinantly or naturally) expressing the polypeptide can be used to produce antibodies which specifically recognise TGF-beta. The polypeptide may be the 'mature' polypeptide of TGF-beta 1, TGF-beta 2 and TGF-beta 3 as shown in SEQ ID NOs: 113, 115 and 117 or a biologically active fragment or derivative thereof. Polypeptides, for use to immunize a host, may be prepared by processes well known in the art from genetically engineered host cells comprising expression systems or they may be recovered from natural biological sources. In the present application, the term "polypeptides" includes peptides, polypeptides and proteins. These are used interchangeably unless otherwise specified. The TGF-beta polypeptide may in some instances be part of a larger protein such as a fusion protein for example fused to an affinity tag, leader sequence, or other sequence.

Antibodies generated against the TGF-beta polypeptide may be obtained, where immunisation of an animal is necessary, by administering the polypeptides to an animal, preferably a non-human animal, using well-known and routine protocols, see for example Handbook of Experimental Immunology, D. M. Weir (ed.), Vol 4, Blackwell Scientific Publishers, Oxford, England, 1986). Many warm-blooded animals, such as rabbits, mice, rats, sheep, cows, camels or pigs may be immunized. However, mice, rabbits, pigs and rats are generally most suitable.

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., 1985, Monoclonal Antibodies and Cancer Therapy, pp 77-96, Alan R Liss, Inc.).

Antibodies may also be generated using single lymphocyte antibody methods by cloning and expressing immunoglobulin variable region cDNAs generated from single lymphocytes selected for the production of specific antibodies by, for example, the methods described by Babcook, J. et al., 1996, Proc. Natl. Acad. Sci. USA 93:7843-7848; WO92/02551; WO04/051268 and International Patent Application number WO04/106377.

Screening for antibodies can be performed using assays to measure binding to human TGF-beta and/or assays to measure the ability to block ligand binding to the receptor. Examples of suitable assays are described in the Examples herein.

'Specific' as employed herein is intended to refer to an antibody that only recognises the antigen to which it is specific or an antibody that has significantly higher binding affinity to the antigen to which it is specific compared to binding to antigens to which it is non-specific, for example at least 5, 6, 7, 8, 9, 10 times higher binding affinity.

The amino acid sequences and the polynucleotide sequences of certain antibodies according to the present disclosure are provided in FIGS. 1 and 2.

In one aspect of the invention the antibody is an antagonistic antibody which binds human TGF-beta 1, human TGF-beta 2 and human TGF-beta 3 comprising a heavy chain, wherein the variable domain of the heavy chain comprises at least one of a CDR having the sequence given in SEQ ID NO:4 for CDR-H1, a CDR having the sequence given in SEQ ID NO:5 for CDR-H2 and a CDR having the sequence given in SEQ ID NO:6, SEQ ID NO:7, SEQ ID NO:8 or SEQ ID NO:9 for CDR-H3. Preferably the variable domain of the heavy chain comprises the sequence given in SEQ ID NO:4 for CDR-H1, the sequence given in SEQ ID NO:5 for CDR-H2 and the sequence given in SEQ ID NO:6, SEQ ID NO:7, SEQ ID NO:8 or SEQ ID NO:9 for CDR-H3.

In a second aspect of the invention the antibody is an antagonistic antibody which binds human TGF-beta 1, human TGF-beta 2 and human TGF-beta 3, comprising a light chain, wherein the variable domain of the light chain comprises at least one of a CDR having the sequence given in SEQ ID NO:1 for CDR-L1, a CDR having the sequence given in SEQ ID NO:2 for CDR-L2 and a CDR having the sequence given in SEQ ID NO:3 for CDR-L3. Preferably the variable domain of the light chain comprises the sequence given in SEQ ID NO:1 for CDR-L1, the sequence given in SEQ ID NO:2 for CDR-L2 and the sequence given in SEQ ID NO:3 for CDR-L3.

The antibody molecules of the present invention suitably comprise a complementary light chain or a complementary heavy chain, respectively.

In one embodiment the antibody of the invention is an antagonistic antibody which binds human TGF-beta 1, human TGF-beta 2 and human TGF-beta 3 comprising a heavy chain as defined above and additionally comprising a light chain wherein the variable domain of the light chain comprises at least one of a CDR having the sequence given in SEQ ID NO: 1 for CDR-L1, a CDR having the sequence given in SEQ ID NO:2 for CDR-L2 and a CDR having the sequence given in SEQ ID NO:3 for CDR-L3. The variable domain of the light chain preferably comprises the sequence given in SEQ ID NO:1 for CDR-L1, the sequence given in SEQ ID NO:2 for CDR-L2 and the sequence given in SEQ ID NO:3 for CDR-L3.

In one embodiment the antibody of the invention is antagonistic antibody which binds human TGF-beta 1, human TGF-beta 2 and human TGF-beta 3 comprising a heavy chain and a light chain, wherein the variable domain of the heavy chain comprises the sequence given in SEQ ID NO:4 for CDR-H1, the sequence given in SEQ ID NO:5 for CDR-H2 and the sequence given in SEQ ID NO:6, SEQ ID NO:7, SEQ ID NO:8 or SEQ ID NO:9 for CDR-H3; and wherein the variable domain of the light chain comprises the sequence given in SEQ ID NO:1 for CDR-L1, the sequence given in SEQ ID NO:2 for CDR-L2 and the sequence given in SEQ ID NO:3 for CDR-L3.

It will be appreciated that one or more amino acid substitutions, additions and/or deletions may be made to the CDRs provided by the present invention without significantly altering the ability of the antibody to bind to TGF-beta 1, TGF-beta 2 and TGF-beta 3 and to neutralise TGF-beta 1, TGF-beta 2 and TGF-beta 3 activity. The effect of any amino acid substitutions, additions and/or deletions can be readily tested by one skilled in the art, for example by using the methods described herein, particularly those illustrated in the Examples, to determine TGF-beta 1, TGF-beta 2 and TGF-beta 3 binding and inhibition of the TGF-beta 1, TGF-beta 2 and TGF-beta 3 and receptor interaction. In one embodiment, at least one amino acid is replaced with a conservative substitution in one or more CDRs selected from the group consisting independently of:

any one of CDR-H1, CDR-H2, CDR-H3, CDR-L1, CDR-L2, CDR-L3;

any one of the combinations CDR-H1 and H2, CDR-H1 and H3, CDR-H1 and L1, CDR-H1 and L2, CDR-H1 and L3, CDR-H2 and H3, CDR-H2 and L1, CDR-H2 and L2, CDR-H2 and L3, CDR-H3 and L1, CDR-H3 and L2, CDR-H3 and L3, CDR-L1 and L2, CDR-L1 and L3, CDR-L2 and L3;

CDR-H1, H2 and H3, CDR-H1, H2 and L1, CDR-H1, H2 and L2, CDR-H1, H2 and L3, CDR-H2, H3 and L1, CDR-H2, H3 and L2, CDR-H2, H3 and L3, CDR-H3, L1 and L2, CDR-H3, L1 and L3, CDR-L1, L2, L3;

any one of the combinations CDR-H1, H2, H3 and L1, CDR-H1, H2, H3 and L2, CDR-H1, H2, H3 and L3, CDR-H2, H3, L1 and L2, CDR-H2, H3, L2 and L3, CDR-H3, L1, L2 and L3, CDR-L1, L2, L3 and H1, CDR-L1, L2, L3 and H2, CDR-L1, L2, L3 and H3, CDR-L2, L3, H1 and H2, CDR-H1, H2, H3, L1 and L2, CDR-H1, H2, H3, L1 and L3, CDR-H1, H2, H3, L2 and L3, CDR-L1, L2, L3, H1 and H2, CDR-L1, L2, L3, H1 and H3, CDR-L1, L2, L3, H2 and H3; and the combination CDR-H1, H2, H3, L1, L2 and L3.

Accordingly, the present invention provides an antagonistic antibody which binds human TGF-beta 1, human TGF-beta 2 and human TGF-beta 3 comprising one or more CDRs selected from CDRH-1 (SEQ ID NO:4), CDRH-2 (SEQ ID NO:5), CDRH-3 (SEQ ID NO:6 or SEQ ID NO:7 or SEQ ID NO:8 or SEQ ID NO:9), CDRL-1 (SEQ ID NO:1), CDRL-2 (SEQ ID NO:2) and CDRL-3 (SEQ ID NO:3) in which one or more amino acids in one or more of the CDRs has been substituted with another amino acid, for example a similar amino acid as defined herein below.

In one embodiment, the present invention provides an antagonistic antibody which binds human TGF-beta 1, human TGF-beta 2 and human TGF-beta 3 comprising CDRH-1 (SEQ ID NO:4), CDRH-2 (SEQ ID NO:5), CDRH-3 (SEQ ID NO:6 or SEQ ID NO:7 or SEQ ID NO:8 or SEQ ID NO:9), CDRL-1 (SEQ ID NO:1), CDRL-2 (SEQ ID NO:2) and CDRL-3 (SEQ ID NO:3), for example in which one or more amino acids in one or more of the CDRs has been substituted with another amino acid, such as a similar amino acid as defined herein below.

In one embodiment, a domain of the heavy chain disclosed herein includes the sequence with 1, 2, 3 or 4 conservative amino acid substitutions, for example wherein the substitutions are in the framework.

In one embodiment, the framework of the heavy chain variable region comprises 1, 2, 3, or 4 amino acids which have been inserted, deleted, substituted or a combination thereof. In one embodiment, the substituted amino acid is a corresponding amino acid from the donor antibody.

In one embodiment, a light variable region disclosed herein includes the sequence with 1, 2, 3 or 4 conservative amino acid substitutions, for example wherein the substitutions are in the framework.

In one embodiment, the framework of the light chain variable region comprises 1, 2, 3 or 4 amino acid which have been inserted, deleted substituted or a combination thereof. In one embodiment the substituted amino is a corresponding amino acid form a donor antibody.

In one aspect of the present invention, there is provided an anti-TGF-beta antibody or binding fragment thereof, wherein the variable domain of the heavy chain comprises three CDRs and the sequence of CDR-H1 has at least 60%, 70%, 80%, 90%, 95%, 96%, 97%, 98%, 99% or more identity or similarity to the sequence given in SEQ ID NO:4, the sequence of CDR-H2 has at least 60%, 70%, 80%, 90% or 95% identity or similarity to the sequence given in SEQ ID NO:5 and the sequence of CDR-H-3 has at least 60%, 70%, 80%, 90%, 95%, 96%, 97%, 98%, 99% or more identity or similarity to the sequence given in SEQ ID NO:6 or SEQ ID NO:7 or SEQ ID NO:8 or SEQ ID NO:9. Preferably, the anti-TGF-beta antibody or binding fragment thereof, additionally comprising a light chain, wherein the variable domain of the light chain comprises three CDRs and the sequence of CDR-L1 has at least 60%, 70%, 80%, 90%, 95%, 96%, 97%, 98%, 99% or more identity or similarity to the sequence given in SEQ ID NO:1, the sequence of CDR-L2 has at least 60%, 70%, 80%, 90%, 95%, 96%, 97%, 98%, 99% or more identity or similarity to the sequence given in SEQ ID NO:2 and the sequence of CDR-L3 has at least 60% identity or similarity to the sequence given in SEQ ID NO:3.

In one embodiment a variable region is provided with at least 60%, 70%, 80%, 90%, 95%, 96%, 97%, 98%, 99% or more identity or similarity to a variable region sequence disclosed herein.

In one embodiment the present invention provides an antagonistic antibody which binds human TGF-beta 1, human TGF-beta 2 and human TGF-beta 3 which contacts a sequence on that is at least 90% identical to amino acids 24-35 of SEQ ID NO:114 and optionally at least one of amino acids 90-95 of SEQ ID NO:114. In a further embodiment, the antibody contacts a sequence that is at least 95%, 96%, 97%, 98%, 99% or 100% identical to SEQ ID NO:114. In a one embodiment the antibody further contacts at least one of amino acids 60, 97 and 101 of SEQ ID NO:114. In a further embodiment, the antibody also contacts amino acids outside the amino acids provided herein. By 'contacts' or 'contacting' it is meant that an interaction can be detected using standard X-ray crystallography techniques at a suitable resolution, such as 5 Å or 4 Å.

In another embodiment there is provided an anti-TGF-beta antibody which competes with the binding of an antibody or fragment of the invention for binding to TbetaRI and/or TbetaRII.

In one embodiment there is provided an anti-TGF-beta antibody which cross-blocks the binding of an antibody comprising a the 6 CDRs given in sequence SEQ ID NO:1 for CDR-L1, SEQ ID NO:2 for CDR-L2, SEQ ID NO:3 for CDR-L3, SEQ ID NO:4 for CDR-H1, SEQ ID NO:5 for CDR-H2 and SEQ ID NO:6 or SEQ ID NO:7 or SEQ ID NO:8 or SEQ ID NO:9 for CDR-H3, in particular wherein the cross blocking is allosteric.

In one embodiment there is provided an anti-TGF-beta antibody which cross-blocks the binding of an antibody comprising the 6 CDRs given in sequence SEQ ID NO:1 for CDR-L1, SEQ ID NO:2 for CDR-L2, SEQ ID NO:3 for CDR-L3, SEQ ID NO:4 for CDR-H1, SEQ ID NO:5 for CDR-H2 and SEQ ID NO:6 or SEQ ID NO:7 or SEQ ID NO:8 or SEQ ID NO:9 for CDR-H3, in particular wherein the antibody cross-blocks the binding by binding the same epitope as the antibody which it blocks.

In one embodiment, the antibody or binding fragment is from a mouse, rat, rabbit, camelid or other mammalian species. For example, the antibody or binding fragment may be from a rabbit. Examples of variable regions for such antibodies are provided in SEQ ID NOs:10-17.

In one embodiment, the antibody or binding fragments is chimeric. Generally, chimeric antibodies or binding fragments comprise elements from two or more species while retaining certain characteristics of that species. For example, a chimeric antibody or binding fragment may have a variable region from one species, such as from a mouse, rat, rabbit or other mammalian species and all or part of a constant region from another species, such as human.

In one embodiment the antibody or binding fragments according to the invention is humanised.

As used herein, the term 'humanised antibody' refers to an antibody or antibody molecule wherein the heavy and/or light chain contains one or more CDRs (including, if desired, one or more modified CDRs) from a donor antibody (e.g. a murine monoclonal antibody) grafted into a heavy and/or light chain variable region framework of an acceptor antibody (e.g. a human antibody) (see, e.g. U.S. Pat. No. 5,585,089; WO91/09967). For a review, see Vaughan et al, Nature Biotechnology, 16, 535-539, 1998. In one embodiment rather than the entire CDR being transferred, only one or more of the specificity determining residues from any one of the CDRs described herein above are transferred to the human antibody framework (see for example, Kashmiri et al., 2005, Methods, 36:25-34). In one embodiment only the specificity determining residues from one or more of the CDRs described herein above are transferred to the human antibody framework. In another embodiment only the specificity determining residues from each of the CDRs described herein above are transferred to the human antibody framework. When the CDRs or specificity determining residues are grafted, any appropriate acceptor variable region framework sequence may be used having regard to the class/type of the donor antibody from which the CDRs are derived, including mouse, primate and human framework regions.

Suitably, the humanised antibody according to the present invention has a variable domain comprising human acceptor framework regions as well as one or more of the CDRs provided specifically herein. Thus, provided in one embodiment is a humanised antibody which binds human TGF-beta 1, TGF-beta 2 and TGF-beta 3 wherein the variable domain comprises human acceptor framework regions and non-human donor CDRs.

Examples of human frameworks which can be used in the present invention are KOL, NEWM, REI, EU, TUR, TEI, LAY and POM (Kabat et al., supra). For example, KOL and NEWM can be used for the heavy chain, REI can be used for the light chain and EU, LAY and POM can be used for both the heavy chain and the light chain. Alternatively, human germline sequences may be used; these are available at: www2.mrc-lmb.cam.ac.uk/vbase or at www.imgt.org, both last accessed 7 Jan. 2016.

In a humanised antibody of the present invention, the acceptor heavy and light chains do not necessarily need to be derived from the same antibody and may, if desired, comprise composite chains having framework regions derived from different chains.

In one embodiment a human framework comprises 1, 2, 3, or 4 amino acid substitutions, additions or deletions, for example 1, 2, 3 or 4 conservative substitutions or substitutions of donor residues.

In one embodiment the sequence employed as a human framework is 80%, 85%, 90%, 95%, 96%, 97%, 98%, 99% or more similar or identical to a sequence disclosed herein.

A suitable framework region for the heavy chain of the humanised antibody of the present invention is derived from the human sub-group VH3 sequence IGHV3-21 together with JH5 (SEQ ID NO:111).

A suitable framework region for the light chain of the humanised antibody of the present invention is derived from the human sub-group VK1 sequence IGKV1-5 sequence together with JK4 (SEQ ID NO:109).

Accordingly, in one example there is provided a humanised antibody comprising the sequence given in SEQ ID NO: 4 for CDR-H1, the sequence given in SEQ ID NO: 5 for CDR-H2 and the sequence given in SEQ ID NO:6 or SEQ ID NO:7 or SEQ ID NO:8 or SEQ ID NO:9 for CDR-H3, wherein the heavy chain framework region is derived from the human subgroup VH3 sequence IGHV3-21 together with JH5 (SEQ ID NO:111).

In one example the heavy chain variable domain of the antibody comprises the sequence given in SEQ ID NO:52, SEQ ID NO:66, SEQ ID NO:80 or SEQ ID NO:94.

A suitable framework region for the light chain of the humanised antibody of the present invention is derived from the human germline sub-group VK1 sequence IGKV1-5 sequence together with JK4 (SEQ ID NO:109).

Accordingly, in one example there is provided a humanised antibody comprising the sequence given in SEQ ID NO: 1 for CDR-L1, the sequence given in SEQ ID NO: 2 for CDR-L2 and the sequence given in SEQ ID NO: 3 for CDR-L3, wherein the light chain framework region is derived from the human subgroup VK1 sequence IGKV1-5 sequence together with JK4 (SEQ ID NO:109).

In one example the light chain variable domain of the antibody comprises the sequence given in SEQ ID NO: 38.

In a humanised antibody of the present invention, the framework regions need not have exactly the same sequence as those of the acceptor antibody. For instance, unusual residues may be changed to more frequently-occurring residues for that acceptor chain class or type. Alternatively, selected residues in the acceptor framework regions may be changed so that they correspond to the residue found at the same position in the donor antibody (see Reichmann et al., 1998, Nature, 332:323-324). Such changes should be kept to the minimum necessary to recover the affinity of the donor antibody. A protocol for selecting residues in the acceptor framework regions which may need to be changed is set forth in WO91/09967.

Donor residue as employed herein refers to a residue from the non-human antibody (e.g. murine or rabbit antibody) which donated the CDRs.

In one embodiment there is provided a humanised antibody wherein the heavy chain variable domain does not contain any donor residues.

Similarly, in one embodiment there is provided an antibody or binding fragment that is 'murinised'. Such an antibody or binding fragment may have a rabbit donor and a murine acceptor. Examples of such antibodies are provided in SEQ ID NOs: 26-33. Examples of murine acceptor sequences are provided in SEQ ID NOs: 34-37.

In a particular embodiment, the present invention provides an antagonistic antibody which binds human TGF-beta 1, human TGF-beta 2 and human TGF-beta 3 having a heavy chain comprising the heavy chain variable domain sequence given in SEQ ID NO:52, SEQ ID NO:66, SEQ ID NO:80 or SEQ ID NO:94 and a light chain comprising the light chain variable domain sequence given in SEQ ID NO: 38.

In one embodiment the disclosure provides an antibody sequence which is 80% similar or identical to a sequence disclosed herein, for example 85%, 90%, 91%, 92%, 93%, 94%, 95% 96%, 97%, 98% or 99% or more over part or whole of the relevant sequence. In one embodiment the relevant sequence is SEQ ID NO:52, SEQ ID NO:66, SEQ ID NO:80 or SEQ ID NO:94. In one embodiment the relevant sequence is SEQ ID NO: 38.

"Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains);
lysine, arginine and histidine (amino acids having basic side chains);
aspartate and glutamate (amino acids having acidic side chains);
asparagine and glutamine (amino acids having amide side chains); and
cysteine and methionine (amino acids having sulphur-containing side chains). Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987, Sequence Analysis Primer, Gribskov, M. and Devereux, J., eds., M Stockton Press, New York, 1991, the BLAST™ software available from NCBI (Altschul, S. F. et al., 1990, J. Mol. Biol. 215:403-410; Gish, W. & States, D. J. 1993, Nature Genet. 3:266-272. Madden, T. L. et al., 1996, Meth. Enzymol. 266:131-141; Altschul, S. F. et al., 1997, Nucleic Acids Res. 25:3389-3402; Zhang, J. & Madden, T. L. 1997, Genome Res. 7:649-656).

The antibody molecules of the present invention may comprise a complete antibody molecule having full length heavy and light chains or a binding fragment thereof and may be, but are not limited to Fab, modified Fab, Fab', modified Fab', F(ab')$_2$, Fv, single domain antibodies (e.g. VH or VL or VHH), scFv, bi, tri or tetra-valent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216:165-181). Other antibody fragments for use in the present invention include the Fab and Fab' fragments described in International patent applications WO05/003169, WO05/003170 and WO05/003171. Multivalent antibodies may comprise multiple specificities e.g. bispecific or may be monospecific (see for example WO92/22853, WO05/113605, WO2009/040562 and WO2010/035012).

Binding fragment of an antibody as employed herein refers to a fragment capable of binding an antigen with affinity to characterise the fragment as specific for the antigen.

In one embodiment the antibody according to the present disclosure is provided as TGF-beta binding antibody fusion protein which comprises an immunoglobulin moiety, for example a Fab or Fab' fragment, and one or two single domain antibodies (dAb) linked directly or indirectly thereto, for example as described in WO2009/040562, WO2010/035012, WO2011/030107, WO2011/061492 and WO2011/086091 all incorporated herein by reference.

In one embodiment the fusion protein comprises two domain antibodies, for example as a variable heavy (VH) and variable light (VL) pairing, optionally linked by a disulphide bond.

In one embodiment the Fab or Fab' element of the fusion protein has the same or similar specificity to the single domain antibody or antibodies. In one embodiment the Fab or Fab' has a different specificity to the single domain antibody or antibodies, that is to say the fusion protein is multivalent. In one embodiment a multivalent fusion protein according to the present invention has an albumin binding site, for example a VH/VL pair therein provides an albumin binding site.

The constant region domains of the antibody molecule of the present invention, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required e.g. for simply blocking TGF-beta activity.

It will be appreciated that sequence variants of these constant region domains may also be used. For example IgG4 molecules in which the serine at position 241 has been changed to proline as described in Angal et al., 1993, Molecular Immunology, 1993, 30:105-108 may be used. Accordingly, in the embodiment where the antibody is an IgG4 antibody, the antibody may include the mutation S241P.

It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, RJ. Journal of Chromatography 705: 129-134, 1995). However, there is no C-terminal Lysine on either heavy or light chain of Ab4856 embodiment of the invention.

In one example one or more CDRs provided herein may be modified to remove undesirable residues or sites, such as cysteine residues or aspartic acid (D) isomerisation sites or asparagine (N) deamidation sites.

For example one or more cysteine residues in any one of the CDRs may be substituted with another amino acid, such as serine.

In one example an Asparagine deamidation site may be removed from one or more CDRs by mutating the asparagine residue (N) and/or a neighbouring residue to any other suitable amino acid. In one example an asparagine deamidation site such as NG or NS may be mutated, for example to NA or NT.

In one example an Aspartic acid isomerisation site may be removed from one or more CDRs by mutating the aspartic acid residue (D) and/or a neighbouring residue to any other suitable amino acid. In one example an aspartic acid isomerisation site such as DG or DS may be mutated, for example to EG, DA or DT.

In one example an N-glycosylation site such as NLS may be removed by mutating the asparagine residue (N) to any other suitable amino acid, for example to SLS or QLS. In one example an N-glycosylation site such as NLS may be removed by mutating the serine residue (S) to any other residue with the exception of threonine (T).

In one embodiment the antibody heavy chain comprises a CH1 domain, a CH2 domain and a CH3 domain and the antibody light chain comprises a CL domain, either kappa or lambda.

In one embodiment the antibody heavy chain comprises a CH1 domain and the antibody light chain comprises a CL domain, either kappa or lambda.

In one embodiment the antibody provided by the present invention is an antagonistic antibody having specificity for human TGF-beta in which the heavy chain constant region comprises a modified hinge region. Accordingly, the present invention provides an antibody in which the heavy chain comprises or consists of the sequence given in SEQ ID NO:59, SEQ ID NO:73, SEQ ID NO:87 or SEQ ID NO:101.

The present invention also provides an antibody in which the light chain comprises or consists of the sequence given in SEQ ID NO:45.

An antibody provided by the present invention has a heavy chain comprising the sequence given in SEQ ID NO:59, SEQ ID NO:73, SEQ ID NO:87 or SEQ ID NO:101 and a light chain comprising the sequence given in SEQ ID NO: 45.

Also provided is an anti-TGF-beta antibody or binding fragment thereof, in which the heavy and light chains are at least 80% (preferably 85%, 90%, 95%, 96%, 97%, 98%, 99% or more) identical or similar to a heavy chain comprising the sequence given in SEQ ID NO:59, SEQ ID NO:73, SEQ ID NO:87 or SEQ ID NO:101 and a light chain comprising the sequence given in SEQ ID NO: 45. In one embodiment, the light chain has or consists of the sequence given in SEQ ID NO: 45 and the heavy chain has or consists of the sequence given in SEQ ID NO:59, SEQ ID NO:73, SEQ ID NO:87 or SEQ ID NO:101. In another embodiment, the light chain has or consists of the sequence of SEQ ID NO: 45 and the heavy chain has or consists of the sequence of SEQ ID NO: 59.

Also provided by the present invention is a specific region or epitope of human TGF-beta 1, 2 or 3 which is bound by an antibody provided by the present invention, in particular an antibody 4856 comprising the heavy chain sequence gH13 (SEQ ID NO: 59) and/or the light chain sequence gL3 (SEQ ID NO:45).

This specific region or epitope of the human TGF-beta 1, 2, or 3 polypeptide can be identified by any suitable epitope mapping method known in the art in combination with any one of the antibodies provided by the present invention. Examples of such methods include screening peptides of varying lengths derived from TGF-beta for binding to the antibody of the present invention with the smallest fragment that can specifically bind to the antibody containing the sequence of the epitope recognised by the antibody (for example a peptide in the region of about 5 to 20, preferably about 7 amino acids in length). The TGF-beta peptides may be produced synthetically or by proteolytic digestion of the TGF-beta polypeptide. Peptides that bind the antibody can be identified by, for example, mass spectrometric analysis. In another example, NMR spectroscopy or X-ray crystallography can be used to identify the epitope bound by an antibody of the present invention. Once identified, the epitopic fragment which binds an antibody of the present invention can be used, if required, as an immunogen to obtain additional antibodies which bind the same epitope.

Antibodies which cross-block the binding of an antibody according to the present invention in particular, an antibody comprising the heavy chain sequence (SEQ ID NO:59) and the light chain sequence (SEQ ID NO:45) may be similarly useful in antagonising TGF-beta 1, 2 and 3 activity. Accordingly, the present invention also provides an antagonistic antibody having specificity for human TGF-beta 1, 2 and 3, which cross-blocks the binding of any one of the antibodies described above to human TGF-beta 1, 2 and/or 3 and/or is cross-blocked from binding TGF-beta 1, 2 and/or 3 by any one of those antibodies. In one embodiment, such an antibody binds to the same epitope as an antibody described herein above. In another embodiment the cross-blocking neutralising antibody binds to an epitope which borders and/or overlaps with the epitope bound by an antibody described herein above. In another embodiment the cross-blocking neutralising antibody of this aspect of the invention does not bind to the same epitope as an antibody of the present invention or an epitope that borders and/or overlaps with said epitope.

Cross-blocking antibodies can be identified using any suitable method in the art, for example by using competition ELISA or BIAcore assays where binding of the cross blocking antibody to human TGF-beta 1, 2 and/or 3 prevents the binding of an antibody of the present invention or vice versa.

In one embodiment there is provided an antagonistic antibody having specificity for human TGF-beta 1, 2 and 3, which cross-blocks the binding of an antibody whose heavy chain comprises the sequence shown in SEQ ID NO: 59 and whose light chain comprises the sequence shown in SEQ ID NO: 45 to human TGF-beta 1, 2 and 3. In one embodiment the cross-blocking antibodies provided by the present invention inhibit the binding of an antibody comprising the heavy chain sequence shown in SEQ ID NO:59 and the light chain sequence shown in SEQ ID NO:45 by greater than 80%, for example by greater than 85%, such as by greater than 90%, in particular by greater than 95%, 96%, 97%, 98%, 99% or more.

Alternatively or in addition, antagonistic antibodies according to this aspect of the invention may be cross-blocked from binding to human TGF-beta 1, 2 and 3 by an antibody comprising the heavy chain sequence shown in SEQ ID NO:59 and the light chain sequence shown in SEQ ID NO: 45. Also provided therefore is an antagonistic antibody molecule having specificity for human TGF-beta 1, 2 and 3 which is cross-blocked from binding human TGF-beta 1, 2 and 3 by an antibody comprising the heavy chain sequence shown in SEQ ID NO: 59 and the light chain sequence shown in SEQ ID NO: 45. In one embodiment the antagonistic antibodies provided by this aspect of the invention are inhibited from binding human TGF-beta 1, 2 and 3 by an antibody comprising the heavy chain sequence shown in SEQ ID NO: 59 and the light chain sequence shown in SEQ ID NO: 45 by greater than 80%, for example by greater than 85%, such as by greater than 90%, in particular by greater than 95%, 96%, 97%, 98%, 99% or more.

In one embodiment the cross-blocking antibodies provided by the present invention are fully human. In one embodiment the cross-blocking antibodies provided by the present invention are humanised. In one embodiment the antibodies of the present invention are suitable for inhaled delivery, for example, by nebulisation. In one example the physical properties of the antibodies of the present invention e.g. binding affinity and potency are not substantially altered by nebulisation. In one example the antibodies of the present invention are highly stable. One measure of antibody stability is melting temperature (Tm). Melting temperature may be determined by any suitable method known in the art, for example using Thermofluor (Ericsson et al, Analytical Biochemistry 357 (2006) 289-298) or DSC (differential scanning calorimetry). Preferably the antibodies provided by the present invention have a high melting temperature (Tm), typically of at least 75° C. In one example the antibody of the present invention has a Tm of at least 75° C. In one example the antibody of the present invention has a Tm of at least 77° C. In one example the antibody of the present invention has a Tm of at least 79° C.

Biological molecules, such as antibodies or fragments, contain acidic and/or basic functional groups, thereby giving the molecule a net positive or negative charge. The amount of overall "observed" charge will depend on the absolute amino acid sequence of the entity, the local environment of the charged groups in the 3D structure and the environmental conditions of the molecule. The isoelectric point (pI) is the pH at which a particular molecule or solvent accessible surface thereof carries no net electrical charge. In one example, the TGF-beta antibody and fragments of the invention may be engineered to have an appropriate isoelectric point. This may lead to antibodies and/or fragments with more robust properties, in particular suitable solubility and/or stability profiles and/or improved purification characteristics.

Thus in one aspect the invention provides a humanised TGF-beta antibody engineered to have an isoelectric point different to that of the originally identified antibody. The antibody may, for example be engineered by replacing an amino acid residue such as replacing an acidic amino acid residue with one or more basic amino acid residues. Alternatively, basic amino acid residues may be introduced or acidic amino acid residues can be removed. Alternatively, if the molecule has an unacceptably high pI value acidic residues may be introduced to lower the pI, as required. It is important that when manipulating the pI care must be taken to retain the desirable activity of the antibody or fragment. Thus in one embodiment the engineered antibody or fragment has the same or substantially the same activity as the "unmodified" antibody or fragment.

Programs such as ** ExPASY www.expasy.ch/tools/pi_tool.html (accessed 21 Dec. 2015) may be used to predict the isoelectric point of the antibody or fragment.

In one embodiment the cross-blocking antibody has an isoelectric point of at least 7, for example at least 8, such as 8.5, 8.6, 8.7, 8.8 or 8.9 or at least 9, such as 9.0, 9.1, 9.2, 9.3 or 9.4.

It will be appreciated that the affinity of antibodies provided by the present invention may be altered using any suitable method known in the art. The present invention therefore also relates to variants of the antibody molecules of the present invention, which have an improved affinity for TGF-beta. Such variants can be obtained by a number of affinity maturation protocols including mutating the CDRs (Yang et al., 1995, J. Mol. Biol., 254:392-403), chain shuffling (Marks et al., 1992, Bio/Technology, 10:779-783), use of mutator strains of *E. coli* (Low et al., 1996, J. Mol. Biol., 250:359-368), DNA shuffling (Patten et al., 1997, Curr. Opin. Biotechnol., 8:724-733), phage display (Thompson et al., J. Mol. Biol., 256, 77-88, 1996) and sexual PCR (Crameri et al., 1998, Nature, 391:288-291). Vaughan et al. (supra) discusses these methods of affinity maturation.

If desired an antibody for use in the present invention may be conjugated to one or more effector molecule(s). It will be appreciated that the effector molecule may comprise a single effector molecule or two or more such molecules so linked as to form a single moiety that can be attached to the antibodies of the present invention. Where it is desired to obtain an antibody fragment linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO93/06231, WO92/22583, WO89/00195, WO89/01476 and WO03/031581. Alternatively, where the effector molecule is a protein or polypeptide the linkage may be achieved using recombinant DNA procedures, for example as described in WO86/01533 and EP0392745.

The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups, such as fluorescent compounds or compounds which may be detected by NMR or ESR spectroscopy.

Examples of effector molecules may include cytotoxins or cytotoxic agents including any agent that is detrimental to (e.g. kills) cells. Examples, include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as $^{111}$In and $^{90}$Y, Lu$^{177}$, Bismuth$^{213}$, Californium$^{252}$, Iridium$^{192}$ and Tungsten$^{188}$/Rhenium$^{188}$; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, pseudomonas exotoxin, or diphtheria toxin, a protein such as insulin, tumour necrosis factor, α-interferon, beta-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), nerve growth factor (NGF) or other growth factor and immunoglobulins.

Other effector molecules may include detectable substances useful, for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO05/117984.

In one embodiment a half-life provided by an effector molecule which is independent of TGF-beta is advantageous.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly (ethyleneglycol), such as methoxypoly(ethyleneglycol) or derivatives thereof.

Specific naturally occurring polymers include lactose, amylose, dextran, glycogen or derivatives thereof.

In one embodiment the polymer is albumin or a fragment thereof, such as human serum albumin or a fragment thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, for example from 5000 to 40000 Da, such as from 20000 to 40000 Da. The polymer size may in particular be selected on the basis of the intended use of the product, for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumour, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Suitable polymers include a polyalkylene polymer, such as a poly(ethyleneglycol) or, especially, a methoxypoly (ethyleneglycol) or a derivative thereof, and especially with a molecular weight in the range from about 15000 Da to about 40000 Da.

In one example antibodies for use in the present invention are attached to poly(ethyleneglycol) (PEG) moieties. In one particular example the antibody is an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. Nos. 5,219,996; 5,667,425; WO98/25971, WO2008/038024). In one example the antibody molecule of the present invention is a modified Fab fragment wherein the modification is the addition to the C-terminal end of its heavy chain one or more amino acids to allow the attachment of an effector molecule. Suitably, the additional amino acids form a modified hinge region containing one or more cysteine residues to which the effector molecule may be attached. Multiple sites can be used to attach two or more PEG molecules.

Suitably PEG molecules are covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

In one embodiment, the antibody is a modified Fab fragment, Fab' fragment or diFab which is PEGylated, i.e. has PEG (poly(ethyleneglycol)) covalently attached thereto, e.g. according to the method disclosed in EP 0948544 or EP1090037 [see also "Poly(ethyleneglycol) Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545].

In one example PEG is attached to a cysteine in the hinge region. In one example, a PEG modified Fab fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20,000 Da. The total molecular weight of the PEG attached to the Fab fragment may therefore be approximately 40,000 Da.

Particular PEG molecules include 2-[3-(N-maleimido) propionamido]ethyl amide of N,N'-bis(methoxypoly(ethylene glycol) MW 20,000) modified lysine, also known as PEG2MAL40K (obtainable from Nektar, formerly Shearwater).

Alternative sources of PEG linkers include NOF who supply GL2-400MA3 (wherein m in the structure below is 5) and GL2-400MA (where m is 2) and n is approximately 450:

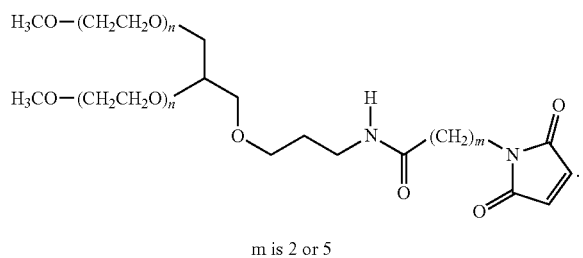

m is 2 or 5

That is to say each PEG is about 20,000 Da.

Thus in one embodiment the PEG is 2,3-Bis(methylpolyoxyethylene-oxy)-1-{[3-(6-maleimido-1-oxohexyl) amino]propyloxy} hexane (the 2 arm branched PEG, —CH$_2$)$_3$NHCO(CH$_2$)$_5$-MAL, Mw 40,000 known as SUNBRIGHT GL2-400MA3.

Further alternative PEG effector molecules of the following type:

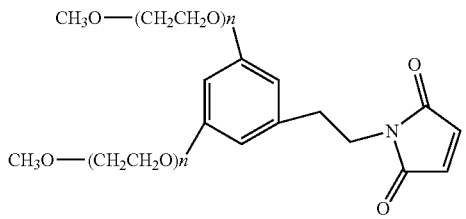

In one embodiment there is provided an antibody, such as a full length antibody, which is PEGylated (for example with a PEG described herein), attached through a cysteine amino acid residue at or about amino acid 226 in the chain, for example amino acid 226 of the heavy chain (by sequential numbering). In one embodiment, PEG is attached to Cys 226 of SEQ ID NO:101.

In one embodiment the present disclosure provides a Fab-PEG molecule comprising one or more PEG polymers, for example 1 or 2 polymers such as a 40 kDa polymer or polymers.

Fab-PEG molecules according to the present disclosure may be particularly advantageous in that they have a half-life independent of the Fc fragment.

In one embodiment there is provided a scFv conjugated to a polymer, such as a PEG molecule, a starch molecule or an albumin molecule.

In one embodiment the antibody or fragment is conjugated to a starch molecule, for example to increase the half-life. Methods of conjugating start to a protein as described in U.S. Pat. No. 8,017,739 incorporated herein by reference.

A reporter molecule as employed herein is a molecule which is capable of being detected, for example a fluorescent dye, radiolabel or other detectable entity.

The present invention also provides an isolated DNA sequence encoding the heavy and/or light chain(s) of an antibody molecule of the present invention. Suitably, the DNA sequence encodes the heavy or the light chain of an antibody molecule of the present invention. The DNA sequence of the present invention may comprise synthetic DNA, for instance produced by chemical processing, cDNA, genomic DNA or any combination thereof.

DNA sequences which encode an antibody molecule of the present invention can be obtained by methods well known to those skilled in the art. For example, DNA sequences coding for part or all of the antibody heavy and light chains may be synthesised as desired from the determined DNA sequences or on the basis of the corresponding amino acid sequences.

DNA coding for acceptor framework sequences is widely available to those skilled in the art and can be readily synthesised on the basis of their known amino acid sequences.

Standard techniques of molecular biology may be used to prepare DNA sequences coding for the antibody molecule of the present invention. Desired DNA sequences may be synthesised completely or in part using oligonucleotide synthesis techniques. Site-directed mutagenesis and polymerase chain reaction (PCR) techniques may be used as appropriate.

Examples of suitable DNA sequences are provided in FIG. 1.

The present invention also relates to a cloning or expression vector comprising one or more DNA sequences of the present invention. Accordingly, provided is a cloning or expression vector comprising one or more DNA sequences encoding an antibody of the present invention. In one embodiment the vector comprises a light chain DNA sequences given in SEQ ID NO:46 or SEQ ID NO:47 and/or a heavy chain DNA sequence given in SEQ ID NO:60, SEQ ID NO:61, SEQ ID NO:74, SEQ ID NO:75, SEQ ID NO:88, SEQ ID NO:89, SEQ ID NO:102 or SEQ ID NO:103. Suitably, the cloning or expression vector comprises two DNA sequences, encoding the light chain and the heavy chain of the antibody molecule of the present invention, preferably SEQ ID NO: 47 and SEQ ID NO: 61, respectively and suitable signal sequences. In one example the vector comprises an intergenic sequence between the heavy and the light chains (see WO03/048208).

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

Also provided is a host cell comprising one or more cloning or expression vectors comprising one or more DNA sequences encoding an antibody of the present invention. Any suitable host cell/vector system may be used for expression of the DNA sequences encoding the antibody molecule of the present invention. Bacterial, for example E. coli, and other microbial systems may be used or eukaryotic, for example mammalian, host cell expression systems may also be used. Suitable mammalian host cells include HEK, CHO, myeloma or hybridoma cells.

The present invention also provides a process for the production of an antibody molecule according to the present invention comprising culturing a host cell containing a vector of the present invention under conditions suitable for leading to expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

The antibodies and fragments according to the present disclosure are expressed at good levels from host cells. Thus the properties of the antibodies and/or binding fragments are suitable for expression on a commercial scale.

Thus there is a provided a process for culturing a host cell and expressing an antibody or fragment thereof, isolating the latter and optionally purifying the same to provide an isolated antibody or fragment. In one embodiment the process further comprises the step of conjugating an effector molecule to the isolated antibody or fragment, for example conjugating to a PEG polymer in particular as described herein.

In one embodiment there is provided a process for purifying an antibody (in particular an antibody or fragment according to the invention) comprising performing anion exchange chromatography in non-binding mode such that the impurities are retained on the column and the antibody is eluted.

In one embodiment the purification employs affinity capture on a TGF-beta column.

In one embodiment the purification employs cibacron blue or similar for purification of albumin fusion or conjugate molecules.

Suitable ion exchange resins for use in the process include Q.FF resin (supplied by GE-Healthcare). The step may, for example be performed at a pH about 8.

The process may further comprise an initial capture step employing cation exchange chromatography, performed for example at a pH of about 4 to 5, such as 4.5. The cation exchange chromatography may, for example employ a resin such as CaptoS resin or SP sepharose FF (supplied by GE-Healthcare). The antibody or fragment can then be eluted from the resin employing an ionic salt solution such as sodium chloride, for example at a concentration of 200 mM.

Thus the chromatography step or steps may include one or more washing steps, as appropriate.

The purification process may also comprise one or more filtration steps, such as a diafiltration step.

Thus in one embodiment there is provided a purified anti-TGF-beta antibody or fragment, for example a humanised antibody or fragment, in particular an antibody or fragment according to the invention, in substantially purified from, in particular free or substantially free of endotoxin and/or host cell protein or DNA.

Purified form as used supra is intended to refer to at least 90% purity, such as 91, 92, 93, 94, 95, 96, 97, 98, 99% w/w or more pure.

Substantially free of endotoxin is generally intended to refer to an endotoxin content of 1 EU per mg antibody product or less such as 0.5 or 0.1 EU per mg product.

Substantially free of host cell protein or DNA is generally intended to refer to host cell protein and/or DNA content 400 pg per mg of antibody product or less such as 100 pg per mg or less, in particular 20 pg per mg, as appropriate.

The present invention also provides an antagonistic antibody which binds human TGF-beta 1, human TGF-beta 2 and human TGF-beta 3 (or pharmaceutical compositions comprising same) according to the disclosure for use as a medicament. The present invention also provides an antagonistic antibody which binds human TGF-beta 1, human TGF-beta 2 and human TGF-beta 3 (or pharmaceutical compositions comprising same) according to the disclosure for use in the treatment or prophylaxis of a pathological disorder that is mediated by TGF-beta 1, 2 and/or 3 or that is associated with an increased level of TGF-beta 1, 2 and/or 3.

The present invention also provides the use of an antagonistic antibody which binds human TGF-beta 1, human TGF-beta 2 and human TGF-beta 3 according to the disclosure in the manufacture of a medicament for the treatment or prophylaxis of a pathological disorder that is mediated by TGF-beta 1, 2 and/or 3 or that is associated with an increased level of TGF-beta 1, 2 and/or 3.

The present invention also provides method for the treatment of a human subject suffering from or at risk of a pathological disorder that is mediated by TGF-beta 1, 2 and/or 3 or that is associated with an increased level of TGF-beta 1, 2 or 3, the method comprising administering to the subject an effective amount of an antibody according to the disclosure. In the present application, the pathological disorder that is mediated by TGF-beta 1, 2 and/or 3 or that is associated with an increased level of TGF-beta 1, 2 and/or 3 may be any suitable disorder. In one embodiment the pathological disorder is selected from the group consisting of: pulmonary fibrosis such as idiopathic pulmonary fibrosis, pulmonary hypertension such as pulmonary arterial hypertension.

The antibody according to the disclosure may be used in the treatment of pulmonary diseases including pulmonary arterial hypertension.

The antibody according to the disclosure may be used in the treatment patients suffering from idiopathic pulmonary fibrosis and pulmonary arterial hypertension.

The present invention also provides an antagonistic antibody Fab or Fab' fragment which binds human TGF-beta 1, human TGF-beta 2 and human TGF-beta 3 for use in the treatment or prophylaxis by inhaled administration of a pathological disorder that is mediated by TGF-beta 1, 2 or 3 and/or that is associated with an increased level of TGF-beta 1, 2 and/or 3.

The present invention also provides an antagonistic antibody Fab or Fab' fragment which binds human TGF-beta 1, human TGF-beta 2 and human TGF-beta 3 in the manufacture of a medicament for the treatment or prophylaxis by inhaled administration of a pathological disorder that is mediated by TGF-beta 1, 2 and/or 3 or that is associated with an increased level of TGF-beta 1, 2 and/or 3.

The present invention also provides a method for the treatment of a human subject suffering from or at risk of a pathological disorder that is mediated by TGF-beta 1, 2 and/or 3 or that is associated with an increased level of TGF-beta 1, 2 and/or 3, the method comprising administering to the subject an effective amount of an antagonistic antibody Fab or Fab' fragment which binds human TGF-beta 1, human TGF-beta 2 and human TGF-beta 3 by inhaled administration.

The pathological disorder suitable for treatment by inhaled administration may be any pulmonary disease that is mediated by TGF-beta 1, 2 and/or 3 or that is associated with an increased level of TGF-beta 1, 2 and/or 3 for example diseases selected from the group consisting of: pulmonary fibrosis such as idiopathic pulmonary fibrosis (IPF), for example mild, moderate and/or severe IPF, and cystic fibrosis and pulmonary hypertension such as pulmonary arterial hypertension (PAH). In another embodiment the antibody may be used to treat mild IPF, such as mild IPF associated with pulmonary hypertension, particularly PAH or disproportionate pulmonary hypertension. In one embodiment, the antibody may be used to treat a patient suffering IPF and pulmonary hypertension, such as IPF and PAH. In another embodiment, the antibody may be used to treated systemic sclerosis. In a further embodiment, the antibody may be used to treat systemic sclerosis associated with at least one of the following: pulmonary fibrosis (SSc-ILD); pulmonary hypertension, for example connective tissue disease-associated pulmonary hypertension; or both IPF and pulmonary hypertension.

The use of an inhaled antibody that binds to human TGF-beta 1, human TGF-beta 2 and human TGF-beta 3 may reduce the risk of side-effects by local administration to the lungs compared to systemic administration of the antibody.

The antibodies and fragments according to the present disclosure may be employed in treatment or prophylaxis.

The antibody molecule of the present invention may also be used in diagnosis, for example in the in vivo diagnosis and imaging of disease states involving TGF-beta.

As the antibodies of the present invention are useful in the treatment and/or prophylaxis of a pathological condition, the present invention also provides a pharmaceutical or diagnostic composition comprising an antibody molecule of the present invention in combination with one or more of a pharmaceutically acceptable excipient, diluent or carrier. Accordingly, provided is the use of an antibody of the invention for the manufacture of a medicament. The composition will usually be supplied as part of a sterile, pharmaceutical composition that will normally include a pharmaceutically acceptable carrier. A pharmaceutical composition of the present invention may additionally comprise a pharmaceutically-acceptable adjuvant.

The present invention also provides a process for preparation of a pharmaceutical or diagnostic composition comprising adding and mixing the antibody molecule of the present invention together with one or more of a pharmaceutically acceptable excipient, diluent or carrier.

The antibody molecule may be the sole active ingredient in the pharmaceutical or diagnostic composition. Alternatively, the antibody may be administered in combination, e.g. simultaneously, sequentially or separately, with one or more other therapeutically active ingredients. According the antibody molecule in the pharmaceutical or diagnostic composition may be accompanied by other active ingredients including other antibody ingredients, for example epidermal growth factor receptor family (EGFR, HER-2), vascular endothelial growth factor receptors (VEGFR), platelet derived growth factor receptor (PDGFR) antibodies, or non-antibody ingredients such as imatinib, dasatinib, nioltinib, basutinib, gefitinib, erlotinib, temsirolimus, vandetanib, vemurafenib, crizotinib, vorinostat, romidepsin, bortezomib, sorafenib, sunitinib, pazopanib, regorafenib, cabozantinib, perfenidone, nintedanib, steroids or other drug molecules, in particular drug molecules whose half-life is independent of TGF-beta binding. In a particular embodiment, the antibody is administered with nintedanib, for example for the treatment of IPF.

Active ingredient as employed herein refers to an ingredient with a pharmacological effect, such as a therapeutic effect, at a relevant dose.

The pharmaceutical compositions suitably comprise a therapeutically effective amount of the antibody of the invention. The term "therapeutically effective amount" as used herein refers to an amount of a therapeutic agent needed to treat, ameliorate or prevent a targeted disease or condition, or to exhibit a detectable therapeutic, pharmacological or preventative effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount will be from 0.01 mg/kg to 500 mg/kg, for example 0.1 mg/kg to 200 mg/kg, such as 100 mg/kg. In particular, the therapeutically effective amount will be between 0.001 to 100 mg/kg.

Pharmaceutical compositions may be conveniently presented in unit dose forms containing a predetermined amount of an active agent of the invention per dose.

Therapeutic doses of the antibodies according the present disclosure show no apparent or limited toxicology effects in vivo.

Compositions may be administered individually to a patient or may be administered in combination (e.g. simultaneously, sequentially or separately) with other agents, drugs or hormones.

The antibodies to be used to treat various inflammatory diseases can be used alone or combined with various other anti-inflammatory agents.

The antibodies to be used to treat various fibrotic diseases can be used alone or combined with various other anti-fibrotic agents. Example of such agents are Pirfenidone and/or Nintedanib.

The dose at which the antibody molecule of the present invention is administered depends on the nature of the condition to be treated, the severity of the condition present and on whether the antibody molecule is being used prophylactically or to treat an existing condition.

The frequency of dose will depend on the half-life of the antibody molecule and the duration of its effect. If the antibody molecule has a short half-life (e.g. 2 to 10 hours) it may be necessary to give one or more doses per day. Alternatively, if the antibody molecule has a long half-life (e.g. 2 to 15 days) and/or long lasting pharmacodynamics (PD) profile it may only be necessary to give a dosage once per day, once per week or even once every 1 or 2 months.

Half-life as employed herein is intended to refer the duration of the molecule in circulation, for example in serum/plasma.

Pharmacodynamics as employed herein refers to the profile and in particular duration of the biological action of the molecule according the present disclosure.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Suitable forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject. The subjects to be treated can be animals. However, in one or more embodiments the compositions are adapted for administration to human subjects.

Suitably in formulations according to the present disclosure, the pH of the final formulation is not similar to the value of the isoelectric point of the antibody or fragment, for example if the pH of the formulation is 7 then a pI of from 8-9 or above may be appropriate. Whilst not wishing to be bound by theory it is thought that this may ultimately provide a final formulation with improved stability, for example the antibody or fragment remains in solution.

In one example the pharmaceutical formulation at a pH in the range of 4.0 to 7.0 comprises: 1 to 200 mg/mL of an antibody according to the present disclosure, 1 to 100 mM of a buffer, 0.001 to 1% of a surfactant, a) 10 to 500 mM of a stabiliser, b) 10 to 500 mM of a stabiliser and 5 to 500 mM of a tonicity agent, or c) 5 to 500 mM of a tonicity agent.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared. Preferably the antibody molecules of the present invention are administered subcutaneously, by inhalation or topically. For example, the antibody may be administered intranasally or orally, such as by inhalation.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

In one embodiment the formulation is provided as a formulation for topical administrations including inhalation.

Suitable inhalable preparations include inhalable powders, metering aerosols containing propellant gases or inhalable solutions free from propellant gases (such as nebulisable solutions or suspensions). Inhalable powders according to the disclosure containing the active substance may consist solely of the abovementioned active substances or of a mixture of the abovementioned active substances with physiologically acceptable excipient.

These inhalable powders may include monosaccharides (e.g. glucose or arabinose), disaccharides (e.g. lactose, saccharose, maltose), oligo- and polysaccharides (e.g. dextranes), polyalcohols (e.g. sorbitol, mannitol, xylitol), salts (e.g. sodium chloride, calcium carbonate) or mixtures of these with one another. Mono- or disaccharides are suitably used, the use of lactose or glucose, particularly but not exclusively in the form of their hydrates.

Particles for deposition in the lung require a particle size less than 10 microns, such as 1-9 microns for example from 0.1 to 5 μm, in particular from 1 to 5 μm. The particle size of the active ingredient (such as the antibody or fragment) is of primary importance as it is thought to correlate with deposition of in areas of the lung suitable for treatment with the antibody or binding fragment of the invention. For example, particles that are 10 μm or less, such as 0.1 to 5 m, in particular from 1 to 5 m, are more likely to deposit in the alveolar structures of the lung.

The propellent gases which can be used to prepare the inhalable aerosols are known in the art. Suitable propellent gases are selected from among hydrocarbons such as n-propane, n-butane or isobutane and halohydrocarbons such as chlorinated and/or fluorinated derivatives of methane, ethane, propane, butane, cyclopropane or cyclobutane. The abovementioned propellent gases may be used on their own or in mixtures thereof.

Particularly suitable propellent gases are halogenated alkane derivatives selected from among TG 11, TG 12, TG 134a and TG227. Of the abovementioned halogenated hydrocarbons, TG134a (1,1,1,2-tetrafluoroethane) and TG227 (1,1,1,2,3,3,3-heptafluoropropane) and mixtures thereof are particularly suitable.

The propellent-gas-containing inhalable aerosols may also contain other ingredients such as cosolvents, stabilisers, surface-active agents (surfactants), antioxidants, lubricants and means for adjusting the pH. All these ingredients are known in the art.

The propellant-gas-containing inhalable aerosols according to the invention may contain up to 5% by weight of active substance. Aerosols according to the invention contain, for example, 0.002 to 5% by weight, 0.01 to 3% by weight, 0.015 to 2% by weight, 0.1 to 2% by weight, 0.5 to 2% by weight or 0.5 to 1% by weight of active ingredient.

Alternatively topical administrations to the lung may also be by administration of a liquid solution or suspension formulation, for example employing a device such as a nebuliser, for example, a nebuliser connected to a compressor.

In one embodiment the formulation is provided as discrete ampoules containing a unit dose for delivery by nebulisation.

In one embodiment the antibody is supplied in lyophilised form, for reconstitutions or alternatively as a suspension formulation.

The antibody of the invention can be delivered dispersed in a solvent, e.g., in the form of a solution or a suspension. It can be suspended in an appropriate physiological solution, e.g., saline or other pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 ml of water so as to achieve a pH of about 4.0 to 5.0. A suspension can employ, for example, lyophilised antibody.

The therapeutic suspensions or solution formulations can also contain one or more excipients. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent/solution used for the formulation, aseptic suspension of the antibody in the sterile buffered solvent solution, and dispensing of the formulation into sterile receptacles by methods familiar to those of ordinary skill in the art.

Nebulisable formulation according to the present disclosure may be provided, for example, as single dose units (e.g., sealed plastic containers or vials) packed in foil envelopes. Each vial contains a unit dose in a volume, e.g., 2 mL, of solvent/solution buffer.

The antibodies disclosed herein are thought to be suitable for delivery via nebulisation.

It is also envisaged that the antibody of the present invention may be administered by use of gene therapy. In order to achieve this, DNA sequences encoding the heavy and light chains of the antibody molecule under the control of appropriate DNA components are introduced into a patient such that the antibody chains are expressed from the DNA sequences and assembled in situ.

In one embodiment the present disclosure comprises use of antibodies or fragments thereof as a reagent or diagnosis, for example conjugated to a reporter molecule. Thus there is provided antibody or fragment according to the disclosure which is labelled. In one aspect there is provided a column comprising an antibody or fragment according to the disclosure.

Thus there is provided an anti-TGF-beta antibody or fragment for use as a reagent for such uses as:
1) purification of TGF-beta protein (or binding fragment thereof)—being conjugated to a matrix and used as an affinity column, or (as a modified form of anti-TGF-beta) as a precipitating agent (e.g. as a form modified with a domain recognised by another molecule, which may be modified), which is optionally precipitated by an anti-Fc reagent)
2) detection and/or quantification of TGF-beta on cells or in cells, live or fixed (cells in vitro or in tissue or cell sections). Uses for this may include quantification of TGF-beta as a biomarker, to follow the effect of anti-TGF-beta treatment. For these purposes, the candidate might be used in a modified form (e.g. by addition another moiety, as a genetic fusion protein or chemical conjugate, such as addition of a reporter molecule, for example a fluorescent tag used for the purposes of detection).
3) purification or sorting of TGF-beta-bearing cells labeled by binding to candidate modified by ways exemplified in (1) and (2).

Comprising in the context of the present specification is intended to mean 'including'.

Where technically appropriate, embodiments of the invention may be combined.

Embodiments are described herein as comprising certain features/elements. The disclosure also extends to separate embodiments consisting or consisting essentially of said features/elements.

Technical references such as patents and applications are incorporated herein by reference.

Any embodiments specifically and explicitly recited herein may form the basis of a disclaimer either alone or in combination with one or more further embodiments.

The present invention is further described by way of illustration only in the following examples:

EXAMPLES

In the following Examples, the use of the terms TGF-beta 1, TGF-beta 2 and TGF-beta 3 refer to the mature sequences of TGF-beta 1, TGF-beta 2 and TGF-beta 3 as shown in FIGS. 3b, 3d and 3f respectively.

Example 1—Immunization and Primary and Secondary Screening of B Cell Culture Supernatants 4 female Half-Lop rabbits (>2 kg) were immunised subcutaneously with 250 ug human TGF-beta1 (FIG. 3b) protein mixed with 250 ug human TGF-beta2 protein (FIG. 3d) to give a total dose of 500 ug per rabbit emulsified in an equal volume of complete Freund's adjuvant (CFA) by vigorously mixing with a syringe. Rabbits were given booster injections at 21 day intervals using incomplete Freund's adjuvant (IFA) with bleeds taken, from the ear, 14 days post immunisation. 3 doses were administered of the isoform1/2 mix before a final dose of human TGF-beta2 protein only (500 ug). Termination occurred 14 days after the final boost with single cell suspensions of spleen, bone marrow and peripheral blood mononuclear cells prepared and frozen in 10% DMSO/FCS at −80° C.

Immune responses generated were determined by ELISA. Nunc-Immuno™ 1 Maxisorp™ 96 well microtitre plates were coated with either human TGF-beta1 protein (Peprotech; #100-21C) at 2 µg/ml in PBS, human TGF-beta2 protein (R&D systems; 302-B2-010/CF) or human TGF-beta-3 protein (R&D systems; 243-B3-010/CF) at 0.5 µg/ml in PBS and incubated overnight at 4° C. Plates were washed after each layer (automated, 4×200 ml washes with PBS+ 0.05% Tween). Wells were blocked with 1% (w/v) casein (VWR Chemicals; 440203H) in PBS by incubation at room temperature (RT) for 1 hr. Sera, log dilutions from 1/100 in 1% casein, were added and incubated for 1½ hours at RT. 100 µl of goat anti-rabbit IgG Fc specific horseradish peroxidase antibody (Jackson; 111-036-046) at a 1/3000 dilution in 1% (w/v) casein in PBS was added to each well and incubated for 1 hour at RT. Substrate, 100 µl of TMB (3,3',5,5' Tetramethylbenzidine, soluble), was added and reaction was stopped with 50 µl 2.5% sodium fluoride solution in dH2O. Optical densities (ODs) were determined at 610 nm using an ELISA reader.

B cell cultures were prepared using a method similar to that described by Zubler et al. (1985). Briefly, peripheral blood mononuclear cell (PBMC)-derived B cells from immunized rabbits, were cultured at a density of approximately 5000 cells per well in bar-coded 96-well tissue culture plates with 200 µl/well RPMI 1640 medium (Gibco BRL) supplemented with 10% FCS (Sigma Aldrich), 2% HEPES (Sigma Aldrich), 2% L-Glutamine (Gibco BRL), 1% penicillin/streptomycin solution (Gibco BRL), 0.1% beta-mercaptoethanol (Gibco BRL), 0.2% Normocin (Invivogen), 1% activated human peripheral blood mononuclear cell (PBMC) supernatant and gamma-irradiated mutant EL4 murine thymoma cells ($5 \times 10^4$/well) for seven days at 37° C. in an atmosphere of 5% $CO_2$.

Primary Screen for TGF-Beta1 Binding:

The presence of TGF-beta1 protein-specific antibodies in B cell culture supernatants was determined using a homogeneous fluorescence-based binding assay using Superavidin™ beads (Bangs Laboratories) coated with biotinylated TGF-beta1 (Peprotech). TGF-beta1 protein was biotinylated using a Lightning-Link® Biotinylation kit (Innova Biosciences) according to manufacturer's instructions.

10 ul of B cell culture supernatant was transferred from barcoded 96-well tissue culture plates into barcoded 384-well black-walled assay plates containing TGF-beta1 immobilised on beads (10 ul/well) using a Bravo automated liquid handler (Agilent). Binding was revealed with a goat anti-rabbit IgG Fcγ-specific FITC conjugate (Jackson ImmunoResearch). Plates were read on a TTP Labtech Mirrorball® detection system.

Following primary screening, positive supernatants for TGF-beta1 binding were consolidated onto 96-well barcoded master plates using a Beckman hit-picking robot and B cells in cell culture plates frozen at −80° C.

Secondary Screen for Binding to TGF-Beta 1, 2 and 3:

To determine the ability of the antibodies to bind different isoforms of TGF-beta, B-cell supernatant in these master plates was screened in an ELISA assay on the 3 different isoforms of TGF-beta. The ELISA assay involved the coating of different TGF-beta isoforms 1, 2, 3 (Peprotech) onto 384-well Maxisorp™ plates (ThermoScientific/Nunc) at 2 ug/ml in PBS. Plates were blocked with 1% BSA in PBS and then incubated with 10 ul/well of B cell culture supernatant. Secondary HRP-conjugated goat anti-rabbit IgG fc antibody (Jackson ImmunoResearch) was added to plates, followed by visualisation of binding with TMB substrate (3,3',5,5'-

Tetramethylbenzidine, from EMD Millipore; 10 μl/well). The optical density was measured at 630 nM using BioTek Synergy 2 microplate reader.

Results from Primary Screen and Secondary Screen

79 Mice, rats and rabbits were immunized with only human TGF-beta1 (SEQ ID NO:114; FIG. 3b) and screened for TGF-beta 1 binding with varying levels of positive TGF-beta 1 binders. From these 79 different immunized rats, mice and rabbit animals 2656 anti-human TGF-beta 1 binders were identified. However, only 831 of these wells showed binding to all three isoforms in the secondary screen.

As described above, 4 rabbits were immunized with both human TGF-beta 1 and human TGF-beta 2. In total sera from these 4 rabbits were analysed in a primary screen and showed 1367 positive wells for TGF-beta 1 binding and were then screened in the secondary screen for binding to all three TGF-beta isoforms 1, 2 and 3 which resulted in 1026 wells with binding to all three isoforms of TGF-beta.

Following Primary and Secondary screening, B cell wells demonstrating binding to all three isoforms were then assayed for blocking activity.

HEK-Blue TGF-Beta Reporter Gene Assay Using Recombinant TGF-Beta 1

A reporter gene assay was developed using HEK-Blue TGF-beta cells (HEK-Blue TGF-beta cell line; Invivogen). The HEK-Blue TGF-beta cell line responds to the presence of TGF-beta by expression of the SEAP which is detected with a colourimetric detection reagent. Antibodies able to neutralise TGF-beta will cause a reduction in the signal generated in the reporter cell line. The ability of test agents to neutralise TGF-beta 1 was assessed.

Antibodies were titrated 3-fold or added at a single concentration and incubated with human TGF-beta isoform 1, 2 or 3 (50 μg/ml TGF-beta isoform) in test medium (DMEM, 4.5 g/l glucose, 10% (v/v) fetal bovine serum, 50 U/ml penicillin, 50 μg/ml streptomycin, 100 μg/ml Normoci, 2 mM L-glutamine) for 30 minutes prior to the addition of 50,000 HEK-Blue TGF-beta cells, and incubated for 16 hours at 37° C. SEAP produced by the cells in response to activation by TGF-beta was detected by addition of Quanti Blue (Invivogen) reagent for 1 hour at 37° C. and detection by absorbance at 630 nm. The maximum signal was generated from wells containing HEK-Blue TGF-beta cells and TGF-beta and the minimum signal was generated using an excess of TGF-beta-neutralising antibody.

B cell culture supernatant containing BSN.4856 was assayed in the single point TGF-beta1 reporter gene assay (Master plate 3142, from well D012). The antibody exhibited 80% inhibition of TGF-beta1. The percent inhibition from concentration response assays was calculated based on the maximum and minimum signals in the assay plate.

Example 2—Cloning of Variable Region Genes from B Cells and Expression and Characterisation of Recombinant Fab Activity in In Vitro Assays Data from binding ELISAs and the blocking reporter gene assays in Example 1 allowed selection of wells for variable region recovery. To recover antibody variable region genes from wells of interest, a deconvolution step had to be performed to enable identification of the antigen-specific B cells in a given well because a heterogeneous population of B cells is present. This was achieved using the fluorescent foci method (Clargo et al., mAbs Vol. 6, Iss. 1, 2014). Briefly, immunoglobulin-secreting B cells from a positive well were mixed with streptavidin beads (New England Biolabs) coated with biotinylated TGF-beta1 and a 1:1200 final dilution of a goat anti-rabbit Fcγ fragment-specific FITC conjugate (Jackson ImmunoResearch). After static incubation at 37° C. for 1 hour, antigen-specific B cells could be identified due to the presence of a fluorescent halo surrounding that B cell. These individual B cells, identified using an Olympus microscope, were then picked with an Eppendorf micromanipulator and deposited into a PCR tube.

Antibody variable region genes were recovered from single cells by reverse transcription (RT)-PCR using heavy and light chain variable region-specific primers. Two rounds of PCR were performed, with the nested 2° PCR incorporating restriction sites at the 3' and 5' ends allowing cloning of the variable region into a rabbit Fab no hinge (VH) or rabbit kappa (VL) mammalian expression vector. Heavy and light chain constructs were co-transfected into Expi-293 cells using ExpiFectamine™ 293 (Invitrogen) and recombinant antibody expressed in a 48 deep well block in a volume of 1 ml or in a conical flask at 30 mL scale. After 7 days expression, unpurified transient supernatants were harvested and tested again for binding by ELISA and blocking in the reporter gene assay as described in Example 1. Binding to all 3 isoforms was confirmed with the recombinant 4856 rabbit Fab in an ELISA. Sequences are provided in FIG. 1B.

The expressed 4856 rabbit Fab molecule was purified by affinity capture using a small scale vacuum based purification system. Briefly, supernatant from the 30 ml cell culture was 0.22 m sterile filtered before 1 ml of GammaBind Plus™ beads (GE Healthcare) were added. The supernatant/bead mixture was then tumbled for an hour before supernatant was removed by applying vacuum. The beads were washed with PBS before elution with 0.1M glycine pH 2.7. The eluted fractions were neutralized and buffer exchanged into PBS before being 0.22 m sterile filtered. The final analysis consisted of concentration determination by A280; purity by SEC-UPLC (BEH200 column, Waters); and endotoxin by PTS-Endosafe™ cartridge system (Charles River).

Example 3—Characterisation of Recombinant Rabbit Fab Activity in In Vitro Assays HEK-SEAP-SBE reporter gene assay using recombinant TGF-beta 1, 2 and 3: The purified rabbit Fab was then tested (n=2) in the TGF-beta reporter gene assay as described in Example 1, in 10 point dose response against TGF-beta 1, 2 and 3. TGF-beta isoforms 1, 2 and 3 were added at 50 μg/ml and the ability of antibody to neutralise TGF-beta 1, 2 and 3 was assessed.

Figure 4B:
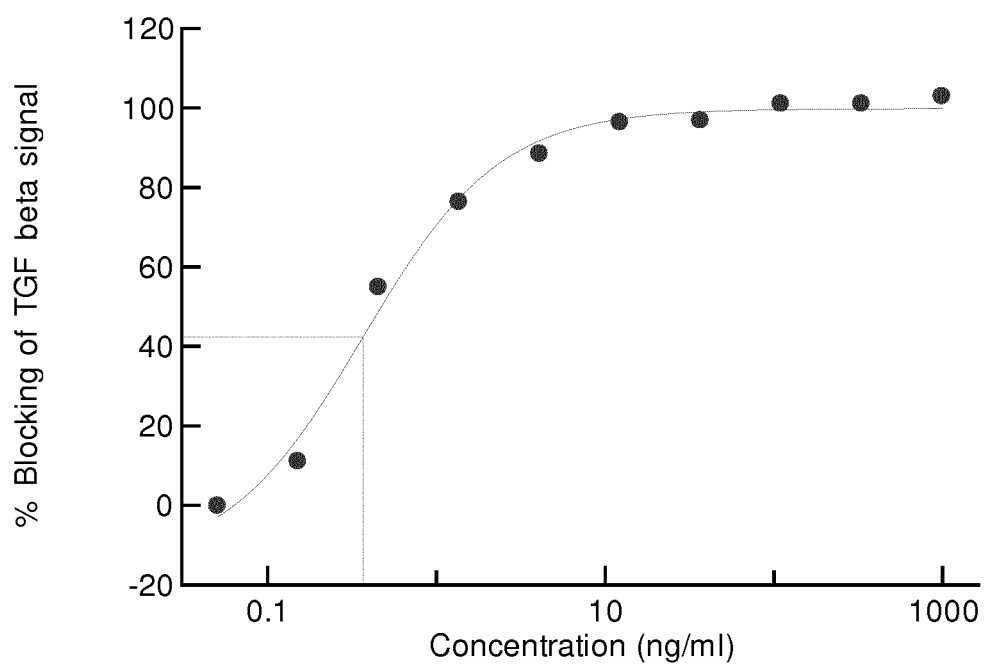
Figure 4C:
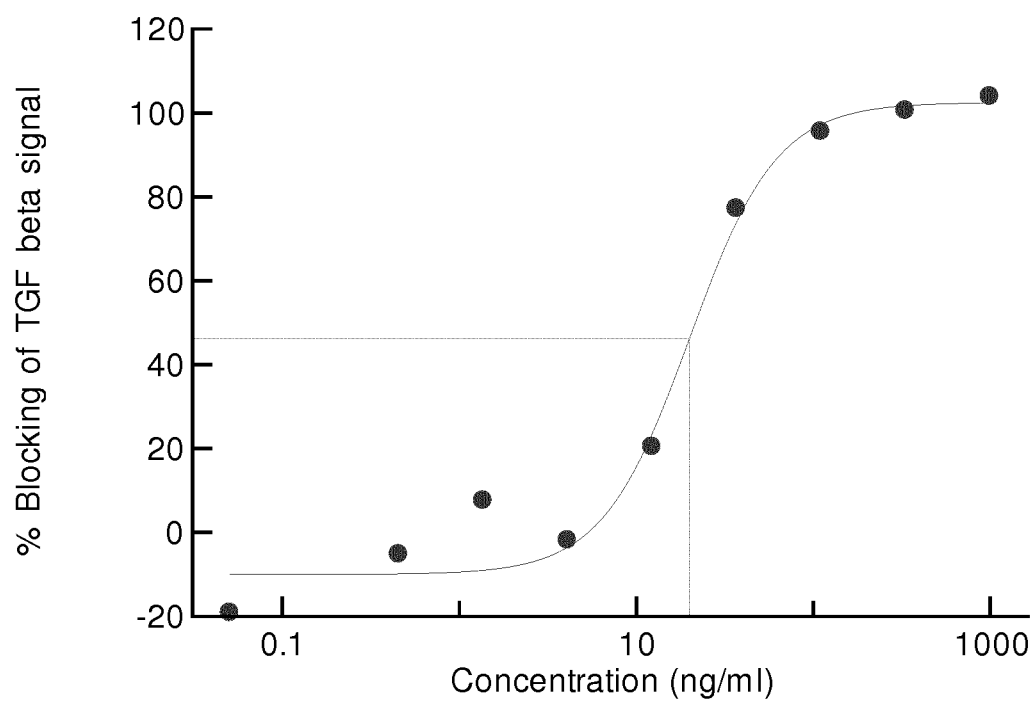

The data was fitted using a 4 parameter logistical fit (FIGS. 4a, 4b and 4c). The IC50 was calculated based on the inflexion point of the curve (Table 1).

TABLE 1

IC50 values of purified 4856 rabbit Fab in the HEK-Blue TGF-beta (Invivogen) reporter gene assay.

| | Geomean IC50 (nM) | | |
|---|---|---|---|
| Identifier | TGF-beta1 | TGF-beta2 | TGF-beta3 |
| BSN.4856.rbFab. (n = 2, of 5 separate samples) | 1.77 (0.04 nM) | 0.30 (0.01 nM) | 24.51 (0.54 nM) |

Purified rabbit Fab 4856 inhibited the TGF-beta1-, TGF-beta2- and TGF-beta3-driven HEK-Blue TGF-beta reporter gene assay with an IC50s of 0.04, 0.01, and 0.54 nM respectively.

Endogenous TGF-Beta BxPC3 and HEK-Blue TGF-Beta Reporter Gene Co-Culture Assay:

A co-culture system was developed consisting of Bx-PC3 cells (ATCC) and the HEK-Blue TGF-beta cell line (Invivogen). The BXPC-3 cells constitutively produce and activate TGF-beta. The HEK-Blue TGF-beta cell line responds to the presence of active TGF-beta by expression of the SEAP which is detected with a colourimetric detection reagent. Antibodies able to neutralise TGF-beta will cause a reduction in the signal generated in the reporter cell line.

HEK-Blue TGF-beta cells were plated out at 100000 cells per well in DMEM with 10% FCS and incubated for 90 minutes at 37° C. Test agents were titrated 3-fold in serum-free DMEM containing 0.2% (w/v) BSA and added to the HEK-Blue TGF-beta cells. BxPC3 cells were added in serum-free DMEM containing 0.2% (w/v) BSA at 50000 cells per well and incubated for 18 hours at 37° C. The maximum signal was generated from wells containing both BX-PC3 and HEK-Blue TGF-beta cells and the minimum signal was generated using an excess of TGF-beta-neutralising antibody. SEAP was detected by addition of QuantiBlue reagent for 1 hour at 37° C. and measuring absorbance at 630 nm.

Figure 5:
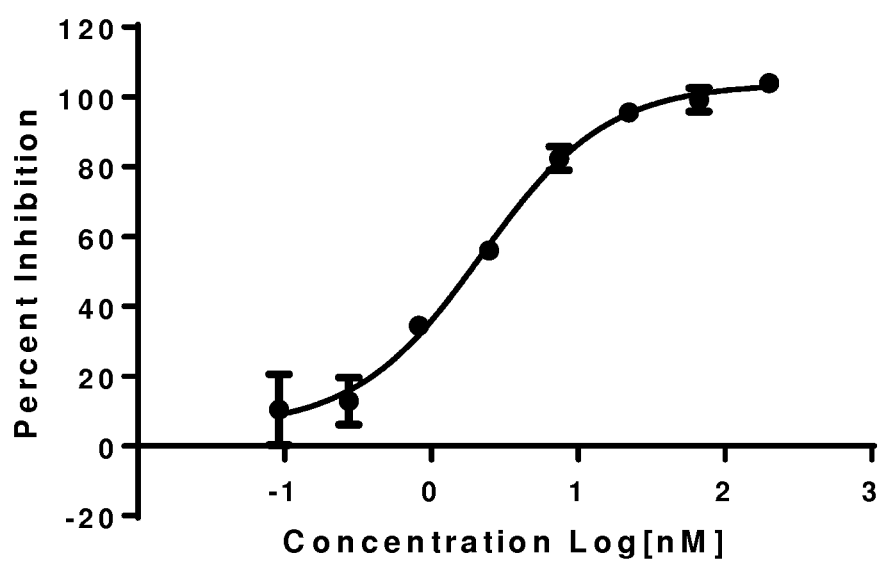
FIG. 5 shows the effect of 4856 rabbit Fab in the endogenous BxPC3-HEK-Blue TGF-beta reporter gene co-culture assay

Purified 4856 rabbit Fab was assayed in the BxPC3-HEK-Blue TGF-beta reporter gene co-culture assay (n=3). The percent inhibition from concentration response assays was calculated based on the maximum and minimum signals in the assay and the data fitted using 4 parameter logistical fit (FIG. 5). The IC50 was calculated based on the inflexion point of the curve (Table 2).

TABLE 2

Potency results of 4856 rabbit Fab in the
BxPC3-HEK-Blue TGF-beta reporter gene
co-culture assay. Five different
samples of 4856 rabbit Fab
were each tested in three independent
experiments.

| Identifier | n | Geomean IC50 (nM) range |
|---|---|---|
| BSN.4856.rbFab | 3 | 3.7; 0.8-16 |

BSN.4856.rbFab inhibits the BxPC3-HEK-Blue TGF-beta reporter gene co-culture assay with an IC50 of 3.7 nM.

Affinity of 4856 Rabbit Fab

The affinity of 4856 rabbit Fab against TGF-β isoforms 1, 2, and 3 was determined by Surface Plasmon Resonance using a Biacore™ T200 (GE Healthcare).

TGF-β isoforms 1, 2, and 3 (Peprotech) were immobilised on CM5 Series S chip via amine coupling chemistry on Flowcell 2, 3 and 4 (respectively) to a level of approximately 150 RU. HBS-EP buffer (10 mM HEPES pH 7.4, 0.15 M NaCl, 3 mM EDTA, 0.05% surfactant P20; GE Healthcare) was used as the running buffer. 4856 rabbit Fab was titrated over all three isoforms at various concentrations (200 nM to 12.5 nM) at a flow rate of 30 μL/min. The surface was regenerated by 2×10 μL injection of 10 mM HCl at a flowrate of 10 uL/min.

Background subtraction binding curves were analysed using the Biacore™ T200 evaluation software (version 1.0) following standard procedures. Kinetic parameters for 4856 rabbit Fab were determined using the 'heterogeneous ligand fitting' algorithm with RI=0. Kinetic parameters are summarized in Table 3.

The immobilisation of each isoform of TGFβ to the Biacore™ sensor chip via lysine residues is believed to have occluded the binding of the antibody to one binding domain and resulted in a secondary weak interaction (KD1). The data has been fitted to a heterogeneous model to account for the two independent binding events. The higher affinity component (KD2) is believed to represent the non-occluded interaction and therefore the most representative affinity measurement of the test antibody.

TABLE 3

Affinity for 4856 rabbit Fab determined using
a Biacore affinity assay, n = 5 for each group.

| | Ka1 (1/Ms) | Kd1 (1/s) | KD1 (M) | ka2 (1/Ms) | kd2 (1/s) | KD2 (M) |
|---|---|---|---|---|---|---|
| TGFb1 | 5.05E+04 | 3.18E−04 | 6.30E−09 | 4.55E+05 | 5.08E−05 | 1.12E−10 |
| TGFb2 | 3.87E+04 | 6.55E−05 | 1.69E−09 | 6.32E+05 | 3.83E−04 | 6.06E−10 |
| TGFb3 | 6.33E+04 | 7.82E−04 | 1.24E−08 | 8.73E+05 | 1.44E−03 | 1.65E−09 |

Example 4—Generation of Chimeric and Humanised Grafts of Antibody 4856

The antibody Fab 4856 was selected for further optimisation based on its excellent inhibitory activity in both the HEK-Blue™-SBE reporter gene assay and the BxPC3-HEK-Blue™-SBE reporter gene co-culture assay combined with its ability to bind all three isoforms of TGF-beta with high affinity.

Chimeric Antibody 4856

The variable regions of antibody 4856 were cloned into separate heavy- and light-chain expression vectors and were expressed as a human Fab (no hinge) fragment.

The VH gene (SEQ ID NO: 17) was cloned into vector pMhFab-HIS6, which contains DNA encoding the human gamma-1 CH1 constant region (G1m17 allotype) with a truncated hinge and a C-terminal tag of six histidine residues. The VL gene (kappa) (SEQ ID NO: 13) was cloned into vector pMhCK, which contains DNA encoding the human kappa constant region (Klm3 allotype).

Antibodies were expressed by transient co-transfection of heavy- and light-chain vectors into Expi293F™ cells.

Humanised Antibody 4856

Antibody 4856 was humanised by grafting the CDRs from the rabbit antibody V-region onto human germline antibody V-region frameworks.

In order to recover the activity of the antibody, a number of framework residues from the rabbit V-region were also retained in the humanised sequence. These residues were selected using the protocol outlined by Adair et al. (1991) (Humanised antibodies. WO91/09967). Alignments of the rabbit antibody (donor) V-region sequences with the human germline (acceptor) V-region sequences are shown in FIGS. 2a and 2b, together with the designed humanised sequences.

The CDRs grafted from the donor to the acceptor sequence are as defined by Kabat et al. (supra), with the exception of CDRH1 where the combined Chothia/Kabat definition is used (see Adair et al. supra).

Genes encoding a number of variant heavy and light chain V-region sequences were designed and constructed by an automated synthesis approach by DNA2.0 Inc. Further variants of both heavy and light chain V-regions were created by modifying the VH and VK genes by oligonucleotide-directed mutagenesis, including, in some cases, mutations within CDRs to modify potential Aspartic acid isomerisation sites.

These genes were cloned into a number of vectors to enable expression of humanised 4856 Fab antibody in E. coli and mammalian cells. The variant chains, and combinations thereof, were assessed for their potency relative to the parent antibody, their biophysical properties and suitability for downstream processing, leading to the selection of the gL3 light chain graft and gH13 heavy chain graft.

Human V-region IGKV1-5 plus JK4 J-region (FIG. 1I, also available from IMGT®, www.imgt.org, last accessed 5 Jan. 2016) was chosen as the acceptor for antibody 4856 light chain CDRs. The light chain framework residues in graft gL3 are all from the human germline gene, with the exception of residues 1, 2, 3 and 71 (Kabat numbering), where the donor residues Alanine (A1), Tyrosine (Y2), Aspartic acid (D3) and Tyrosine (Y71) were retained, respectively. Retention of residues A1, Y2, D3 and Y71 was essential for full potency of the humanised antibody.

Human V-region IGHV3-21 plus JH5 J-region (FIG. 1I, also available from IMGT®, www.imgt.org, last accessed 5 Jan. 2016) was chosen as the acceptor for the heavy chain CDRs of antibody 4856. In common with many rabbit antibodies, the VH gene of antibody 4856 is shorter than the selected human acceptor. When aligned with the human acceptor sequence, framework 1 of the VH region of antibody 4856 lacks the N-terminal residue, which is retained in the humanised antibody (FIG. 2b). Framework 3 of the 4856 rabbit VH region also lacks two residues (75 and 76) in the loop between beta sheet strands D and E: in graft gH13 the gap is filled with the corresponding residues (Lysine 75, K75; Asparagine 76, N76) from the selected human acceptor sequence (FIG. 2b). The heavy chain framework residues in grafts gH13, gH23 and gH29 are all from the human germline gene, with the exception of residues 48, 49, 73 and 78 (Kabat numbering), where the donor residues Isoleucine (I48), Glycine (G49), Serine (S73) and Valine (V78) were retained, respectively. Retention of residues E1, V2, Q3, I48, G49, S73 and V78 was essential for full potency of the humanised antibody.

In graft gH20, framework residues are all from the human germline gene, with the exception of residues 48, 69, 71, 73 and 78 (Kabat numbering), where the donor residues Isoleucine (I48), Methionine (M69), Lysine (K71), Serine (S73) and Valine (V78) were retained, respectively.

Residue 98 in CDRH3 of grafts gH13, gH20, gH23 and gH29 was mutated from a Glycine (G98) to an Alanine (A98) residue, thus removing a potential Aspartic acid isomerization site from the gH13, gH20, gH23 and gH29 sequences.

A potential Asparagine deamidation site at residues N100e and G100f (FIG. 2b), was removed in the gH23 graft by mutating G100f to A100f and was removed in the gH29 graft by mutating N100e to D100e.

Expression of Humanised 4856 Fab

The original 4856 Fab fragments were constructed and tested as mammalian expression vectors. In order to achieve the highest yield the codon usage of the grafts was changed to suit E. coli periplasmic expression. The grafts were aligned with the previous humanized Fabs which historically gave consistently high yields and corresponding codons altered to match the framework sequences.

For expression of humanised 4856 Fab in E. coli, the humanised heavy chain V-region gene (SEQ ID NO: 54, SEQ ID NO: 68, SEQ ID NO:82 or SEQ ID NO: 96) and light chain V-region gene (SEQ ID NO:40) were cloned into the UCB expression vector pTTOD, which contains DNA encoding the human C-kappa constant region (Klm3 allotype) and the human gamma-1 CH1 region (G1m17 allotype). The E. coli fkpA and dsbC genes were also introduced into the expression plasmid, as co-expression of these chaperone proteins was found to improve the yield of the humanised Fab in E. coli strain MXE016 during batch-fed fermentation, using IPTG to induce Fab expression. The 4856 Fab light and heavy chains and FkpA and DsbC polypeptides were all expressed from a single multi-cistron under the control of the IPTG-inducible tac promoter.

Expression of the Fab was tested in the E. coli production strain MXE016 using a 5 ml auto induction method. The combination of FkpA and DsbC chaperones increased the yield of Fab obtained substantially.

For expression of humanised 4856 Fab in mammalian cells, the humanised light chain V-region gene was joined to a DNA sequence encoding the human C-kappa constant region (Klm3 allotype), to create a contiguous light chain gene (SEQ ID NO:41). The humanised heavy chain V-region gene was joined to a DNA sequence encoding the human gamma-I CH1 region (G1m17 allotype), to create a contiguous heavy chain gene (SEQ ID NO: 55, SEQ ID NO: 69, SEQ ID NO: 83 or SEQ ID NO: 97). The heavy and light chain genes were cloned into the mammalian expression vector pMXE692 Cellca vector DGV 4856 gL3 gH13 VL VH.

Biacore Affinity Determination of E. coli Derived 4856 Fab gL3gH13

Antibody 4856 gL3gH13 produced in E. coli according to the method described above was tested for affinity against TGF-β isoforms 1, 2, and 3 determined by Surface Plasmon Resonance using a Biacore T200 (GE Healthcare). Human TGF-β isoforms 1, 2, and 3 (Peprotech) were immobilised on CM5 Series S chip via amine coupling chemistry on Flowcell 2, 3 and 4 (respectively) to a level of approximately 20 RU. HBS-EP buffer (10 mM HEPES pH 7.4, 0.15 M NaCl, 3 mM EDTA, 0.05% Surfactant P20, GE Healthcare) was used as the running buffer. Antibody 4856 gL3gH13Fab was titrated over all three isoforms at various concentrations (200 nM to 1.56 nM) at a flow rate of 30 µL/min. The surface was regenerated by 2×10 µL injection of 10 mM HCl at a flowrate of 10 uL/min.

Background subtraction binding curves were analysed using the T200 evaluation software (version 1.0; GE Healthcare) following standard procedures. Kinetic parameters were determined using heterogeneous fitting algorithm with RI=0), as described in Example 3, and the values are provided in Table 4. As before with the rabbit version of the Fab in Table 3, the KD2 of Table 4 is believed to represent the unoccluded binding value for antibody 4856 gL3gH13Fab.

TABLE 4

Affinity for 4856 humanised Fab determined using
a Biacore affinity assay, n = 4 for each group.

| TGFb isoform | ka1 (1/Ms) | kd1 (1/s) | KD1 (M) | ka2 (1/Ms) | kd2 (1/s) | KD2 (M) |
|---|---|---|---|---|---|---|
| TGFb1 | 7.49E+04 | 7.09E−04 | 9.48E−09 | 7.04E+05 | 5.56E−05 | 8.08E−11 |
| TGFb2 | 5.77E+04 | 2.11E−04 | 3.67E−09 | 9.04E+05 | 1.70E−04 | 1.96E−10 |
| TGFb3 | 9.32E+04 | 1.46E−03 | 1.57E−08 | 2.00E+06 | 3.39E−03 | 1.72E−09 |

Analytical gel filtration was performed to determine whether the antibody graft 4856 gL3gH13 binds to the full length sequence of TGF-beta 1 including the latency associated peptide. The data showed that antibody 4856 gL3gH13 does not bind full length TGF-beta 1 including the latency associated peptide (data not shown).

Example 5—In Vitro Inhibitory Activity of Humanised Grafts

Inhibitory Activity in HEK-Blue TGF-Beta Reporter Gene Assay Using Recombinant TGF-Beta 1, 2 and 3:

The inhibitory activity of 4856 humanised grafts gL3gH13, gL3gH2O, gL3gH23 and gL3gH29, was analysed in the HEK-Blue TGF-beta reporter gene assay using recombinant TGF-beta 1, 2 and 3, as described in Example 1, in 10 point dose response against TGF-beta 1, 2 and 3. TGF-beta isoforms 1, 2 and 3 were added at 50 µg/ml and the ability of antibody to neutralise TGF-beta 1, 2 and 3 was assessed. The data was fitted using a 4 parameter logistical fit. The IC50 was calculated based on the inflexion point of the curve (Table 5). It can be seen from Table 5 that the humanized grafts, particularly gL3gH13 and gL3gH20 were effective in neutralizing TGF-beta 1, 2 and 3 activity.

TABLE 5

Inhibition of exogenous TGF-beta isoforms 1, 2 and 3.

| | N | Geometric mean (nM) | 95% CI (range where N =< 4) |
|---|---|---|---|
| TGF-beta1 | | | |
| 4856gL3gH29 | 9 | 0.255 | 0.173-0.376 |
| 4856gL3gH23 | 8 | 0.41 | 0.313-0.538 |
| 4856gL3gH13 | 11 | 0.074 | 0.053-0.104 |
| 4856gL3gH20 | 12 | 0.038 | 0.024-0.062 |
| TGF-beta 2 | | | |
| 4856gL3gH29 | 3 | 0.016 | 0.013-0.018 (range) |
| 4856gL3gH23 | 3 | 0.017 | 0.015-0.022 (range) |
| 4856gL3gH13 | 3 | 0.01 | 0.007-0.019 (range) |
| 4856gL3gH20 | 5 | 0.011 | 0.010-0.027 |
| TGF-beta 3 | | | |
| 4856gL3gH29 | 3 | 1.954 | 1.6-2.46 (range) |
| 4856gL3gH23 | 4 | 1.987 | 1.21-1.88 (range) |
| 4856gL3gH13 | 4 | 0.475 | 0.248-0.909 |
| 4856gL3gH20 | 5 | 0.302 | 0.141-0.647 |

Inhibitory Activity in Endogeneous TGF-Beta BxPC3 and HEK-Blue TGF-Beta Reporter Gene Co-Culture Assay:

The inhibitory activity of 4856 humanized grafts gL3gH13, gL3gH20, gL3gH23 and gL3gH29, was analysed in the BxPC3 and HEK-Blue TGF-beta reporter gene co-culture assay as described in Example 3. The percent inhibition from concentration response assays was calculated based on the maximum and minimum signals in the assay and the data fitted using 4 parameter logistical fit. The IC50 was calculated based on the inflexion point of the curve and the results are shown in Table 6. It can be seen from Table 6 that the humanized grafts, particularly gL3gH13, gL3gH20 and gL3gH29 were effective in neutralizing TGF-beta expressed and activated by cells in this assay.

TABLE 6

Inhibition of TGF-beta expressed by BxPC3 cells in a co-culture assay withHEK-Blue TGF-beta cells.

| Endogenous assay | N | Geometric mean (nM) | 95% CI (range where N =<4) |
|---|---|---|---|
| 4856gL3gH23 | 4 | 9.104 | 3.89-21.31 |
| 4856gL3gH29 | 4 | 3.773 | 0.71-20.05 |
| 4856gL3gH13 | 4 | 3.949 | 2.52-6.19 |
| 4856gL3gH20 | 3 | 4.626 | 3.01-6.41 (range) |

Example 6—Inhibitory Activity of Humanised 4856 Grafts in an Adriamycin-Induced In Vitro Model of Kidney Fibrosis Adriamycin-induced nephropathy is a well characterised rodent model of acquired kidney fibrosis with pathological features similar to human glomerulosclerosis and tubulointerstitial fibrosis. Mesangial cells are one of the main cell types involved in the fibrotic phenotype in response to Adriamycin. A human in vitro model for the fibrotic response to Adriamycin treatment was established and the ability of TGF-beta-neutralizing grafts gL3gH13, gL3gH20, gL3gH23 and gL3gH29 of antibody 4856 Fab to modulate the deposition of extracellular matrix (ECM) components in this system was assessed.

Primary human renal mesangial cells (HRMCs, Innoprot) were plated at $1.6 \times 10^4$ cells/cm$^2$ in the presence of 10 nM Adriamycin and of test 4856 Fab grafts gL3gH13, gL3gH20, gL3gH23 and gL3gH29 and a control Fab, (3-fold sequential dilutions ranging from 0.2 to 6000 nM). Cells were incubated for 6 days at 37° C., 5% CO$_2$, then lysed in 0.25M NH$_4$OH/25 mM Tris (30 min at 37° C.) and the deposited ECM fixed in ice-cold Methanol (30 min at −20° C.). Deposition of the individual ECM components was detected by high content imaging after immunostaining for Fibronectin (AlexaFluor488-conjugated Ebioscience 53-9869-82), Collagens I and III (Millipore rabbit polyclonal antibodies AB745 and AB747), and Collagen type IV (Efluor660-conjugated Ebioscience 50-9871-80). Images were acquired and the fluorescence intensity detected by a Cellomics Arrayscan. The maximum signal was generated from wells containing Adriamycin-treated cells in the absence of Fab and the minimum signal was obtained in wells where cells had not been exposed to Adriamycin.

The percent inhibition from concentration response assays was calculated based on the maximum and minimum fluorescence intensities in the assay and the data fitted using 4 parameter logistical fit. Images and plots shown are representative of three replicate experiments.

Figure 6:
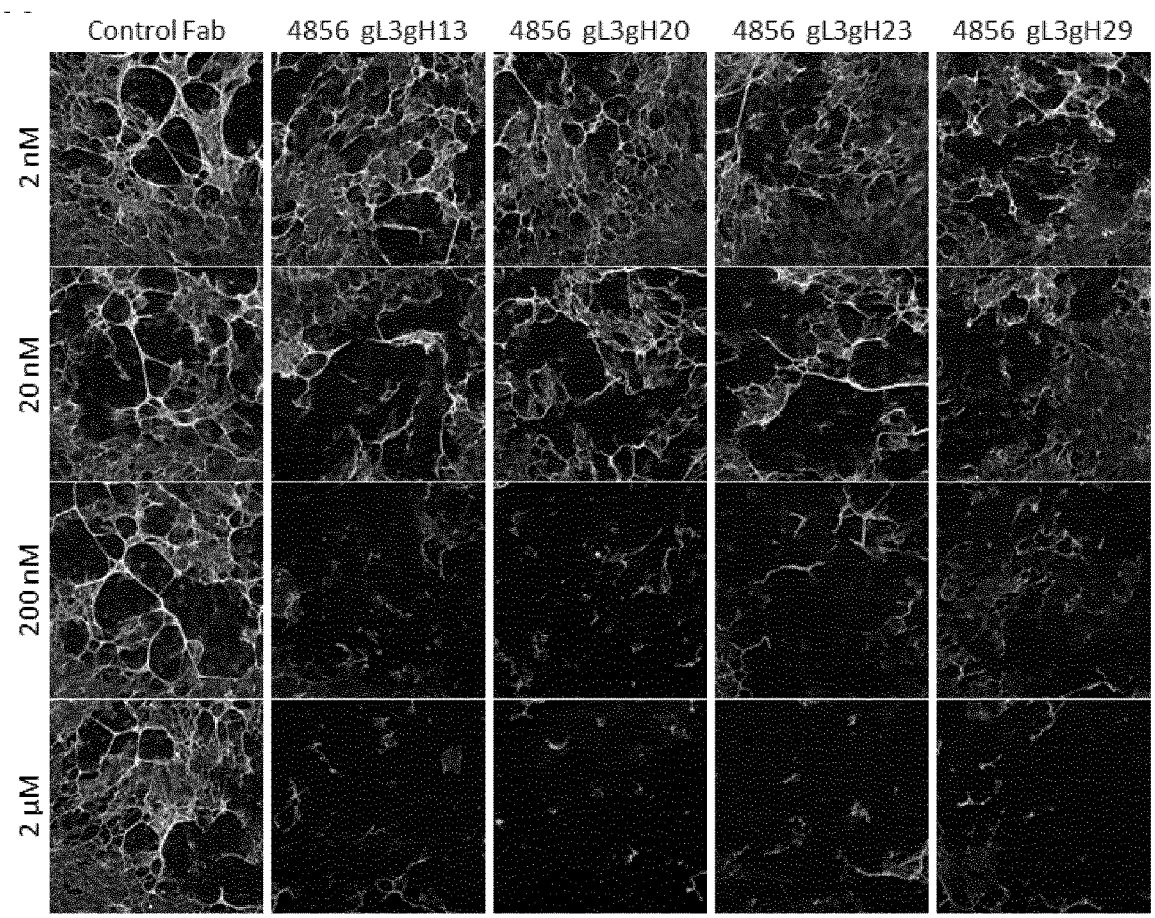
FIG. 6 shows images of ECM deposition by HRMCs in response to 10 nM Adriamycin and in the presence of increasing concentrations of 4856 Fab grafts gL3gH13, gL3gH20, gL3gH23 and gL3gH29 or control Fab FIGS. 7A, B and C show the effect of 4856 Fab grafts gL3gH13, gL3gH20, gL3gH23 and gL3gH29 on the deposition of (A) fibronectin, (B) collagen I and III and (C) collagen IV from HRMCs treated with Adriamycin

FIG. 6 shows representative images of ECM deposition by HRMCs in response to 10 nM Adriamycin and in the presence of the indicated concentrations of TGF-beta-neutralising 4856 Fab grafts gL3gH13, gL3gH20, gL3gH23 and gL3gH29 or control Fab.

Figure 7A:
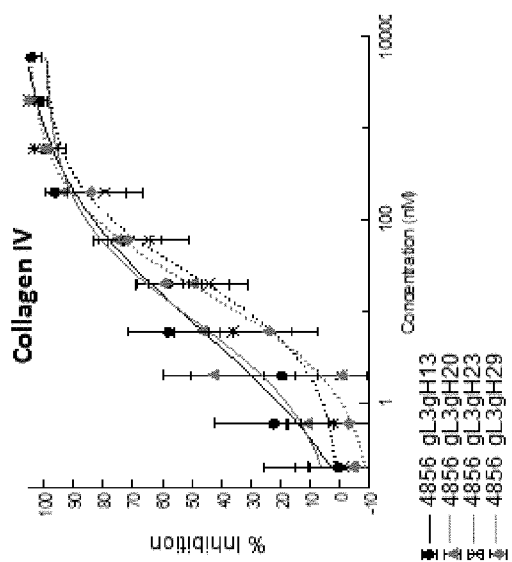
Figure 7B:
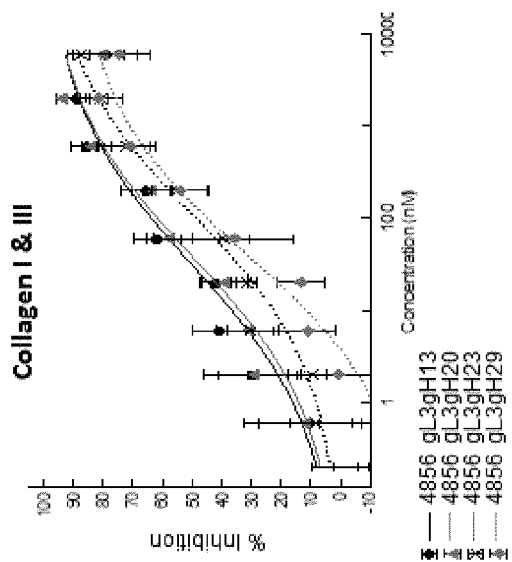
Figure 7C:
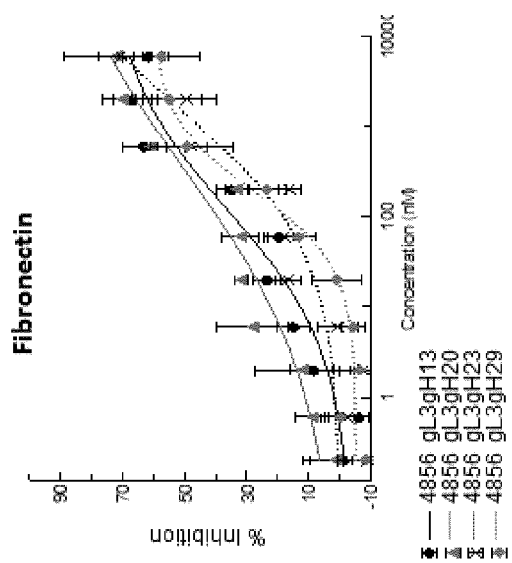

FIG. 7 shows representative concentration response curves for 4856 Fab grafts gL3gH13, gL3gH20, gL3gH23 and gL3gH29 in the Adriamycin in vitro assay.

The four tested TGF-beta-neutralising Fab grafts inhibited Adriamycin-induced ECM deposition by HRMCs (Table 7).

TABLE 7

Inhibition of ECM deposition by 4856 Fab grafts gL3gH13, gL3gH20, gL3gH23 and gL3gH29 in the Adriamycin-Induced Model of Kidney Fibrosis (Geomean from 3 replicate experiments).

| 4856 Fab graft | Fibronetin | | Collagen I&III | | Collagen IV | |
|---|---|---|---|---|---|---|
| | Geomean IC50 (nM) | range n = 3 | Geomean IC50 (nM) | range n = 3 | Geomean IC50 (nM) | range n = 3 |
| gL3gH29 | 105.96 | 49.3-190.1 | 90.10 | 40.2-178.1 | 22.93 | 6.0-50.7 |
| gL3gH23 | 227.29 | 40.6-1387.7 | 198.35 | 110.4-540.2 | 44.86 | 24.8-99.8 |
| gL3gH13 | 57.30 | 32.9-118.6 | 57.94 | 31.0-87.7 | 10.39 | 9.2-11.8 |
| gL3gH20 | 104.84 | 52.1-329.4 | 33.86 | 16.8-60.2 | 16.65 | 8.3-51.0 |

Note, the upper and lower asymptotes of some curves were fixed at minimum or maximum values.

Example 7—Inhibitory Activity of Humanized 4856 Graft in an In Vitro Model of Human Lung Interstitial Fibrosis Epithelial damage and fibroblast activation are crucial events leading to ECM accumulation during the fibrotic process. In order to establish an in-vitro model of lung interstitial fibrosis, an assay was developed using primary human small airway epithelial cells (SAEpCs, ATCC) and lung fibroblasts (ATCC) isolated from an IPF patient. The co-culture of these two cell types in epithelial cell media induces significant ECM deposition even in the absence of additional stimulus, allowing the study of anti-fibrotic agents.

$1.8 \times 10^4$ primary human small airway epithelial cells (SAEpCs) and equal number of IPF lung fibroblasts were plated per $cm^2$ (total of $3.6 \times 10^4$ cells/$cm^2$) and co-cultured for 7 days at 37° C., 5% $CO_2$. 4856 Fab graft gL3gH13, and a control Fab were titrated 3-fold within the range of 0.03 to 1000 nM. After the 7 day co-culture, cell viability was assessed with Presto Blue, the cells were then lysed in in 0.25M $NH_4OH$/25 mM Tris (30 min at 37° C.) and the deposited ECM fixed in ice-cold Methanol (30 min at −20° C.). Deposition of the individual ECM components was detected by high content imaging after immunostaining for Fibronectin and Collagens type I, III, IV and V. Images were acquired and the fluorescence intensity detected by a Cellomics Arrayscan. The maximum signal was generated in untreated co-cultures and the minimum signal was generated using excess Fab.

The percent inhibition from concentration response assays was calculated based on the maximum and minimum signals in the assay and the data fitted using 4 parameter logistical fit. The IC50 was calculated based on the inflexion point of the curve. Images and plots shown are representative of three replicate experiments.

Figure 8:
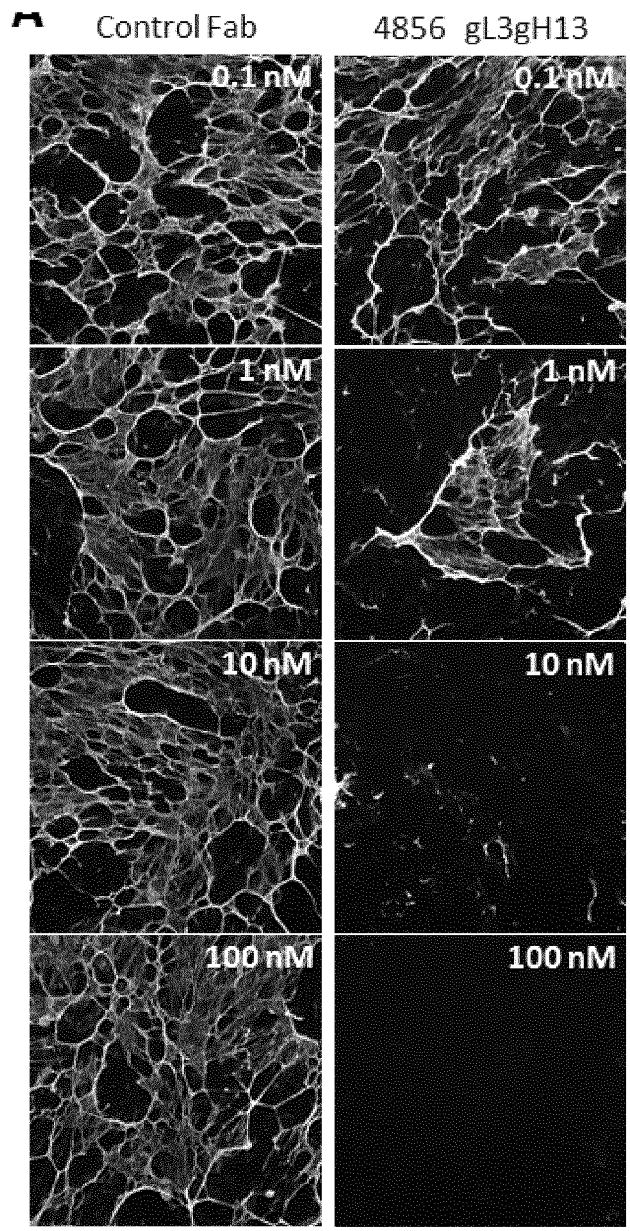
FIG. 8 shows images of ECM deposition by SAEpCs and IPF fibroblasts co-cultures in the presence of increasing concentrations of 4856 Fab graft gL3gH13 and a control Fab FIGS. 9A, B and C show the effect of 4856 Fab graft gL3gH13 and a control Fab on the deposition of (A) fibronectin, (B) collagen I and III and (C) collagen IV from SAEpCs and IPF fibroblasts co-cultures FIGS. 10A, B and C show the effect of 4856 Fab graft gL3gH13 on the inhibition of (A) TGF-beta 1, (B) TGF-beta 2 and (C) TGF-beta 3 induced fibronectin deposition from a mono-culture of human renal proximal tubular epithelial cells

FIG. 8 shows images of ECM deposition by SAEpCs and IPF fibroblasts co-cultures in the presence of the indicated concentrations of 4856 Fab graft gL3gH13 and a control Fab.

Figure 9A:
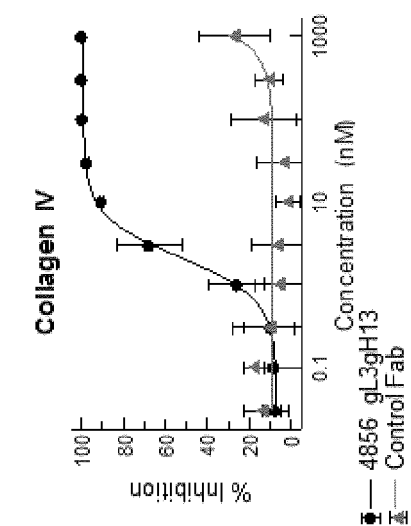
Figure 9B:
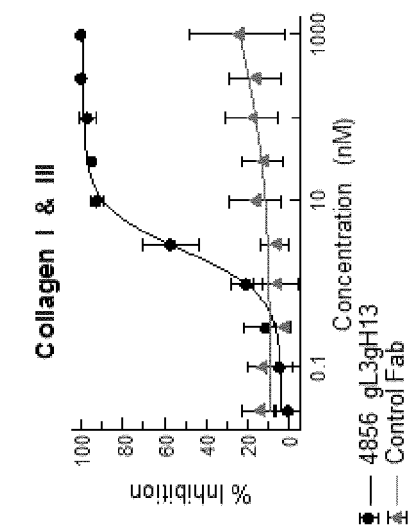
Figure 9C:
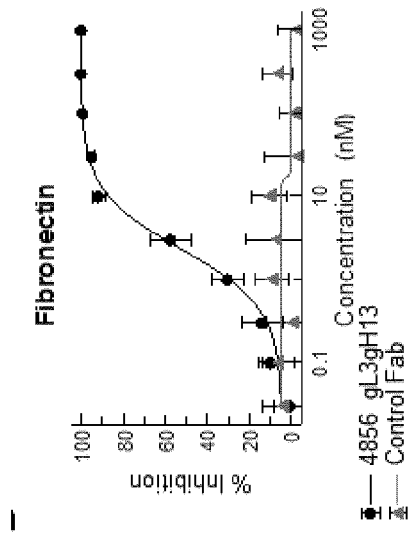

FIG. 9 shows concentration response curves of the 4856 Fab graft gL3gH13 and a control Fab in the human lung co-culture assay.

Table 7 shows the potency results for the inhibition of ECM deposition by 4856 Fab graft gL3gH13 in the lung co-culture assay (Geomean from 3 replicate experiments)

| ECM protein | Geomean IC50 (nM) (range) n = 3 4856 gL3gH13 |
|---|---|
| Fibronectin | 2.42 (1.6-3.9) |
| Collagen I & III | 2.66 (2.3-3.2) |
| Collagen IV | 2.91 (2.1-5.5) |
| Collagen V | 2.70 (1.8-4.5) |

ECM deposition in co-cultures of SAEpCs and IPF fibroblasts was inhibited by 4856 Fab graft gL3gH13.

Example 8—Inhibitory Activity of Humanized 4856 Graft in an In Vitro Model of Human Kidney Fibrosis The capacity of 4856 Fab gL3gH13 to inhibit fibronectin and collagen deposition in human primary kidney cells was assessed using extra cellular matrix (ECM) accumulation assays on a mono-culture of human renal proximal tubular epithelial cells (RPTEC) stimulated with TGF-beta 1, 2 or 3 and a co-culture of human renal proximal tubular epithelial cells (RPTEC) with human renal fibroblasts (HRF) (no stimulation).

Human renal proximal tubular epithelial cells (RPTEC, Innoprot) and human renal fibroblasts (HRF, InnoProt) were seeded at 2,000 cells per well (ratio 1:1 in the co-culture) in a 384-well black clear-bottomed plate (Corning) in the presence of 0.1 to 100 μg/mL (0.2-2000 nM) of anti-TGF-beta antibody (gL3gH13 Fab) or control Fab and 10 ng/ml TGF-beta1 (Peprotech), TGF-beta2 (R&D) or TGF-beta3 (R&D) for the mono-culture of RPTEC, or no exogenous TGF-beta (no stimulation) for the co-culture of RPTEC and HRF, in a final volume of 50 μL in Renal Epithelial Cell Basal medium+0.5% Fcs and supplements (ATCC).

After 7 days incubation at 37° C. 5% $CO_2$, cells were washed in PBS and lysed with 20 µl 0.25 M NH4OH/25 mM Tris for 15 min at 37° C. Matrix was washed 3 times in PBS, fixed in 40 µl 100% methanol for 30 min at −20° C. and washed 3 times in PBS before being stained using anti-Fibronectin (eBiosciences), anti-Collagen I (Millipore), anti-Collagen III (Millipore), anti-Collagen IV (eBiosciences) and anti-Collagen V (Abcam) antibodies. Plates were scanned on the Cellomics Arrayscan HC reader using a 3-channel protocol under the "Cellomics CellHealth" profiling bioapplication and a 10× objective (new X1 camera) with 2×2 binning (1104×1104 pixels/field).

Although data was generated for the Collagen IV readout, the results have been excluded due to unacceptable assay windows and variability.

Figure 10A:
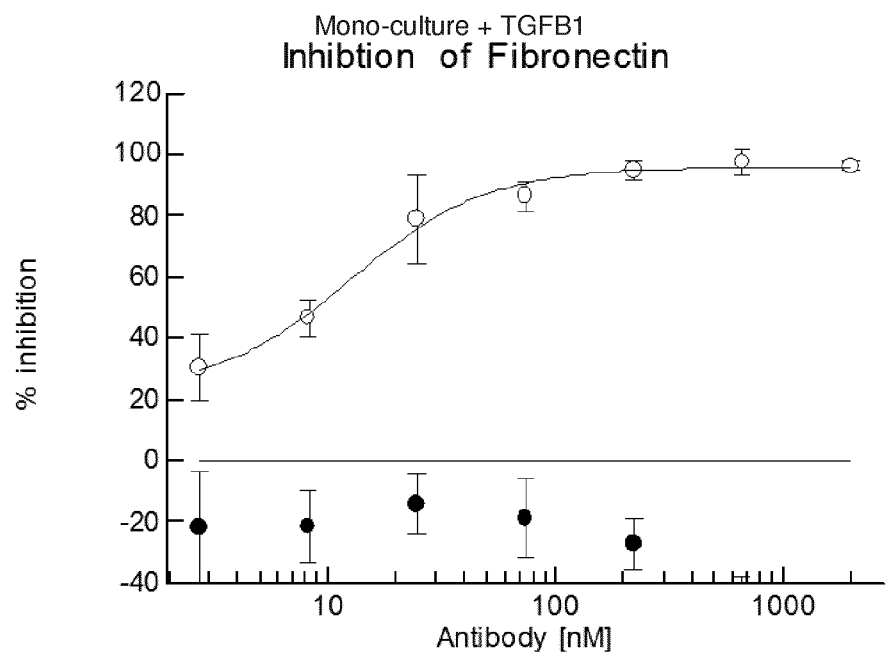
FIG. 10D shows the effect of 4856 Fab graft gL3gH13 on the inhibition of fibronectin deposition from a co-culture of human renal proximal tubular epithelial cells and human renal fibroblasts FIGS. 11A and B the effect of 4856 Fab graft gL3gH13 on the inhibition of TGF-beta 1 induced (A) collagen I and III, (B) collagen V deposition from a mono-culture of human renal proximal tubular epithelial cells FIG. 12 Comparison of the effect of intranasal administration of the indicated 4856 Fabs on the expression of PAI-1 in mice at day 7 after challenge with bleomycin.
Figure 10B:
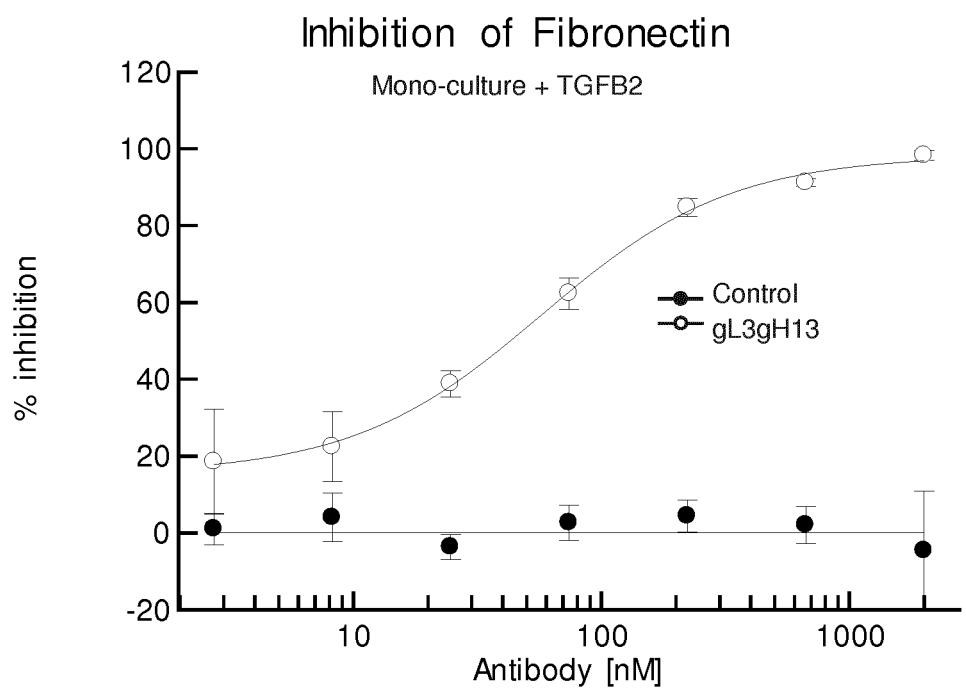
Figure 10C:
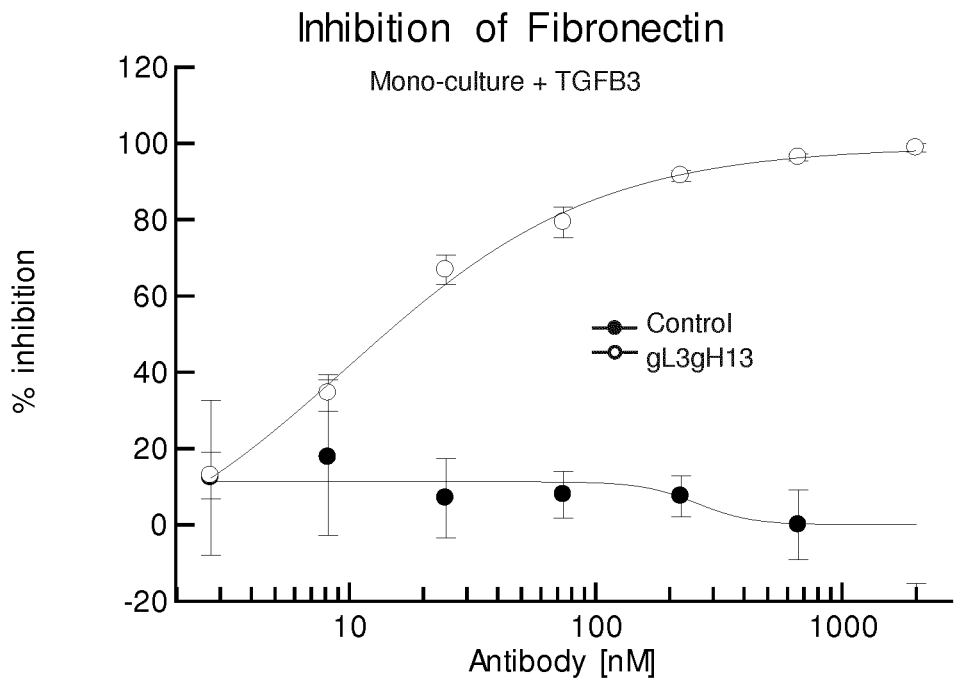
Figure 10D:
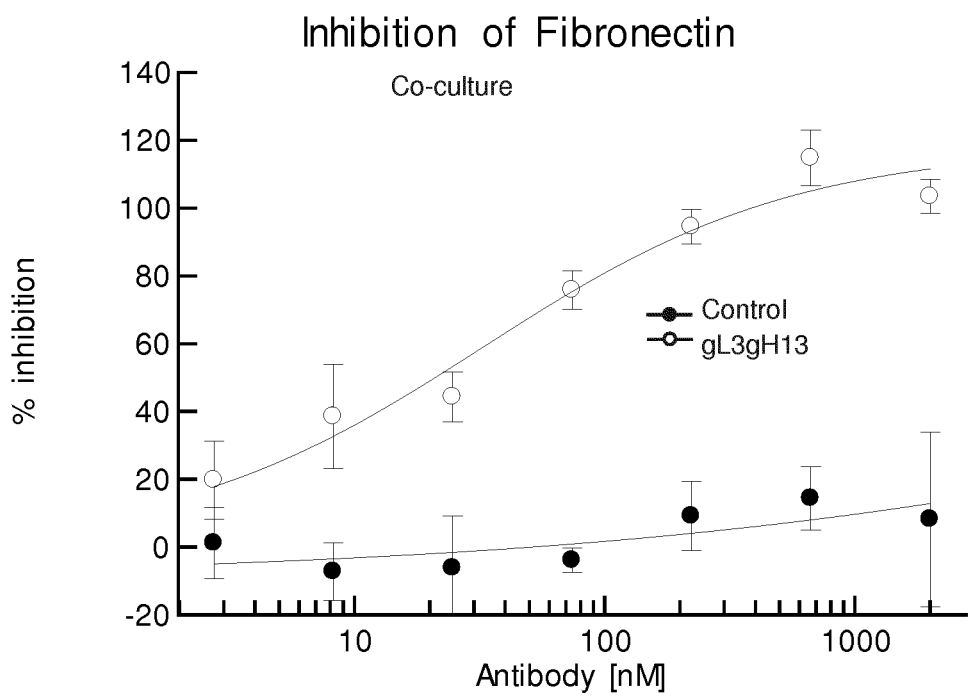
Figure 11A:
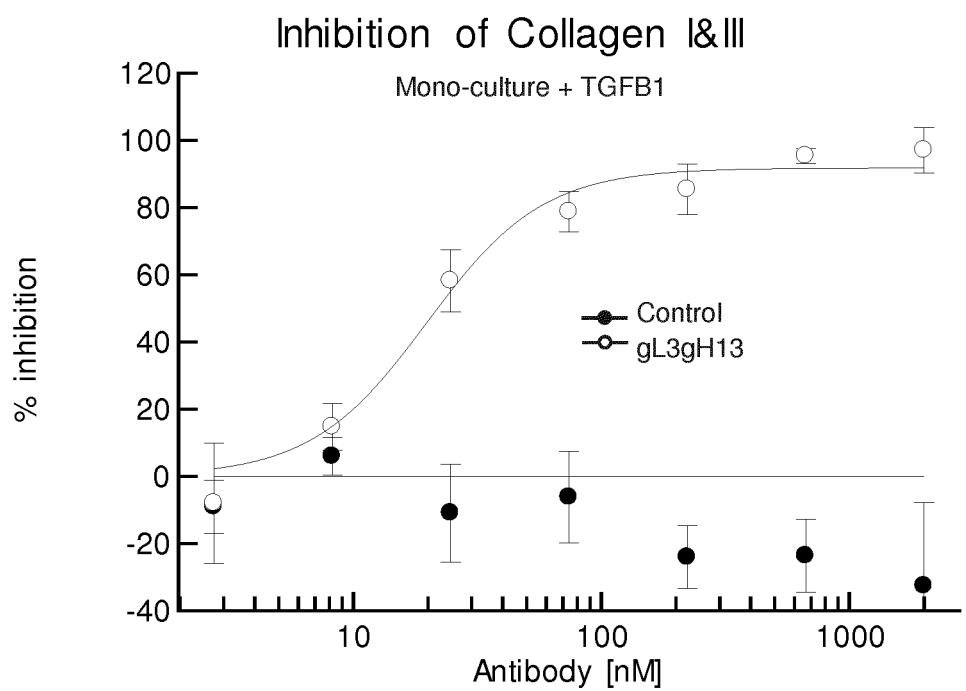
Figure 11B:
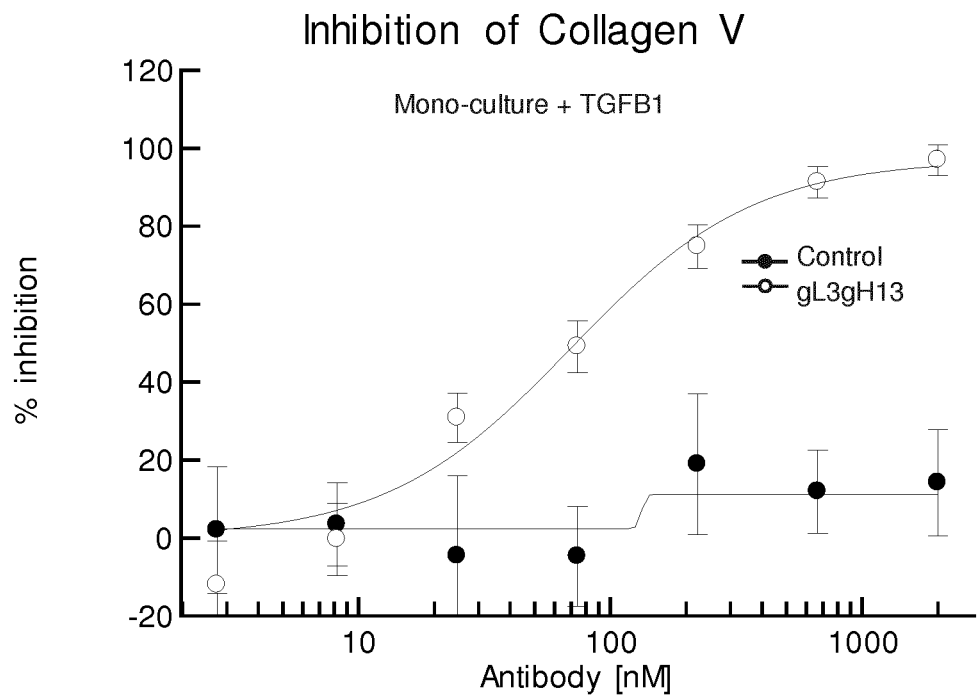

Results are shown in Table 9 and FIG. 10a, b, c and d and FIGS. 11a and b which shows that gL3gH13 Fab is able to inhibit TGF-beta1, 2 and 3 induced accumulation of Fibronectin and Collagen I, III and V in the RPTEC monoculture system, and by endogenously produced TGF-beta in the RPTEC and HRF co-culture system.

Figure 12:
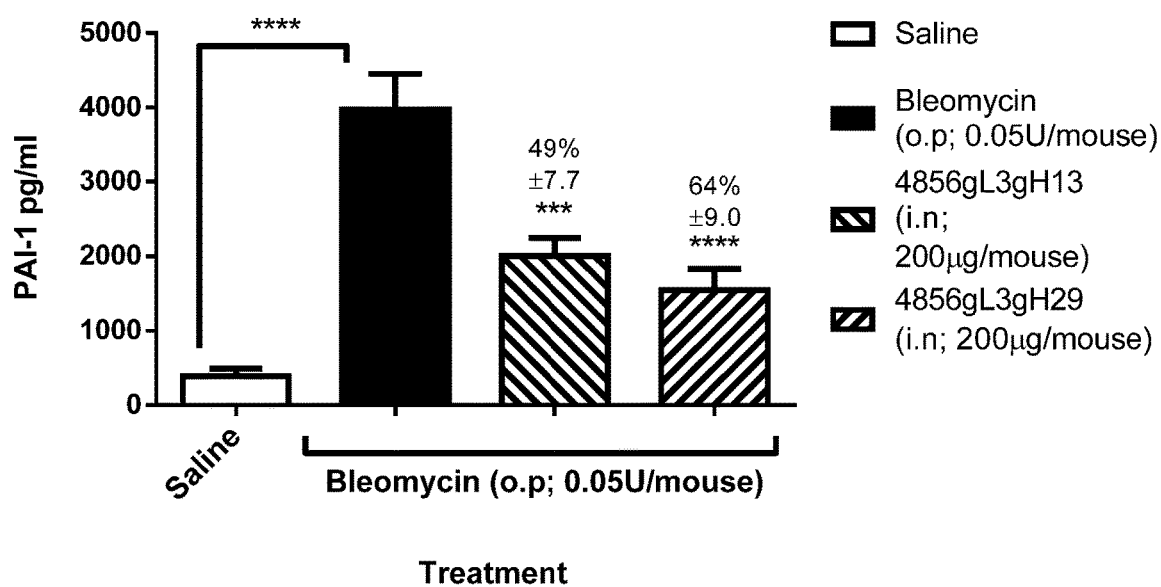

The results of this administration of the two 4856Fabs (4856gL3gH13 and 4856gL3gH29) is shown in FIG. 12. FIG. 12 demonstrates that mice challenged with bleomycin had greatly elevated PAI-1 levels in the BAL compared to saline challenged control mice and that humanised Fabs 4856gL3gH13 and 4856gL3gH29 were capable of inhibiting bleomycin-induced PAI-1 by 49% and 64% respectively when delivered directly to the lung.

In a second study C57/BL6 mice were administered humanised 4856gL3gH13 (i.n; 20, 60, 200 g/mouse) 1 hour before bleomycin challenge (o.p; 0.05 U/mouse) and 6 hours after. Mice subsequently received 4856gL3gH13 every 12 hours until they were terminated on day 7. Immediately after termination BAL was collected and total PAI-1 concentrations were determined by ELISA. Statistical analysis performed by one-way ANOVA versus bleomycin treated control group. *$p<0.05$, $p<0.005$, *$p<0.0005$, ****$p<0.00005$.

Figure 13:
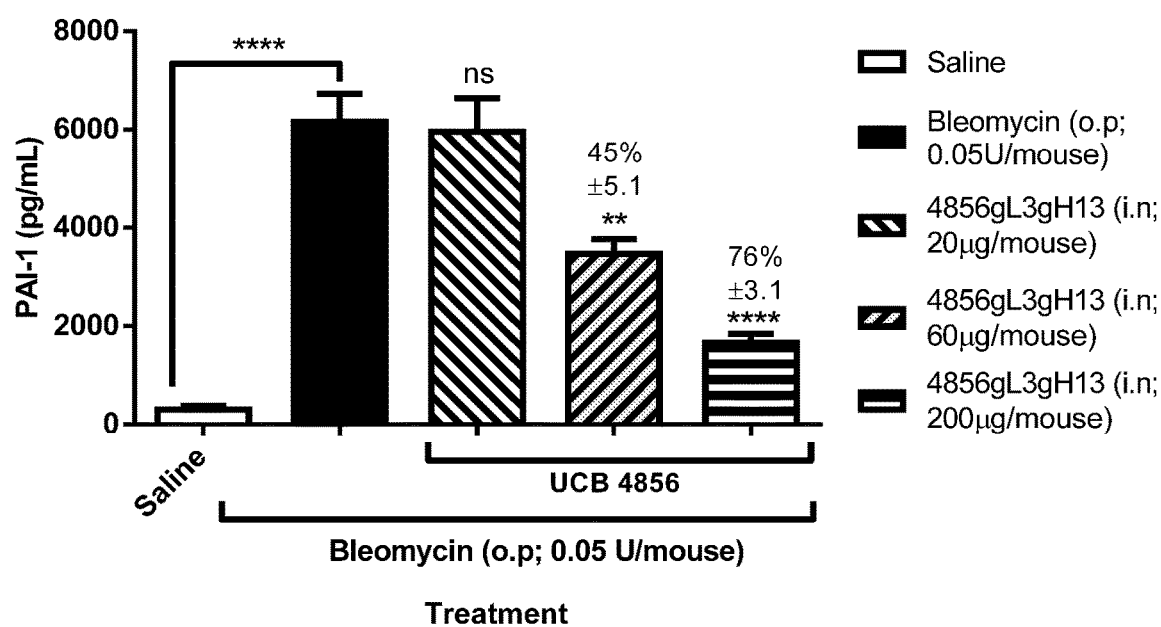
FIG. 13 Dose comparison of intranasally administered 4856 gL3gH13 Fab on the expression of PAI-1 in mice at day 7 after challenge with bleomycin FIGS. 14A-B The effect of intranasally administered 4856 gL3gH13 Fab from day 1-28 on A) bleomycin-induced collagen deposition (PSR stain) and (B) hydroxyproline content in the lung.

In order to demonstrate superior efficacy of 4856gL3gH13 in this system, FIG. 13 illustrates the effect of 4856gL3gH13 on bleomycin-induced PAI-1 at different doses. As previously shown, bleomycin induces an increase in BAL PAI-1 levels that can be significantly inhibited up to 76% using 200 g/mouse i.n 4856gL3gH13 and up to 45% using 60 g/mouse i.n 4856gL3gH13.

This demonstrates that locally delivered (i.n) 4856gL3gH13 significantly inhibits acute bleomycin-induced PAI-1 and that it is possible to locally inhibit TGF-beta in the lung, potentially avoiding unwanted systemic events.

TABLE 9

IC50s and Geometric Mean IC50s (nM) (N = 3) for gL3gH13:

| Marker | Antibody | Mono-culture + TGFB1 | | | | Mono-culture + TGFB2 | | | | Mono-culture + TGFB3 | | | | Co-culture | | |
|---|---|---|---|---|---|---|---|---|---|---|---|---|---|---|---|---|
| | | N = 1 | N = 2 | N = 3 | Geo Mean | N = 1 | N = 2 | N = 3 | Geo Mean | N = 1 | N = 2 | N = 3 | Geo Mean | N = 1 | N = 2 | Geo Mean |
| Fibronectin | gL3gH13 | 12.6 | 57.4 | 9.8 | 19.2 | 0.16 | 0.76 | 0.22 | 0.30 | 51.5 | 140.0 | 76.8 | 82.1 | 32.6 | 27.1 | 29.7 |
| Collagen I &III | gL3gH13 | 5.1 | 13.8 | 19.8 | 11.2 | <2 | 0.60 | 0.13 | 0.30 | 64.3 | 123.8 | 67.2 | 81.2 | 22.4 | 48.0 | 32.8 |
| Collagen V | gL3gH13 | 13.1 | 92.1 | 69.4 | 43.7 | 0.52 | 10.5 | 5.29 | 3.1 | 140.8 | 336.3 | 146.6 | 190.8 | 38.9 | 81.6 | 56.3 |

Example 9—In Vivo Murine Model of Lung Fibrosis i) 7 Day Challenge

The acute bleomycin-induced model of lung injury involves the local administration of the glycopeptide bleomycin directly to the lungs of mice. This induces an inflammatory response associated with an increase in Plasminogen Activator Inhibitor-1 (PAI-1) and ultimately results in pulmonary fibrosis. PAI-1 is transcriptionally regulated by TGF-beta and can act as a potent fibrogenic mediator inducing the recruitment of inflammatory cells and the deposition of extracellular matrix (ECM) (Ghosh and Vaughan, 2012, J Cell Physiol, 227: 493-507).

Any effect on test anti-TGF-beta Fabs to limit fibrogenesis such as PAI-1 inhibition provides supporting evidence that a pan-specific anti-TGF-beta blocking Fab delivered directly to the lung is a viable therapeutic for pulmonary fibrosis in humans.

4856 Fab grafts (humanised) were locally administered directly to the lungs of mice via the intranasal (i.n) route. C57/BL6 mice were administered with 4856gL3gH13 or 4856gL3gH29 (i.n; 200 g/mouse) 1 hour before bleomycin challenge (o.p; 0.05 U/mouse) and 6 hours after. Mice subsequently received 4856gL3gH13 or 4856gL3gH29 (i.n; 200 g/mouse) every 12 hours until they were terminated on day 7. Immediately after termination bronchoalveloar lavage fluid (BAL) was collected and total PAI-1 concentrations were determined by ELISA. Statistical analysis performed by one-way ANOVA versus bleomycin treated control group.

ii) 28 Day Challenge

The longer term effects of bleomycin challenge results in pulmonary fibrosis, and a similar study was therefore performed in mice for 28 days with murinised 4856gL3gH13 (called 4856 hereafter) dosed prophylactically from day 1 as well as from day 13 of the bleomycin challenge. This later administration of 4856 allows fibrosis to become more fully established in the lung before treatment is started.

The impact of 4856 on bleomycin-induced pulmonary fibrosis was assessed by the attenuation of ECM deposition and myofibroblast differentiation in the lung. ECM deposition was determined histologically in paraffin-embedded lung tissue by staining for collagen using Picro Sirius Red (PSR). This was supported by more quantitative analysis of hydroxyproline levels in digested lung tissue. Hydroxyproline is a major component of collagen and can be used to estimate the amount of collagen in tissues. In addition, the number of myofibroblasts; the predominant cell type believed to be responsible for collagen deposition in the lung, was determined using immunohistochemical (IHC) staining for α-Smooth Muscle Actin (α-SMA). Furthermore, inhibition of phosphorylated-Mothers against decapentaplegic homolog 2 and 3 (p-Smad2/3) was also determined by IHC to demonstrate specific inhibition of the TGFβ signaling pathway by 4856. All statistics were determined using unpaired t-test against the assigned bleomycin challenged control group. *p=0.05; p=0.01; *p=0.001; ****p=0.0001.

a) 4856 Ameliorates Bleomycin-Induced Collagen Deposition in the Lungs

Treatment with 4856 from day 1-28 Mice (Male c57BL/6; n=8/group) were treated with saline (i.t, 50 μL) or bleomycin (i.t, 50 μL; 0.5 mg/mL) for 28 days. In addition mice were treated with either vehicle (i.n, 25 μL) or 4856 (i.n, 25 μL; 400 g/mouse) twice daily from day 1-28.

Treatment with 4856 from day 13-28 Mice (Male c57BL/6; n=8/group) were treated with saline (i.t, 50 μL) or bleomycin (i.t, 50 μL; 0.5 mg/mL) for 12 or 28 days. In addition mice were treated with either vehicle (i.n, 25 μL) or 4856 (i.n, 25 μL; 400 g/mouse) twice daily from day 13-28.

Assay The entire left lobe was fixed in 4% formalin for 6 h and embedded in paraffin. 5 m sections were cut and stained with PSR. Images were captured using a Nikon Eclipse 80i microscope (Nikon, Badhoevedorp, Netherlands) and the fibrotic area in a minimum of four fields per mouse was analysed using ImageJ (V. 1.42q, National Institutes of Health, USA). The amount of collagen protein in the three lower lobes of the right lung (azygous lobe, cardiac lobe and diaphramatic lobe) was determined via hydroxyproline assay. After digestion in 6 M HCl for three hours at 120° C., the pH of the samples was adjusted to 6 with 6 M NaOH. Afterwards, 0.06 M chloramine T was added to each sample and incubated for 20 min at room temperature. Next, 3.15 M perchloric acid and 20% p-dimethylaminobenzaldehyde were added and samples were incubated for additional 20 min at 60° C. The absorbance was determined at 557 nm with a Spectra MAX 190 microplate spectrophotometer.

Figure 14A:
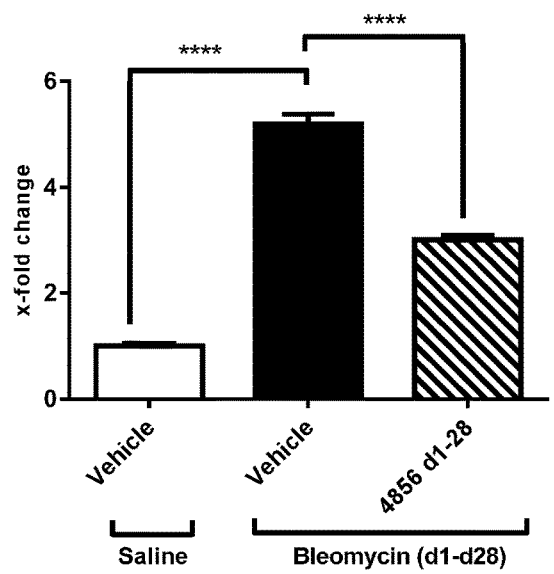

Results Intratracheal (i.t) instillation of bleomycin using a micro-sprayer (50 μL; 0.5 mg/mL) induced prominent pulmonary fibrosis compared to control mice treated with i.t instillation of saline (0.9% NaCl, the solvent of bleomycin). This is demonstrated by enhanced PSR staining and elevated hydroxyproline content in the lung (FIGS. 14 and 15). In addition, these fibrotic changes were more pronounced after 28 days than after 12 days (FIG. 15) suggesting that the severity of fibrosis progressed over time.

Figure 14B:
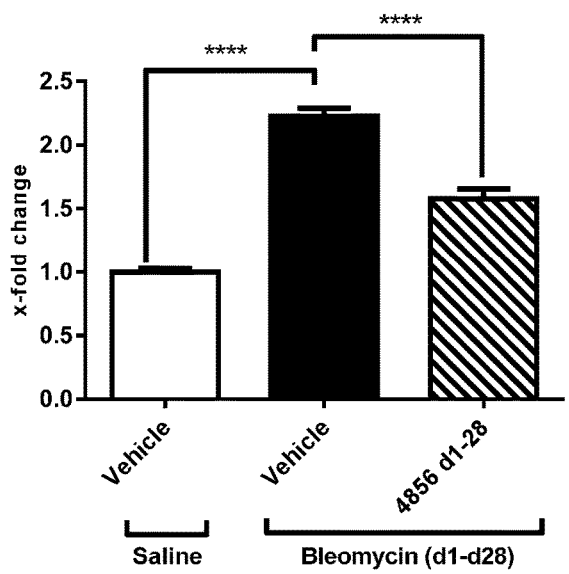
Figure 15A:
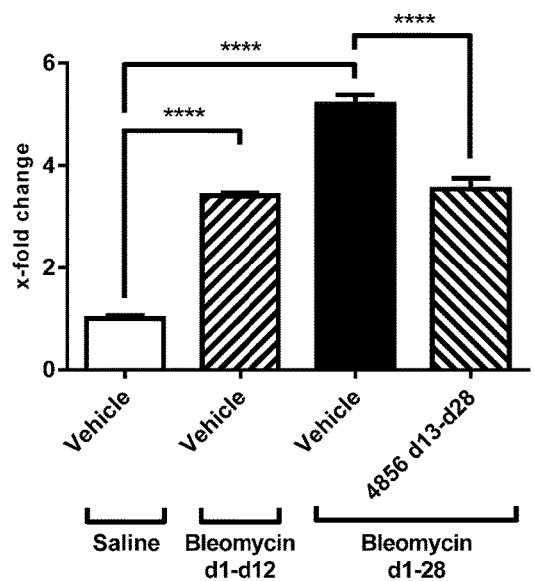
FIGS. 15A-B The effect of intranasally administered 4856 gL3gH13 Fab from day 13-28 on A) bleomycin-induced collagen deposition (PSR stain) and B) hydroxyproline content in the lung.
Figure 15B:
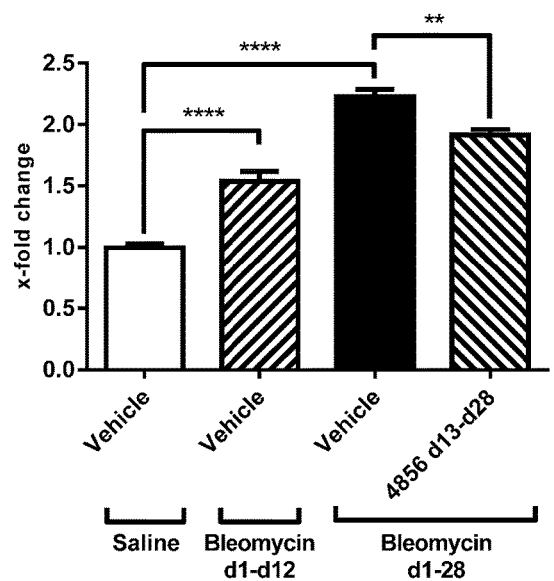

Treatment with 4856 from day 1-28 (25 μL i.n; 400 μg/mouse; twice daily) resulted in a significant reduction in both PSR (FIG. 14A) and hydroxyproline content in the lung (FIG. 14B). This suggests that 4856 can prevent bleomycin-induced pulmonary fibrosis. Furthermore, administration of 4856 to bleomycin challenged mice from day 13-28 significantly limited the progressive increase in PSR (FIG. 15A) and hydroxyproline (FIG. 15B) observed at day 28 when compared to vehicle treated mice. This suggests that 4856 is capable of limiting the progression of disease when given after fibrosis is already evident.

b) 4856 Ameliorates Bleomycin-Induced Myofibroblast Differentiation in the Lungs Mice (Male c57BL/6; n=8/group) were treated with saline (i.t, 50 μL) or bleomycin (i.t, 50 μL; 0.5 mg/mL) for 12 or 28 days. In addition mice were treated with either vehicle (i.n, 25 μL) or 4856 (i.n, 25 μL; 400 μg/mouse) twice daily from day 1-28 or 13-28. Myofibroblasts are characterized by the expression of α-smooth muscle actin (α-SMA). Fibroblasts positive for α-SMA were detected by incubation with monoclonal anti-αSMA antibodies (clone 1A4, Sigma-Aldrich, Steinheim, Germany). The expression was visualized with horseradish peroxidase labeled secondary antibodies and 3,3-diaminobenzidine tetrahydrochloride (DAB) (Sigma-Aldrich). Monoclonal mouse IgG antibodies (Calbiochem, San Diego, Calif., USA) were used for isotype controls. Four different fields were evaluated per mouse.

Figure 16A:
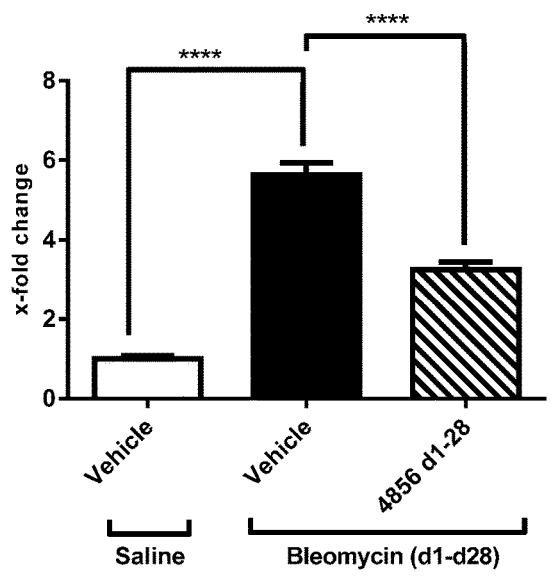
FIGS. 16A-B The effect of intranasally administered 4856 gL3gH13 Fab from day A) 1-28 or B) 13-28 on bleomycin-induced myofibroblast differentiation in the lung.
Figure 16B:
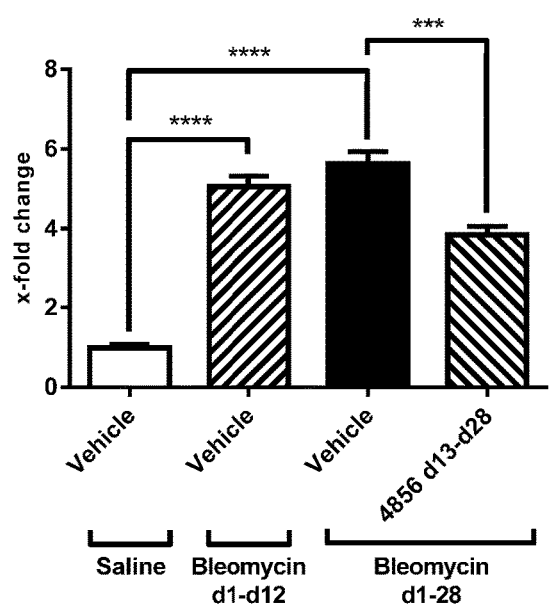

The administration of bleomycin also induced an increase in myofibroblast differentiation in the lungs characterized by the expression of α-SMA by IHC (FIG. 16). FIG. 16A illustrates that bleomycin-induced myofibroblast differentiation in the lung was inhibited by i.n administration of 4856 from day 1-28. Additionally, although there was not a significant increase in α-SMA expression between day 12 and 28 of bleomycin treatment, administration of 4856 from day 13-28 also caused a significant attenuation in myofibroblast differentiation. Furthermore, this was reduced to below the level of α-SMA expression observed after bleomycin treatment alone for 12 days suggesting a possible reversal of fibrotic processes at this time point (FIG. 16B).

c) 4856 Inhibits Bleomycin-Induced TGF-β Signaling in the Lungs.

Mice (Male c57BL/6; n=8/group) were treated with saline (i.t, 50 μL) or bleomycin (i.t, 50 μL; 0.5 mg/mL) for 12 or 28 days. In addition mice were treated with either vehicle (i.n, 25 μL) or 4856 (i.n, 25 μL; 400 μg/mouse) twice daily from day 1-28 or 13-28. Lung sections were stained with goat anti-pSmad2/3 antibodies (Santa Cruz Biotechnology, Heidelberg, Germany) and type I collagen antibodies (Abcam, Cambridge, UK). HRP-conjugated- or Alexa Fluor antibodies (Life Technologies, Darmstadt, Germany) were used as secondary antibodies. Irrelevant isotype matched antibodies served as controls. Nuclei were stained using DAPI (Santa Cruz Biotechnology). Staining was visualized using a Nikon Eclipse 80i microscope (Nikon, Badhoevedorp, Netherlands). The expression of pSmad2/3 in type 1 collagen positive cells was assessed in three different fields per mouse.

Bleomycin-induced lung fibrosis was associated with an increase in pSmad2/3 expression in type 1 collagen positive cells at both day 12 and to a greater extent at day 28 compared to saline treated controls (FIG. 17B). Treatment with 4856 from day 1-28 (FIG. 17A) and from day 13-28 (FIG. 17B) significantly inhibited pSmad2/3 expression to below that of saline treated control mice, suggesting that TGFβ-dependent Smad2/3 phosphorylation was completely blocked by 4856. In addition, 4856 dosed from day 13-28 can reverse the bleomycin-induced increase in pSmad2/3 expression observed after 12 days of bleomycin challenge plus vehicle, which correlates with the effect seen on myofibroblast differentiation.

d) Summary 4856 exerted potent anti-fibrotic effects in a murine model of bleomycin-induced pulmonary fibrosis and ameliorated histological changes in collagen deposition (PSR staining), collagen accumulation (hydroxyproline assay), myofibroblast differentiation (α-SMA expression), and activation of canonical TGF-β signaling (pSmad2/3 expression). Furthermore, 4856 proved efficacious when dosed either prophylactically from day 1-28 or as an intervention from day 13-28 after fibrotic changes were already evident. This supports the hypothesis that it is possible to locally inhibit TGFβ in the lung, potentially avoiding unwanted systemic events.

Example 10—Biophysical Analysis of Humanized 4856 Fab Grafts

The humanized grafts of antibody 4856: gL3gH13, gL3gH20, gL3gH23, gL3gH29 were subjected to a series of biochemical and biophysical analyses to screen and select the most robust molecule for development and administration stability. The analyses included comparison of characteristics such as $T_m$ (melting temperature at mid-point of unfolding); experimental pI, and aggregation stability at an air-liquid interface (mimic of shear stress in manufacture and nebulization stability); and deamidation propensity.

Thermal Stability Measurement (Tm)

A fluorescence-based thermal shift assay (also referred to as the thermofluor assay) was performed to obtain the $T_m$ (temperature at the mid-point of unfolding) to assess the thermal stabilities of purified molecules. The reaction mix contained 5 µl of 30×SYPRO® Orange dye (Invitrogen), diluted with PBS from 5000× stock solution and 45 µl of sample at 0.12 mgml$^{-1}$, (in PBS pH 7.4). 10 µl of the mix was dispensed in quadruplicate into a 384 PCR optical well plate and was run on a 7900HT Fast Real-Time PCR System (Applied Biosystems). The PCR system heating device was set at 20° C. to 99° C. with a ramp rate of 1.1° C. min$^{-1}$. A charge-coupled device monitored fluorescence changes in the wells. Intensity increases were plotted, the inflection point of the slope(s) was used to generate the $T_m$.

$T_m$ (the temperature at the midpoint of unfolding) was determined by the thermofluor assay. In this method, SYPRO orange (fluorescent dye) is used to monitor the unfolding process by binding to hydrophobic regions that become exposed during thermal ramping. A higher $T_m$ value equates to a greater molecular stability and robustness to developability and nebulisation stress.

One unfolding domain, as expected, was observed for all molecules, equivalent to the Fab unfolding domain. The results are summarised in Table 10.

It was possible to rank the molecules based on their melting temperature: gL3gH13 was shown to have the highest melting temperature, the substitution of N109G with D109G in the HC CDR3 (gL3gH29) resulted in a 2° C. decrease in the melting temperature and both gL3gH23 and gL3gH20 exhibited a further 2° C. decrease in the melting temperature. gL3gH13 had the highest melting temperature of 79° C. which makes it an excellent candidate for use in local delivery to the lung via nebulization where the Fab has to retain sufficient biological activity following nebulization.

TABLE 10

$T_m$ Analysis:
Thermofluor Assay:
gL3gH13 > gL3gH29 > gL3gH20 = gL3gH23

| Antibody 4856 Fab graft | Tm° C. |
|---|---|
| gL3gH13 | 79.0 |
| gL3gH20 | 75.3 |
| gL3gH23 | 75.7 |
| gL3gH29 | 77.0 |

Experimental pI and Analysis of Charge Variants Purified samples were analysed using whole-capillary imaged cIEF ICE3 system (ProteinSimple). Samples were prepared by mixing the following: 30 µl sample (from a 1 mg/ml stock in HPLC grade water), 35 µl of 1% methylcellulose solution (Protein Simple), 4 µl pH3-10 ampholytes (Pharmalyte), 0.5 µl of 4.65 and 0.5 µl 9.77 synthetic pI markers (ProteinSimple), 12.5 µl of 8M urea solution (Sigma-Aldrich). HPLC grade water was used to make up the final volume to 100 µl. The mixture was vortexed briefly to ensure complete mixing and centrifuged at 10,000 rpm for 3 minutes to remove air bubbles before analysis. Samples were focused for 1 min at 1.5 kV, followed by 5 min at 3 kV, and $A_{280}$ images of the capillary were taken using the ProteinSimple software. The resulting electropherograms were first analysed using iCE3 software and pI values were assigned (linear relationship between the pI markers). The calibrated electropherograms were then integrated using Empower software (Waters).

The pI of all lead candidates was high (see Table 11) such that it is unlikely that the molecules would have approximately zero overall molecular charge (where there is increased risk of aggregation) at the expected formulation pH. The experimental pI was found to be similar for all molecules and so could not discriminate between them.

TABLE 11

Experimental pI

| | Experimental pI |
|---|---|
| gL3gH13 | 9.34 |
| gL3gH20 | 9.25 |
| gL3gH23 | 9.34 |
| gL3gH29 | 9.10 |

Aggregation Propensity at an Air-Liquid Interface

Purified samples (3×250 µl aliquots) in PBS pH 7.4 at 1 mg $ml^{-1}$ were vortexed at 1400 rpm at 25° C. in 1.5 ml eppendorfs using an Eppendorf Mixmate. Samples were analysed for turbidity generation at various time-points post vortexing by obtaining absorption at 595 nm using a spectrophotometer (Varian). The data was plotted versus time.

All lead candidates were subjected to stress by vortexing to provide information on aggregation stability at an air-liquid interface. This served to mimic shear during manufacture as well as potential stability during nebulisation. Aggregation stability was monitored by measurement of turbidity at 595 nm up to 144 hours. The rate of aggregation was slow (low absorbance values) and no difference was observed between the grafts.

Analysis of Deamidation Status Asn(N)109 (Heavy Chain CDR3).

A deamidation motif in the heavy chain CDR3 for gL3gH13, gL3gH20 (both N109G) and gL3gH23 (N109A) is present. Chemical instability at this site could result in product heterogeneity and immunogenicity. Graft gL3gH29 has D109G at this site (the deamidated product) to test suitability as a candidate whilst minimising the risk of deamidation.

The basal percent deamidation at N109 in the heavy chain CDR3 for gL3gH13, gL3gH20 and gL3gH23 immediately post purification was determined by (i) tryptic digestion/peptide mapping/mass spectrometry and (ii) capillary imaged isoelectric focusing (ICE3). The rate/propensity for the N109 site to deamidate (loss of ammonia; generation of acidic species) was determined by subjecting the three molecules to accelerated stress conditions known to promote deamidation (pH 8, 37° C.).

(i) Mass Spectrometry

Aliquots (50 µg) were reduced with DTT, alkylated with iodoacetamide then digested with trypsin (1:20w/w) overnight at room temperature. The digest (~2 µg) was analysed by injection onto a C18 column (1×150 mm BEH-300) equilibrated with 0.2% formic acid/water. The resultant peptides were eluted at 20 µL/minute with an acetonitrile gradient into a Thermo Fusion mass spectrometer operated in +ve-ion mode. Data dependent acquisition (DDA) consisted of an orbitrap full scan (120000 resolution) followed by HCD fragmentation and ion-trap measurement of the most intense precursors. MS data was analysed using Thermo Pepfinder to match acquired spectra against the expected sequence of the antibody.

The percent basal level of deamidation (ammonia loss) at site N109G (heavy chain CDR3) in gL3gH13 and gL3gH20 was similar (~4%), whereas, no deamidation was noted at N109A for gL3gH23.

After accelerated stress (pH 8 for 2 weeks at 4° C. and 37° C.), there was no change in the levels of deamidation for any Fab graft (Table 12).

Overall, substitution of N109G with N109A resulted in gL3gH23 having a potentially lower deamidation risk. However, since the basal level was low for all and there was no increased propensity post accelerated stress, all molecules have a deamidation level that would be suitable for a therapeutic candidate.

TABLE 12

Percent deamidation pre and post accelerated stress (pH 8).

| | gL3gH13 | gL3gH20 | gL3gH23 | gL3gH29 |
|---|---|---|---|---|
| Site (Heavy Chain CDR3) | N109G | N109G | N109A | D109G |
| T0 (basal level) | 4.70% | 4.10% | not detected | not detected |
| 2 weeks/4° C. | 4.40% | 4.00% | not detected | not detected |
| 2 weeks/37° C. | 3.40% | 2.40% | not detected | not detected |

(ii) Capillary Imaged Isoelectric Focusing (ICE3)

ICE3 was performed as described above for pI measurement and the results showed no significant differences between the gL3gH13, gL3gH2O, gL3gH23 and gL3gH29 grafts in % charged Species Pre and Post Accelerated Stress (pH 8).

Example 11—Nebulization Study of Humanized 4856 Fab Graft gL3gH13

The aggregation stability to the shear forces exerted by nebulisation of Fab 4856 graft gL3gH13 (referred to hereafter as 4856) was determined utilising an investigational PARI eFlow® nebulizer (PARI Pharma GmBh, Grafeling, Germany) *E. coli* expressed Fab 4856 at ~100 mg/mL in a pH 6.0 buffer diluted to nominal concentrations 20 mg/mL, 50 mg/mL and 80 mg/mL and a pH 7.4 buffer diluted to nominal concentrations 20 mg/mL and 50 mg/mL.

Pre-filtered/sterile samples of the 4856 samples (~1.0 mL) at different concentrations and buffers were nebulised using the eFlow® nebuliser.

(i) Effect of Nebulisation on Concentration

Diluted samples (<1 AU at 280 nm) were measured using a Varian Cary 50-Bio UV/Vis Spectrophotometer. Concentration was calculated using an extinction coefficient of 1.72 AU (280 nm, 1 mg/mL, and lcm path length).

No difference in concentration (mg/mL) was observed between the pre and post nebulised samples.

(ii) Size Exclusion HPLC (SEC HPLC)

This analysis monitored the generation of soluble aggregates and fragmented material.

Samples were diluted to 1 mg/mL (25 μL injection volume) or 5 mg/mL (20 μL injection volume). Analysis was performed using a TSK G3000SW (7.7 mm I.D×30.0 cm) column connected to an Agilent 1100 system, eluted isocratically using 0.2 M sodium phosphate, pH 7 at 1.0 mL/min for 17 minutes, 30° C. The peaks were monitored at 280 nm.

No difference was observed in the percent of high molecular weight species (HMW) present in the pre- and post-nebulised material. Hence nebulisation did not result in the generation of soluble aggregate. There was no evidence for any low molecular weight material hence no fragmentation observed as a consequence of nebulisation.

(iii) Dynamic Light Scattering (DLS)

This analysis monitored the generation of large molecular weight species (insoluble particulate material that would be filtered by SEC HPLC column matrix). Fab 4856 in buffer comprising histidine and sodium chloride, at pH 6.0 was tested by dynamic light scattering using a Malvern Nano ZS instrument.

No difference was observed in the main peak intensity (%) from the intensity size distribution profile (SDP) for 4856 up to 50 mg/mL in the pre and post nebulization samples. With regards to percent poly-dispersity (% PD), the intensity distribution is heavily weighted to larger molecular weight material (scattering is proportional to the square of the molecular weight) and when this is converted to volume distribution describing the relative proportion of multiple species present, minimal insignificant changes were observed up to 50 mg/mL.

(iv) SDS PAGE (Non-Reducing and Reducing Conditions)

This analysis monitored the generation of aggregation/fragmentation in buffer comprising histidine and NaCl, at pH 6.0.

For non-reducing conditions, 10 μL of sample at 1 mg/mL was mixed with 10 μL of Tris/Glycine SDS Sample Buffer (2×, Invitrogen) and 2 μL of 100 mM N-ethylmaleimide; heated at 100° C. for 2 minutes.

For reducing conditions, 10 μL of sample at 1 mg/mL was mixed with 10 μL of Tris/Glycine SDS Sample Buffer (2×, Invitrogen) and 2 μL of DTT (10× Invitrogen); heated at 100° C. for 3 minutes.

After centrifugation, 10 μL (4.5 μg) of each sample was loaded onto a Novex Tris/Glycine (4-20%) gel (Invitrogen) and electrophoresed at 125 mV (constant voltage) for 100 minutes. The bands were visualised by Coomassie Blue.

No difference was observed between pre and post nebulisation samples up to 20 mg/mL.

(vi) Functional In Vitro Assay.

This analysis was performed in histidine pH 6.0, NaCl, at 20, 50 and 80 mg/mL.

HEK-Blue TGF-beta reporter gene assay using recombinant TGF-beta 1 was carried out as described in Example 3.

No significant differences in IC50 were observed between pre and post nebulised samples at any concentration.

(v) Aerosol Characterisation of the Nebulised Antibody in a Breath Simulation

This analysis monitored the droplet size as well as delivered dose and nebulisation times of Fab 4856 at a concentration of 50 mg/mL (pH 6.0) using the PARI eFlow® nebuliser. Briefly, the nebuliser was connected to a sinus pump and aerosol droplets containing the nebulised material was collected on an inspiratory collection filter. An adult breathing pattern was used, with a tidal volume of 500 ml at 15 breaths per minute and an inhalation:exhalation ratio of 50:50. After completion, the collection filter was washed to extract the nebulised material, which was analysed by HPLC (Table 13).

TABLE 13

Data from the breath simulation experiments using two different nebuliser heads.

| Mass Median Diameter (MMD) | | 2.9 μm | | 3.7 μm | |
|---|---|---|---|---|---|
| | | Mean | SD (n = 6) | Mean | SD (n = 6) |
| Nebulization time | min | 14.10* After back flushing: 5.75 | 5.00 | 3.62 | 0.34 |
| DD | mg | 71.5 | 5.5 | 66.4 | 3.5 |
| DD | % | 68.0 | 5.1 | 63.5 | 3.4 |
| Residue | mg | 14.7 | 3.2 | 22.9 | 2.1 |
| Residue | % | 14.0 | 3.1 | 21.9 | 2.0 |
| RD <5 μm | mg | 66.6 | 5.0 | 52.1 | 4.3 |
| RD <5 μm | % | 63.4 | 4.6 | 49.8 | 4.2 |
| RD <3.3 μm | mg | 45.2 | 4.9 | 25.7 | 3.1 |
| RD <3.3 μm | % | 43.1 | 4.7 | 24.6 | 2.9 |
| DDR | mg/min | 2.2 | 1.2 | 20.8 | 3.3 |
| DDR | %/min | 2.1 | 1.1 | 19.9 | 3.2 |

Delivered Dose (DD) was determined by breath simulation experiments. The DD [%] was 68% (2.9 μm MMD) and 64% (3.7 μm MMD), which is judged to be a typical good result as DD values are rarely over 70%. The residue was 14% (2.9 μm MMD) and 21.9% (3.7 μm MMD), which is also in the typical range. The Respirable Doses <5 μm (RD<5 μm) are 6300 (2.9 μm MMD) vs. 50% (3.7 μm MMD). Particle size affects delivery to the different regions of the respiratory pathway, and RD<5 μm corresponds to alveolar delivery.

These data confirm the suitability of the 4856 Fab for delivery by nebulisation.

Example 12—X-Ray Crystallography Structure

The antibody 4856 was crystallised with TGF-beta1 to determine the amino acid residues that the antibody contacts.

i) Sample Preparation 2 ml of mature TGF-beta 1 at 2.25 mg/ml in 5 mM HCl was adjusted to pH7 by addition of 30 ul 2M Tris pH8. After incubation at RT for 1 hr the precipitate was removed by centrifugation leaving 2 ml at 2.1 mg/ml. To this was added 0.46 ml Fab4856gL3gH13 at 32 mg/ml (14.7 mg) an approximate molar ratio of 1:1.1 TGF-beta 1:Fab. This was left at RT for 1 hr then loaded onto an S200 16/160 column pre-equilibrated in 50 mM NaCl, 25 mM Tris, 5% glycerol, pH 7.5. Peak fractions of the complex were pooled and concentrated to 10 mg/ml for crystallography.

ii) Crystallization

| Crystallization experiment type | Sitting drop, vapour diffusion | | |
|---|---|---|---|
| Crystallization condition | 0.1 M Sodium phosphate citrate pH4.2, 40% PEG300 | | |
| Protein concentration | 10 mg/ml | Drop volume/ratio | 0.4 ul Protein + 0.4 ul Reservoir |
| Crystal growth time | 8-21 days | | |
| Cryoprotection | Crystals were harvested from the drop and flash-frozen in liquid nitrogen (−180° C.) within 10 seconds. | | |

Screening was performed using the various conditions that were available from Qiagen (approximately 2000 conditions). The incubation and imaging was performed by Formulatrix RockImager 1000 (for a total incubation period of 21 days).

iii) Data Collection and Structure Refinement

| X-ray source | Diamond synchrotron | | |
|---|---|---|---|
| Experiment Type | oscillation | Wavelength | 0.92819 Å |
| Processing Software | Mosflm | | |
| Resolution Limits | 40-2.48 | Space group | $P6_522$ |
| Unit Cell parameters | a = 114.0 Å $\alpha$ = 90° | b =114.0 Å $\beta$ = 90° | c = 289.5 Å $\gamma$ = 120° |
| Completeness | 99.9 (100.0) | Multiplicity | 18.3 (19.0) |
| $I/\sigma(I)$ | 20.1 (3.7) | $R_{merge}$ | 11.2% (83.2%) |
| Number of reflections | 741045 (109123) | Number of unique reflections | 40392 (5758) |
| Comments | | | |

| Structure determination method | Molecular Replacement | Program(s) used | Phaser |
|---|---|---|---|
| Structure template | internal human Fab, 3KFD | | |
| Refinement program | Refmac | Resolution limits | 40-2.48 |
| R factor | 22.18% | Free R factor | 25.14% |
| Number of non-hydrogen atoms | | 4175 | |

| Structure determination method | Molecular Replacement | Program(s) used | Phaser |
|---|---|---|---|
| RMSD bond length | 0.0205 Å | RMSD bond angle | 2.057° |
| Ramachandran favoured | 515 (94.5%) | Ramachandran outliers | 2 (0.37%) |
| Comments | rebuilt using Coot | | |

TGF-beta 1 residues interacting with 4856gL3gH13 Fab are given in FIGS. 18A and 18B. 4856gL3gH13 Fab binds in a region that overlays with the receptor binding region suggesting that receptor blockade by 4856gL3gH13 Fab is by competition, the anti-TGF-beta 1 being effective by superior affinity. A variant of 4856gL3H13 containing an asparagine substitution for threonine in the light chain (position 5 of SEQ ID NO:45) was also tested and found to cause no change in the structure.

Similarly, the single chain antibody format of antibody 4856 (scFv 4856, SEQ ID NO: 108) was crystallised with TGF-beta 2 (SEQ ID NO: 116) to determine the amino acid residues that the antibody contacts. The TGF-beta 2 residues interacting with scFv 4856 are given in FIG. 18C, showing binding in the same region as shown for the Fab binding of TGF-beta 1.

SEQUENCE LISTING

```
<160> NUMBER OF SEQ ID NOS: 118

<210> SEQ ID NO 1
<211> LENGTH: 11
<212> TYPE: PRT
<213> ORGANISM: Artificial Sequence
<220> FEATURE:
<223> OTHER INFORMATION: CDRL1

<400> SEQUENCE: 1

Gln Ala Ser Glu Ser Ile Tyr Ser Gly Leu Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: CDRL2

<400> SEQUENCE: 2

Ala Ala Ser Asp Leu Ala Ser
1               5

<210> SEQ ID NO 3
<211> LENGTH: 12
<212> TYPE: PRT
<213> ORGANISM: Artificial Sequence
<220> FEATURE:
<223> OTHER INFORMATION: CDRL3

<400> SEQUENCE: 3

Gln Gln Thr Trp Thr Asp Gly Gly Ile Asp Asn Pro
1               5                   10

<210> SEQ ID NO 4
<211> LENGTH: 10
<212> TYPE: PRT
<213> ORGANISM: Artificial Sequence
<220> FEATURE:
<223> OTHER INFORMATION: CDRH1

<400> SEQUENCE: 4

Gly Phe Ser Leu Ser Ser Tyr Asp Met Ser
1               5                   10
```

```
<210> SEQ ID NO 5
<211> LENGTH: 17
<212> TYPE: PRT
<213> ORGANISM: Artificial Sequence
<220> FEATURE:
<223> OTHER INFORMATION: CDRH2

<400> SEQUENCE: 5

Ile Ile Tyr Gly Gly Ser Gly Ser Thr Trp Tyr Ala Ser Trp Ala Lys
1               5                   10                  15

Gly

<210> SEQ ID NO 6
<211> LENGTH: 15
<212> TYPE: PRT
<213> ORGANISM: Artificial Sequence
<220> FEATURE:
<223> OTHER INFORMATION: CDRH3

<400> SEQUENCE: 6

Gly Arg Asp Gly Gly Ala Gly Gly Ser Arg Asn Gly Tyr Ser Leu
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: CDRH3 var1

<400> SEQUENCE: 7

Gly Arg Asp Ala Gly Ala Gly Gly Ser Arg Asn Gly Tyr Ser Leu
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: CDRH3 var 2

<400> SEQUENCE: 8

Gly Arg Asp Ala Gly Ala Gly Gly Ser Arg Asn Ala Tyr Ser Leu
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: CDRH3 var3

<400> SEQUENCE: 9

Gly Arg Asp Ala Gly Ala Gly Gly Ser Arg Asp Gly Tyr Ser Leu
1               5                   10                  15

<210> SEQ ID NO 10
<211> LENGTH: 110
<212> TYPE: PRT
<213> ORGANISM: Artificial Sequence
<220> FEATURE:
<223> OTHER INFORMATION: Rabbit 4856 VL

<400> SEQUENCE: 10

Ala Tyr Asp Met Thr Gln Thr Pro Ala Ser Val Glu Val Ala Val Gly
1               5                   10                  15
```

Gly Thr Val Thr Ile Lys Cys Gln Ala Ser Glu Ser Ile Tyr Ser Gly
            20                  25                  30

Leu Ala Trp Tyr Gln Gln Thr Pro Gly Gln Arg Pro Lys Leu Leu Ile
        35                  40                  45

Tyr Ala Ala Ser Asp Leu Ala Ser Gly Val Pro Ser Arg Phe Lys Gly
50                  55                  60

Ser Gly Ser Gly Thr Glu Tyr Thr Leu Thr Ile Ser Gly Val Glu Cys
65                  70                  75                  80

Ala Asp Ala Ala Thr Tyr Tyr Cys Gln Gln Thr Trp Thr Asp Gly Gly
                85                  90                  95

Ile Asp Asn Pro Phe Gly Gly Thr Glu Val Val Val Lys
            100                 105                 110

<210> SEQ ID NO 11
<211> LENGTH: 330
<212> TYPE: DNA
<213> ORGANISM: Artificial Sequence
<220> FEATURE:
<223> OTHER INFORMATION: Rabbit 4856 VL

<400> SEQUENCE: 11
gcctatgata tgacccagac tccagcctct gtggaggtag ctgtgggagg cacagtcacc      60
atcaagtgcc aggccagtga gagcatttac agtggtttgg cctggtatca gcagacacca     120
gggcagcgtc ccaagctcct gatctatgct gcatccgatc tggcatctgg ggtcccatcg     180
cgattcaaag gcagtggatc tgggacagag tacactctca ccatcagcgg cgtggagtgt     240
gccgatgctg ccacttacta ctgtcaacag acttggactg atggtggtat tgataatcct     300
ttcggcggag ggaccgaggt ggtggtcaaa                                       330

<210> SEQ ID NO 12
<211> LENGTH: 132
<212> TYPE: PRT
<213> ORGANISM: Artificial Sequence
<220> FEATURE:
<223> OTHER INFORMATION: Rabbit 4856 VL region with signal sequence

<400> SEQUENCE: 12

Met Asn Met Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Glu Val Ala Val Gly Gly Thr Val Thr Ile Lys Cys Gln Ala Ser
        35                  40                  45

Glu Ser Ile Tyr Ser Gly Leu Ala Trp Tyr Gln Gln Thr Pro Gly Gln
    50                  55                  60

Arg Pro Lys Leu Leu Ile Tyr Ala Ala Ser Asp Leu Ala Ser Gly Val
65                  70                  75                  80

Pro Ser Arg Phe Lys Gly Ser Gly Ser Gly Thr Glu Tyr Thr Leu Thr
                85                  90                  95

Ile Ser Gly Val Glu Cys Ala Asp Ala Ala Thr Tyr Tyr Cys Gln Gln
            100                 105                 110

Thr Trp Thr Asp Gly Gly Ile Asp Asn Pro Phe Gly Gly Thr Glu
        115                 120                 125

Val Val Val Lys
    130

<210> SEQ ID NO 13
<211> LENGTH: 396
<212> TYPE: DNA
<213> ORGANISM: Artificial Sequence
<220> FEATURE:
<223> OTHER INFORMATION: Rabbit 4856 VL with signal sequence

<400> SEQUENCE: 13

```
atgaacatga gggcccccac tcagctgctg gggctcctgc tgctctggct cccaggtgcc      60
agatgtgcct atgatatgac ccagactcca gcctctgtgg aggtagctgt gggaggcaca     120
gtcaccatca agtgccaggc cagtgagagc atttacagtg gtttggcctg gtatcagcag     180
acaccagggc agcgtcccaa gctcctgatc tatgctgcat ccgatctggc atctggggtc     240
ccatcgcgat tcaaaggcag tggatctggg acagagtaca ctctcaccat cagcggcgtg     300
gagtgtgccg atgctgccac ttactactgt caacagactt ggactgatgg tggtattgat     360
aatcctttcg gcggagggac cgaggtggtg gtcaaa                                396
```

<210> SEQ ID NO 14
<211> LENGTH: 121
<212> TYPE: PRT
<213> ORGANISM: Artificial Sequence
<220> FEATURE:
<223> OTHER INFORMATION: Rabbit 4856 VH

<400> SEQUENCE: 14

```
Gln Ser Leu Glu Glu Ser Gly Gly Arg Leu Val Thr Pro Gly Thr Pro
1               5                   10                  15
Leu Thr Leu Thr Cys Thr Ala Ser Gly Phe Ser Leu Ser Ser Tyr Asp
            20                  25                  30
Met Ser Trp Val Arg Gln Ala Pro Gly Lys Gly Leu Glu Trp Ile Gly
        35                  40                  45
Ile Ile Tyr Gly Gly Ser Gly Ser Thr Trp Tyr Ala Ser Trp Ala Lys
    50                  55                  60
Gly Arg Phe Thr Met Ser Lys Thr Ser Thr Thr Val Asp Leu Lys Ile
65                  70                  75                  80
Thr Ser Pro Thr Thr Glu Asp Met Ala Thr Tyr Phe Cys Ala Arg Gly
                85                  90                  95
Arg Asp Gly Gly Ala Gly Gly Ser Arg Asn Gly Tyr Ser Leu Trp Gly
            100                 105                 110
Gln Gly Thr Leu Val Thr Val Ser Ser
        115                 120
```

<210> SEQ ID NO 15
<211> LENGTH: 363
<212> TYPE: DNA
<213> ORGANISM: Artificial Sequence
<220> FEATURE:
<223> OTHER INFORMATION: Rabbit 4856 VH

<400> SEQUENCE: 15

```
cagtcgctgg aggagtccgg gggtcgcctg gtcacgcctg gacacccct gacactcacc       60
tgcacagcct ctggattctc cctcagcagc tacgacatga gctgggtccg ccaggctcca    120
gggaagggc tggaatggat cggaatcatt tatggtggta gtggtagcac atggtacgcg     180
agctgggcga aaggccgatt caccatgtcc aaaacgtcga ccacggtgga tctgaaaatc    240
accagtccga cgaccgagga catggccacc tatttctgtg ccagaggacg ggatggtggt    300
gctggtggtt ctcgtaatgg ctattccttg tggggccaag gcaccctggt caccgtctcg    360
```

<210> SEQ ID NO 16
<211> LENGTH: 140
<212> TYPE: PRT
<213> ORGANISM: Artificial Sequence
<220> FEATURE:
<223> OTHER INFORMATION: Rabbit 4856 VH with signal sequence

<400> SEQUENCE: 16

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Ala Ser Gly Phe Ser Leu Ser
        35                  40                  45

Ser Tyr Asp Met Ser Trp Val Arg Gln Ala Pro Gly Lys Gly Leu Glu
    50                  55                  60

Trp Ile Gly Ile Ile Tyr Gly Gly Ser Gly Ser Thr Trp Tyr Ala Ser
65                  70                  75                  80

Trp Ala Lys Gly Arg Phe Thr Met Ser Lys Thr Ser Thr Thr Val Asp
                85                  90                  95

Leu Lys Ile Thr Ser Pro Thr Thr Glu Asp Met Ala Thr Tyr Phe Cys
            100                 105                 110

Ala Arg Gly Arg Asp Gly Gly Ala Gly Gly Ser Arg Asn Gly Tyr Ser
        115                 120                 125

Leu Trp Gly Gln Gly Thr Leu Val Thr Val Ser Ser
    130                 135                 140

<210> SEQ ID NO 17
<211> LENGTH: 420
<212> TYPE: DNA
<213> ORGANISM: Artificial Sequence
<220> FEATURE:
<223> OTHER INFORMATION: Rabbit 4856 VH with signal sequence

<400> SEQUENCE: 17
atggagactg ggctgcgctg gcttctcctg gtcgctgtgc tcaaaggtgt ccagtgtcag       60
tcgctggagg agtccggggg tcgcctggtc acgcctggga caccctgac actcacctgc      120 acagcctctg gattctccct cagcagctac gacatgagct gggtccgcca ggctccaggg     180
aaggggctgg aatggatcgg aatcatttat ggtggtagtg gtagcacatg gtacgcgagc     240
tgggcgaaag gccgattcac catgtccaaa acgtcgacca cggtggatct gaaaatcacc     300
agtccgacga ccgaggacat ggccacctat ttctgtgcca gaggacggga tggtggtgct     360
ggtggttctc gtaatggcta ttccttgtgg ggccaaggca ccctggtcac cgtctcgagt     420

<210> SEQ ID NO 18
<211> LENGTH: 214
<212> TYPE: PRT
<213> ORGANISM: Artificial Sequence
<220> FEATURE:
<223> OTHER INFORMATION: rabbit 4856 light chain

<400> SEQUENCE: 18

Ala Tyr Asp Met Thr Gln Thr Pro Ala Ser Val Glu Val Ala Val Gly
1               5                   10                  15

Gly Thr Val Thr Ile Lys Cys Gln Ala Ser Glu Ser Ile Tyr Ser Gly
            20                  25                  30

```
Leu Ala Trp Tyr Gln Gln Thr Pro Gly Gln Arg Pro Lys Leu Leu Ile
         35                  40                  45

Tyr Ala Ala Ser Asp Leu Ala Ser Gly Val Pro Ser Arg Phe Lys Gly
 50                  55                  60

Ser Gly Ser Gly Thr Glu Tyr Thr Leu Thr Ile Ser Gly Val Glu Cys
 65                  70                  75                  80

Ala Asp Ala Ala Thr Tyr Tyr Cys Gln Gln Thr Trp Thr Asp Gly Gly
                 85                  90                  95

Ile Asp Asn Pro Phe Gly Gly Gly Thr Glu Val Val Val Lys Arg Thr
                100                 105                 110

Pro Val Ala Pro Thr Val Leu Ile Phe Pro Pro Ala Ala Asp Gln Val
            115                 120                 125

Ala Thr Gly Thr Val Thr Ile Val Cys Val Ala Asn Lys Tyr Phe Pro
        130                 135                 140

Asp Val Thr Val Thr Trp Glu Val Asp Gly Thr Thr Gln Thr Thr Gly
145                 150                 155                 160

Ile Glu Asn Ser Lys Thr Pro Gln Asn Ser Ala Asp Cys Thr Tyr Asn
                165                 170                 175

Leu Ser Ser Thr Leu Thr Leu Thr Ser Thr Gln Tyr Asn Ser His Lys
                180                 185                 190

Glu Tyr Thr Cys Lys Val Thr Gln Gly Thr Thr Ser Val Val Gln Ser
            195                 200                 205

Phe Asn Arg Gly Asp Cys
    210

<210> SEQ ID NO 19
<211> LENGTH: 642
<212> TYPE: DNA
<213> ORGANISM: Artificial Sequence
<220> FEATURE:
<223> OTHER INFORMATION: rabbit 4856 light chain

<400> SEQUENCE: 19
gcctatgata tgacccagac tccagcctct gtggaggtag ctgtgggagg cacagtcacc      60
atcaagtgcc aggccagtga gagcatttac agtggtttgg cctggtatca gcagacacca     120
gggcagcgtc ccaagctcct gatctatgct gcatccgatc tggcatctgg ggtcccatcg     180
cgattcaaag gcagtggatc tgggacagag tacactctca ccatcagcgg cgtggagtgt     240
gccgatgctg ccacttacta ctgtcaacag acttggactg atggtggtat tgataatcct     300
ttcggcggag ggaccgaggt ggtggtcaaa cgtacgccag ttgcacctac tgtcctcatc     360
ttcccaccag ctgctgatca ggtggcaact ggaacagtca ccatcgtgtg tgtggcgaat     420
aaatactttc ccgatgtcac cgtcacctgg gaggtggatg gcaccaccca aacaactggc     480
atcgagaaca gtaaaacacc gcagaattct gcagattgta cctacaacct cagcagcact     540
ctgacactga ccagcacaca gtacaacagc cacaaagagt acacctgcaa ggtgacccag     600
ggcacgacct cagtcgtcca gagcttcaat aggggtgact gt                         642

<210> SEQ ID NO 20
<211> LENGTH: 236
<212> TYPE: PRT
<213> ORGANISM: Artificial Sequence
<220> FEATURE:
<223> OTHER INFORMATION: Rabbit 4856 light chain with signal sequence

<400> SEQUENCE: 20

Met Asn Met Arg Ala Pro Thr Gln Leu Leu Gly Leu Leu Leu Leu Trp
```

```
1               5                   10                  15
Leu Pro Gly Ala Arg Cys Ala Tyr Asp Met Thr Gln Thr Pro Ala Ser
                20                  25                  30
Val Glu Val Ala Val Gly Gly Thr Val Thr Ile Lys Cys Gln Ala Ser
                35                  40                  45
Glu Ser Ile Tyr Ser Gly Leu Ala Trp Tyr Gln Gln Thr Pro Gly Gln
    50                  55                  60
Arg Pro Lys Leu Leu Ile Tyr Ala Ala Ser Asp Leu Ala Ser Gly Val
65                  70                  75                  80
Pro Ser Arg Phe Lys Gly Ser Gly Ser Gly Thr Glu Tyr Thr Leu Thr
                85                  90                  95
Ile Ser Gly Val Glu Cys Ala Asp Ala Ala Thr Tyr Tyr Cys Gln Gln
                100                 105                 110
Thr Trp Thr Asp Gly Gly Ile Asp Asn Pro Phe Gly Gly Gly Thr Glu
                115                 120                 125
Val Val Val Lys Arg Thr Pro Val Ala Pro Thr Val Leu Ile Phe Pro
    130                 135                 140
Pro Ala Asp Gln Val Ala Thr Gly Thr Val Thr Ile Val Cys Val
145                 150                 155                 160
Ala Asn Lys Tyr Phe Pro Asp Val Thr Val Thr Trp Glu Val Asp Gly
                165                 170                 175
Thr Thr Gln Thr Thr Gly Ile Glu Asn Ser Lys Thr Pro Gln Asn Ser
                180                 185                 190
Ala Asp Cys Thr Tyr Asn Leu Ser Ser Thr Leu Thr Leu Thr Ser Thr
                195                 200                 205
Gln Tyr Asn Ser His Lys Glu Tyr Thr Cys Lys Val Thr Gln Gly Thr
    210                 215                 220
Thr Ser Val Val Gln Ser Phe Asn Arg Gly Asp Cys
225                 230                 235

<210> SEQ ID NO 21
<211> LENGTH: 708
<212> TYPE: DNA
<213> ORGANISM: Artificial Sequence
<220> FEATURE:
<223> OTHER INFORMATION: Rabbit 4856 light chain with signal sequence
      underlined

<400> SEQUENCE: 21
atgaacatga gggcccccac tcagctgctg gggctcctgc tgctctggct cccaggtgcc      60
agatgtgcct atgatatgac ccagactcca gcctctgtgg aggtagctgt gggaggcaca     120
gtcaccatca gtgccaggc cagtgagagc atttacagtg gtttggcctg gtatcagcag      180
acaccagggc agcgtcccaa gctcctgatc tatgctgcat ccgatctggc atctggggtc     240
ccatcgcgat tcaaaggcag tggatctggg acagagtaca ctctcaccat cagcggcgtg     300
gagtgtgccg atgctgccac ttactactgt caacagactt ggactgatgg tggtattgat     360
aatccttcg gcggagggac cgaggtggtg gtcaaacgta cgccagttgc acctactgtc     420
ctcatcttcc caccagctgc tgatcaggtg gcaactggaa cagtcaccat cgtgtgtgtg     480
gcgaataaat actttcccga tgtcaccgtc acctgggagg tggatggcac acccaaaca     540
actggcatcg agaacagtaa aaccgcag aattctgcag attgtaccta caacctcagc      600
agcactctga cactgaccag cacacagtac aacagccaca agagtacac ctgcaaggtg      660
acccagggca cgacctcagt cgtccagagc ttcaataggg gtgactgt                  708
```

<210> SEQ ID NO 22
<211> LENGTH: 216
<212> TYPE: PRT
<213> ORGANISM: Artificial Sequence
<220> FEATURE:
<223> OTHER INFORMATION: Rabbit 4856 Fab heavy chain

<400> SEQUENCE: 22

```
Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Asp
            20                  25                  30

Met Ser Trp Val Arg Gln Ala Pro Gly Lys Gly Leu Glu Trp Ile Gly
        35                  40                  45

Ile Ile Tyr Gly Gly Ser Gly Ser Thr Trp Tyr Ala Ser Trp Ala Lys
    50                  55                  60

Gly Arg Phe Thr Met Ser Lys Thr Ser Thr Thr Val Asp Leu Lys Ile
65                  70                  75                  80

Thr Ser Pro Thr Thr Glu Asp Met Ala Thr Tyr Phe Cys Ala Arg Gly
                85                  90                  95

Arg Asp Gly Gly Ala Gly Gly Ser Arg Asn Gly Tyr Ser Leu Trp Gly
            100                 105                 110

Gln Gly Thr Leu Val Thr Val Ser Ser Gly Gln Pro Lys Ala Pro Ser
        115                 120                 125

Val Phe Pro Leu Ala Pro Cys Cys Gly Asp Thr Pro Ser Ser Thr Val
    130                 135                 140

Thr Leu Gly Cys Leu Val Lys Gly Tyr Leu Pro Glu Pro Val Thr Val
145                 150                 155                 160

Thr Trp Asn Ser Gly Thr Leu Thr Asn Gly Val Arg Thr Phe Pro Ser
                165                 170                 175

Val Arg Gln Ser Ser Gly Leu Tyr Ser Leu Ser Ser Val Val Ser Val
            180                 185                 190

Thr Ser Ser Ser Gln Pro Val Thr Cys Asn Val Ala His Pro Ala Thr
        195                 200                 205

Asn Thr Lys Val Asp Lys Thr Val
    210                 215
```

<210> SEQ ID NO 23
<211> LENGTH: 648
<212> TYPE: DNA
<213> ORGANISM: Artificial Sequence
<220> FEATURE:
<223> OTHER INFORMATION: Rabbit 4856 Fab heavy chain

<400> SEQUENCE: 23

```
cagtcgctgg aggagtccgg gggtcgcctg gtcacgcctg ggacacccct gacactcacc      60
tgcacagcct ctggattctc cctcagcagc tacgacatga gctgggtccg ccaggctcca     120
gggaaggggc tggaatggat cggaatcatt tatggtggta gtggtagcac atggtacgcg     180
agctgggcga aaggccgatt caccatgtcc aaaacgtcga ccacggtgga tctgaaaatc     240
accagtccga cgaccgagga catggccacc tatttctgtg ccagaggacg ggatggtggt     300
gctggtggtt ctcgtaatgg ctattccttg tggggccaag gcaccctggt caccgtctcg     360
agtgggcaac taaggctcc atcagtcttc ccactggccc cctgctgcgg ggacacaccc      420
agctccacgg tgaccctggg ctgcctggtc aaaggctacc tcccggagcc agtgaccgtg     480
acctggaact cgggcaccct caccaatggg gtacgcacct tcccgtccgt ccggcagtcc     540
```

```
tcaggcctct actcgctgag cagcgtggtg agcgtgacct caagcagcca gcccgtcacc    600
tgcaacgtgg cccacccagc caccaacacc aaagtggaca agaccgtt                 648
```

<210> SEQ ID NO 24
<211> LENGTH: 235
<212> TYPE: PRT
<213> ORGANISM: Artificial Sequence
<220> FEATURE:
<223> OTHER INFORMATION: Rabbit 4856 Fab heavy chain with signal
      sequence underlined

<400> SEQUENCE: 24

```
Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Ala Ser Gly Phe Ser Leu Ser
        35                  40                  45

Ser Tyr Asp Met Ser Trp Val Arg Gln Ala Pro Gly Lys Gly Leu Glu
    50                  55                  60

Trp Ile Gly Ile Ile Tyr Gly Gly Ser Gly Ser Thr Trp Tyr Ala Ser
65                  70                  75                  80

Trp Ala Lys Gly Arg Phe Thr Met Ser Lys Thr Ser Thr Thr Val Asp
                85                  90                  95

Leu Lys Ile Thr Ser Pro Thr Thr Glu Asp Met Ala Thr Tyr Phe Cys
            100                 105                 110

Ala Arg Gly Arg Asp Gly Gly Ala Gly Gly Ser Arg Asn Gly Tyr Ser
        115                 120                 125

Leu Trp Gly Gln Gly Thr Leu Val Thr Val Ser Ser Gly Gln Pro Lys
    130                 135                 140

Ala Pro Ser Val Phe Pro Leu Ala Pro Cys Cys Gly Asp Thr Pro Ser
145                 150                 155                 160

Ser Thr Val Thr Leu Gly Cys Leu Val Lys Gly Tyr Leu Pro Glu Pro
                165                 170                 175

Val Thr Val Thr Trp Asn Ser Gly Thr Leu Thr Asn Gly Val Arg Thr
            180                 185                 190

Phe Pro Ser Val Arg Gln Ser Ser Gly Leu Tyr Ser Leu Ser Ser Val
        195                 200                 205

Val Ser Val Thr Ser Ser Ser Gln Pro Val Thr Cys Asn Val Ala His
    210                 215                 220

Pro Ala Thr Asn Thr Lys Val Asp Lys Thr Val
225                 230                 235
```

<210> SEQ ID NO 25
<211> LENGTH: 705
<212> TYPE: DNA
<213> ORGANISM: Artificial Sequence
<220> FEATURE:
<223> OTHER INFORMATION: Rabbit 4856 Fab heavy chain with signal
      sequence

<400> SEQUENCE: 25

```
atggagactg ggctgcgctg gcttctcctg gtcgctgtgc tcaaaggtgt ccagtgtcag    60
tcgctggagg agtccggggg tcgcctggtc acgcctggga cacccctgac actcacctgc   120
acagcctctg gattctccct cagcagctac gacatgagct gggtccgcca ggctccaggg   180
aaggggctgg aatggatcgg aatcatttat ggtggtagtg gtagcacatg gtacgcgagc   240
```

```
tgggcgaaag gccgattcac catgtccaaa acgtcgacca cggtggatct gaaaatcacc    300
agtccgacga ccgaggacat ggccacctat ttctgtgcca gaggacggga tggtggtgct    360
ggtggttctc gtaatggcta ttccttgtgg ggccaaggca ccctggtcac cgtctcgagt    420
gggcaaccta aggctccatc agtcttccca ctggcccct gctgcgggga cacacccagc     480
tccacggtga ccctgggctg cctggtcaaa ggctacctcc ggagccagt gaccgtgacc      540 tggaactcgg gcaccctcac caatggggta cgcaccttcc cgtccgtccg gcagtcctca    600
ggcctctact cgctgagcag cgtggtgagc gtgacctcaa gcagccagcc cgtcacctgc    660
aacgtggccc acccagccac caacaccaaa gtggacaaga ccgtt                    705
```

```
<210> SEQ ID NO 26
<211> LENGTH: 110
<212> TYPE: PRT
<213> ORGANISM: Artificial Sequence
<220> FEATURE:
<223> OTHER INFORMATION: Murinised 4856 mL1.1 V-region

<400> SEQUENCE: 26

Ala Tyr Asp Met Asn Gln Ser Pro Ser Ser Leu Ser Ala Ser Leu Gly
1               5                   10                  15

Asp Thr Ile Thr Ile Thr Cys Gln Ala Ser Glu Ser Ile Tyr Ser Gly
            20                  25                  30

Leu Ala Trp Tyr Gln Gln Lys Pro Gly Asn Ile Pro Lys Leu Leu Ile
        35                  40                  45

Tyr Ala Ala Ser Asp Leu Ala Ser Gly Val Pro Ser Arg Phe Lys Gly
    50                  55                  60

Ser Gly Ser Gly Thr Glu Tyr Thr Leu Thr Ile Ser Ser Leu Gln Pro
65                  70                  75                  80

Glu Asp Ile Ala Thr Tyr Tyr Cys Gln Gln Thr Trp Thr Asp Gly Gly
                85                  90                  95

Ile Asp Asn Pro Phe Gly Gly Gly Thr Lys Leu Glu Ile Lys
            100                 105                 110
```

```
<210> SEQ ID NO 27
<211> LENGTH: 330
<212> TYPE: DNA
<213> ORGANISM: Artificial Sequence
<220> FEATURE:
<223> OTHER INFORMATION: Murinised 4856 mL1.1 V-region

<400> SEQUENCE: 27
gcctacgaca tgaaccagtc gccatcaagc ctgagcgcct cccttggcga caccatcacc     60
attacttgcc aagcctccga aagcatctac tccggactcg cctggtatca gcagaaaccg    120
gggaacattc ccaagctcct gatctacgcc gcttccgact ggcatcggg agtgccgtca     180 cggttcaagg ggtccggatc gggaaccgag tacaccctga ctatctcctc cctgcaaccc    240
gaggatattg cgacctacta ctgtcagcag acttggacgg atggtggaat cgacaaccct    300
ttcggtggcg gcaccaagct ggaaatcaag                                     330
```

```
<210> SEQ ID NO 28
<211> LENGTH: 130
<212> TYPE: PRT
<213> ORGANISM: Artificial Sequence
<220> FEATURE:
<223> OTHER INFORMATION: Murinised 4856 mL1.1 V-region with signal
      sequence
```

<400> SEQUENCE: 28

```
Met Ser Val Pro Thr Gln Val Leu Gly Leu Leu Leu Trp Leu Thr
1               5                   10                  15

Asp Ala Arg Cys Ala Tyr Asp Met Asn Gln Ser Pro Ser Ser Leu Ser
            20                  25                  30

Ala Ser Leu Gly Asp Thr Ile Thr Ile Thr Cys Gln Ala Ser Glu Ser
        35                  40                  45

Ile Tyr Ser Gly Leu Ala Trp Tyr Gln Gln Lys Pro Gly Asn Ile Pro
    50                  55                  60

Lys Leu Leu Ile Tyr Ala Ala Ser Asp Leu Ala Ser Gly Val Pro Ser
65                  70                  75                  80

Arg Phe Lys Gly Ser Gly Ser Gly Thr Glu Tyr Thr Leu Thr Ile Ser
                85                  90                  95

Ser Leu Gln Pro Glu Asp Ile Ala Thr Tyr Tyr Cys Gln Gln Thr Trp
            100                 105                 110

Thr Asp Gly Gly Ile Asp Asn Pro Phe Gly Gly Gly Thr Lys Leu Glu
        115                 120                 125

Ile Lys
    130
```

<210> SEQ ID NO 29
<211> LENGTH: 390
<212> TYPE: DNA
<213> ORGANISM: Artificial Sequence
<220> FEATURE:
<223> OTHER INFORMATION: Murinised 4856 mL1.1 V-region with signal
      sequence

<400> SEQUENCE: 29

```
atgtctgtcc ccacccaagt cctcggactc ctgctactct ggcttacaga tgccagatgc      60
gcctacgaca tgaaccagtc gccatcaagc ctgagcgcct cccttggcga caccatcacc     120
attacttgcc aagcctccga aagcatctac tccggactcg cctggtatca gcagaaaccg     180
gggaacattc ccaagctcct gatctacgcc gcttccgact ggcatcgggg agtgccgtca     240
cggttcaagg gtccggatc gggaaccgag tacacccctg ctatctcctc cctgcaaccc      300
gaggatattg cgacctacta ctgtcagcag acttggacgg atggtggaat cgacaaccct     360
ttcggtggcg gcaccaagct ggaaatcaag                                       390
```

<210> SEQ ID NO 30
<211> LENGTH: 124
<212> TYPE: PRT
<213> ORGANISM: Artificial Sequence
<220> FEATURE:
<223> OTHER INFORMATION: Murinised 4856 mH2.1 V-region

<400> SEQUENCE: 30

```
Glu Val Lys Leu Leu Glu Ser Gly Gly Gly Leu Val Gln Pro Gly Gly
1               5                   10                  15

Ser Leu Lys Leu Ser Cys Thr Ala Ser Gly Phe Ser Leu Ser Ser Tyr
            20                  25                  30

Asp Met Ser Trp Val Arg Gln Ala Pro Gly Lys Gly Leu Glu Trp Ile
        35                  40                  45

Gly Ile Ile Tyr Gly Gly Ser Gly Ser Thr Trp Tyr Ala Ser Trp Ala
    50                  55                  60

Lys Gly Lys Phe Ile Met Ser Lys Asp Ser Ala Lys Asn Thr Val Tyr
65                  70                  75                  80
```

Leu Gln Met Ser Lys Val Arg Ser Glu Asp Met Ala Thr Tyr Phe Cys
                85                  90                  95

Ala Arg Gly Arg Asp Gly Gly Ala Gly Gly Ser Arg Asn Gly Tyr Ser
            100                 105                 110

Leu Trp Gly Gln Gly Thr Leu Val Thr Val Ser Ser
        115                 120

<210> SEQ ID NO 31
<211> LENGTH: 372
<212> TYPE: DNA
<213> ORGANISM: Artificial Sequence
<220> FEATURE:
<223> OTHER INFORMATION: Murinised 4856 mH2.1 V-region

<400> SEQUENCE: 31
gaggtcaagc tgctggaatc gggggagggt ctggtgcagc cgggcggatc tctgaagctg    60
tcatgcaccg catccgggtt tagcctttcg tcctacgaca tgtcctgggt gcgccaggcc   120
cccggaaagg gattggaatg gatcggcatt atctacgggg gctccggttc cacttggtac   180
gcgagctggg ccaaggggaa gttcatcatg tcgaaggact ccgctaagaa caccgtgtac   240
ctccaaatga gcaaagtccg gagcgaggat atggccacct atttctgcgc cggggaagg   300 gacggaggag ccggcggttc cagaaacggc tactcactgt ggggacaggg caccctcgtg   360
actgtctcga gt                                                      372

<210> SEQ ID NO 32
<211> LENGTH: 143
<212> TYPE: PRT
<213> ORGANISM: Artificial Sequence
<220> FEATURE:
<223> OTHER INFORMATION: Murinised 4856 mH2.1 V-region with signal
      sequence

<400> SEQUENCE: 32

Met Glu Trp Ser Trp Val Phe Leu Phe Leu Ser Val Thr Thr Gly
1               5                   10                  15

Val His Ser Glu Val Lys Leu Leu Glu Ser Gly Gly Gly Leu Val Gln
                20                  25                  30

Pro Gly Gly Ser Leu Lys Leu Ser Cys Thr Ala Ser Gly Phe Ser Leu
            35                  40                  45

Ser Ser Tyr Asp Met Ser Trp Val Arg Gln Ala Pro Gly Lys Gly Leu
        50                  55                  60

Glu Trp Ile Gly Ile Ile Tyr Gly Gly Ser Gly Ser Thr Trp Tyr Ala
65                  70                  75                  80

Ser Trp Ala Lys Gly Lys Phe Ile Met Ser Lys Asp Ser Ala Lys Asn
                85                  90                  95

Thr Val Tyr Leu Gln Met Ser Lys Val Arg Ser Glu Asp Met Ala Thr
            100                 105                 110

Tyr Phe Cys Ala Arg Gly Arg Asp Gly Gly Ala Gly Gly Ser Arg Asn
        115                 120                 125

Gly Tyr Ser Leu Trp Gly Gln Gly Thr Leu Val Thr Val Ser Ser
    130                 135                 140

<210> SEQ ID NO 33
<211> LENGTH: 429
<212> TYPE: DNA
<213> ORGANISM: Artificial Sequence
<220> FEATURE:
<223> OTHER INFORMATION: Murinised 4856 mH2.1 V-region with signal
      sequence

<400> SEQUENCE: 33

```
atggaatgga gctgggtctt tctcttcttc ctgtcagtaa ctacaggagt ccattctgag      60
gtcaagctgc tggaatcggg gggaggtctg gtgcagccgg gcggatctct gaagctgtca     120
tgcaccgcat ccgggtttag cctttcgtcc tacgacatgt cctgggtgcg ccaggccccc     180
ggaaagggat tggaatggat cggcattatc tacgggggct ccggttccac ttggtacgcg     240
agctgggcca aggggaagtt catcatgtcg aaggactccg ctaagaacac cgtgtacctc     300
caaatgagca agtccggag cgaggatatg ccacctatt tctgcgcccg ggaagggac        360 ggaggagccg gcggttccag aaacggctac tcactgtggg acagggcac cctcgtgact      420 gtctcgagt                                                            429
```

<210> SEQ ID NO 34
<211> LENGTH: 107
<212> TYPE: PRT
<213> ORGANISM: Artificial Sequence
<220> FEATURE:
<223> OTHER INFORMATION: Mouse IGKV15-103 JK1 acceptor framework

<400> SEQUENCE: 34

```
Asp Ile Gln Met Asn Gln Ser Pro Ser Ser Leu Ser Ala Ser Leu Gly
1               5                   10                  15

Asp Thr Ile Thr Ile Thr Cys His Ala Ser Gln Asn Ile Asn Val Trp
            20                  25                  30

Leu Ser Trp Tyr Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Ser Tyr Pro Trp
                85                  90                  95

Thr Phe Gly Gly Gly Thr Lys Leu Glu Ile Lys
            100                 105
```

<210> SEQ ID NO 35
<211> LENGTH: 321
<212> TYPE: DNA
<213> ORGANISM: Artificial Sequence
<220> FEATURE:
<223> OTHER INFORMATION: Mouse IGKV15-103 JK1 acceptor framework

<400> SEQUENCE: 35

```
gacatccaga tgaaccagtc tccatccagt ctgtctgcat cccttggaga cacaattacc      60
atcacttgcc atgccagtca gaacattaat gtttggttaa gctggtacca gcagaaacca    120
ggaaatattc ctaaactatt gatctataag gcttccaact tgcacacagg cgtcccatca    180
aggtttagtg gcagtggatc tggaacaggt ttcacattaa ccatcagcag cctgcagcct    240
gaagacattg ccacttacta ctgtcaacag ggtcaaagtt atccttggac gttcggtgga    300
ggcaccaagc tggaaatcaa a                                              321
```

<210> SEQ ID NO 36
<211> LENGTH: 113
<212> TYPE: PRT
<213> ORGANISM: Artificial Sequence
<220> FEATURE:
<223> OTHER INFORMATION: Mouse IGHV4-S1 JH3 acceptor framework

<400> SEQUENCE: 36

```
Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Thr Pro Ser Leu
50                  55                  60

Lys Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Arg Trp Phe Ala Tyr Trp Gly Gln Gly Thr Leu Val Thr Val Ser
            100                 105                 110

Ala
```

<210> SEQ ID NO 37
<211> LENGTH: 339
<212> TYPE: DNA
<213> ORGANISM: Artificial Sequence
<220> FEATURE:
<223> OTHER INFORMATION: Mouse IGHV4-S1 JH3 acceptor framework

<400> SEQUENCE: 37

```
gaggtgaagc ttctcgagtc tggaggtggc ctggtgcagc ctggaggatc cctgaaactc     60
tcctgtgcag cctcaggatt cgattttagt agatactgga tgagttgggt ccggcaggct    120
ccagggaaag gctagaatg gattggagaa attaatccag atagcagtac gataaactat    180
acgccatctc taaaggataa attcatcatc tccagagaca acgccaaaaa tacgctgtac    240
ctgcaaatga gcaaagtgag atctgaggac acagcccttt attactgtgc aagatggttt    300
gcttactggg gccaagggac tctggtcact gtctctgca                           339
```

<210> SEQ ID NO 38
<211> LENGTH: 110
<212> TYPE: PRT
<213> ORGANISM: Artificial Sequence
<220> FEATURE:
<223> OTHER INFORMATION: 4856 gL3 V-region

<400> SEQUENCE: 38

```
Ala Tyr Asp Met Thr Gln Ser Pro Ser Thr Leu Ser Ala Ser Val Gly
1               5                   10                  15

Asp Arg Val Thr Ile Thr Cys Gln Ala Ser Glu Ser Ile Tyr Ser Gly
            20                  25                  30

Leu Ala Trp Tyr Gln Gln Lys Pro Gly Lys Ala Pro Lys Leu Leu Ile
        35                  40                  45

Tyr Ala Ala Ser Asp Leu Ala Ser Gly Val Pro Ser Arg Phe Ser Gly
50                  55                  60

Ser Gly Ser Gly Thr Glu Tyr Thr Leu Thr Ile Ser Ser Leu Gln Pro
65                  70                  75                  80

Asp Asp Phe Ala Thr Tyr Tyr Cys Gln Gln Thr Trp Thr Asp Gly Gly
                85                  90                  95

Ile Asp Asn Pro Phe Gly Gly Gly Thr Lys Val Glu Ile Lys
            100                 105                 110
```

<210> SEQ ID NO 39
<211> LENGTH: 330
<212> TYPE: DNA
<213> ORGANISM: Artificial Sequence
<220> FEATURE:
<223> OTHER INFORMATION: 4856 gL3 V-region (mammalian expression)

<400> SEQUENCE: 39

```
gcctacgaca tgacccagtc ccctcaacc ctctccgctt ccgtgggaga tcgcgtgacc      60
atcacttgcc aagcctccga atcgatctac tcgggtctgg cctggtatca gcagaagcca    120
gggaaggcac ctaagctgtt gatctacgcg gcctcagacc tggccagcgg agtgcccagc    180
cggttctccg gctccggaag cggcactgag tacaccctga ccatttcctc gcttcaaccg    240
gatgacttcg cgacctacta ctgtcagcag acttggacgg acgggggcat cgacaacccg    300
tttggtggag gcaccaaagt cgagattaag                                      330
```

<210> SEQ ID NO 40
<211> LENGTH: 330
<212> TYPE: DNA
<213> ORGANISM: Artificial Sequence
<220> FEATURE:
<223> OTHER INFORMATION: 4856 gL3 V-region (E. coli expression)

<400> SEQUENCE: 40

```
gcgtatgata tgacccagag tccaagcacc ctctccgcca gcgtaggcga tcgtgtgact     60
attacctgtc aggccagtga aagcatctat agcggcctgg cgtggtatca gcaaaaaccg    120
ggcaaagccc cgaagctgct catctatgcg gcgtccgatc tggcgagcgg tgtgccaagc    180
cgtttcagtg gcagcggcag cggcaccgaa tataccctca aatttcgtc tctccagccg     240
gatgatttcg ccacttacta ttgtcagcaa acctggaccg atggcggcat tgataacccg    300
ttcggtggcg gcactaaagt agaaatcaaa                                      330
```

<210> SEQ ID NO 41
<211> LENGTH: 128
<212> TYPE: PRT
<213> ORGANISM: Artificial Sequence
<220> FEATURE:
<223> OTHER INFORMATION: 4856 gL3 V-region with signal sequence

<400> SEQUENCE: 41

```
Met Lys Trp Val Thr Phe Ile Ser Leu Leu Phe Leu Phe Ser Ser Ala
1               5                   10                  15

Tyr Ser Ala Tyr Asp Met Thr Gln Ser Pro Ser Thr Leu Ser Ala Ser
            20                  25                  30

Val Gly Asp Arg Val Thr Ile Thr Cys Gln Ala Ser Glu Ser Ile Tyr
        35                  40                  45

Ser Gly Leu Ala Trp Tyr Gln Gln Lys Pro Gly Lys Ala Pro Lys Leu
    50                  55                  60

Leu Ile Tyr Ala Ala Ser Asp Leu Ala Ser Gly Val Pro Ser Arg Phe
65                  70                  75                  80

Ser Gly Ser Gly Ser Gly Thr Glu Tyr Thr Leu Thr Ile Ser Ser Leu
                85                  90                  95

Gln Pro Asp Asp Phe Ala Thr Tyr Tyr Cys Gln Gln Thr Trp Thr Asp
            100                 105                 110

Gly Gly Ile Asp Asn Pro Phe Gly Gly Gly Thr Lys Val Glu Ile Lys
        115                 120                 125
```

```
<210> SEQ ID NO 42
<211> LENGTH: 384
<212> TYPE: DNA
<213> ORGANISM: Artificial Sequence
<220> FEATURE:
<223> OTHER INFORMATION: 4856 gL3 V-region with signal sequence

<400> SEQUENCE: 42
atgaagtggg tcaccttcat ctccctgctg tttctgttct cctccgccta ctccgcctac      60
gacatgaccc agtcccccctc aaccctctcc gcttccgtgg gagatcgcgt gaccatcact     120
tgccaagcct ccgaatcgat ctactcgggt ctggcctggt atcagcagaa gccagggaag     180
gcacctaagc tgttgatcta cgcggcctca gacctggcca gcggagtgcc cagccggttc     240
tccggctccg gaagcggcac tgagtacacc ctgaccattt cctcgcttca accggatgac     300
ttcgcgacct actactgtca gcagacttgg acggacgggg gcatcgacaa cccgtttggt     360
ggaggcacca aagtcgagat taag                                            384

<210> SEQ ID NO 43
<211> LENGTH: 131
<212> TYPE: PRT
<213> ORGANISM: Artificial Sequence
<220> FEATURE:
<223> OTHER INFORMATION: 4856 gL3 V-region with signal sequence (E. coli
      expression)

<400> SEQUENCE: 43

Met Lys Lys Thr Ala Ile Ala Ile Ala Val Ala Leu Ala Gly Phe Ala
1               5                   10                  15

Thr Val Ala Gln Ala Ala Tyr Asp Met Thr Gln Ser Pro Ser Thr Leu
            20                  25                  30

Ser Ala Ser Val Gly Asp Arg Val Thr Ile Thr Cys Gln Ala Ser Glu
        35                  40                  45

Ser Ile Tyr Ser Gly Leu Ala Trp Tyr Gln Gln Lys Pro Gly Lys Ala
    50                  55                  60

Pro Lys Leu Leu Ile Tyr Ala Ala Ser Asp Leu Ala Ser Gly Val Pro
65                  70                  75                  80

Ser Arg Phe Ser Gly Ser Gly Ser Gly Thr Glu Tyr Thr Leu Thr Ile
                85                  90                  95

Ser Ser Leu Gln Pro Asp Asp Phe Ala Thr Tyr Tyr Cys Gln Gln Thr
            100                 105                 110

Trp Thr Asp Gly Gly Ile Asp Asn Pro Phe Gly Gly Gly Thr Lys Val
        115                 120                 125

Glu Ile Lys
    130

<210> SEQ ID NO 44
<211> LENGTH: 393
<212> TYPE: DNA
<213> ORGANISM: Artificial Sequence
<220> FEATURE:
<223> OTHER INFORMATION: 4856 gL3 V-region with signal sequence (E. coli
      expression)

<400> SEQUENCE: 44
atgaaaaaga cagctatcgc aattgcagtg gccttggctg gtttcgctac cgtagcgcaa      60
gctgcgtatg atatgaccca gagtccaagc accctctccg ccagcgtagg cgatcgtgtg     120
actattacct gtcaggccag tgaaagcatc tatagcggcc tggcgtggta tcagcaaaaa     180
ccgggcaaag ccccgaagct gctcatctat gcggcgtccg atctggcgag cggtgtgcca     240
```

```
agccgtttca gtggcagcgg cagcggcacc gaatatacce tcacaatttc gtctctccag    300
ccggatgatt tcgccactta ctattgtcag caaacctgga ccgatggcgg cattgataac    360
ccgttcggtg gcggcactaa agtagaaatc aaa                                 393
```

```
<210> SEQ ID NO 45
<211> LENGTH: 217
<212> TYPE: PRT
<213> ORGANISM: Artificial Sequence
<220> FEATURE:
<223> OTHER INFORMATION: 4856 gL3 light chain

<400> SEQUENCE: 45
```

```
Ala Tyr Asp Met Thr Gln Ser Pro Ser Thr Leu Ser Ala Ser Val Gly
1               5                   10                  15

Asp Arg Val Thr Ile Thr Cys Gln Ala Ser Glu Ser Ile Tyr Ser Gly
            20                  25                  30

Leu Ala Trp Tyr Gln Gln Lys Pro Gly Lys Ala Pro Lys Leu Leu Ile
        35                  40                  45

Tyr Ala Ala Ser Asp Leu Ala Ser Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Asp Asp Phe Ala Thr Tyr Tyr Cys Gln Gln Thr Trp Thr Asp Gly Gly
                85                  90                  95

Ile Asp Asn Pro Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

```
<210> SEQ ID NO 46
<211> LENGTH: 651
<212> TYPE: DNA
<213> ORGANISM: Artificial Sequence
<220> FEATURE:
<223> OTHER INFORMATION: 4856 gL3 light chain (mammalian expression)

<400> SEQUENCE: 46
```

```
gcctacgaca tgacccagtc cccctcaacc ctctccgctt ccgtgggaga tcgcgtgacc    60
atcacttgcc aagcctccga atcgatctac tcgggtctgg cctggtatca gcagaagcca    120
gggaaggcac ctaagctgtt gatctacgcg gcctcagacc tggccagcgg agtgcccagc    180
cggttctccg gctccggaag cggcactgag tacaccctga ccatttcctc gcttcaaccg    240
gatgacttcg cgacctacta ctgtcagcag acttggacgg acggggggcat cgacaacccg    300
```

```
tttggtggag gcaccaaagt cgagattaag cgtacggtag cggccccatc tgtcttcatc    360
ttcccgccat ctgatgagca gttgaaatct ggaactgcct ctgttgtgtg cctgctgaat    420
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgagctcgcc cgtcacaaag agcttcaaca ggggagagtg t             651
```

<210> SEQ ID NO 47
<211> LENGTH: 651
<212> TYPE: DNA
<213> ORGANISM: Artificial Sequence
<220> FEATURE:
<223> OTHER INFORMATION: 4856 gL3 light chain (E.coli expression)

<400> SEQUENCE: 47

```
gcgtatgata tgacccagag tccaagcacc ctctccgcca gcgtaggcga tcgtgtgact     60
attacctgtc aggccagtga agcatctat agcggcctgg cgtggtatca gcaaaaaccg    120
ggcaaagccc cgaagctgct catctatgcg gcgtccgatc tggcgagcgg tgtgccaagc    180
cgtttcagtg gcagcggcag cggcaccgaa atatccctca aatttcgtc tctccagccg    240 gatgatttcg ccacttacta ttgtcagcaa acctggaccg atggcggcat tgataacccg    300
ttcggtggcg gcactaaagt agaaatcaaa cgtacggtag cggccccatc tgtcttcatc    360
ttcccgccat ctgatgagca gttgaaatct ggaactgcct ctgttgtgtg cctgctgaat    420
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgagctcacc agtaacaaaa agtttaata gaggggagtg t              651
```

<210> SEQ ID NO 48
<211> LENGTH: 235
<212> TYPE: PRT
<213> ORGANISM: Artificial Sequence
<220> FEATURE:
<223> OTHER INFORMATION: 4856 gL3 light chain with signal sequence

<400> SEQUENCE: 48

Met Lys Trp Val Thr Phe Ile Ser Leu Leu Phe Leu Phe Ser Ser Ala
1               5                   10                  15

Tyr Ser Ala Tyr Asp Met Thr Gln Ser Pro Ser Thr Leu Ser Ala Ser
            20                  25                  30

Val Gly Asp Arg Val Thr Ile Thr Cys Gln Ala Ser Glu Ser Ile Tyr
        35                  40                  45

Ser Gly Leu Ala Trp Tyr Gln Gln Lys Pro Gly Lys Ala Pro Lys Leu
    50                  55                  60

Leu Ile Tyr Ala Ala Ser Asp Leu Ala Ser Gly Val Pro Ser Arg Phe
65                  70                  75                  80

Ser Gly Ser Gly Ser Gly Thr Glu Tyr Thr Leu Thr Ile Ser Ser Leu
                85                  90                  95

Gln Pro Asp Asp Phe Ala Thr Tyr Tyr Cys Gln Gln Thr Trp Thr Asp
            100                 105                 110

Gly Gly Ile Asp Asn Pro Phe Gly Gly Gly Thr Lys Val Glu Ile Lys
        115                 120                 125

Arg Thr Val Ala Ala Pro Ser Val Phe Ile Phe Pro Pro Ser Asp Glu

```
              130                 135                 140
Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
                180                 185                 190

Thr Tyr Ser Leu Ser Ser Thr Leu Thr Leu Ser Lys Ala Asp Tyr Glu
            195                 200                 205

Lys His Lys Val Tyr Ala Cys Glu Val Thr His Gln Gly Leu Ser Ser
        210                 215                 220

Pro Val Thr Lys Ser Phe Asn Arg Gly Glu Cys
225                 230                 235

<210> SEQ ID NO 49
<211> LENGTH: 705
<212> TYPE: DNA
<213> ORGANISM: Artificial Sequence
<220> FEATURE:
<223> OTHER INFORMATION: 4856 gL3 light chain with signal sequence
      (mammalian expression)

<400> SEQUENCE: 49
atgaagtggg tcaccttcat ctccctgctg tttctgttct cctccgccta ctccgcctac    60
gacatgaccc agtcccccte aaccctctcc gcttccgtgg agatcgcgt gaccatcact   120 tgccaagcct ccgaatcgat ctactcgggt ctggcctggt atcagcagaa gccaggaag   180 gcacctaagc tgttgatcta cgcggcctca gacctggcca gcggagtgcc cagccggttc   240
tccggctccg gaagcggcac tgagtacacc ctgaccattt cctcgcttca accggatgac   300
ttcgcgacct actactgtca gcagacttgg acggacgggg catcgacaa cccgtttggt   360 ggaggcacca agtcgagat taagcgtacg gtagcggccc catctgtctt catcttcccg   420
ccatctgatg agcagttgaa atctggaact gcctctgttg tgtgcctgct gaataacttc   480
tatcccagag aggccaaagt acagtggaag gtggataacg ccctccaatc gggtaactcc   540
caggagagtg tcacagagca ggacagcaag acagcacct acagcctcag cagcaccctg   600
acgctgagca agcagacta cgagaaacac aaagtctacg cctgcgaagt cacccatcag   660
ggcctgagct cgcccgtcac aaagagcttc aacagggag agtgt                     705

<210> SEQ ID NO 50
<211> LENGTH: 238
<212> TYPE: PRT
<213> ORGANISM: Artificial Sequence
<220> FEATURE:
<223> OTHER INFORMATION: 4856 gL3 light chain with signal sequence (E.
      coli expression)

<400> SEQUENCE: 50

Met Lys Lys Thr Ala Ile Ala Ile Ala Val Ala Leu Ala Gly Phe Ala
1               5                   10                  15

Thr Val Ala Gln Ala Ala Tyr Asp Met Thr Gln Ser Pro Ser Thr Leu
            20                  25                  30

Ser Ala Ser Val Gly Asp Arg Val Thr Ile Thr Cys Gln Ala Ser Glu
        35                  40                  45

Ser Ile Tyr Ser Gly Leu Ala Trp Tyr Gln Gln Lys Pro Gly Lys Ala
    50                  55                  60

Pro Lys Leu Leu Ile Tyr Ala Ala Ser Asp Leu Ala Ser Gly Val Pro
```

```
                65                  70                  75                  80
Ser Arg Phe Ser Gly Ser Gly Ser Gly Thr Glu Tyr Thr Leu Thr Ile
                    85                  90                  95

Ser Ser Leu Gln Pro Asp Asp Phe Ala Thr Tyr Tyr Cys Gln Gln Thr
                    100                 105                 110

Trp Thr Asp Gly Gly Ile Asp Asn Pro Phe Gly Gly Thr Lys Val
                    115                 120                 125

Glu Ile Lys Arg Thr Val Ala Ala Pro Ser Val Phe Ile Phe Pro Pro
                    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                    165                 170                 175

Ala Leu Gln Ser Gly Asn Ser Gln Glu Ser Val Thr Glu Gln Asp Ser
                    180                 185                 190

Lys Asp Ser Thr Tyr Ser Leu Ser Ser Thr Leu Thr Leu Ser Lys Ala
                    195                 200                 205

Asp Tyr Glu Lys His Lys Val Tyr Ala Cys Glu Val Thr His Gln Gly
            210                 215                 220

Leu Ser Ser Pro Val Thr Lys Ser Phe Asn Arg Gly Glu Cys
225                 230                 235

<210> SEQ ID NO 51
<211> LENGTH: 714
<212> TYPE: DNA
<213> ORGANISM: Artificial Sequence
<220> FEATURE:
<223> OTHER INFORMATION: 4856 gL3 light chain with signal sequence (E.
      coli expression)

<400> SEQUENCE: 51
atgaaaaaga cagctatcgc aattgcagtg gccttggctg gtttcgctac cgtagcgcaa      60
gctgcgtatg atatgaccca gagtccaagc accctctccg ccagcgtagg cgatcgtgtg     120
actattacct gtcaggccag tgaaagcatc tatagcggcc tggcgtggta tcagcaaaaa     180
ccgggcaaag ccccgaagct gctcatctat gcggcgtccg atctggcgag cggtgtgcca     240
agccgtttca gtggcagcgg cagcggcacc gaatatacccc tcacaatttc gtctctccag    300
ccggatgatt tcgccactta ctattgtcag caaacctgga ccgatggcgg cattgataac     360
ccgttcggtg gcggcactaa agtagaaatc aaacgtacgg tagcggcccc atctgtcttc     420
atcttcccgc catctgatga gcagttgaaa tctggaactg cctctgttgt gtgcctgctg     480
aataacttct atcccagaga ggccaaagta cagtggaagg tggataacgc cctccaatcg     540
ggtaactccc aggagagtgt cacagagcag gacagcaagg acagcaccta cagcctcagc     600
agcaccctga cgctgagcaa agcagactac gagaaacaca agtctacgc ctgcgaagtc      660 acccatcagg gcctgagctc accagtaaca aaagttttta tagagggga gtgt            714

<210> SEQ ID NO 52
<211> LENGTH: 124
<212> TYPE: PRT
<213> ORGANISM: Artificial Sequence
<220> FEATURE:
<223> OTHER INFORMATION: 4856gH13 V-region

<400> SEQUENCE: 52

Glu Val Gln Leu Val Glu Ser Gly Gly Gly Leu Val Lys Pro Gly Gly
1               5                   10                  15
```

```
Ser Leu Arg Leu Ser Cys Ala Ala Ser Gly Phe Ser Leu Ser Ser Tyr
         20                  25                  30

Asp Met Ser Trp Val Arg Gln Ala Pro Gly Lys Gly Leu Glu Trp Ile
             35                  40                  45

Gly Ile Ile Tyr Gly Ser Gly Ser Thr Tyr Tyr Ala Ser Trp Ala
 50                  55                  60

Lys Gly Arg Phe Thr Ile Ser Arg Asp Ser Ala Lys Asn Ser Val Tyr
 65                  70                  75                  80

Leu Gln Met Asn Ser Leu Arg Ala Glu Asp Thr Ala Val Tyr Tyr Cys
                 85                  90                  95

Ala Arg Gly Arg Asp Ala Gly Ala Gly Gly Ser Arg Asn Gly Tyr Ser
             100                 105                 110

Leu Trp Gly Gln Gly Thr Leu Val Thr Val Ser Ser
             115                 120
```

```
<210> SEQ ID NO 53
<211> LENGTH: 372
<212> TYPE: DNA
<213> ORGANISM: Artificial Sequence
<220> FEATURE:
<223> OTHER INFORMATION: 4856gH13 V-region (mammalian expression)

<400> SEQUENCE: 53
gaagtgcaac tggtggaaag cggaggaggt ttggtgaaac cggagggtc actgcggctc      60 tcctgtgccg cctccggatt cagcctctcg tcctacgaca tgagctgggt cagacaggcc    120
cccgggaagg gcctggagtg gattggtatc atctacggcg ctccggctc gacttggtac     180 gcttcgtggg ccaagggacg gttcaccatc tcccgcgatt ccgcgaagaa cagcgtgtat    240
ctgcagatga actctctgcg ggccgaggac accgcagtgt actactgcgc gaggggcgc     300 gacgccggcg ccgggggatc acgcaacggt tactcccttt ggggacaggg aaccctggtc    360
actgtctcca gc                                                        372

<210> SEQ ID NO 54
<211> LENGTH: 372
<212> TYPE: DNA
<213> ORGANISM: Artificial Sequence
<220> FEATURE:
<223> OTHER INFORMATION: 4856gH13 V-region (E. coli expression)

<400> SEQUENCE: 54
gaggttcagc tggtcgagtc tggaggcggg cttgtcaaac tggagggag cctgcgtctc      60 tcttgtgcag caagcggctt cagcctgtcc tcttacgata tgtcctgggt gcgccaggca    120
cctgggaagg gcctggagtg gattggcatt atttatggcg gcagcggcag cacatggtac    180
gcgagctggg cgaagggccg tttcaccatc tcccgggaca gcgcaaagaa tagcgtgtac    240
ctccagatga actctctccg cgcagaggac acagcagtct attactgtgc gcggggccgc    300
gatgcaggcg cgggcggcag ccgcaacggc tatagcctgt ggggacaggg gacccttgtg    360
acagtctcga gc                                                        372

<210> SEQ ID NO 55
<211> LENGTH: 142
<212> TYPE: PRT
<213> ORGANISM: Artificial Sequence
<220> FEATURE:
<223> OTHER INFORMATION: 4856gH13 V-region with signal sequence
      (mammalian expression)
```

<400> SEQUENCE: 55

```
Met Lys Trp Val Thr Phe Ile Ser Leu Leu Phe Leu Phe Ser Ser Ala
1               5                   10                  15

Tyr Ser Glu Val Gln Leu Val Glu Ser Gly Gly Gly Leu Val Lys Pro
            20                  25                  30

Gly Gly Ser Leu Arg Leu Ser Cys Ala Ala Ser Gly Phe Ser Leu Ser
        35                  40                  45

Ser Tyr Asp Met Ser Trp Val Arg Gln Ala Pro Gly Lys Gly Leu Glu
50                  55                  60

Trp Ile Gly Ile Ile Tyr Gly Gly Ser Gly Ser Thr Trp Tyr Ala Ser
65                  70                  75                  80

Trp Ala Lys Gly Arg Phe Thr Ile Ser Arg Asp Ser Ala Lys Asn Ser
                85                  90                  95

Val Tyr Leu Gln Met Asn Ser Leu Arg Ala Glu Asp Thr Ala Val Tyr
            100                 105                 110

Tyr Cys Ala Arg Gly Arg Asp Ala Gly Ala Gly Gly Ser Arg Asn Gly
        115                 120                 125

Tyr Ser Leu Trp Gly Gln Gly Thr Leu Val Thr Val Ser Ser
130                 135                 140
```

<210> SEQ ID NO 56
<211> LENGTH: 426
<212> TYPE: DNA
<213> ORGANISM: Artificial Sequence
<220> FEATURE:
<223> OTHER INFORMATION: 4856gH13 V-region with signal sequence
      (mammalian expression)

<400> SEQUENCE: 56

```
atgaagtggg tcaccttcat ctccctgctg tttctgttct ccagcgccta ctccgaagtg    60
caactggtgg aaagcggagg aggtttggtg aaaccgggag gtcactgcg gctctcctgt   120
gccgcctccg gattcagcct ctcgtcctac gacatgagct gggtcagaca ggcccccggg   180
aagggcctgg agtggattgg tatcatctac ggcggctccg gctcgacttg gtacgcttcg   240
tgggccaagg gacggttcac catctcccgc gattccgcga agaacagcgt gtatctgcag   300
atgaactctc tgcgggccga ggacaccgca gtgtactact gcgcgagggg cgcgacgcc   360
ggcgccgggg gatcacgcaa cggttactcc ctttggggac agggaaccct ggtcactgtc   420
tccagc                                                             426
```

<210> SEQ ID NO 57
<211> LENGTH: 145
<212> TYPE: PRT
<213> ORGANISM: Artificial Sequence
<220> FEATURE:
<223> OTHER INFORMATION: 4856gH13 V-region with signal sequence (E. coli
      expression)

<400> SEQUENCE: 57

```
Met Lys Lys Thr Ala Ile Ala Ile Ala Val Ala Leu Ala Gly Phe Ala
1               5                   10                  15

Thr Val Ala Gln Ala Glu Val Gln Leu Val Glu Ser Gly Gly Gly Leu
            20                  25                  30

Val Lys Pro Gly Gly Ser Leu Arg Leu Ser Cys Ala Ala Ser Gly Phe
        35                  40                  45

Ser Leu Ser Ser Tyr Asp Met Ser Trp Val Arg Gln Ala Pro Gly Lys
50                  55                  60
```

```
Gly Leu Glu Trp Ile Gly Ile Ile Tyr Gly Gly Ser Gly Ser Thr Trp
 65                  70                  75                  80

Tyr Ala Ser Trp Ala Lys Gly Arg Phe Thr Ile Ser Arg Asp Ser Ala
                 85                  90                  95

Lys Asn Ser Val Tyr Leu Gln Met Asn Ser Leu Arg Ala Glu Asp Thr
            100                 105                 110

Ala Val Tyr Tyr Cys Ala Arg Gly Arg Asp Ala Gly Ala Gly Gly Ser
        115                 120                 125

Arg Asn Gly Tyr Ser Leu Trp Gly Gln Gly Thr Leu Val Thr Val Ser
    130                 135                 140

Ser
145

<210> SEQ ID NO 58
<211> LENGTH: 435
<212> TYPE: DNA
<213> ORGANISM: Artificial Sequence
<220> FEATURE:
<223> OTHER INFORMATION: 4856gH13 V-region with signal sequence (E. coli
      expression)

<400> SEQUENCE: 58
atgaagaaga ctgctatagc aattgcagtg gcgctagctg gtttcgccac cgtggcgcaa     60
gctgaggttc agctggtcga gtctggaggc gggcttgtca aacctggagg gagcctgcgt    120
ctctcttgtg cagcaagcgg cttcagcctg tcctcttacg atatgtcctg ggtgcgccag    180
gcacctggga agggcctgga gtggattggc attatttatg gcggcagcgg cagcacatgg    240
tacgcgagct gggcgaaggg ccgtttcacc atctcccggg acagcgcaaa gaatagcgtg    300
tacctccaga tgaactctct ccgcgcagag gacacagcag tctattactg tgcgcggggc    360
cgcgatgcag gcgcgggcgg cagccgcaac ggctatagcc tgtggggaca ggggaccctt    420
gtgacagtct cgagc                                                    435

<210> SEQ ID NO 59
<211> LENGTH: 227
<212> TYPE: PRT
<213> ORGANISM: Artificial Sequence
<220> FEATURE:
<223> OTHER INFORMATION: 4856 gH13 Fab heavy chain

<400> SEQUENCE: 59

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Ser Leu Ser Ser Tyr
             20                  25                  30

Asp Met Ser Trp Val Arg Gln Ala Pro Gly Lys Gly Leu Glu Trp Ile
         35                  40                  45

Gly Ile Ile Tyr Gly Gly Ser Gly Ser Thr Trp Tyr Ala Ser Trp Ala
     50                  55                  60

Lys Gly Arg Phe Thr Ile Ser Arg Asp Ser Ala Lys Asn Ser Val Tyr
 65                  70                  75                  80

Leu Gln Met Asn Ser Leu Arg Ala Glu Asp Thr Ala Val Tyr Tyr Cys
                 85                  90                  95

Ala Arg Gly Arg Asp Ala Gly Ala Gly Gly Ser Arg Asn Gly Tyr Ser
            100                 105                 110

Leu Trp Gly Gln Gly Thr Leu Val Thr Val Ser Ser Ala Ser Thr Lys
        115                 120                 125
```

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys
225

<210> SEQ ID NO 60
<211> LENGTH: 681
<212> TYPE: DNA
<213> ORGANISM: Artificial Sequence
<220> FEATURE:
<223> OTHER INFORMATION: 4856 gH13 Fab heavy chain (mammalian
      expression)

<400> SEQUENCE: 60
gaagtgcaac tggtggaaag cggaggaggt ttggtgaaac cgggagggtc actgcggctc        60
tcctgtgccg cctccggatt cagcctctcg tcctacgaca tgagctgggt cagacaggcc      120
cccgggaagg gcctggagtg gattggtatc atctacggcg gctccggctc gacttggtac      180
gcttcgtggg ccaagggacg gttcaccatc tcccgcgatt ccgcgaagaa cagcgtgtat      240
ctgcagatga actctctgcg ggccgaggac accgcagtgt actactgcgc gaggggcgc       300 gacgccggcg ccgggggatc acgcaacggt tactcccttt ggggacaggg aaccctggtc      360
actgtctcca gcgcttctac aaagggccca tcggtcttcc ccctggcacc ctcctccaag      420
agcacctctg ggggcacagc ggccctgggc tgcctggtca aggactactt ccccgaaccg      480
gtgacggtgt cgtggaactc aggcgccctg accagcggcg tgcacacctt cccggctgtc      540
ctacagtcct caggactcta ctccctcagc agcgtggtga ccgtgccctc cagcagcttg      600
ggcacccaga cctacatctg caacgtgaat cacaagccca gcaacaccaa ggtggacaag      660
aaagttgagc ccaaatcttg t                                                681

<210> SEQ ID NO 61
<211> LENGTH: 681
<212> TYPE: DNA
<213> ORGANISM: Artificial Sequence
<220> FEATURE:
<223> OTHER INFORMATION: 4856 gH13 Fab heavy chain (E. coli expression)

<400> SEQUENCE: 61
gaggttcagc tggtcgagtc tggaggcggg cttgtcaaac tggaggggag cctgcgtctc        60
tcttgtgcag caagcggctt cagcctgtcc tcttacgata tgtcctgggt cgccaggca       120 cctgggaagg gcctggagtg gattggcatt atttatggcg gcagcggcag cacatggtac      180
gcgagctggg cgaagggccg tttcaccatc tcccgggaca gcgcaaagaa tagcgtgtac      240
ctccagatga actctctccg cgcagaggac acagcagtct attactgtgc gcggggccgc      300
gatgcaggcg cgggcggcag ccgcaacggc tatagcctgt ggggacaggg gacccttgtg      360
acagtctcga gcgcttctac aaagggccca tcggtcttcc ccctggcacc ctcctccaag      420

```
agcacctctg ggggcacagc ggccctgggc tgcctggtca aggactactt ccccgaaccg    480
gtgacggtgt cgtggaactc aggcgccctg accagcggcg tgcacacctt cccggctgtc    540
ctacagtcct caggactcta ctccctcagc agcgtggtga ccgtgccctc agcagcttg     600 ggcacccaga cctacatctg caacgtgaat cacaagccca gcaacaccaa ggtcgacaag    660
aaagttgagc ccaaatcttg t                                              681
```

<210> SEQ ID NO 62
<211> LENGTH: 245
<212> TYPE: PRT
<213> ORGANISM: Artificial Sequence
<220> FEATURE:
<223> OTHER INFORMATION: 4856 gH13 Fab heavy chain with signal sequence
      (mammalian expression)

<400> SEQUENCE: 62

```
Met Lys Trp Val Thr Phe Ile Ser Leu Leu Phe Leu Phe Ser Ser Ala
1               5                   10                  15

Tyr Ser Glu Val Gln Leu Val Glu Ser Gly Gly Gly Leu Val Lys Pro
            20                  25                  30

Gly Gly Ser Leu Arg Leu Ser Cys Ala Ala Ser Gly Phe Ser Leu Ser
        35                  40                  45

Ser Tyr Asp Met Ser Trp Val Arg Gln Ala Pro Gly Lys Gly Leu Glu
    50                  55                  60

Trp Ile Gly Ile Ile Tyr Gly Gly Ser Gly Ser Thr Trp Tyr Ala Ser
65                  70                  75                  80

Trp Ala Lys Gly Arg Phe Thr Ile Ser Arg Asp Ser Ala Lys Asn Ser
                85                  90                  95

Val Tyr Leu Gln Met Asn Ser Leu Arg Ala Glu Asp Thr Ala Val Tyr
            100                 105                 110

Tyr Cys Ala Arg Gly Arg Asp Ala Gly Ala Gly Gly Ser Arg Asn Gly
        115                 120                 125

Tyr Ser Leu Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys
                245
```

<210> SEQ ID NO 63
<211> LENGTH: 735
<212> TYPE: DNA
<213> ORGANISM: Artificial Sequence
<220> FEATURE:
<223> OTHER INFORMATION: 4856 gH13 Fab heavy chain with signal sequence
      (mammalian expression)

<400> SEQUENCE: 63

```
atgaagtggg tcaccttcat ctccctgctg tttctgttct ccagcgccta ctccgaagtg      60
caactggtgg aaagcggagg aggtttggtg aaaccgggag ggtcactgcg gctctcctgt     120
gccgcctccg gattcagcct ctcgtcctac gacatgagct gggtcagaca ggcccccggg     180
aagggcctgg agtggattgg tatcatctac ggcggctccg gctcgacttg gtacgcttcg     240
tgggccaagg gacggttcac catctcccgc gattccgcga agaacagcgt gtatctgcag     300
atgaactctc tgcgggccga ggacaccgca gtgtactact gcgcgagggg gcgcgacgcc     360
ggcgccgggg gatcacgcaa cggttactcc ctttggggac agggaaccct ggtcactgtc     420
tccagcgctt ctacaaaggg cccatcggtc ttccccctgg caccctcctc caagagcacc     480
tctgggggca gcggccctg ggctgcctg gtcaaggact acttccccga accggtgacg       540
gtgtcgtgga actcaggcgc cctgaccagc ggcgtgcaca ccttcccggc tgtcctacag     600
tcctcaggac tctactccct cagcagcgtg gtgaccgtgc cctccagcag cttgggcacc     660
cagacctaca tctgcaacgt gaatcacaag cccagcaaca ccaaggtgga caagaaagtt     720
gagcccaaat cttgt                                                     735
```

<210> SEQ ID NO 64
<211> LENGTH: 248
<212> TYPE: PRT
<213> ORGANISM: Artificial Sequence
<220> FEATURE:
<223> OTHER INFORMATION: 4856 gH13 Fab heavy chain with signal sequence
      (E. coli expression)

<400> SEQUENCE: 64

```
Met Lys Lys Thr Ala Ile Ala Ile Ala Val Ala Leu Ala Gly Phe Ala
1               5                   10                  15

Thr Val Ala Gln Ala Glu Val Gln Leu Val Glu Ser Gly Gly Gly Leu
            20                  25                  30

Val Lys Pro Gly Gly Ser Leu Arg Leu Ser Cys Ala Ala Ser Gly Phe
        35                  40                  45

Ser Leu Ser Ser Tyr Asp Met Ser Trp Val Arg Gln Ala Pro Gly Lys
    50                  55                  60

Gly Leu Glu Trp Ile Gly Ile Ile Tyr Gly Gly Ser Gly Ser Thr Trp
65                  70                  75                  80

Tyr Ala Ser Trp Ala Lys Gly Arg Phe Thr Ile Ser Arg Asp Ser Ala
                85                  90                  95

Lys Asn Ser Val Tyr Leu Gln Met Asn Ser Leu Arg Ala Glu Asp Thr
            100                 105                 110

Ala Val Tyr Tyr Cys Ala Arg Gly Arg Asp Ala Gly Ala Gly Gly Ser
        115                 120                 125

Arg Asn Gly Tyr Ser Leu Trp Gly Gln Gly Thr Leu Val Thr Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
```

Thr Tyr Ile Cys Asn Val Asn His Lys Pro Ser Asn Thr Lys Val Asp
225                 230                 235                 240

Lys Lys Val Glu Pro Lys Ser Cys
                245

<210> SEQ ID NO 65
<211> LENGTH: 744
<212> TYPE: DNA
<213> ORGANISM: Artificial Sequence
<220> FEATURE:
<223> OTHER INFORMATION: 4856 gH13 Fab heavy chain with signal sequence
      (E. coli expression)

<400> SEQUENCE: 65
atgaagaaga ctgctatagc aattgcagtg gcgctagctg gtttcgccac cgtggcgcaa    60
gctgaggttc agctggtcga gtctggaggc gggcttgtca aacctggagg gagcctgcgt   120
ctctcttgtg cagcaagcgg cttcagcctg tcctcttacg atatgtcctg ggtgcgccag   180
gcacctggga agggcctgga gtggattggc attatttatg gcggcagcgg cagcacatgg   240
tacgcgagct gggcgaaggg ccgtttcacc atctcccggg acagcgcaaa gaatagcgtg   300
tacctccaga tgaactctct ccgcgcagag gacacagcag tctattactg cgcgggggc   360
cgcgatgcag gcgcgggcgg cagccgcaac ggctatagcc tgtggggaca ggggaccctt   420
gtgacagtct cgagcgcttc tacaaagggc ccatcggtct tccccctggc accctcctcc   480
aagagcacct ctgggggcac agcggccctg ggctgcctgg tcaaggacta cttccccgaa   540
ccggtgacgg tgtcgtggaa ctcaggcgcc ctgaccagcg gcgtgcacac cttcccggct   600
gtcctacagt cctcaggact ctactccctc agcagcgtgg tgaccgtgcc ctccagcagc   660
ttgggcaccc agacctacat ctgcaacgtg aatcacaagc ccagcaacac caaggtcgac   720
aagaaagttg agcccaaatc ttgt                                          744

<210> SEQ ID NO 66
<211> LENGTH: 124
<212> TYPE: PRT
<213> ORGANISM: Artificial Sequence
<220> FEATURE:
<223> OTHER INFORMATION: 4856gH20 V-region

<400> SEQUENCE: 66

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Leu Ser Ser Tyr
            20                  25                  30

Asp Met Ser Trp Val Arg Gln Ala Pro Gly Lys Gly Leu Glu Trp Ile
        35                  40                  45

Ser Ile Ile Tyr Gly Gly Ser Gly Ser Thr Trp Tyr Ala Ser Trp Ala
    50                  55                  60

Lys Gly Arg Phe Thr Met Ser Lys Asp Ser Ala Lys Asn Ser Val Tyr
65                  70                  75                  80

Leu Gln Met Asn Ser Leu Arg Ala Glu Asp Thr Ala Val Tyr Tyr Cys
                85                  90                  95

Ala Arg Gly Arg Asp Ala Gly Ala Gly Gly Ser Arg Asn Gly Tyr Ser
            100                 105                 110

Leu Trp Gly Gln Gly Thr Leu Val Thr Val Ser Ser
        115                 120

<210> SEQ ID NO 67
<211> LENGTH: 372
<212> TYPE: DNA
<213> ORGANISM: Artificial Sequence
<220> FEATURE:
<223> OTHER INFORMATION: 4856gH20 V-region

<400> SEQUENCE: 67

```
gaagtgcaac tggtggaaag cggaggaggt ttggtgaaac cgggagggtc actgcggctc    60
tcctgtgccg cctccggatt cagcctctcg tcctacgaca tgagctgggt cagacaggcc   120
cccgggaagg gcctggagtg gatttccatc atctacggcg gctccggctc gacttggtac   180
gcttcgtggg ccaagggacg gttcaccatg tccaaggatt ccgcgaagaa cagcgtgtat   240
ctgcagatga actctctgcg ggccgaggac accgcagtgt actactgcgc gaggggcgc    300
gacgccggcg ccgggggatc acgcaacggt tactcccttt ggggacaggg aaccctggtc   360
actgtctcca gc                                                        372
```

<210> SEQ ID NO 68
<211> LENGTH: 372
<212> TYPE: DNA
<213> ORGANISM: Artificial Sequence
<220> FEATURE:
<223> OTHER INFORMATION: 4856gH20 V-region (E. coli expression)

<400> SEQUENCE: 68

```
gaggttcagc tggtcgagtc tggaggcggg cttgtcaaac tggagggag cctgcgtctc     60
tcttgtgcag caagcggctt cagcctgtcc tcttacgata tgtcctgggt gcgccaggca   120
cctgggaagg gcctggagtg gatttctatt atttatggcg gcagcggcag cacatggtac   180
gcgagctggg cgaagggccg tttcaccatg tccaaagaca cgcaaagaa tagcgtgtac    240
ctccagatga actctctccg cgcagaggac acagcagtct attactgtgc gcggggccgc   300
gatgcaggcg cgggcggcag ccgcaatggg tatagcctgt ggggacaggg gacccttgtg   360
acagtctcga gc                                                        372
```

<210> SEQ ID NO 69
<211> LENGTH: 142
<212> TYPE: PRT
<213> ORGANISM: Artificial Sequence
<220> FEATURE:
<223> OTHER INFORMATION: 4856gH20 V-region with signal sequence
      (mammalian expression)

<400> SEQUENCE: 69

```
Met Lys Trp Val Thr Phe Ile Ser Leu Leu Phe Leu Phe Ser Ser Ala
1               5                   10                  15

Tyr Ser Glu Val Gln Leu Val Glu Ser Gly Gly Gly Leu Val Lys Pro
            20                  25                  30

Gly Gly Ser Leu Arg Leu Ser Cys Ala Ala Ser Gly Phe Ser Leu Ser
        35                  40                  45

Ser Tyr Asp Met Ser Trp Val Arg Gln Ala Pro Gly Lys Gly Leu Glu
    50                  55                  60

Trp Ile Ser Ile Ile Tyr Gly Gly Ser Gly Ser Thr Trp Tyr Ala Ser
65                  70                  75                  80

Trp Ala Lys Gly Arg Phe Thr Met Ser Lys Asp Ser Ala Lys Asn Ser
                85                  90                  95

Val Tyr Leu Gln Met Asn Ser Leu Arg Ala Glu Asp Thr Ala Val Tyr
            100                 105                 110
```

Tyr Cys Ala Arg Gly Arg Asp Ala Gly Ala Gly Gly Ser Arg Asn Gly
            115                 120                 125

Tyr Ser Leu Trp Gly Gln Gly Thr Leu Val Thr Val Ser Ser
        130                 135                 140

<210> SEQ ID NO 70
<211> LENGTH: 426
<212> TYPE: DNA
<213> ORGANISM: Artificial Sequence
<220> FEATURE:
<223> OTHER INFORMATION: 4856gH20 V-region with signal sequence
      (mammalian expression)

<400> SEQUENCE: 70
atgaagtggg tcaccttcat ctccctgctg tttctgttct ccagcgccta ctccgaagtg     60
caactggtgg aaagcggagg aggtttggtg aaaccgggag ggtcactgcg gctctcctgt    120
gccgcctccg gattcagcct ctcgtcctac gacatgagct gggtcagaca ggccccgggg    180
aagggcctgg agtggatttc catcatctac ggcggctccg gctcgacttg gtacgcttcg    240
tgggccaagg gacggttcac catgtccaag gattccgcga agaacagcgt gtatctgcag    300
atgaactctc tgcgggccga ggacaccgca gtgtactact gcgcgagggg cgcgacgcc    360 ggcgccgggg gatcacgcaa cggttactcc ctttggggac agggaaccct ggtcactgtc    420
tccagc                                                              426

<210> SEQ ID NO 71
<211> LENGTH: 145
<212> TYPE: PRT
<213> ORGANISM: Artificial Sequence
<220> FEATURE:
<223> OTHER INFORMATION: 4856gH20 V-region with signal sequence (E. coli
      expression)

<400> SEQUENCE: 71

Met Lys Lys Thr Ala Ile Ala Ile Ala Val Ala Leu Ala Gly Phe Ala
1               5                   10                  15

Thr Val Ala Gln Ala Glu Val Gln Leu Val Glu Ser Gly Gly Gly Leu
            20                  25                  30

Val Lys Pro Gly Gly Ser Leu Arg Leu Ser Cys Ala Ala Ser Gly Phe
        35                  40                  45

Ser Leu Ser Ser Tyr Asp Met Ser Trp Val Arg Gln Ala Pro Gly Lys
    50                  55                  60

Gly Leu Glu Trp Ile Ser Ile Ile Tyr Gly Gly Ser Gly Ser Thr Trp
65                  70                  75                  80

Tyr Ala Ser Trp Ala Lys Gly Arg Phe Thr Met Ser Lys Asp Ser Ala
                85                  90                  95

Lys Asn Ser Val Tyr Leu Gln Met Asn Ser Leu Arg Ala Glu Asp Thr
            100                 105                 110

Ala Val Tyr Tyr Cys Ala Arg Gly Arg Asp Ala Gly Ala Gly Gly Ser
        115                 120                 125

Arg Asn Gly Tyr Ser Leu Trp Gly Gln Gly Thr Leu Val Thr Val Ser
    130                 135                 140

Ser
145

<210> SEQ ID NO 72
<211> LENGTH: 435
<212> TYPE: DNA

```
<213> ORGANISM: Artificial Sequence
<220> FEATURE:
<223> OTHER INFORMATION: 4856gH20 V-region with signal sequence (E. coli
      expression)

<400> SEQUENCE: 72
atgaagaaga ctgctatagc aattgcagtg gcgctagctg gtttcgccac cgtggcgcaa      60
gctgaggttc agctggtcga gtctggaggc gggcttgtca aacctggagg gagcctgcgt     120
ctctcttgtg cagcaagcgg cttcagcctg tcctcttacg atatgtcctg ggtgcgccag     180
gcacctggga agggcctgga gtggatttct attatttatg cggcagcgg cagcacatgg      240 tacgcgagct gggcgaaggg ccgtttcacc atgtccaaag acagcgcaaa gaatagcgtg     300
tacctccaga tgaactctct ccgcgcagag gacacagcag tctattactg tgcgcgggc      360 cgcgatgcag gcgcgggcgg cagccgcaat gggtatagcc tgtggggaca ggggacccttt   420 gtgacagtct cgagc                                                      435
```

<210> SEQ ID NO 73
<211> LENGTH: 227
<212> TYPE: PRT
<213> ORGANISM: Artificial Sequence
<220> FEATURE:
<223> OTHER INFORMATION: 4856 gH20 Fab heavy chain

<400> SEQUENCE: 73

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Leu Ser Ser Tyr
            20                  25                  30

Asp Met Ser Trp Val Arg Gln Ala Pro Gly Lys Gly Leu Glu Trp Ile
        35                  40                  45

Ser Ile Ile Tyr Gly Gly Ser Gly Ser Thr Trp Tyr Ala Ser Trp Ala
    50                  55                  60

Lys Gly Arg Phe Thr Met Ser Lys Asp Ser Ala Lys Asn Ser Val Tyr
65                  70                  75                  80

Leu Gln Met Asn Ser Leu Arg Ala Glu Asp Thr Ala Val Tyr Tyr Cys
                85                  90                  95

Ala Arg Gly Arg Asp Ala Gly Ala Gly Gly Ser Arg Asn Gly Tyr Ser
            100                 105                 110

Leu Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys
225
```

<210> SEQ ID NO 74
<211> LENGTH: 681
<212> TYPE: DNA
<213> ORGANISM: Artificial Sequence
<220> FEATURE:
<223> OTHER INFORMATION: 4856 gH20 Fab heavy chain (V + human gamma-1
CH1) (mammalian expression)

<400> SEQUENCE: 74

```
gaagtgcaac tggtggaaag cggaggaggt ttggtgaaac cgggagggtc actgcggctc    60
tcctgtgccg cctccggatt cagcctctcg tcctacgaca tgagctgggt cagacaggcc   120
cccgggaagg gcctggagtg gatttccatc atctacggcg ctccggctc gacttggtac    180 gcttcgtggg ccaagggacg gttcaccatg tccaaggatt ccgcgaagaa cagcgtgtat   240
ctgcagatga actctctgcg ggccgaggac accgcagtgt actactgcgc gaggggcgc    300 gacgccggcg ccggggatc acgcaacggt tactcccttt ggggacaggg aaccctggtc    360
actgtctcca gcgcttctac aaagggccca tcggtcttcc cctggcacc ctcctccaag    420 agcacctctg gggcacagc ggccctgggc tgcctggtca aggactactt ccccgaaccg    480
gtgacggtgt cgtggaactc aggcgccctg accagcggcg tgcacacctt cccggctgtc   540
ctacagtcct caggactcta ctccctcagc agcgtggtga ccgtgccctc cagcagcttg    600
ggcacccaga cctacatctg caacgtgaat cacaagccca gcaacaccaa ggtggacaag    660
aaagttgagc ccaaatcttg t                                              681
```

<210> SEQ ID NO 75
<211> LENGTH: 681
<212> TYPE: DNA
<213> ORGANISM: Artificial Sequence
<220> FEATURE:
<223> OTHER INFORMATION: 4856 gH20 Fab heavy chain (V + human gamma-1
CH1) (E. coli expression)

<400> SEQUENCE: 75

```
gaggttcagc tggtcgagtc tggaggcggg cttgtcaaac tggaggagag cctgcgtctc    60
tcttgtgcag caagcggctt cagcctgtcc tcttacgata tgtcctgggt cgccaggca    120 cctgggaagg gcctggagtg gatttctatt atttatggcg cagcggcag cacatggtac    180 gcgagctggg cgaagggccg tttcaccatg tccaagaca gcgcaaagaa tagcgtgtac   240
ctccagatga actctctccg cgcagaggac acagcagtct attactgtgc gcggggccgc   300
gatgcaggcg cgggcggcag ccgcaatggg tatagcctgt ggggacaggg gaccctgtg    360 acagtctcga gcgcttctac aaagggccca tcggtcttcc cctggcacc ctcctccaag    420 agcacctctg gggcacagc ggccctgggc tgcctggtca aggactactt ccccgaaccg    480
gtgacggtgt cgtggaactc aggcgccctg accagcggcg tgcacacctt cccggctgtc   540
ctacagtcct caggactcta ctccctcagc agcgtggtga ccgtgccctc cagcagcttg    600
ggcacccaga cctacatctg caacgtgaat cacaagccca gcaacaccaa ggtcgacaag    660
aaagttgagc ccaaatcttg t                                              681
```

<210> SEQ ID NO 76
<211> LENGTH: 245
<212> TYPE: PRT
<213> ORGANISM: Artificial Sequence
<220> FEATURE:
<223> OTHER INFORMATION: 4856 gH20 Fab heavy chain with signal sequence
(mammalian expression)

<400> SEQUENCE: 76

```
Met Lys Trp Val Thr Phe Ile Ser Leu Leu Phe Leu Phe Ser Ser Ala
1               5                   10                  15

Tyr Ser Glu Val Gln Leu Val Glu Ser Gly Gly Gly Leu Val Lys Pro
            20                  25                  30

Gly Gly Ser Leu Arg Leu Ser Cys Ala Ala Ser Gly Phe Ser Leu Ser
        35                  40                  45

Ser Tyr Asp Met Ser Trp Val Arg Gln Ala Pro Gly Lys Gly Leu Glu
    50                  55                  60

Trp Ile Ser Ile Ile Tyr Gly Gly Ser Gly Ser Thr Trp Tyr Ala Ser
65                  70                  75                  80

Trp Ala Lys Gly Arg Phe Thr Met Ser Lys Ser Ala Lys Asn Ser
                85                  90                  95

Val Tyr Leu Gln Met Asn Ser Leu Arg Ala Glu Asp Thr Ala Val Tyr
                100                 105                 110

Tyr Cys Ala Arg Gly Arg Asp Ala Gly Ala Gly Gly Ser Arg Asn Gly
            115                 120                 125

Tyr Ser Leu Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
                180                 185                 190

His Thr Phe Pro Ala Val Leu Gln Ser Ser Gly Leu Tyr Ser Leu Ser
            195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys
                245
```

<210> SEQ ID NO 77
<211> LENGTH: 735
<212> TYPE: DNA
<213> ORGANISM: Artificial Sequence
<220> FEATURE:
<223> OTHER INFORMATION: 4856 gH20 Fab heavy chain with signal sequence
      (mammalian expression)

<400> SEQUENCE: 77

```
atgaagtggg tcaccttcat ctccctgctg tttctgttct ccagcgccta ctccgaagtg    60
caactggtgg aaagcggagg aggtttggtg aaaccgggag gtcactgcg gctctcctgt   120 gccgcctccg gattcagcct ctcgtcctac gacatgagct gggtcagaca ggcccccggg   180
aagggcctgg agtggatttc catcatctac ggcggctccg gctcgacttg gtacgcttcg   240
tgggccaagg gacggttcac catgtccaag gattccgcga agaacagcgt gtatctgcag   300
atgaactctc tgcgggccga ggacaccgca gtgtactact gcgcgagggg cgcgacgcc   360 ggcgccgggg gatcacgcaa cggttactcc ctttggggac agggaaccct ggtcactgtc   420
tccagcgctt ctacaaaggg cccatcggtc ttccccctgg caccctcctc caagagcacc   480 tctggggca cagcggccct gggctgcctg gtcaaggact acttccccga accggtgacg   540
gtgtcgtgga actcaggcgc cctgaccagc ggcgtgcaca ccttcccggc tgtcctacag   600
```

```
tcctcaggac tctactccct cagcagcgtg gtgaccgtgc cctccagcag cttgggcacc    660
cagacctaca tctgcaacgt gaatcacaag cccagcaaca ccaaggtgga caagaaagtt    720
gagcccaaat cttgt                                                    735
```

<210> SEQ ID NO 78
<211> LENGTH: 248
<212> TYPE: PRT
<213> ORGANISM: Artificial Sequence
<220> FEATURE:
<223> OTHER INFORMATION: 4856 gH20 Fab heavy chain with signal sequence
     (E. coli expression)

<400> SEQUENCE: 78

```
Met Lys Lys Thr Ala Ile Ala Ile Ala Val Ala Leu Ala Gly Phe Ala
1               5                   10                  15

Thr Val Ala Gln Ala Glu Val Gln Leu Val Glu Ser Gly Gly Gly Leu
            20                  25                  30

Val Lys Pro Gly Gly Ser Leu Arg Leu Ser Cys Ala Ala Ser Gly Phe
        35                  40                  45

Ser Leu Ser Ser Tyr Asp Met Ser Trp Val Arg Gln Ala Pro Gly Lys
    50                  55                  60

Gly Leu Glu Trp Ile Ser Ile Ile Tyr Gly Gly Ser Gly Ser Thr Trp
65                  70                  75                  80

Tyr Ala Ser Trp Ala Lys Gly Arg Phe Thr Met Ser Lys Asp Ser Ala
                85                  90                  95

Lys Asn Ser Val Tyr Leu Gln Met Asn Ser Leu Arg Ala Glu Asp Thr
            100                 105                 110

Ala Val Tyr Tyr Cys Ala Arg Gly Arg Asp Ala Gly Ala Gly Gly Ser
        115                 120                 125

Arg Asn Gly Tyr Ser Leu Trp Gly Gln Gly Thr Leu Val Thr Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240

Lys Lys Val Glu Pro Lys Ser Cys
                245
```

<210> SEQ ID NO 79
<211> LENGTH: 744
<212> TYPE: DNA
<213> ORGANISM: Artificial Sequence
<220> FEATURE:
<223> OTHER INFORMATION: 4856 gH20 Fab heavy chain with signal sequence
     (E. coli expression)

<400> SEQUENCE: 79

```
atgaagaaga ctgctatagc aattgcagtg gcgctagctg gtttcgccac cgtggcgcaa    60
```

```
gctgaggttc agctggtcga gtctggaggc gggcttgtca aacctggagg gagcctgcgt    120
ctctcttgtg cagcaagcgg cttcagcctg tcctcttacg atatgtcctg ggtgcgccag    180
gcacctggga agggcctgga gtggatttct attatttatg gcggcagcgg cagcacatgg    240
tacgcgagct gggcgaaggg ccgtttcacc atgtccaaag acagcgcaaa gaatagcgtg    300
tacctccaga tgaactctct ccgcgcagag gacacagcag tctattactg tgcgcggggc    360
cgcgatgcag gcgcgggcgg cagccgcaat gggtatagcc tgtggggaca ggggacccTT    420
gtgacagtct cgagcgcttc tacaaagggc ccatcggtct tccccctggc accctcctcc    480
aagagcacct ctgggggcac agcggccctg ggctgcctgg tcaaggacta cttccccgaa    540
ccggtgacgg tgtcgtggaa ctcaggcgcc ctgaccagcg gcgtgcacac cttcccggct    600
gtcctacagt cctcaggact ctactccctc agcagcgtgg tgaccgtgcc ctccagcagc    660
ttgggcaccc agacctacat ctgcaacgtg aatcacaagc ccagcaacac caaggtcgac    720
aagaaagttg agcccaaatc ttgt                                           744
```

```
<210> SEQ ID NO 80
<211> LENGTH: 124
<212> TYPE: PRT
<213> ORGANISM: Artificial Sequence
<220> FEATURE:
<223> OTHER INFORMATION: 4856gH23 V-region

<400> SEQUENCE: 80

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Leu Ser Ser Tyr
            20                  25                  30

Asp Met Ser Trp Val Arg Gln Ala Pro Gly Lys Gly Leu Glu Trp Ile
        35                  40                  45

Gly Ile Ile Tyr Gly Gly Ser Gly Ser Thr Trp Tyr Ala Ser Trp Ala
    50                  55                  60

Lys Gly Arg Phe Thr Ile Ser Arg Asp Ser Ala Lys Asn Ser Val Tyr
65                  70                  75                  80

Leu Gln Met Asn Ser Leu Arg Ala Glu Asp Thr Ala Val Tyr Tyr Cys
                85                  90                  95

Ala Arg Gly Arg Asp Ala Gly Ala Gly Gly Ser Arg Asn Ala Tyr Ser
            100                 105                 110

Leu Trp Gly Gln Gly Thr Leu Val Thr Val Ser Ser
        115                 120
```

```
<210> SEQ ID NO 81
<211> LENGTH: 372
<212> TYPE: DNA
<213> ORGANISM: Artificial Sequence
<220> FEATURE:
<223> OTHER INFORMATION: 4856gH23 V-region

<400> SEQUENCE: 81
gaagtgcaac tggtggaaag cggaggaggt ttggtgaaac cgggagggtc actgcggctc     60
tcctgtgccg cctccggatt cagcctctcg tcctacgaca tgagctgggt cagacaggcc    120
cccgggaagg gcctggagtg gattggtatc atctacggcg gctccggctc gacttggtac    180
gcttcgtggg ccaagggacg gttcaccatc tcccgcgatt ccgcgaagaa cagcgtgtat    240
ctgcagatga actctctgcg ggccgaggac accgcagtgt actactgcgc gagggggcgc    300
gacgccggcg ccgggggatc acgcaacgcc tactcccttt ggggacaggg aaccctggtc    360
```

| | |
|---|---|
| actgtctcca gc | 372 |

<210> SEQ ID NO 82
<211> LENGTH: 372
<212> TYPE: DNA
<213> ORGANISM: Artificial Sequence
<220> FEATURE:
<223> OTHER INFORMATION: 4856gH23 V-region (E. coli expression)

<400> SEQUENCE: 82

| | |
|---|---|
| gaggttcagc tggtcgagtc tggaggcggg cttgtcaaac tggagggag cctgcgtctc | 60 |
| tcttgtgcag caagcggctt cagcctgtcc tcttacgata tgtcctgggt gcgccaggca | 120 |
| cctgggaagg gcctggagtg gattggcatt atttatggcg gcagcggcag cacatggtac | 180 |
| gcgagctggg cgaagggccg tttcaccatc tcccgggaca cgcaaagaa tagcgtgtac | 240 |
| ctccagatga actctctccg cgcagaggac acagcagtct attactgtgc gcggggccgc | 300 |
| gatgcaggcg cgggcggcag ccgcaacgcg tatagcctgt ggggacaggg gacccttgtg | 360 |
| acagtctcga gc | 372 |

<210> SEQ ID NO 83
<211> LENGTH: 142
<212> TYPE: PRT
<213> ORGANISM: Artificial Sequence
<220> FEATURE:
<223> OTHER INFORMATION: 4856gH23 V-region with signal sequence
      (mammalian expression)

<400> SEQUENCE: 83

Met Lys Trp Val Thr Phe Ile Ser Leu Leu Phe Leu Phe Ser Ser Ala
1               5                   10                  15

Tyr Ser Glu Val Gln Leu Val Glu Ser Gly Gly Gly Leu Val Lys Pro
            20                  25                  30

Gly Gly Ser Leu Arg Leu Ser Cys Ala Ala Ser Gly Phe Ser Leu Ser
        35                  40                  45

Ser Tyr Asp Met Ser Trp Val Arg Gln Ala Pro Gly Lys Gly Leu Glu
    50                  55                  60

Trp Ile Gly Ile Ile Tyr Gly Gly Ser Gly Ser Thr Trp Tyr Ala Ser
65                  70                  75                  80

Trp Ala Lys Gly Arg Phe Thr Ile Ser Arg Asp Ser Ala Lys Asn Ser
                85                  90                  95

Val Tyr Leu Gln Met Asn Ser Leu Arg Ala Glu Asp Thr Ala Val Tyr
            100                 105                 110

Tyr Cys Ala Arg Gly Arg Asp Ala Gly Ala Gly Gly Ser Arg Asn Ala
        115                 120                 125

Tyr Ser Leu Trp Gly Gln Gly Thr Leu Val Thr Val Ser Ser
    130                 135                 140

<210> SEQ ID NO 84
<211> LENGTH: 426
<212> TYPE: DNA
<213> ORGANISM: Artificial Sequence
<220> FEATURE:
<223> OTHER INFORMATION: 4856gH23 V-region with signal sequence
      (mammalian expression)

<400> SEQUENCE: 84

| | |
|---|---|
| atgaagtggg tcaccttcat ctccctgctg tttctgttct ccagcgccta ctccgaagtg | 60 |
| caactggtgg aaagcggagg aggtttggtg aaaccgggag gtcactgcg gctctcctgt | 120 |

```
gccgcctccg gattcagcct ctcgtcctac gacatgagct gggtcagaca ggccccgggg      180
aagggcctgg agtggattgg tatcatctac ggcggctccg gctcgacttg gtacgcttcg      240
tgggccaagg gacggttcac catctcccgc gattccgcga agaacagcgt gtatctgcag      300
atgaactctc tgcgggccga ggacaccgca gtgtactact gcgcgagggg gcgcgacgcc      360
ggcgccgggg gatcacgcaa cgcctactcc ctttggggac agggaaccct ggtcactgtc      420
tccagc                                                                426
```

```
<210> SEQ ID NO 85
<211> LENGTH: 145
<212> TYPE: PRT
<213> ORGANISM: Artificial Sequence
<220> FEATURE:
<223> OTHER INFORMATION: 4856gH23 V-region with signal sequence (E. coli
      expression)

<400> SEQUENCE: 85
```

```
Met Lys Lys Thr Ala Ile Ala Ile Ala Val Ala Leu Ala Gly Phe Ala
1               5                   10                  15

Thr Val Ala Gln Ala Glu Val Gln Leu Val Glu Ser Gly Gly Gly Leu
            20                  25                  30

Val Lys Pro Gly Gly Ser Leu Arg Leu Ser Cys Ala Ala Ser Gly Phe
        35                  40                  45

Ser Leu Ser Ser Tyr Asp Met Ser Trp Val Arg Gln Ala Pro Gly Lys
    50                  55                  60

Gly Leu Glu Trp Ile Gly Ile Ile Tyr Gly Gly Ser Gly Ser Thr Trp
65                  70                  75                  80

Tyr Ala Ser Trp Ala Lys Gly Arg Phe Thr Ile Ser Arg Asp Ser Ala
                85                  90                  95

Lys Asn Ser Val Tyr Leu Gln Met Asn Ser Leu Arg Ala Glu Asp Thr
            100                 105                 110

Ala Val Tyr Tyr Cys Ala Arg Gly Arg Asp Ala Gly Ala Gly Gly Ser
        115                 120                 125

Arg Asn Ala Tyr Ser Leu Trp Gly Gln Gly Thr Leu Val Thr Val Ser
    130                 135                 140

Ser
145
```

```
<210> SEQ ID NO 86
<211> LENGTH: 435
<212> TYPE: DNA
<213> ORGANISM: Artificial Sequence
<220> FEATURE:
<223> OTHER INFORMATION: 4856gH23 V-region with signal sequence (E. coli
      expression)

<400> SEQUENCE: 86
```

```
atgaagaaga ctgctatagc aattgcagtg gcgctagctg gtttcgccac cgtggcgcaa      60
gctgaggttc agctggtcga gtctggaggc gggcttgtca aacctggagg agcctgcgt      120 ctctcttgtg cagcaagcgg cttcagcctg tcctcttacg atatgtcctg ggtgcgccag      180
gcacctggaa agggcctgga gtggattggc attatttatg gcggcagcgg cagcacatgg      240
tacgcgagct gggcgaaggg ccgtttcacc atctcccggg acagcgcaaa gaatagcgtg      300
tacctccaga tgaactctct ccgcgcagag gacacagcag tctattactg tgcgcggggc      360
cgcgatgcag gcgcgggcgg cagccgcaac gcgtatagcc tgtggggaca ggggaccctt      420
```

```
gtgacagtct cgagc                                                       435
```

<210> SEQ ID NO 87
<211> LENGTH: 227
<212> TYPE: PRT
<213> ORGANISM: Artificial Sequence
<220> FEATURE:
<223> OTHER INFORMATION: 4856 gH23 Fab heavy chain (V + human gamma-1 CH1)

<400> SEQUENCE: 87

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Leu Ser Ser Tyr
            20                  25                  30

Asp Met Ser Trp Val Arg Gln Ala Pro Gly Lys Gly Leu Glu Trp Ile
        35                  40                  45

Gly Ile Ile Tyr Gly Gly Ser Gly Ser Thr Trp Tyr Ala Ser Trp Ala
    50                  55                  60

Lys Gly Arg Phe Thr Ile Ser Arg Asp Ser Ala Lys Asn Ser Val Tyr
65                  70                  75                  80

Leu Gln Met Asn Ser Leu Arg Ala Glu Asp Thr Ala Val Tyr Tyr Cys
                85                  90                  95

Ala Arg Gly Arg Asp Ala Gly Ala Gly Gly Ser Arg Asn Ala Tyr Ser
            100                 105                 110

Leu Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys
225
```

<210> SEQ ID NO 88
<211> LENGTH: 681
<212> TYPE: DNA
<213> ORGANISM: Artificial Sequence
<220> FEATURE:
<223> OTHER INFORMATION: 4856 gH23 Fab heavy chain (V + human gamma-1 CH1) (mammalian expression)

<400> SEQUENCE: 88

```
gaagtgcaac tggtggaaag cggaggaggt ttggtgaaac cgggagggtc actgcggctc    60
tcctgtgccg cctccggatt cagcctctcg tcctacgaca tgagctgggt cagacaggcc   120
cccgggaagg gcctggagtg gattggtatc atctacggcg gctccggctc gacttggtac   180
gcttcgtggg ccaagggacg gttcaccatc tcccgcgatt ccgcgaagaa cagcgtgtat   240
ctgcagatga actctctgcg ggccgaggac accgcagtgt actactgcgc gagggggcgc   300
```

```
gacgccggcg ccgggggatc acgcaacgcc tactcccttt ggggacaggg aaccctggtc    360
actgtctcca gcgcttctac aaagggccca tcggtcttcc ccctggcacc ctcctccaag    420
agcacctctg ggggcacagc ggccctgggc tgcctggtca aggactactt ccccgaaccg    480
gtgacggtgt cgtggaactc aggcgccctg accagcggcg tgcacacctt cccggctgtc    540
ctacagtcct caggactcta ctccctcagc agcgtggtga ccgtgccctc cagcagcttg    600
ggcacccaga cctacatctg caacgtgaat cacaagccca gcaacaccaa ggtggacaag    660
aaagttgagc ccaaatcttg t                                              681
```

<210> SEQ ID NO 89
<211> LENGTH: 681
<212> TYPE: DNA
<213> ORGANISM: Artificial Sequence
<220> FEATURE:
<223> OTHER INFORMATION: 4856 gH23 Fab heavy chain (V + human gamma-1 CH1) (E. coli expression)

<400> SEQUENCE: 89

```
gaggttcagc tggtcgagtc tggaggcggg cttgtcaaac ctggagggag cctgcgtctc     60
tcttgtgcag caagcggctt cagcctgtcc tcttacgata tgtcctgggt cgcgccaggca   120 cctgggaagg gcctggagtg gattggcatt atttatggcg gcagcggcag cacatggtac   180
gcgagctggg cgaagggccg tttcaccatc tcccgggaca cgcaaagaa  tagcgtgtac    240 ctccagatga actctctccg cgcagaggac acagcagtct attactgtgc gcggggccgc   300
gatgcaggcg cgggcggcag ccgcaacgcg tatagcctgt ggggacaggg gacccttgtg   360
acagtctcga gcgcttctac aaagggccca tcggtcttcc ccctggcacc ctcctccaag   420
agcacctctg ggggcacagc ggccctgggc tgcctggtca aggactactt ccccgaaccg   480
gtgacggtgt cgtggaactc aggcgccctg accagcggcg tgcacacctt cccggctgtc   540
ctacagtcct caggactcta ctccctcagc agcgtggtga ccgtgccctc cagcagcttg   600
ggcacccaga cctacatctg caacgtgaat cacaagccca gcaacaccaa ggtcgacaag   660
aaagttgagc ccaaatcttg t                                             681
```

<210> SEQ ID NO 90
<211> LENGTH: 245
<212> TYPE: PRT
<213> ORGANISM: Artificial Sequence
<220> FEATURE:
<223> OTHER INFORMATION: 4856 gH23 Fab heavy chain with signal sequence (mammalian expression)

<400> SEQUENCE: 90

```
Met Lys Trp Val Thr Phe Ile Ser Leu Leu Phe Leu Phe Ser Ser Ala
1               5                   10                  15

Tyr Ser Glu Val Gln Leu Val Glu Ser Gly Gly Gly Leu Val Lys Pro
            20                  25                  30

Gly Gly Ser Leu Arg Leu Ser Cys Ala Ala Ser Gly Phe Ser Leu Ser
        35                  40                  45

Ser Tyr Asp Met Ser Trp Val Arg Gln Ala Pro Gly Lys Gly Leu Glu
    50                  55                  60

Trp Ile Gly Ile Ile Tyr Gly Gly Ser Gly Ser Thr Trp Tyr Ala Ser
65                  70                  75                  80

Trp Ala Lys Gly Arg Phe Thr Ile Ser Arg Asp Ser Ala Lys Asn Ser
                85                  90                  95

Val Tyr Leu Gln Met Asn Ser Leu Arg Ala Glu Asp Thr Ala Val Tyr
```

```
                100                 105                 110
Tyr Cys Ala Arg Gly Arg Asp Ala Gly Ala Gly Gly Ser Arg Asn Ala
            115                 120                 125
Tyr Ser Leu Trp Gly Gln Gly Thr Leu Val Thr Val Ser Ser Ala Ser
        130                 135                 140
Thr Lys Gly Pro Ser Val Phe Pro Leu Ala Pro Ser Ser Lys Ser Thr
145                 150                 155                 160
Ser Gly Gly Thr Ala Ala Leu Gly Cys Leu Val Lys Asp Tyr Phe Pro
                165                 170                 175
Glu Pro Val Thr Val Ser Trp Asn Ser Gly Ala Leu Thr Ser Gly Val
            180                 185                 190
His Thr Phe Pro Ala Val Leu Gln Ser Ser Gly Leu Tyr Ser Leu Ser
        195                 200                 205
Ser Val Val Thr Val Pro Ser Ser Ser Leu Gly Thr Gln Thr Tyr Ile
    210                 215                 220
Cys Asn Val Asn His Lys Pro Ser Asn Thr Lys Val Asp Lys Lys Val
225                 230                 235                 240
Glu Pro Lys Ser Cys
                245
```

```
<210> SEQ ID NO 91
<211> LENGTH: 735
<212> TYPE: DNA
<213> ORGANISM: Artificial Sequence
<220> FEATURE:
<223> OTHER INFORMATION: 4856 gH23 Fab heavy chain with signal sequence
      (mammalian expression)

<400> SEQUENCE: 91
atgaagtggg tcaccttcat ctccctgctg tttctgttct ccagcgccta ctccgaagtg      60
caactggtgg aaagcggagg aggtttggtg aaaccgggag gtcactgcg gctctcctgt     120
gccgcctccg gattcagcct ctcgtcctac gacatgagct gggtcagaca ggcccccggg     180
aagggcctgg agtggattgg tatcatctac ggcggctccg gctcgacttg gtacgcttcg     240
tgggccaagg gacggttcac catctcccgc gattccgcga agaacagcgt gtatctgcag     300
atgaactctc tgcgggccga ggacaccgca gtgtactact gcgcgagggg cgcgacgcc     360
ggcgccgggg gatcacgcaa cgcctactcc ctttggggac agggaaccct ggtcactgtc     420
tccagcgctt ctacaaaggg cccatcggtc ttccccctgg caccctcctc caagagcacc     480
tctggggca cagcggccct gggctgcctg gtcaaggact acttccccga accggtgacg     540
gtgtcgtgga actcaggcgc cctgaccagc ggcgtgcaca ccttcccggc tgtcctacag     600
tcctcaggac tctactccct cagcagcgtg gtgaccgtgc cctccagcag cttgggcacc     660
cagacctaca tctgcaacgt gaatcacaag cccagcaaca ccaaggtgga caagaaagtt     720
gagcccaaat cttgt                                                      735

<210> SEQ ID NO 92
<211> LENGTH: 248
<212> TYPE: PRT
<213> ORGANISM: Artificial Sequence
<220> FEATURE:
<223> OTHER INFORMATION: 4856 gH23 Fab heavy chain with signal sequence
      (E. coli expression)

<400> SEQUENCE: 92

Met Lys Lys Thr Ala Ile Ala Ile Ala Val Ala Leu Ala Gly Phe Ala
1               5                   10                  15
```

Thr Val Ala Gln Ala Glu Val Gln Leu Val Glu Ser Gly Gly Gly Leu
            20                  25                  30

Val Lys Pro Gly Gly Ser Leu Arg Leu Ser Cys Ala Ala Ser Gly Phe
        35                  40                  45

Ser Leu Ser Ser Tyr Asp Met Ser Trp Val Arg Gln Ala Pro Gly Lys
 50                  55                  60

Gly Leu Glu Trp Ile Gly Ile Ile Tyr Gly Gly Ser Gly Ser Thr Trp
 65                  70                  75                  80

Tyr Ala Ser Trp Ala Lys Gly Arg Phe Thr Ile Ser Arg Asp Ser Ala
                85                  90                  95

Lys Asn Ser Val Tyr Leu Gln Met Asn Ser Leu Arg Ala Glu Asp Thr
            100                 105                 110

Ala Val Tyr Tyr Cys Ala Arg Gly Arg Asp Ala Gly Ala Gly Gly Ser
        115                 120                 125

Arg Asn Ala Tyr Ser Leu Trp Gly Gln Gly Thr Leu Val Thr Val Ser
130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240

Lys Lys Val Glu Pro Lys Ser Cys
                245

<210> SEQ ID NO 93
<211> LENGTH: 744
<212> TYPE: DNA
<213> ORGANISM: Artificial Sequence
<220> FEATURE:
<223> OTHER INFORMATION: 4856 gH23 Fab heavy chain with signal sequence
      (E. coli expression)

<400> SEQUENCE: 93
atgaagaaga ctgctatagc aattgcagtg gcgctagctg gtttcgccac cgtggcgcaa      60
gctgaggttc agctggtcga gtctggaggc gggcttgtca aacctggagg gagcctgcgt     120
ctctcttgtg cagcaagcgg cttcagcctg tcctcttacg atatgtcctg ggtgcgccag     180
gcacctggga agggcctgga gtggattggc attatttatg gcggcagcgg cagcacatgg     240
tacgcgagct gggcgaaggg ccgtttcacc atctcccggg acagcgcaaa gaatagcgtg     300
tacctccaga tgaactctct ccgcgcagag gacacagcag tctattactg tgcgcggggc     360
cgcgatgcag gcgcgggcgg cagccgcaac gcgtatagcc tgtggggaca ggggaccctt     420
gtgacagtct cgagcgcttc tacaaagggc ccatcggtct tccccctggc accctcctcc     480
aagagcacct ctgggggcac agcggccctg ggctgcctgg tcaaggacta cttccccgaa     540
ccggtgacgg tgtcgtggaa ctcaggcgcc ctgaccagcg gcgtgcacac cttcccggct     600
gtcctacagt cctcaggact ctactccctc agcagcgtgg tgaccgtgcc ctccagcagc     660

```
ttgggcaccc agacctacat ctgcaacgtg aatcacaagc ccagcaacac caaggtcgac    720
aagaaagttg agcccaaatc ttgt                                           744
```

<210> SEQ ID NO 94
<211> LENGTH: 124
<212> TYPE: PRT
<213> ORGANISM: Artificial Sequence
<220> FEATURE:
<223> OTHER INFORMATION: 4856gH29 V-region

<400> SEQUENCE: 94

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Leu Ser Ser Tyr
            20                  25                  30

Asp Met Ser Trp Val Arg Gln Ala Pro Gly Lys Gly Leu Glu Trp Ile
        35                  40                  45

Gly Ile Ile Tyr Gly Gly Ser Gly Ser Thr Trp Tyr Ala Ser Trp Ala
    50                  55                  60

Lys Gly Arg Phe Thr Ile Ser Arg Asp Ser Ala Lys Asn Ser Val Tyr
65                  70                  75                  80

Leu Gln Met Asn Ser Leu Arg Ala Glu Asp Thr Ala Val Tyr Tyr Cys
                85                  90                  95

Ala Arg Gly Arg Asp Ala Gly Ala Gly Gly Ser Arg Asp Gly Tyr Ser
            100                 105                 110

Leu Trp Gly Gln Gly Thr Leu Val Thr Val Ser Ser
        115                 120
```

<210> SEQ ID NO 95
<211> LENGTH: 372
<212> TYPE: DNA
<213> ORGANISM: Artificial Sequence
<220> FEATURE:
<223> OTHER INFORMATION: 4856gH29 V-region (mammalian expression)

<400> SEQUENCE: 95

```
gaagtgcaac tggtggaaag cggaggaggt ttggtgaaac cgggagggtc actgcggctc    60
tcctgtgccg cctccggatt cagcctctcg tcctacgaca tgagctgggt cagacaggcc   120
cccgggaagg gcctggagtg gattggtatc atctacggcg gctccggctc gacttggtac   180
gcttcgtggg ccaagggacg gttcaccatc tcccgcgatt ccgcgaagaa cagcgtgtat   240
ctgcagatga actctctgcg ggccgaggac accgcagtgt actactgcgc gagggggcgc   300
gacgccggcg ccgggggatc acgcgacggt tactcccttt ggggacaggg aaccctggtc   360
actgtctcca gc                                                        372
```

<210> SEQ ID NO 96
<211> LENGTH: 372
<212> TYPE: DNA
<213> ORGANISM: Artificial Sequence
<220> FEATURE:
<223> OTHER INFORMATION: 4856gH29 V-region (E. coli expression)

<400> SEQUENCE: 96

```
gaggttcagc tggtcgagtc tggaggcggg cttgtcaaac tggaggag cctgcgtctc     60 tcttgtgcag caagcggctt cagcctgtcc tcttacgata tgtcctgggt gcgccaggca   120
cctgggaagg gcctggagtg gattggcatt atttatggcg gcagcggcag cacatggtac   180
gcgagctggg cgaagggccg tttcaccatc tcccgggaca gcgcaaagaa tagcgtgtac   240
```

```
ctccagatga actctctccg cgcagaggac acagcagtct attactgtgc gcggggccgc    300
gatgcaggcg cgggcggcag ccgcgatggg tatagcctgt ggggacaggg gacccttgtg    360
acagtctcga gc                                                       372
```

<210> SEQ ID NO 97
<211> LENGTH: 142
<212> TYPE: PRT
<213> ORGANISM: Artificial Sequence
<220> FEATURE:
<223> OTHER INFORMATION: 4856gH29 V-region with signal sequence
      (mammalian expression)

<400> SEQUENCE: 97

```
Met Lys Trp Val Thr Phe Ile Ser Leu Leu Phe Leu Phe Ser Ser Ala
1               5                   10                  15

Tyr Ser Glu Val Gln Leu Val Glu Ser Gly Gly Gly Leu Val Lys Pro
            20                  25                  30

Gly Gly Ser Leu Arg Leu Ser Cys Ala Ala Ser Gly Phe Ser Leu Ser
        35                  40                  45

Ser Tyr Asp Met Ser Trp Val Arg Gln Ala Pro Gly Lys Gly Leu Glu
    50                  55                  60

Trp Ile Gly Ile Ile Tyr Gly Gly Ser Gly Ser Thr Trp Tyr Ala Ser
65                  70                  75                  80

Trp Ala Lys Gly Arg Phe Thr Ile Ser Arg Asp Ser Ala Lys Asn Ser
                85                  90                  95

Val Tyr Leu Gln Met Asn Ser Leu Arg Ala Glu Asp Thr Ala Val Tyr
            100                 105                 110

Tyr Cys Ala Arg Gly Arg Asp Ala Gly Ala Gly Gly Ser Arg Asp Gly
        115                 120                 125

Tyr Ser Leu Trp Gly Gln Gly Thr Leu Val Thr Val Ser Ser
    130                 135                 140
```

<210> SEQ ID NO 98
<211> LENGTH: 426
<212> TYPE: DNA
<213> ORGANISM: Artificial Sequence
<220> FEATURE:
<223> OTHER INFORMATION: 4856gH29 V-region with signal sequence
      (mammalian expression)

<400> SEQUENCE: 98

```
atgaagtggg tcaccttcat ctccctgctg tttctgttct ccagcgccta ctccgaagtg     60
caactggtgg aaagcggagg aggtttggtg aaaccgggag gtcactgcg gctctcctgt    120 gccgcctccg gattcagcct ctcgtcctac gacatgagct gggtcagaca ggcccccggg    180
aagggcctgg agtggattgg tatcatctac ggcggctccg gctcgacttg gtacgcttcg    240
tgggccaagg gacggttcac catctcccgc gattccgcga agaacagcgt gtatctgcag    300
atgaactctc tgcgggccga ggacaccgca gtgtactact cgcgaggggg gcgcgacgcc    360
ggcgccgggg gatcacgcga cggttactcc ctttggggac agggaacccct ggtcactgtc    420 tccagc                                                              426
```

<210> SEQ ID NO 99
<211> LENGTH: 145
<212> TYPE: PRT
<213> ORGANISM: Artificial Sequence
<220> FEATURE:
<223> OTHER INFORMATION: 4856gH29 V-region with signal sequence (E. coli expression)

<400> SEQUENCE: 99

Met Lys Lys Thr Ala Ile Ala Ile Ala Val Ala Leu Ala Gly Phe Ala
1               5                   10                  15

Thr Val Ala Gln Ala Glu Val Gln Leu Val Glu Ser Gly Gly Gly Leu
            20                  25                  30

Val Lys Pro Gly Gly Ser Leu Arg Leu Ser Cys Ala Ala Ser Gly Phe
        35                  40                  45

Ser Leu Ser Ser Tyr Asp Met Ser Trp Val Arg Gln Ala Pro Gly Lys
    50                  55                  60

Gly Leu Glu Trp Ile Gly Ile Ile Tyr Gly Ser Gly Ser Thr Trp
65                  70                  75                  80

Tyr Ala Ser Trp Ala Lys Gly Arg Phe Thr Ile Ser Arg Asp Ser Ala
                85                  90                  95

Lys Asn Ser Val Tyr Leu Gln Met Asn Ser Leu Arg Ala Glu Asp Thr
            100                 105                 110

Ala Val Tyr Tyr Cys Ala Arg Gly Arg Asp Ala Gly Ala Gly Gly Ser
        115                 120                 125

Arg Asp Gly Tyr Ser Leu Trp Gly Gln Gly Thr Leu Val Thr Val Ser
    130                 135                 140

Ser
145

<210> SEQ ID NO 100
<211> LENGTH: 435
<212> TYPE: DNA
<213> ORGANISM: Artificial Sequence
<220> FEATURE:
<223> OTHER INFORMATION: 4856gH29 V-region with signal sequence (E. coli
      expression)

<400> SEQUENCE: 100
atgaagaaga ctgctatagc aattgcagtg gcgctagctg gtttcgccac cgtggcgcaa      60
gctgaggttc agctggtcga gtctggaggc gggcttgtca aacctggagg gagcctgcgt     120
ctctcttgtg cagcaagcgg cttcagcctg tcctcttacg atatgtcctg ggtgcgccag     180
gcacctggga agggcctgga gtggattggc attatttatg gcggcagcgg cagcacatgg     240
tacgcgagct gggcgaaggg ccgtttcacc atctcccggg acagcgcaaa gaatagcgtg     300
tacctccaga tgaactctct ccgcgcagag gacacagcag tctattactg tgcgcggggc     360
cgcgatgcag gcgcgggcgg cagccgcgat gggtatagcc tgtggggaca ggggaccctt     420
gtgacagtct cgagc                                                      435

<210> SEQ ID NO 101
<211> LENGTH: 227
<212> TYPE: PRT
<213> ORGANISM: Artificial Sequence
<220> FEATURE:
<223> OTHER INFORMATION: 4856 gH29 Fab heavy chain (V + human gamma-1
      CH1)

<400> SEQUENCE: 101

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Leu Ser Ser Tyr
            20                  25                  30

Asp Met Ser Trp Val Arg Gln Ala Pro Gly Lys Gly Leu Glu Trp Ile

```
            35                  40                  45
Gly Ile Ile Tyr Gly Gly Ser Gly Ser Thr Trp Tyr Ala Ser Trp Ala
 50                  55                  60

Lys Gly Arg Phe Thr Ile Ser Arg Asp Ser Lys Asn Ser Val Tyr
 65                  70                  75                  80

Leu Gln Met Asn Ser Leu Arg Ala Glu Asp Thr Ala Val Tyr Tyr Cys
                 85                  90                  95

Ala Arg Gly Arg Asp Ala Gly Ala Gly Gly Ser Arg Asp Gly Tyr Ser
                100                 105                 110

Leu Trp Gly Gln Gly Thr Leu Val Thr Val Ser Ser Ala Ser Thr Lys
                115                 120                 125

Gly Pro Ser Val Phe Pro Leu Ala Pro Ser Ser Lys Ser Thr Ser Gly
            130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Lys Val Glu Pro
    210                 215                 220

Lys Ser Cys
225

<210> SEQ ID NO 102
<211> LENGTH: 681
<212> TYPE: DNA
<213> ORGANISM: Artificial Sequence
<220> FEATURE:
<223> OTHER INFORMATION: 4856 gH29 Fab heavy chain (V + human gamma-1
      CH1) (mammalian expression)

<400> SEQUENCE: 102
gaagtgcaac tggtggaaag cggaggaggt ttggtgaaac cgggagggtc actgcggctc      60
tcctgtgccg cctccggatt cagcctctcg tcctacgaca tgagctgggt cagacaggcc    120
cccgggaagg gctggagtg gattggtatc atctacggcg gctccggctc gacttggtac     180
gcttcgtggg ccaagggacg gttcaccatc tcccgcgatt ccgcgaagaa cagcgtgtat    240
ctgcagatga actctctgcg ggccgaggac accgcagtgt actactgcgc gaggggcgc    300 gacgccggcg ccgggggatc acgcgacggt tactcccttt ggggacaggg aaccctggtc    360
actgtctcca gcgcttctac aaagggccca tcggtcttcc cctggcacc ctcctccaag    420 agcacctctg ggggcacagc ggccctgggc tgcctggtca aggactactt ccccgaaccg    480
gtgacggtgt cgtggaactc aggcgccctg accagcggcg tgcacacctt ccggctgtc    540 ctacagtcct caggactcta ctccctcagc agcgtggtga ccgtgccctc agcagcttg    600 ggcacccaga cctacatctg caacgtgaat cacaagccca gcaacaccaa ggtggacaag    660
aaagttgagc ccaaatcttg t                                              681

<210> SEQ ID NO 103
<211> LENGTH: 681
<212> TYPE: DNA
<213> ORGANISM: Artificial Sequence
<220> FEATURE:
```

<223> OTHER INFORMATION: 4856 gH29 Fab heavy chain (V + human gamma-1
CH1) (E. coli expression)

<400> SEQUENCE: 103

```
gaggttcagc tggtcgagtc tggaggcggg cttgtcaaac ctggagggag cctgcgtctc    60
tcttgtgcag caagcggctt cagcctgtcc tcttacgata tgtcctgggt cgcccaggca   120
cctgggaagg gcctggagtg gattggcatt atttatggcg gcagcggcag cacatggtac   180
gcgagctggg cgaagggccg tttcaccatc tcccgggaca cgcaaagaa tagcgtgtac    240
ctccagatga actctctccg cgcagaggac acagcagtct attactgtgc gcggggccgc   300
gatgcaggcg cgggcggcag ccgcgatggg tatagcctgt ggggacaggg gacccttgtg   360
acagtctcga gcgcttctac aaagggccca tcggtcttcc ccctggcacc ctcctccaag   420
agcacctctg ggggcacagc ggccctgggc tgcctggtca aggactactt ccccgaaccg   480
gtgacggtgt cgtggaactc aggcgccctg accagcggcg tgcacacctt cccggctgtc   540
ctacagtcct caggactcta ctccctcagc agcgtggtga ccgtgccctc cagcagcttg   600
ggcacccaga cctacatctg caacgtgaat cacaagccca gcaacaccaa ggtcgacaag   660
aaagttgagc ccaaatcttg t                                              681
```

<210> SEQ ID NO 104
<211> LENGTH: 245
<212> TYPE: PRT
<213> ORGANISM: Artificial Sequence
<220> FEATURE:
<223> OTHER INFORMATION: 4856 gH29 Fab heavy chain with signal sequence
(mammalian expression)

<400> SEQUENCE: 104

Met Lys Trp Val Thr Phe Ile Ser Leu Leu Phe Leu Phe Ser Ser Ala
1               5                   10                  15

Tyr Ser Glu Val Gln Leu Val Glu Ser Gly Gly Gly Leu Val Lys Pro
            20                  25                  30

Gly Gly Ser Leu Arg Leu Ser Cys Ala Ala Ser Gly Phe Ser Leu Ser
        35                  40                  45

Ser Tyr Asp Met Ser Trp Val Arg Gln Ala Pro Gly Lys Gly Leu Glu
    50                  55                  60

Trp Ile Gly Ile Ile Tyr Gly Gly Ser Gly Ser Thr Trp Tyr Ala Ser
65                  70                  75                  80

Trp Ala Lys Gly Arg Phe Thr Ile Ser Arg Asp Ser Ala Lys Asn Ser
                85                  90                  95

Val Tyr Leu Gln Met Asn Ser Leu Arg Ala Glu Asp Thr Ala Val Tyr
            100                 105                 110

Tyr Cys Ala Arg Gly Arg Asp Ala Gly Ala Gly Gly Ser Arg Asp Gly
        115                 120                 125

Tyr Ser Leu Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Leu Gly Thr Gln Thr Tyr Ile
    210                 215                 220

Cys Asn Val Asn His Lys Pro Ser Asn Thr Lys Val Asp Lys Val
225                 230                 235                 240

Glu Pro Lys Ser Cys
                245

<210> SEQ ID NO 105
<211> LENGTH: 735
<212> TYPE: DNA
<213> ORGANISM: Artificial Sequence
<220> FEATURE:
<223> OTHER INFORMATION: 4856 gH29 Fab heavy chain with signal sequence
      (mammalian expression)

<400> SEQUENCE: 105

```
atgaagtggg tcaccttcat ctccctgctg tttctgttct ccagcgccta ctccgaagtg      60
caactggtgg aaagcggagg aggtttggtg aaaccgggag gtcactgcg gctctcctgt     120
gccgcctccg gattcagcct ctcgtcctac gacatgagct gggtcagaca ggccccggg     180
aagggcctgg agtggattgg tatcatctac ggcggctccg gctcgacttg gtacgcttcg     240
tgggccaagg gacggttcac catctcccgc gattccgcga agaacagcgt gtatctgcag     300
atgaactctc tgcgggccga ggacaccgca gtgtactact gcgcgagggg cgcgacgcc     360
ggcgccgggg gatcacgcga cggttactcc ctttggggac agggaaccct ggtcactgtc     420
tccagcgctt ctacaaaggg cccatcggtc ttccccctgg caccctcctc aagagcacc     480
tctgggggca gcggccct gggctgcctg gtcaaggact acttccccga accggtgacg     540
gtgtcgtgga actcaggcgc cctgaccagc ggcgtgcaca ccttcccggc tgtcctacag     600
tcctcaggac tctactccct cagcagcgtg gtgaccgtgc cctccagcag cttgggcacc     660
cagacctaca tctgcaacgt gaatcacaag cccagcaaca ccaaggtgga caagaaagtt     720
gagcccaaat cttgt                                                     735
```

<210> SEQ ID NO 106
<211> LENGTH: 248
<212> TYPE: PRT
<213> ORGANISM: Artificial Sequence
<220> FEATURE:
<223> OTHER INFORMATION: 4856 gH29 Fab heavy chain with signal sequence
      (E. coli expression)

<400> SEQUENCE: 106

Met Lys Lys Thr Ala Ile Ala Ile Ala Val Ala Leu Ala Gly Phe Ala
1               5                   10                  15

Thr Val Ala Gln Ala Glu Val Gln Leu Val Glu Ser Gly Gly Gly Leu
            20                  25                  30

Val Lys Pro Gly Gly Ser Leu Arg Leu Ser Cys Ala Ala Ser Gly Phe
        35                  40                  45

Ser Leu Ser Ser Tyr Asp Met Ser Trp Val Arg Gln Ala Pro Gly Lys
    50                  55                  60

Gly Leu Glu Trp Ile Gly Ile Ile Tyr Gly Gly Ser Gly Ser Thr Trp
65                  70                  75                  80

Tyr Ala Ser Trp Ala Lys Gly Arg Phe Thr Ile Ser Arg Asp Ser Ala
                85                  90                  95

Lys Asn Ser Val Tyr Leu Gln Met Asn Ser Leu Arg Ala Glu Asp Thr
            100                 105                 110

Ala Val Tyr Tyr Cys Ala Arg Gly Arg Asp Ala Gly Ala Gly Gly Ser

|   |   |   | 115 |   |   |   | 120 |   |   |   | 125 |   |
|---|---|---|---|---|---|---|---|---|---|---|---|---|
Arg Asp Gly Tyr Ser Leu Trp Gly Gln Gly Thr Leu Val Thr Val Ser
          130                     135                     140

Ser Ala Ser Thr Lys Gly Pro Ser Val Phe Pro Leu Ala Pro Ser Ser
145                     150                     155                 160

Lys Ser Thr Ser Gly Gly Thr Ala Ala Leu Gly Cys Leu Val Lys Asp
              165                     170                     175

Tyr Phe Pro Glu Pro Val Thr Val Ser Trp Asn Ser Gly Ala Leu Thr
                180                     185                     190

Ser Gly Val His Thr Phe Pro Ala Val Leu Gln Ser Ser Gly Leu Tyr
          195                     200                     205

Ser Leu Ser Ser Val Val Thr Val Pro Ser Ser Ser Leu Gly Thr Gln
      210                     215                     220

Thr Tyr Ile Cys Asn Val Asn His Lys Pro Ser Asn Thr Lys Val Asp
225                     230                     235                 240

Lys Lys Val Glu Pro Lys Ser Cys
              245

<210> SEQ ID NO 107
<211> LENGTH: 744
<212> TYPE: DNA
<213> ORGANISM: Artificial Sequence
<220> FEATURE:
<223> OTHER INFORMATION: 4856 gH29 Fab heavy chain with signal sequence
      (E. coli expression)

<400> SEQUENCE: 107
atgaagaaga ctgctatagc aattgcagtg gcgctagctg gtttcgccac cgtggcgcaa      60
gctgaggttc agctggtcga gtctggaggc gggcttgtca aacctggagg gagcctgcgt     120
ctctcttgtg cagcaagcgg cttcagcctg tcctcttacg atatgtcctg ggtgcgccag     180
gcacctggga agggcctgga gtggattggc attatttatg cggcagcgg cagcacatgg      240 tacgcgagct gggcgaaggg ccgtttcacc atctcccggg acagcgcaaa gaatagcgtg     300
tacctccaga tgaactctct ccgcgcagag gacacagcag tctattactg tgcgcggggc     360
cgcgatgcag gcgcgggcgg cagccgcgat gggtatagcc tgtggggaca ggggacccct     420
gtgacagtct cgagcgcttc tacaaagggc ccatcggtct tccccctggc accctcctcc     480
aagagcacct ctgggggcac agcggccctg ggctgcctgg tcaaggacta cttccccgaa     540
ccggtgacgg tgtcgtggaa ctcaggcgcc ctgaccagcg gcgtgcacac cttcccggct     600
gtcctacagt cctcaggact ctactccctc agcagcgtgg tgaccgtgcc ctccagcagc     660
ttgggcaccc agacctacat ctgcaacgtg aatcacaagc ccagcaacac caaggtcgac     720
aagaaagttg agcccaaatc ttgt                                            744

<210> SEQ ID NO 108
<211> LENGTH: 262
<212> TYPE: PRT
<213> ORGANISM: Artificial Sequence
<220> FEATURE:
<223> OTHER INFORMATION: 4856 scFv

<400> SEQUENCE: 108

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ser Leu Ser Ser Tyr
            20                  25                  30

-continued

Asp Met Ser Trp Val Arg Gln Ala Pro Gly Lys Cys Leu Glu Trp Ile
                35                  40                  45

Gly Ile Ile Tyr Gly Gly Ser Gly Ser Thr Trp Tyr Ala Ser Trp Ala
 50                  55                  60

Lys Gly Arg Phe Thr Ile Ser Arg Asp Ser Ala Lys Asn Ser Val Tyr
 65                  70                  75                  80

Leu Gln Met Asn Ser Leu Arg Ala Glu Asp Thr Ala Val Tyr Tyr Cys
                 85                  90                  95

Ala Arg Gly Arg Asp Ala Gly Ala Gly Ser Arg Asn Gly Tyr Ser
                100                 105                 110

Leu Trp Gly Gln Gly Thr Leu Val Thr Val Ser Ser Gly Gly Gly Gly
            115                 120                 125

Ser Gly Gly Gly Gly Ser Gly Gly Gly Gly Ser Gly Gly Gly Gly Ser
130                 135                 140

Ala Tyr Asp Met Thr Gln Ser Pro Ser Thr Leu Ser Ala Ser Val Gly
145                 150                 155                 160

Asp Arg Val Thr Ile Thr Cys Gln Ala Ser Glu Ser Ile Tyr Ser Gly
                165                 170                 175

Leu Ala Trp Tyr Gln Gln Lys Pro Gly Lys Ala Pro Lys Leu Leu Ile
            180                 185                 190

Tyr Ala Ala Ser Asp Leu Ala Ser Gly Val Pro Ser Arg Phe Ser Gly
        195                 200                 205

Ser Gly Ser Gly Thr Glu Tyr Thr Leu Thr Ile Ser Ser Leu Gln Pro
    210                 215                 220

Asp Asp Phe Ala Thr Tyr Tyr Cys Gln Gln Thr Trp Thr Asp Gly Gly
225                 230                 235                 240

Ile Asp Asn Pro Phe Gly Cys Gly Thr Lys Val Glu Ile Lys Arg Thr
                245                 250                 255

Glu Asn Leu Tyr Phe Gln
            260

<210> SEQ ID NO 109
<211> LENGTH: 107
<212> TYPE: PRT
<213> ORGANISM: Artificial Sequence
<220> FEATURE:
<223> OTHER INFORMATION: Human IGKV1-5 JK4 acceptor framework

<400> SEQUENCE: 109

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Tyr Ser Leu
                 85                  90                  95

Thr Phe Gly Gly Gly Thr Lys Val Glu Ile Lys
            100                 105

<210> SEQ ID NO 110
<211> LENGTH: 321

<212> TYPE: DNA
<213> ORGANISM: Artificial Sequence
<220> FEATURE:
<223> OTHER INFORMATION: Human IGKV1-5 JK4 acceptor framework

<400> SEQUENCE: 110

```
gacatccaga tgacccagtc tccttccacc ctgtctgcat ctgtaggaga cagagtcacc    60
atcacttgcc gggccagtca gagtattagt agctggttgg cctggtatca gcagaaacca   120
gggaaagccc ctaagctcct gatctatgat gcctccagtt tggaaagtgg ggtcccatca   180
aggttcagcg gcagtggatc tgggacagaa ttcactctca ccatcagcag cctgcagcct   240
gatgattttg caacttatta ctgccaacag tataatagtt attctctcac tttcggcgga   300
gggaccaagg tggagatcaa a                                             321
```

<210> SEQ ID NO 111
<211> LENGTH: 114
<212> TYPE: PRT
<213> ORGANISM: Artificial Sequence
<220> FEATURE:
<223> OTHER INFORMATION: Human IGHV3-21 JH5 acceptor framework

<400> SEQUENCE: 111

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asn Trp Phe Asp Ser Trp Gly Gln Gly Thr Leu Val Thr Val
            100                 105                 110

Ser Ser
```

<210> SEQ ID NO 112
<211> LENGTH: 342
<212> TYPE: DNA
<213> ORGANISM: Artificial Sequence
<220> FEATURE:
<223> OTHER INFORMATION: Human IGHV3-21 JH5 acceptor framework

<400> SEQUENCE: 112

```
gaggtgcagc tggtggagtc tgggggaggc ctggtcaagc ctggggggtc cctgagactc    60
tcctgtgcag cctctggatt caccttcagt agctatagca tgaactgggt ccgccaggct   120
ccagggaagg ggctggagtg gtctcatcc attagtagta gtagtagtta catatactac   180
gcagactcag tgaagggccg attcaccatc tccagagaca acgccaagaa ctcactgtat   240
ctgcaaatga acagcctgag agccgaggac acggctgtgt attactgtgc gagaaactgg   300
ttcgactcct ggggccaagg aaccctggtc accgtctcct ca                      342
```

<210> SEQ ID NO 113
<211> LENGTH: 361
<212> TYPE: PRT
<213> ORGANISM: Artificial Sequence
<220> FEATURE:
<223> OTHER INFORMATION: Human LAP and TGFb1

<400> SEQUENCE: 113

```
Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
    130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Arg Asp Asn Thr Leu Gln Val Asp Ile Asn
        195                 200                 205

Gly Phe Thr Thr Gly Arg Arg Gly Asp Leu Ala Thr Ile His Gly Met
    210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg Ala Leu Asp Thr Asn Tyr Cys
                245                 250                 255

Phe Ser Ser Thr Glu Lys Asn Cys Cys Val Arg Gln Leu Tyr Ile Asp
            260                 265                 270

Phe Arg Lys Asp Leu Gly Trp Lys Trp Ile His Glu Pro Lys Gly Tyr
        275                 280                 285

His Ala Asn Phe Cys Leu Gly Pro Cys Pro Tyr Ile Trp Ser Leu Asp
    290                 295                 300

Thr Gln Tyr Ser Lys Val Leu Ala Leu Tyr Asn Gln His Asn Pro Gly
305                 310                 315                 320

Ala Ser Ala Ala Pro Cys Cys Val Pro Gln Ala Leu Glu Pro Leu Pro
                325                 330                 335

Ile Val Tyr Tyr Val Gly Arg Lys Pro Lys Val Glu Gln Leu Ser Asn
            340                 345                 350

Met Ile Val Arg Ser Cys Lys Cys Ser
            355                 360
```

<210> SEQ ID NO 114
<211> LENGTH: 112
<212> TYPE: PRT
<213> ORGANISM: Artificial Sequence
<220> FEATURE:
<223> OTHER INFORMATION: mature human TGFb1

<400> SEQUENCE: 114

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110

<210> SEQ ID NO 115
<211> LENGTH: 394
<212> TYPE: PRT
<213> ORGANISM: Artificial Sequence
<220> FEATURE:
<223> OTHER INFORMATION: Human LAP and TGFb2

<400> SEQUENCE: 115

Leu Ser Thr Cys Ser Thr Leu Asp Met Asp Gln Phe Met Arg Lys Arg
1               5                   10                  15

Ile Glu Ala Ile Arg Gly Gln Ile Leu Ser Lys Leu Lys Leu Thr Ser
            20                  25                  30

Pro Pro Glu Asp Tyr Pro Glu Pro Glu Glu Val Pro Pro Glu Val Ile
        35                  40                  45

Ser Ile Tyr Asn Ser Thr Arg Asp Leu Leu Gln Glu Lys Ala Ser Arg
    50                  55                  60

Arg Ala Ala Ala Cys Glu Arg Glu Arg Ser Asp Glu Glu Tyr Tyr Ala
65                  70                  75                  80

Lys Glu Val Tyr Lys Ile Asp Met Pro Pro Phe Phe Pro Ser Glu Asn
                85                  90                  95

Ala Ile Pro Pro Thr Phe Tyr Arg Pro Tyr Phe Arg Ile Val Arg Phe
            100                 105                 110

Asp Val Ser Ala Met Glu Lys Asn Ala Ser Asn Leu Val Lys Ala Glu
        115                 120                 125

Phe Arg Val Phe Arg Leu Gln Asn Pro Lys Ala Arg Val Pro Glu Gln
    130                 135                 140

Arg Ile Glu Leu Tyr Gln Ile Leu Lys Ser Lys Asp Leu Thr Ser Pro
145                 150                 155                 160

Thr Gln Arg Tyr Ile Asp Ser Lys Val Val Lys Thr Arg Ala Glu Gly
                165                 170                 175

Glu Trp Leu Ser Phe Asp Val Thr Asp Ala Val His Glu Trp Leu His
            180                 185                 190

His Lys Asp Arg Asn Leu Gly Phe Lys Ile Ser Leu His Cys Pro Cys
        195                 200                 205

Cys Thr Phe Val Pro Ser Asn Asn Tyr Ile Ile Pro Asn Lys Ser Glu
    210                 215                 220

Glu Leu Glu Ala Arg Phe Ala Gly Ile Asp Gly Thr Ser Thr Tyr Thr

```
                    225                 230                 235                 240

Ser Gly Asp Gln Lys Thr Ile Lys Ser Thr Arg Lys Lys Asn Ser Gly
                245                 250                 255

Lys Thr Pro His Leu Leu Leu Met Leu Leu Pro Ser Tyr Arg Leu Glu
                260                 265                 270

Ser Gln Gln Thr Asn Arg Arg Lys Arg Ala Leu Asp Ala Ala Tyr
            275                 280                 285

Cys Phe Arg Asn Val Gln Asp Asn Cys Cys Leu Arg Pro Leu Tyr Ile
        290                 295                 300

Asp Phe Lys Arg Asp Leu Gly Trp Lys Trp Ile His Glu Pro Lys Gly
305                 310                 315                 320

Tyr Asn Ala Asn Phe Cys Ala Gly Ala Cys Pro Tyr Leu Trp Ser Ser
                325                 330                 335

Asp Thr Gln His Ser Arg Val Leu Ser Leu Tyr Asn Thr Ile Asn Pro
            340                 345                 350

Glu Ala Ser Ala Ser Pro Cys Cys Val Ser Gln Asp Leu Glu Pro Leu
        355                 360                 365

Thr Ile Leu Tyr Tyr Ile Gly Lys Thr Pro Lys Ile Glu Gln Leu Ser
370                 375                 380

Asn Met Ile Val Lys Ser Cys Lys Cys Ser
385                 390

<210> SEQ ID NO 116
<211> LENGTH: 112
<212> TYPE: PRT
<213> ORGANISM: Artificial Sequence
<220> FEATURE:
<223> OTHER INFORMATION: mature human TGFb2

<400> SEQUENCE: 116

Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Trp Lys Trp
            20                  25                  30

Ile His Glu Pro Lys Gly Tyr Asn Ala Asn Phe Cys Ala Gly Ala Cys
        35                  40                  45

Pro Tyr Leu Trp Ser Ser Asp Thr Gln His Ser Arg Val Leu Ser Leu
    50                  55                  60

Tyr Asn Thr Ile Asn Pro Glu Ala Ser Ala Ser Pro Cys Cys Val Ser
65                  70                  75                  80

Gln Asp Leu Glu Pro Leu Thr Ile Leu Tyr Tyr Ile Gly Lys Thr Pro
                85                  90                  95

Lys Ile Glu Gln Leu Ser Asn Met Ile Val Lys Ser Cys Lys Cys Ser
            100                 105                 110

<210> SEQ ID NO 117
<211> LENGTH: 389
<212> TYPE: PRT
<213> ORGANISM: Artificial Sequence
<220> FEATURE:
<223> OTHER INFORMATION: Human LAP and TGFb3

<400> SEQUENCE: 117

Leu Ser Thr Cys Thr Thr Leu Asp Phe Gly His Ile Lys Lys Lys Arg
1               5                   10                  15

Val Glu Ala Ile Arg Gly Gln Ile Leu Ser Lys Leu Arg Leu Thr Ser
            20                  25                  30
```

```
Pro Pro Glu Pro Thr Val Met Thr His Val Pro Tyr Gln Val Leu Ala
            35                  40                  45
Leu Tyr Asn Ser Thr Arg Glu Leu Leu Glu Glu Met His Gly Glu Arg
 50                  55                  60
Glu Glu Gly Cys Thr Gln Glu Asn Thr Glu Ser Glu Tyr Tyr Ala Lys
 65                  70                  75                  80
Glu Ile His Lys Phe Asp Met Ile Gln Gly Leu Ala Glu His Asn Glu
                 85                  90                  95
Leu Ala Val Cys Pro Lys Gly Ile Thr Ser Lys Val Phe Arg Phe Asn
            100                 105                 110
Val Ser Ser Val Glu Lys Asn Arg Thr Asn Leu Phe Arg Ala Glu Phe
            115                 120                 125
Arg Val Leu Arg Val Pro Asn Pro Ser Ser Lys Arg Asn Glu Gln Arg
130                 135                 140
Ile Glu Leu Phe Gln Ile Leu Arg Pro Asp Glu His Ile Ala Lys Gln
145                 150                 155                 160
Arg Tyr Ile Gly Gly Lys Asn Leu Pro Thr Arg Gly Thr Ala Glu Trp
                165                 170                 175
Leu Ser Phe Asp Val Thr Asp Thr Val Arg Glu Trp Leu Leu Arg Arg
            180                 185                 190
Glu Ser Asn Leu Gly Leu Glu Ile Ser Ile His Cys Pro Cys His Thr
            195                 200                 205
Phe Gln Pro Asn Gly Asp Ile Leu Glu Asn Ile His Glu Val Met Glu
            210                 215                 220
Ile Lys Phe Lys Gly Val Asp Asn Glu Asp Asp His Gly Arg Gly Asp
225                 230                 235                 240
Leu Gly Arg Leu Lys Lys Gln Lys Asp His His Asn Pro His Leu Ile
                245                 250                 255
Leu Met Met Ile Pro Pro His Arg Leu Asp Asn Pro Gly Gln Gly Gly
            260                 265                 270
Gln Arg Lys Lys Arg Ala Leu Asp Thr Asn Tyr Cys Phe Arg Asn Leu
            275                 280                 285
Glu Glu Asn Cys Cys Val Arg Pro Leu Tyr Ile Asp Phe Arg Gln Asp
            290                 295                 300
Leu Gly Trp Lys Trp Val His Glu Pro Lys Gly Tyr Tyr Ala Asn Phe
305                 310                 315                 320
Cys Ser Gly Pro Cys Pro Tyr Leu Arg Ser Ala Asp Thr Thr His Ser
                325                 330                 335
Thr Val Leu Gly Leu Tyr Asn Thr Leu Asn Pro Glu Ala Ser Ala Ser
            340                 345                 350
Pro Cys Cys Val Pro Gln Asp Leu Glu Pro Leu Thr Ile Leu Tyr Tyr
            355                 360                 365
Val Gly Arg Thr Pro Lys Val Glu Gln Leu Ser Asn Met Val Val Lys
            370                 375                 380
Ser Cys Lys Cys Ser
385

<210> SEQ ID NO 118
<211> LENGTH: 112
<212> TYPE: PRT
<213> ORGANISM: Artificial Sequence
<220> FEATURE:
<223> OTHER INFORMATION: Mature human TGFb3

<400> SEQUENCE: 118
```

-continued

```
Ala Leu Asp Thr Asn Tyr Cys Phe Arg Asn Leu Glu Glu Asn Cys Cys
1               5                   10                  15

Val Arg Pro Leu Tyr Ile Asp Phe Arg Gln Asp Leu Gly Trp Lys Trp
            20                  25                  30

Val His Glu Pro Lys Gly Tyr Tyr Ala Asn Phe Cys Ser Gly Pro Cys
        35                  40              45

Pro Tyr Leu Arg Ser Ala Asp Thr Thr His Ser Thr Val Leu Gly Leu
    50              55                  60

Tyr Asn Thr Leu Asn Pro Glu Ala Ser Ala Ser Pro Cys Cys Val Pro
65              70              75                      80

Gln Asp Leu Glu Pro Leu Thr Ile Leu Tyr Tyr Val Gly Arg Thr Pro
            85                  90                  95

Lys Val Glu Gln Leu Ser Asn Met Val Val Lys Ser Cys Lys Cys Ser
            100                 105                 110
```

What is claimed is:

1. An isolated DNA sequence encoding a heavy chain variable domain of an antagonistic antibody, which antagonistic antibody binds human TGF-beta 1, human TGF-beta 2 and human TGF-beta 3, wherein the encoded heavy chain variable domain comprises a CDR having SEQ ID NO:4 for CDR-H1, a CDR having SEQ ID NO:5 for CDR-H2 and a CDR having SEQ ID NO:6, SEQ ID NO:7, SEQ ID NO:8 or SEQ ID NO:9 for CDR-H3.

2. An The isolated DNA sequence according to claim 1, wherein the isolated DNA sequence comprises SEQ ID NO: 53; SEQ ID NO:54; SEQ ID NO: 67; SEQ ID NO: 68; SEQ ID NO:81; SEQ ID NO:82; SEQ ID NO:95 or SEQ ID NO:96.

3. A cloning or expression vector comprising the DNA sequence according to claim 2.

4. The isolated DNA sequence according to claim 1, wherein the isolated DNA sequence further encodes a constant domain of the heavy chain and comprises SEQ ID NO: 60, SEQ ID NO: 61, SEQ ID NO: 74, SEQ ID NO: 75, SEQ ID NO: 88, SEQ ID NO: 89, SEQ ID NO: 102, or SEQ ID NO: 103.

5. A cloning or expression vector comprising the DNA sequence according to claim 4.

6. A cloning or expression vector comprising the DNA sequence according to claim 1.

7. An isolated DNA sequence encoding a light chain variable domain of an antagonistic antibody, which antagonistic antibody binds human TGF-beta 1, human TGF-beta 2 and human TGF-beta 3, wherein the encoded light chain variable domain comprises a CDR having SEQ ID NO:1 for CDR-L1, a CDR having SEQ ID NO:2 for CDR-L2 and a CDR having SEQ ID NO:3 for CDR-L3.

8. The isolated DNA sequence according to claim 7, wherein the isolated DNA sequence comprises SEQ ID NO: 39 or SEQ ID NO:40.

9. A cloning or expression vector comprising the DNA sequence according to claim 8.

10. The isolated DNA sequence according to claim 7, wherein the isolated DNA sequence further encodes a constant domain of the light chain and comprises SEQ ID NO: 46 or SEQ ID NO:47.

11. A cloning or expression vector comprising the DNA sequence according to claim 7.

12. An isolated DNA sequence encoding a heavy chain variable domain and a light chain variable domain of an antagonistic antibody, which antagonistic antibody binds human TGF-beta 1, human TGF-beta 2 and human TGF-beta 3, wherein the isolated DNA sequence comprises:
a first DNA sequence encoding the heavy chain variable domain, wherein the heavy chain variable domain comprises a CDR having SEQ ID NO:4 for CDR-H1, a CDR having SEQ ID NO:5 for CDR-H2 and a CDR having SEQ ID NO:6, SEQ ID NO:7, SEQ ID NO:8 or SEQ ID NO:9 for CDR-H3, and
a second DNA sequence encoding the light chain variable domain, wherein the light chain variable domain comprises a CDR having SEQ ID NO:1 for CDR-L1, a CDR having SEQ ID NO:2 for CDR-L2 and a CDR having SEQ ID NO:3 for CDR-L3.

13. A cloning or expression vector comprising the DNA sequence according to claim 12.

14. A cloning or expression vector according to claim 13, wherein the vector comprises SEQ ID NO: 39 or SEQ ID NO:40, and/or SEQ ID NO: 53, SEQ ID NO:54, SEQ ID NO: 67, SEQ ID NO:68, SEQ ID NO: 81, SEQ ID NO:82, SEQ ID NO:95 or SEQ ID NO: 96.

15. A host cell comprising one or more cloning or expression vectors according to claim 14.

16. A process for producing an antagonistic antibody, comprising culturing the host cell of claim 15 and isolating the antibody.

17. The isolated DNA sequence according to claim 12, wherein the isolated DNA sequence comprises SEQ ID NO: 53; SEQ ID NO:54; SEQ ID NO: 67; SEQ ID NO: 68; SEQ ID NO:81; SEQ ID NO:82; SEQ ID NO:95 or SEQ ID NO:96.

18. The isolated DNA sequence according to claim 12, wherein the isolated DNA sequence further encodes a constant domain of the heavy chain and comprises SEQ ID NO: 60, SEQ ID NO: 61, SEQ ID NO: 74, SEQ ID NO: 75, SEQ ID NO: 88, SEQ ID NO: 89, SEQ ID NO: 102, or SEQ ID NO: 103.

19. The isolated DNA sequence according to claim 12, wherein the isolated DNA sequence comprises SEQ ID NO: 39 or SEQ ID NO:40.

20. The isolated DNA sequence according to claim 12, wherein the isolated DNA sequence further encodes a constant domain of the light chain and comprises SEQ ID NO: 46 or SEQ ID NO:47.

* * * * *